United States Patent
Greene et al.

(10) Patent No.: US 9,352,010 B2
(45) Date of Patent: *May 31, 2016

(54) TREATMENT OF HIV-1 INFECTION AND AIDS

(71) Applicant: The J. David Gladstone Institutes, San Franciscio, CA (US)

(72) Inventors: Warner C. Greene, Hillsborough, CA (US); Gilad Doitsh, San Francisco, CA (US); Orlando Zepeda, San Francisco, CA (US); Nicole Galloway, Portland, OR (US)

(73) Assignee: The J. David Gladstone Institutes, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/846,652

(22) Filed: Sep. 4, 2015

(65) Prior Publication Data

US 2016/0008420 A1 Jan. 14, 2016

Related U.S. Application Data

(63) Continuation of application No. 14/731,259, filed on Jun. 4, 2015, which is a continuation of application No. 13/556,054, filed on Jul. 23, 2012.

(60) Provisional application No. 61/572,883, filed on Jul. 22, 2011, provisional application No. 61/511,023, filed on Jul. 23, 2011, provisional application No. 61/575,324, filed on Aug. 17, 2011.

(51) Int. Cl.
*A61K 38/06* (2006.01)
*A61K 45/06* (2006.01)

(52) U.S. Cl.
CPC ............... *A61K 38/06* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,430,128 A | 7/1995 | Chapman et al. |
| 5,434,248 A | 7/1995 | Chapman et al. |
| 5,462,939 A | 10/1995 | Dolle et al. |
| 5,552,400 A | 9/1996 | Dolle et al. |
| 5,565,430 A | 10/1996 | Dolle et al. |
| 5,585,357 A | 12/1996 | Dolle et al. |
| 5,585,486 A | 12/1996 | Dolle et al. |
| 5,622,967 A | 4/1997 | Dolle et al. |
| 5,639,745 A | 6/1997 | Dolle et al. |
| 5,656,627 A | 8/1997 | Bemis et al. |
| 5,670,494 A | 9/1997 | Dolle et al. |
| 5,677,283 A | 10/1997 | Dolle et al. |
| 5,716,929 A | 2/1998 | Bemis et al. |
| 5,739,279 A | 4/1998 | Robinson |
| 5,756,465 A | 5/1998 | Sleath et al. |
| 5,756,466 A | 5/1998 | Bemis et al. |
| 5,798,247 A | 8/1998 | Albrecht et al. |
| 5,798,442 A | 8/1998 | Gallant et al. |
| 5,834,514 A | 11/1998 | Dolle et al. |
| 5,843,904 A | 12/1998 | Bemis et al. |
| 5,843,905 A | 12/1998 | Singh et al. |
| 5,847,135 A | 12/1998 | Bemis et al. |
| 5,866,545 A | 2/1999 | Hagmann et al. |
| 5,869,519 A | 2/1999 | Karanewsky et al. |
| 5,874,424 A | 2/1999 | Batchelor et al. |
| 5,932,549 A | 8/1999 | Allen et al. |
| 5,985,838 A | 11/1999 | Dolle et al. |
| 6,184,210 B1 | 2/2001 | Keana et al. |
| 6,184,244 B1 | 2/2001 | Karanewsky et al. |
| 6,187,771 B1 | 2/2001 | Karanewsky et al. |
| 6,197,750 B1 | 3/2001 | Karanewsky et al. |
| 6,242,422 B1 | 6/2001 | Karanewsky et al. |
| 6,576,614 B1 | 6/2003 | Dolle et al. |
| 6,632,962 B2 | 10/2003 | Golec et al. |
| 6,689,784 B2 | 2/2004 | Bebbington et al. |
| 7,053,057 B2 | 5/2006 | Golec et al. |
| 7,074,782 B2 | 7/2006 | Bebbington et al. |
| 7,205,327 B2 | 4/2007 | Kay et al. |
| 7,417,029 B2 | 8/2008 | Wannamaker et al. |
| 7,517,987 B2 | 4/2009 | Golec et al. |
| 7,531,570 B2 | 5/2009 | Randle |

(Continued)

FOREIGN PATENT DOCUMENTS

EP 519748 A2 12/1992
EP 547699 A1 6/1993

(Continued)

OTHER PUBLICATIONS

Cornelis et al., "Inflammatory Caspases: targets for novel therapies," Curr. Pharma. Design 13:367-385 (2007).*

Ohnimus et al., "Apoptotic cell death upon contact of CD4+ T lymphocytes with HIV glycoprotein-expressing cells is mediated by caspases but bypasses CD95 (Fas/Apo-1) and TNF receptor 1," J. Immunol. 159:5246-5252 (1997).*

(Continued)

*Primary Examiner* — Julie Ha
*Assistant Examiner* — Kristina M Hellman
(74) *Attorney, Agent, or Firm* — Duane Morris, LLP; Siegfried J. W. Ruppert

(57) ABSTRACT

Provided herein are compositions and methods for the treatment of a patient having an HIV-1 infection and/or AIDS. More specifically this invention provides treatment of an HIV-1 infection and/or AIDS using small molecule compounds, such as inhibitors for the activation and/or activity of caspase-1. Inhibitors for the activation and/or activity of caspase-1 also prevent the cell death of CD4 T-cells in a population of CD4 T-cells comprising HIV-1 infected CD4 T-cells and uninfected CD4 T-cells. In addition, caspase-1 inhibitors inhibit inflammation, and pyroptosis.

75 Claims, 45 Drawing Sheets

(56) References Cited

U.S. PATENT DOCUMENTS

| | | |
|---|---|---|
| 2003/0092703 A1 | 5/2003 | Mortimore et al. |
| 2003/0096737 A1 | 5/2003 | Diu-Hercend et al. |
| 2003/0232846 A1 | 12/2003 | Golec et al. |
| 2004/0019017 A1 | 1/2004 | Mortimore et al. |
| 2004/0048895 A1 | 3/2004 | Allen et al. |
| 2004/0072850 A1 | 4/2004 | Knegtel et al. |
| 2004/0116355 A1 | 6/2004 | Cai et al. |
| 2004/0192612 A1 | 9/2004 | Charrier et al. |
| 2004/0242494 A1 | 12/2004 | Brenchley et al. |
| 2005/0233979 A1 | 10/2005 | Charrier et al. |
| 2006/0128696 A1 | 6/2006 | Vezzani et al. |
| 2006/0160862 A1 | 7/2006 | Charrier et al. |
| 2007/0010457 A1 | 1/2007 | Diu-hercend et al. |
| 2007/0155718 A1 | 7/2007 | Durrant et al. |
| 2008/0015172 A1 | 1/2008 | Mortimore et al. |
| 2008/0286201 A1 | 11/2008 | Guilbert et al. |
| 2009/0093416 A1 | 4/2009 | Brenchley et al. |
| 2009/0131456 A1 | 5/2009 | Golec et al. |
| 2009/0149436 A1 | 6/2009 | Nakada et al. |
| 2009/0215736 A1 | 8/2009 | Mortimore et al. |
| 2009/0281128 A1 | 11/2009 | Knegtel et al. |
| 2010/0040607 A1 | 2/2010 | Tracey et al. |
| 2010/0105914 A1 | 4/2010 | Charrier et al. |
| 2010/0137359 A1 | 6/2010 | Charrier et al. |
| 2011/0003824 A1 | 1/2011 | Charrier et al. |
| 2011/0077190 A1 | 3/2011 | Ahlfors et al. |
| 2011/0130436 A1 | 6/2011 | Golec et al. |
| 2011/0137037 A1 | 6/2011 | Durrant et al. |
| 2011/0144074 A1 | 6/2011 | Mortimore et al. |
| 2015/0343011 A1 | 12/2015 | Greene |

FOREIGN PATENT DOCUMENTS

| | | |
|---|---|---|
| EP | 618223 A2 | 10/1994 |
| EP | 623592 A1 | 11/1994 |
| EP | 623606 A2 | 11/1994 |
| EP | 628550 A2 | 12/1994 |
| EP | 644198 A1 | 3/1995 |
| WO | WO 93/05071 A1 | 3/1993 |
| WO | WO 93/09135 A1 | 5/1993 |
| WO | WO 93/14777 A1 | 8/1993 |
| WO | WO 95/26958 A1 | 10/1995 |
| WO | WO 95/29672 A1 | 11/1995 |
| WO | WO 95/33751 A1 | 12/1995 |
| WO | WO 95/35308 A1 | 12/1995 |
| WO | WO 96/03982 A1 | 2/1996 |
| WO | WO 96/30395 A2 | 10/1996 |
| WO | WO 97/07805 A1 | 3/1997 |
| WO | WO 97/08174 A1 | 3/1997 |
| WO | WO 97/22618 A1 | 6/1997 |
| WO | WO 97/22619 A1 | 6/1997 |
| WO | WO 97/27220 A2 | 7/1997 |
| WO | WO 98/11109 A1 | 3/1998 |
| WO | WO 98/11129 A1 | 3/1998 |
| WO | WO 98/16502 A1 | 4/1998 |
| WO | WO 98/16504 A2 | 4/1998 |
| WO | WO 98/16505 A1 | 4/1998 |
| WO | WO 98/24804 A2 | 6/1998 |
| WO | WO 98/24805 A1 | 6/1998 |
| WO | WO 99/47545 A2 | 9/1999 |
| WO | WO 00/55114 A1 | 9/2000 |
| WO | WO 00/61542 A1 | 10/2000 |
| WO | WO 01/16093 A1 | 3/2001 |
| WO | WO 01/90063 A2 | 11/2001 |
| WO | WO 02/22611 A2 | 3/2002 |
| WO | WO 02/085899 A1 | 10/2002 |

OTHER PUBLICATIONS

De Clercq, "Antiviral drugs: current state of the art," J. Clin. Virol. 22:73-89 (2001).*

Aranda, Victoria, et al; "Taming IL-17 inflammation"; *Nature Medicine*, vol. 17, No. 1; Jan. 2011; pp. 52-53.

Beaumont, et al; "Design of Ester Prodrugs to Enhance Oral Absorption of Poorly Permeable Compounds: Challenges to the Discovery Scientist"; *Current Drug Metabolism* vol. 4 (2003) pp. 461-485.

Bergsbaken, et al; "Pyroptosis: host cell death and inflammation"; *Nat. Rev. Microbiol.* vol. 7, (2009) pp. 99-109.

Caspase-1, 4, 5 Inhibitor (Z-WEHD-FMK) [1 nM] from G Biosciences, Product literature; accessed Aug. 6, 2013 at URL: http://www.biocompare.com/10821-Caspase-Inhibitor-Sets-Samplers/2204006-Caspase1-4-5-Inhibitor-ZWEHDFMK-1mM/.

CD4 Count; accessed Aug. 11, 2013 at URL aids.gov/hiv-aids-basics/just-diagnosed-with-hiv-aids/understand-your-test-resuts/cd4-count/.

Denton Paul W.and Garcia J. Victor; "Humanized Mouse Models of HIV Infection"; AIDS Rev. 2011 Jul.-Sep.; 13(3): 135-148; 24 pages.

Doitsh G,et al; "Abortive HIV Infection Mediates CD4 T Cell Depletion and Inflammation in Human Lymphoid Tissue"; *Cell* vol. 143 (2010) pp. 789-801.

Doitsh Gilad, Galloway Nicole L. K., Geng Xin, Yang Zhiyuan, Monroe Kathryn M., Zepeda Orlando, Hunt Peter W., Hatano Hiroyu, Sowinski Stefanie, Muñoz-Arias Isa, and Greene Warner; "Cell Death by Pyroptosis Drives CD4 T-Cell Depletion in HIV-1 Infection"; Nature. Jan. 23, 2014;505(7484):509-14. doi: 10.1038/nature12940; 18 pages.

Doitsh G,et al; "Death before infection: T cells pushed to suicide by failed HIV transcription"; *Future Virol*. vol. 6, No. 1; (2011) pp. 9-11.

Dolle et al.; "$P_1$ Aspartate-Based Peptide α-((2,6-Dichlorobenzoyl)oxy) methyl Ketones as Potent Time-Dependent Inhibitors of Interleukin-1β-Converting Enzyme"; Journal of Medicinal Chemistry 37: (1994); pp. 563-564.

Dolle et al.; "Aspartyl α-((1-Phenyl-3-(trifluoromethyl)-pyrazol-5-yl)oxy)methyl Ketones as Interleukin-1β Converting Enzyme Inhibitors. Significance of the $P_1$ and $P_3$ Amido Nitrogens for Enzyme-Peptide Inhibitor Binding"; *Journal of Medicinal Chemistry*, vol. 37, No. 23; Nov. 11, 1994; pp. 3863-3866.

Dolle et al.; "Aspartyl α-((Diphenylphosphinyl)oxy)methyl Ketones as Novel Inhibitors of Interleukin-1β Converting Enzyme."; *Journal of Medicinal Chemistry* 38: (1995); pp. 220-222.

Eckstein Daniel A.; "HIV-1 Actively Replicates in Native CD4+ T Cells Residing within Human Lymphoid Tissues"; Immunity, vol. 15, 671-682, Oct. 2001, by Cell Press; 12 pages.

Estaquier, et al; "Fas-mediated apoptosis of CD4+ and CD8+ T cells from human immunodeficiency virus-infected persons: differential in vitro preventive effect of cytokines and protease antagonists"; *Blood* vol. 87, (1996) pp. 4959-4966.

Ettmayer P,et al; "Lessons learned from marketed and investigational prodrugs"; *J. Med. Chem.* vol. 47, No. 10; (2004) pp. 2393-2404.

Fink Susan L. and Cookson Brad T.; "Caspase-1-Dependent Pore Formation During Pyroptosis Leads to Osmotic Lysis of Infected Host Macrophages"; Cell Microbiol. Nov. 2006;8(11):1812-25. Epub Jul. 4, 2006; 14 pages.

Foley, et al; "Ritonavir and disulfiram have potential to inhibit caspase-1 mediated inflammation and reduce neurological sequelae after minor blast exposure"; *Med. Hypo*. vol. 72; (2009) pp. 150-152.

Franchi,et al; "The inflammasome: a caspase-1-activation platform that regulates immune responses and disease pathogenesis"; *Nat. Immunol*. vol. 10, (2009) pp. 241-247.

Graybill et al., "α-((Tetronoyl)Oxy)- and α-((Tetramoyl)Oxy)Methyl Ketone Inhibitors of the Interleukin-1β Converting Enzyme (ICE)"; *Bioorganic & Medicinal Chemistry Letters*, vol. 7, No. 1; (1997); pp. 41-46.

Han, H.-K. "Targeted prodrug design to optimize drug delivery"; *AAPS Pharmsci*. vol. 2, No. 1; (2000) Article 6:1-11.

Health Day News; "Scientists May Have Solved an HIV Mystery: Mechanism for death of critical immune cells identified in study"; *US News and World Report*; Nov. 24, 2010; 1 page; http:/__/health.__usnews.com/health-news/family-healthlsexual-and-reproductive-healthlarticl . . . .

Howard Gary; "Deciphering how CD4 T cells die during HIV infection"; *EurekAiert!*: Nov. 24, 2010; 2 pages; http:/__/www.eurekalert.org/pub__releases/2010-11/gi-dhc111610.php.

(56) References Cited

OTHER PUBLICATIONS

Huang, et al; "Functional Proteomic Analyses of Cd4+ T Lymphocyte Surveillance of the HIV-1 Infected Macrophage"; *J. Neuroimmune Pharmacol.* vol. 5(Suppl. 1):S3-S59 at S13; (Mar. 2010).

Mjalli et al., "Phenylalkyl Ketones as Potent Reversible Inhibitors of Interleukin-1β Converting Enzyme"; *Bioorganic & Medicinal Chemistry Letters*, vol. 3, No. 12; (1993); pp. 2689-2693.

Mjalli et al.; "Activated Ketones as Potent Reversible Inhibitors of Interleukin-1β Converting Enzyme"; *Bioorganic & Medicinal Chemistry Letters*, vol. 4, No. 16; (1994); pp. 1965-1968.

Mjalli et al., "Inhibition of Interleukin-1β Converting Enzyme by N-Acyl-Aspartyl Aryloxymethyl Ketones"; *Bioorganic & Medicinal Chemistry Letters*, vol. 5, No. 13; (1995); pp. 1405-1408.

Mjalli et al., "Inhibition of Interleukin-I~ Converting Enzyme by N-Acyl-Aspartic Acid Ketones"; *Bioorganic & Medicinal Chemistry Letters*, vol. 5, No. 13;: (1995); pp. 1409-1414.

Muller, Christa E; "Prodrug Approaches for Enhancing the Bioavailability of Drugs with Low Solubility"; *Chemistry & Biodiversity*, vol. 6 (2009) pp. 2071-2083.

Okamoto et al.; Peptide Based Interleukin-1β Converting Enzyme (ICE) Inhibitors: Synthesis, Structure Activity Relationships and Crystallographic Study of the ICE-inhibitor Complex; *Chem Pharm Bull* 47(1); Jan. 1999; pp. 11-21.

Osuka Akinori, Hanschen Marc, Stoecklein Veit, and Lederer James A.; "A Protective Role for Inflammasome Activation Following Injury"; Shock. Jan. 2012; 37(1): 47-55. doi: 10.1097/SHK. 0b013e318234f7ff; 21 pages.

Schneider, et al; "Revised Surveillance Case definitions for HIV infection among adults, adolescents, and children aged <18 months and for HIV infection and AIDS among children aged 18 months to <13 years—United States, 2008"; CDC Recommendations and Reports (Dec. 2008).

Science Daily; "An answer to a longstanding question: How HIV infection kills T cells"; Nov. 24, 2010; 3 pages; http://www.sciencedaily.com/releases/20__10111/101124124022.htm.

Semple et al.; "Peptidomimetic Aminomethylene Ketone Inhibitors of Interleukin-1β-Converting Enzyme (ICE)"; *Bioorganic & Medicinal Chemistry Letters 8*; (1998); pp. 959-964.

Singh, Yashveer et al; "Recent Trends in Targeted Anticancer Prodrug and Conjugate"; *Design Curr Med Chem.* vol. 15, No. 18 (2008) pp. 1802-1826.

Sloand, et al; "Human immunodeficiency Virus Type 1 protease inhibitor modulates activation of peripheral blood CD4+ T cells and decreases their susceptibility to apoptosis in vitro and in vivo"; *Blood* vol. 94, (1999) pp. 1021-1027.

Sloand, et al; "Protease inhibitors stimulate hematopoiesis and decrease apoptosis and ICE expression in CD34+ cells"; *Blood* vol. 96, (2000) pp. 2735-2739.

Stierle et al.; "Caspase-1 Inhibitors from an Extremophilic Fungus That Target Specific Leukemia Cell Lines"; *Journal of National Products* 75; (2012); pp. 344-350.

Stierle et al., "Caspase-1 and -3 Inhibiting Drimane Sesquiterpenoids from the Extremophilic Fungus *Penicillium solitum*"; Journal of National Products 75; (2012); pp. 262-266.

Testa, B.; "Prodrug research: futile or fertile?"; Biochemical Pharmacology vol. 68, (2004) pp. 2097-2106.

Thornberry et al., "Inactivation of Interleukin-1β Converting Enzyme by Peptide (Acyloxy)methyl Ketones"; *Biochemistry* 3; (1994); pp. 3934-3940.

Galloway, Nicole LK, et al; "Cell-to-Cell transmission of HIV-1 is required to trigger pyroptotic death of lymphoid tissue-derived CD4 T cells"; *Cell Rep.*, vol. 12, No. 10, Sep. 8, 2015; pp. 1555-1563.

Hodge, Nicholas, C, et al; "Improved cyclic urea inhibitors of the HIV-1 protease: synthesis, potency, resistance profile, human pharmacokinetics and X-ray crystal structure of DMP 450"; *Chemistry & Biology* vol. 3, Apr. 1996; pp. 301-314.

Muñoz-Arias, Isa, et al; "Blood-Derived CD4 T Cells Naturally Resist Pyroptosis during Abortive HIV-1 Infection"; *Cell Host & Microbe*, vol. 18, Oct. 14, 2015; pp. 463-470.

Wannamaker, Woods, et al; "(S)-1-((S)-2-{[1-(4-Amino-3-chlorophenyl)-methanoyl]0amino}-3,3-dimethyl-butanoyl)-pyrrolidine-2-carboxylic acid ((2R,3S)-2-ethoxy-5-oxo-tetrahydro-furan-3-yl)-amide (VX-765), an Orally Available Selective Interleukin (IL)-Converting Enzyme/Caspase-1 Inhibitor, Exhibits Potent Anti-Inflammatory Activities by Inhibiting the Release of IL-1β and IL-18"; *J. Pharm. & Exp. Ther.*, vol. 321, No. 2, 2007; pp. 509-516.

Product Data Sheet—Z-VAD-FMK (http://www.enzolifesciences.com/ALX-260-020/z-vad-fmk/ (last visited Jan. 7, 2016).

Product Data Sheet—YVAD-FMK (http://www.biocompare.com/10204-Biomolecule/236316-caspase1-Inhibitor-YVADFMK-2mM/ (last visited Jan. 7, 2016).

Product Data Sheet—Z-YVAD-FMK (http://www.enzolifesciences.com/alx-260-154/z-yvad-fmk-ready-to-use/; (last visited Jan. 7, 2016).

Product Data Sheet—Z-YVAD-FMK (https://www.mdsystems.com/products/caspase-4-inhibitor-z-yvad-fmk__fmk005 (last visited Jan. 7, 2016).

Product Data Sheet—AC-YVAD-CMK (http://www.enzolifesciences.com/alx-260-028/ac-yvad-cmk/ (last visited Jan. 7, 2016).

Lasinavir; https://en.wikipedia.org/wiki/Lasinavir (last visited Jan. 7, 2016).

Lasinavir; CAS 175385-62-3; http://www.chemnet.com/cas/en/175385-62-3/Lasinavir.html (last visited Jan. 7, 2016).

Proleukin__Aldesleukin__IL-2; http://chemocare.com/chemotherapy/drug-info/aldesleukin.aspx (last visited Jan. 7, 2016).

\* cited by examiner

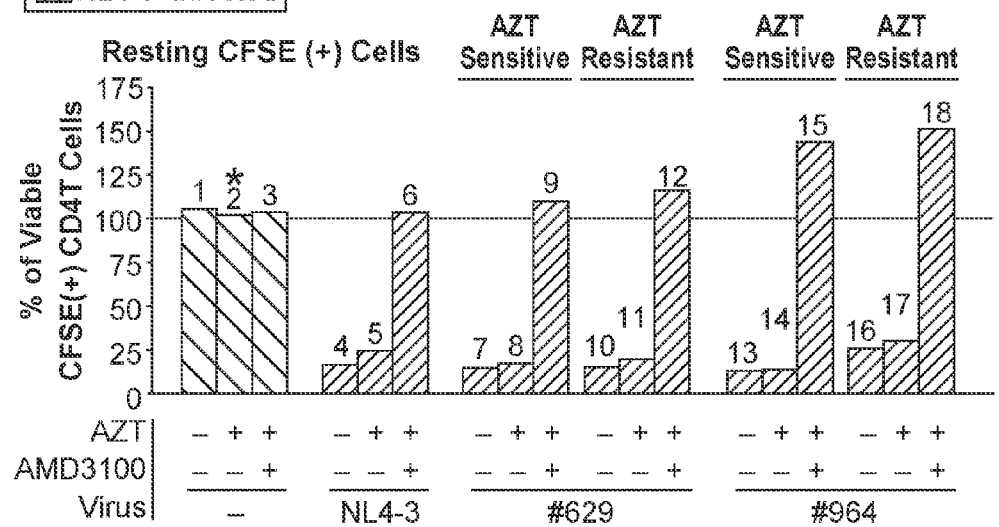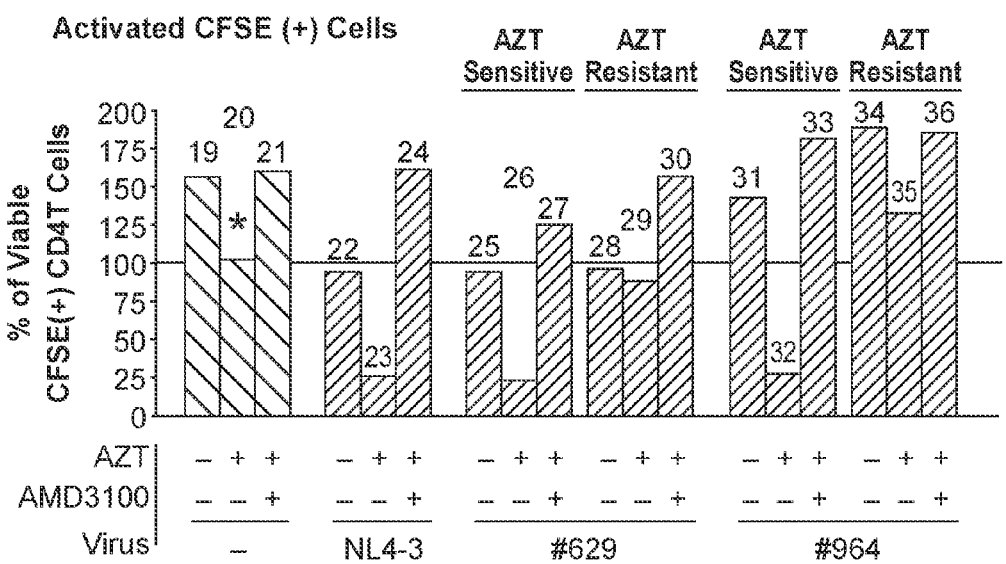
FIG. 8 (Cont. 1)

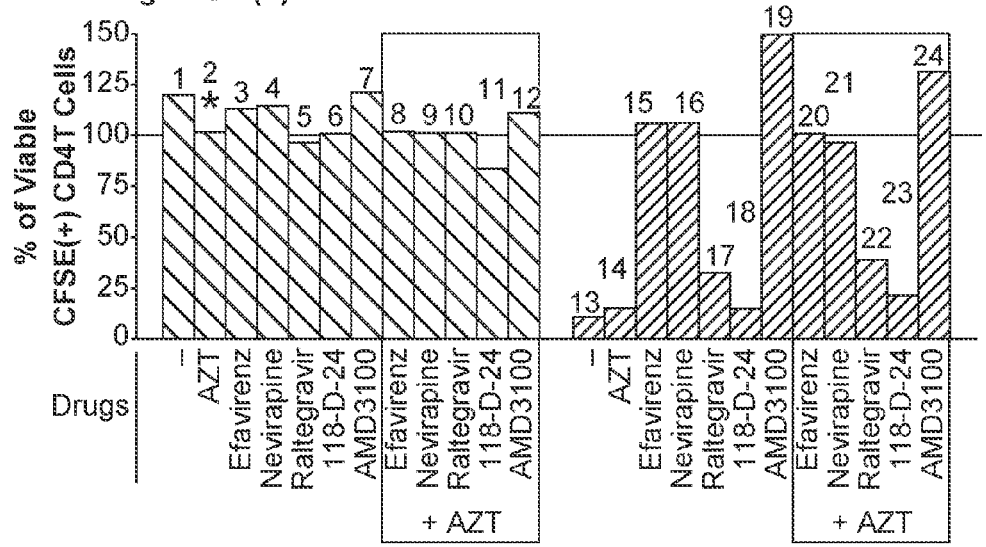
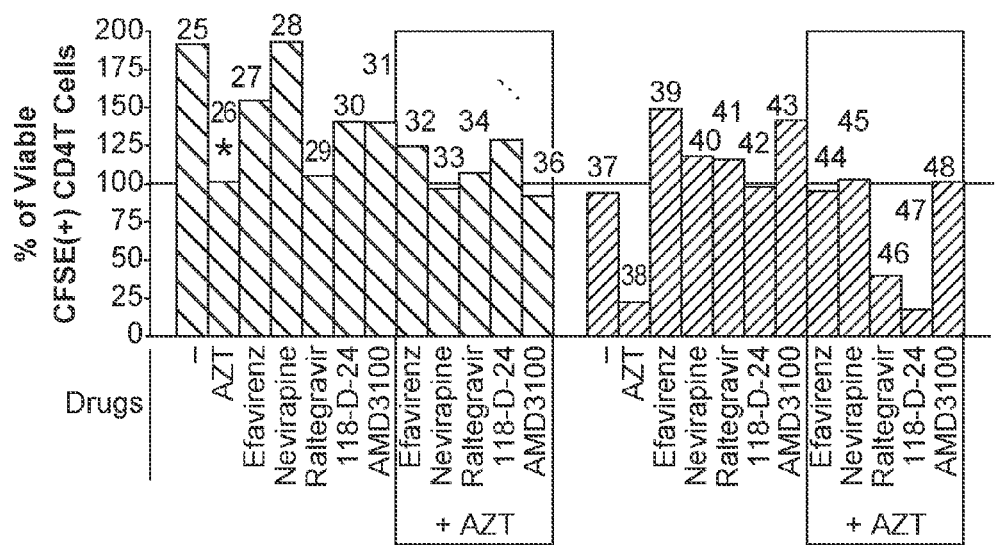
FIG. 8 (Cont. 2)

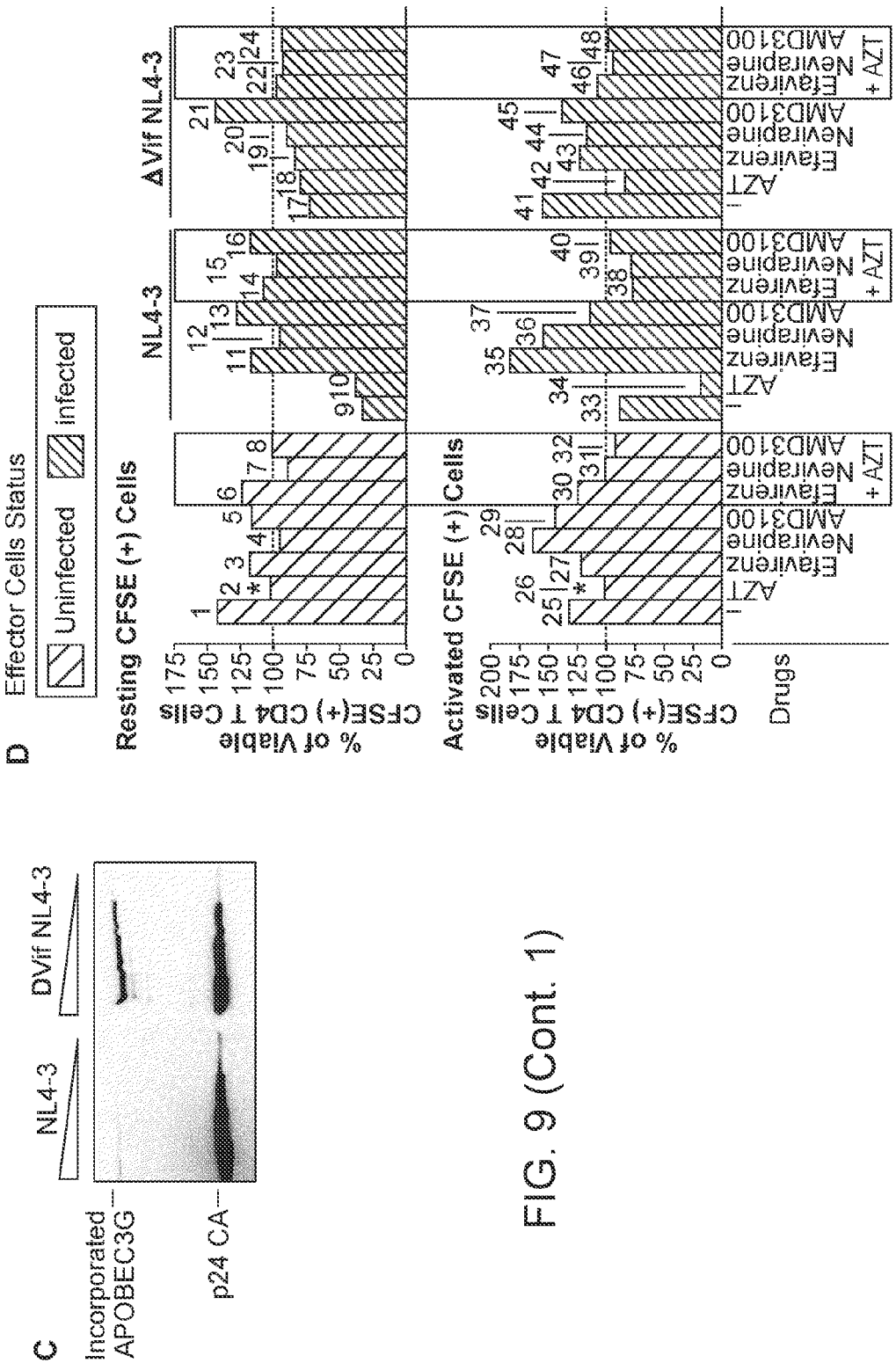
FIG. 9 (Cont. 1)

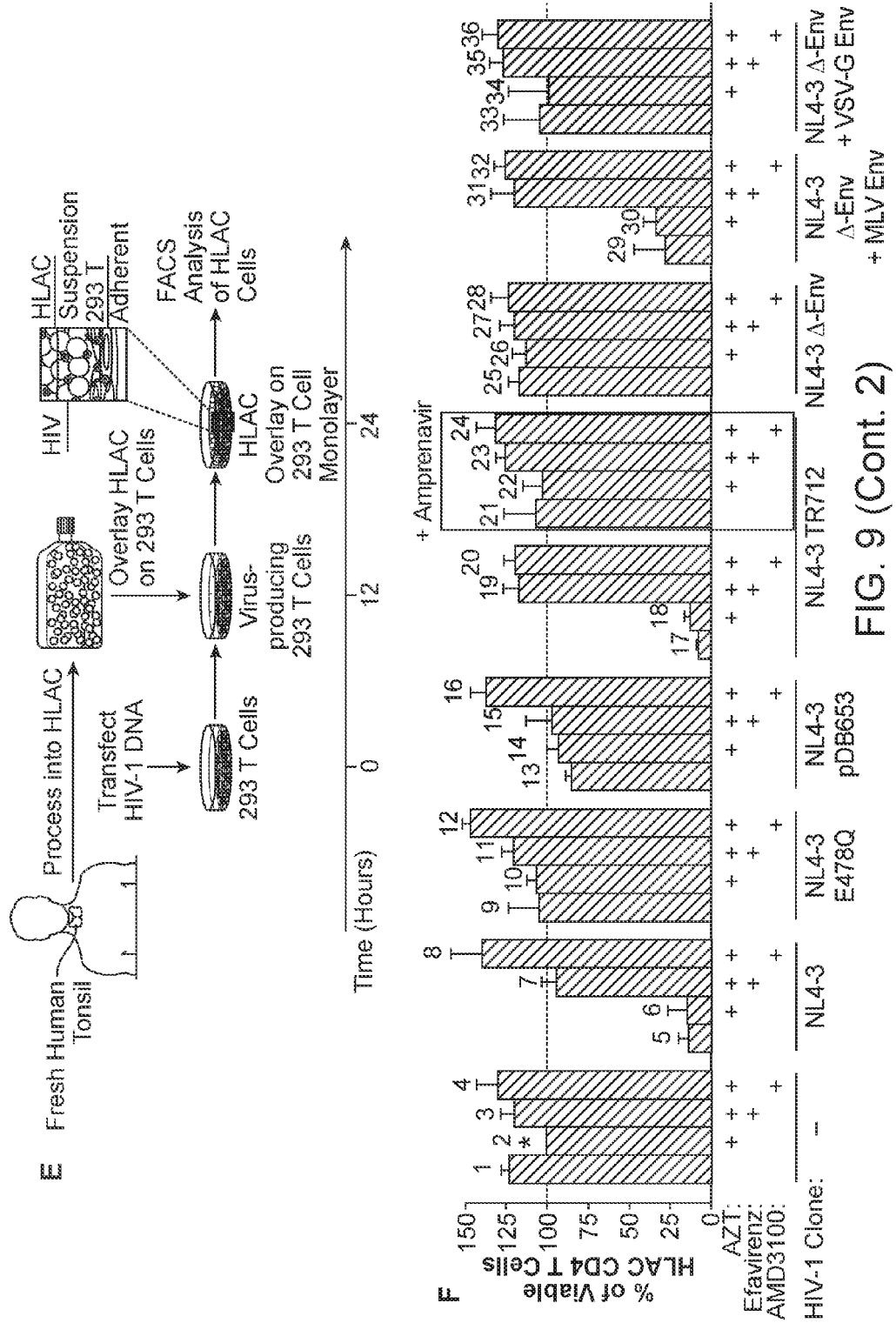
FIG. 9 (Cont. 2)

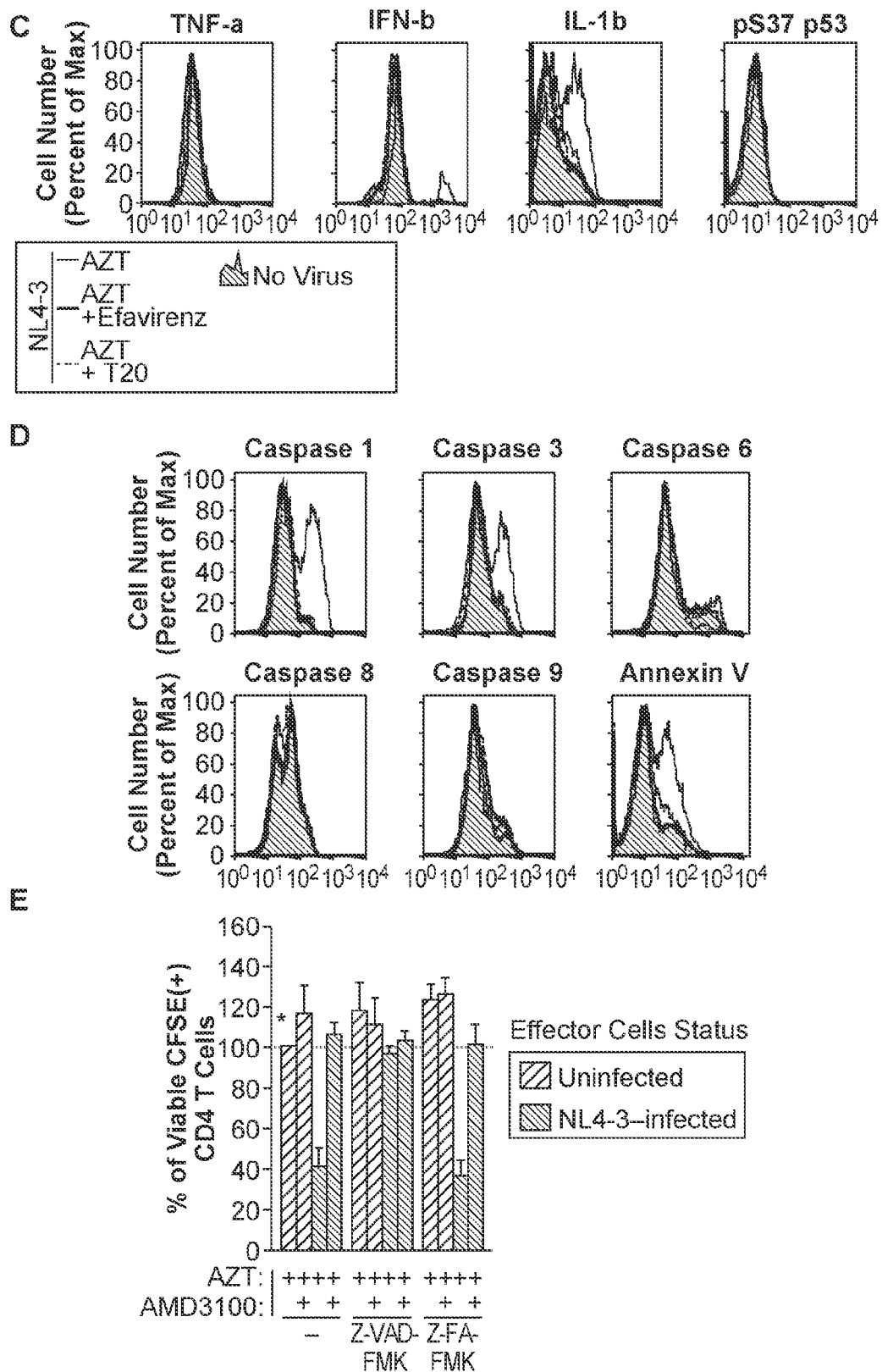
FIG. 10 (Cont. 1)

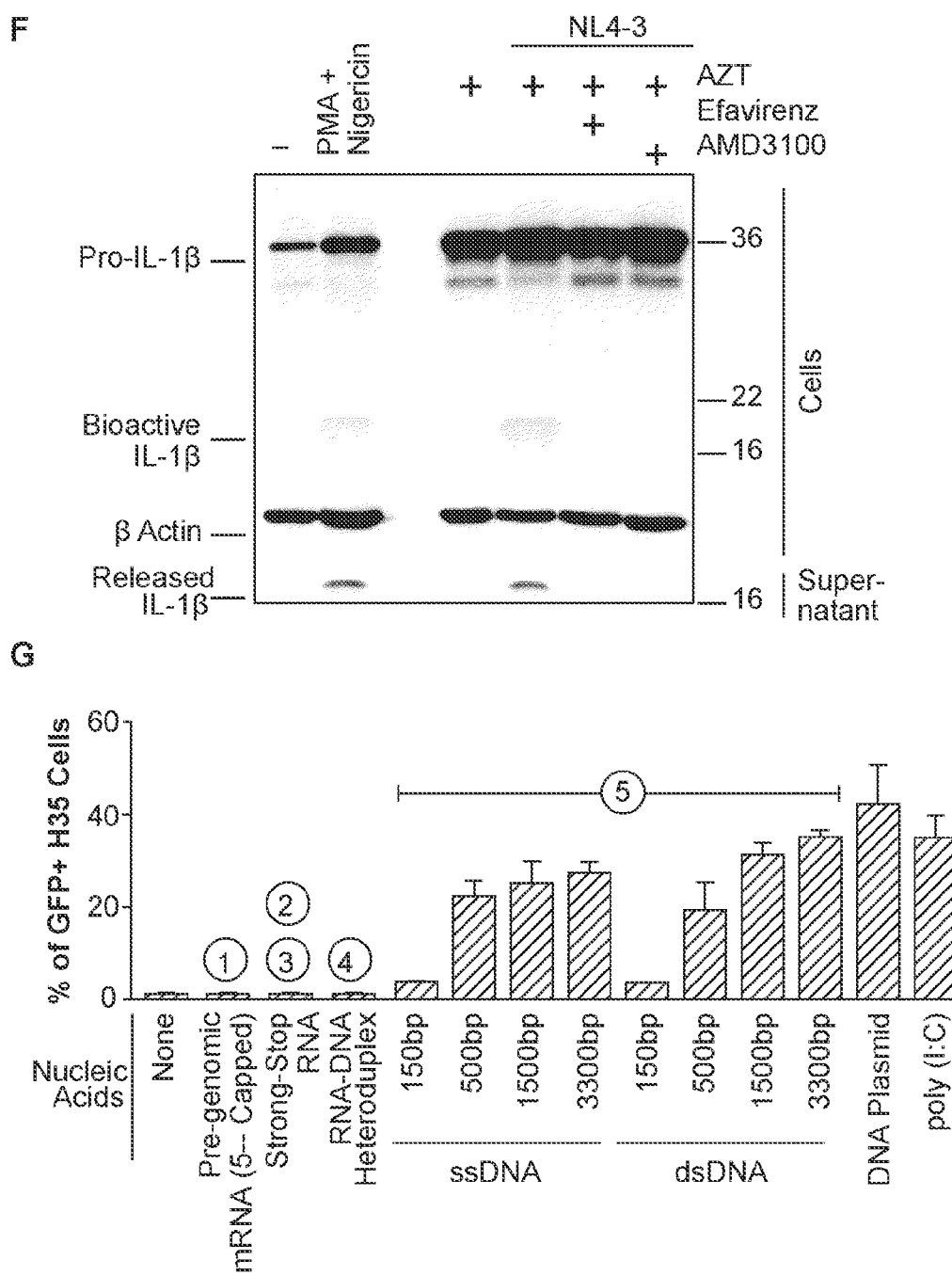
FIG. 10 (Cont. 2)

FIG. 13A
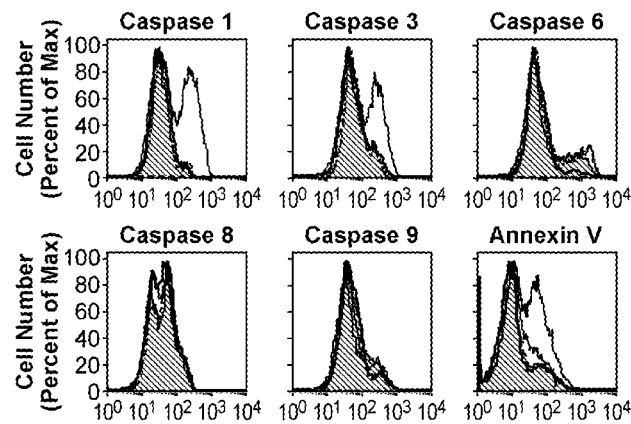
FIG. 13B
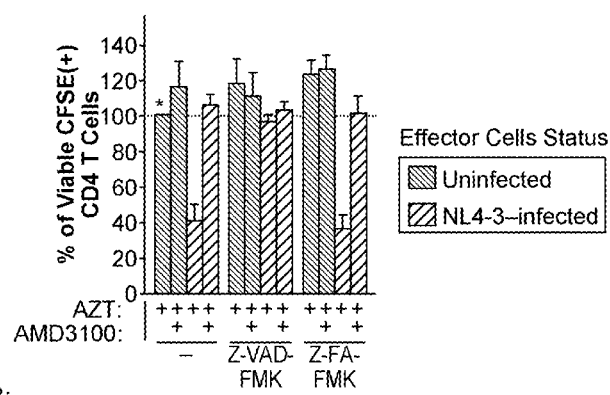
FIG. 13C
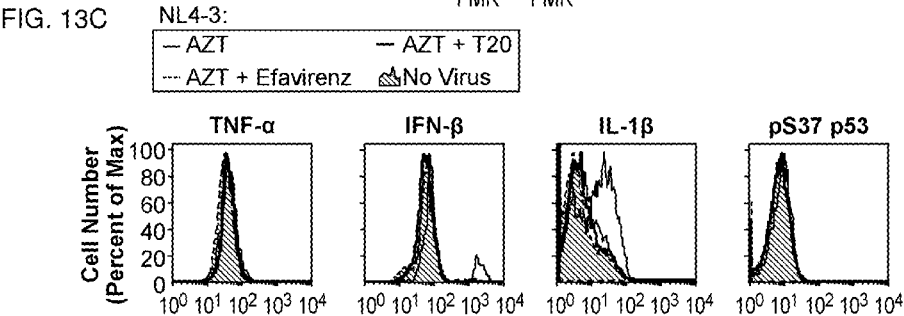
FIG. 13

FIG. 13D
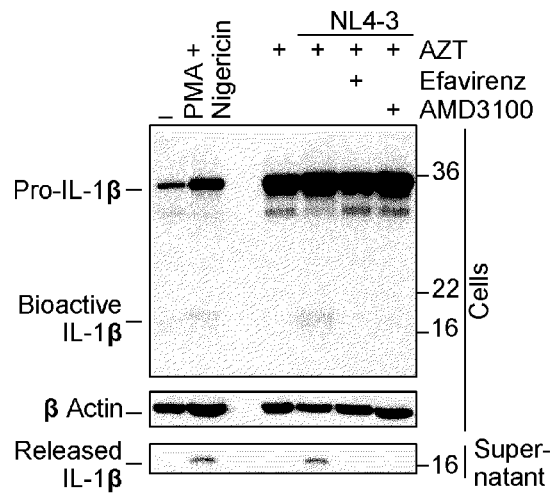
FIG. 13E
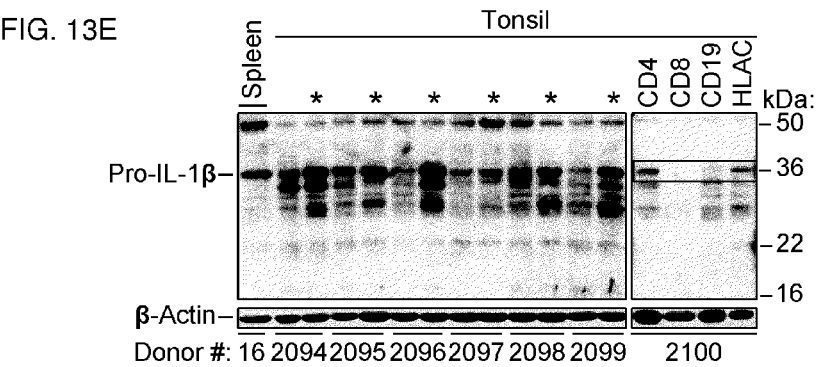
FIG. 13F
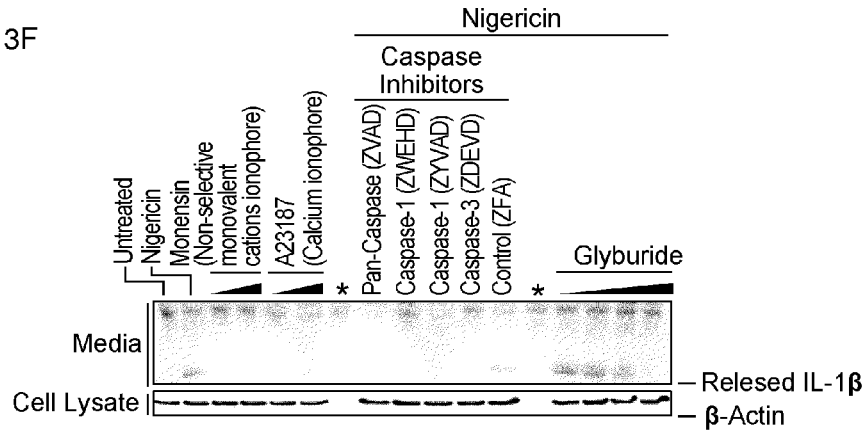
FIG. 13 (Cont.)

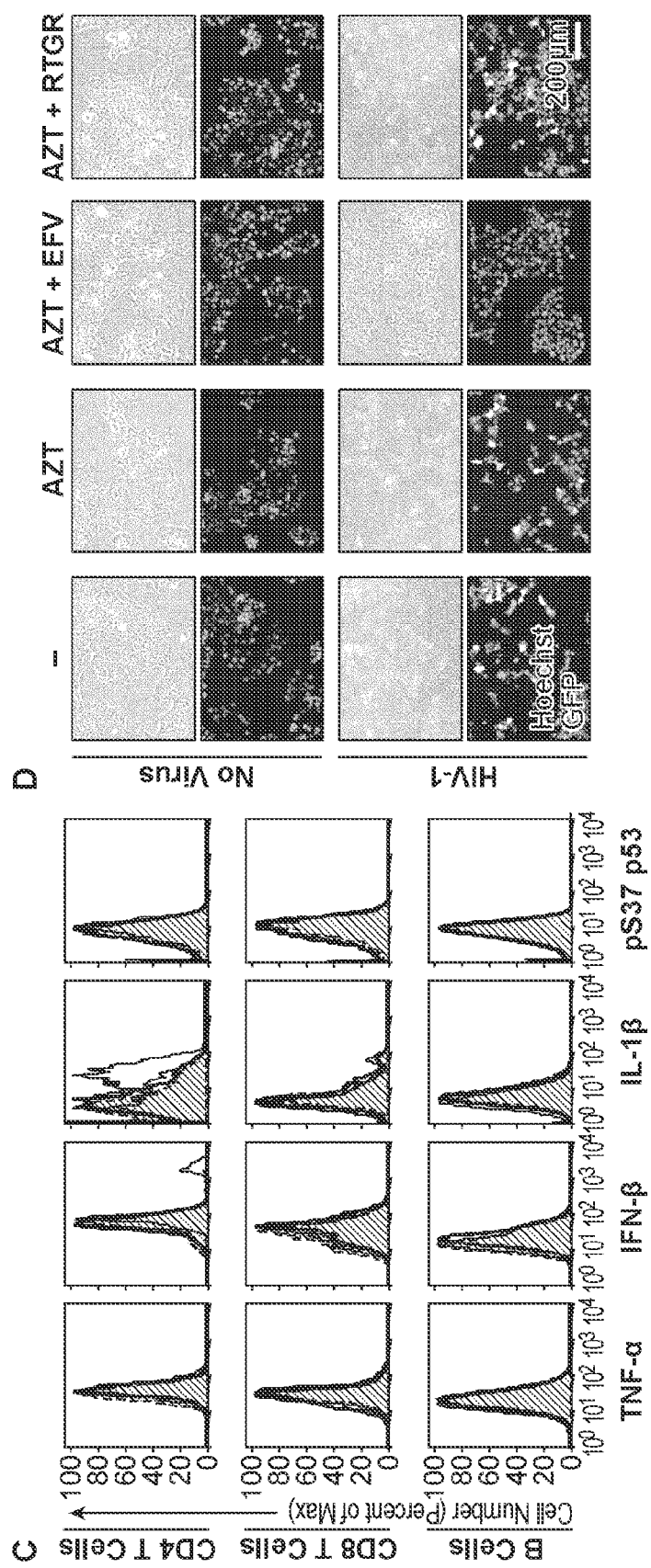
FIG. 14 (Cont. 1)

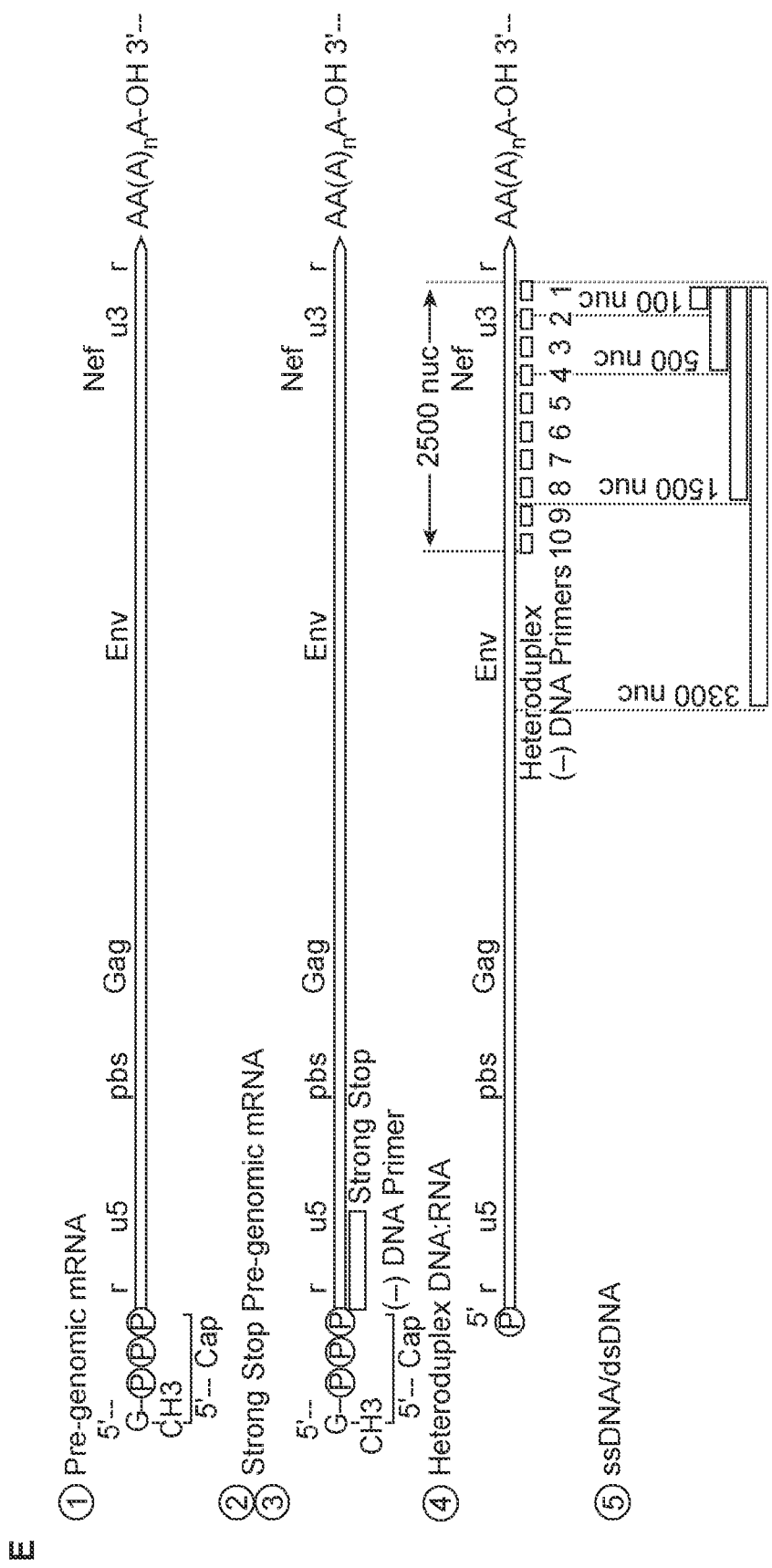
FIG. 14 (Cont. 2)

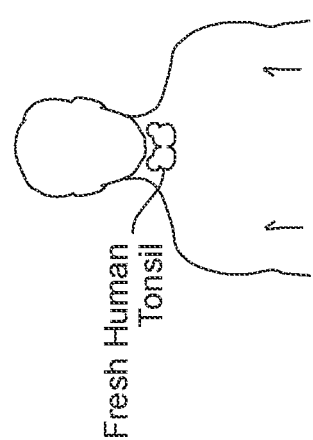
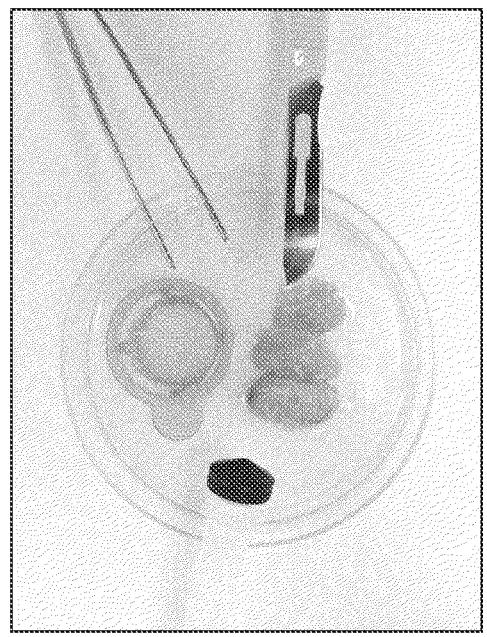
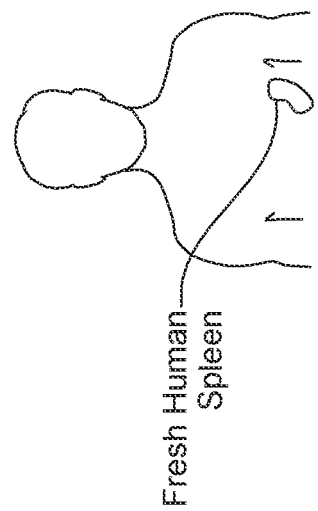
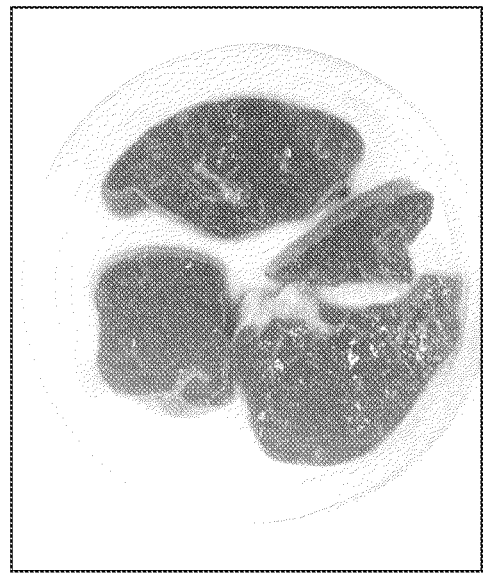
FIG. 19

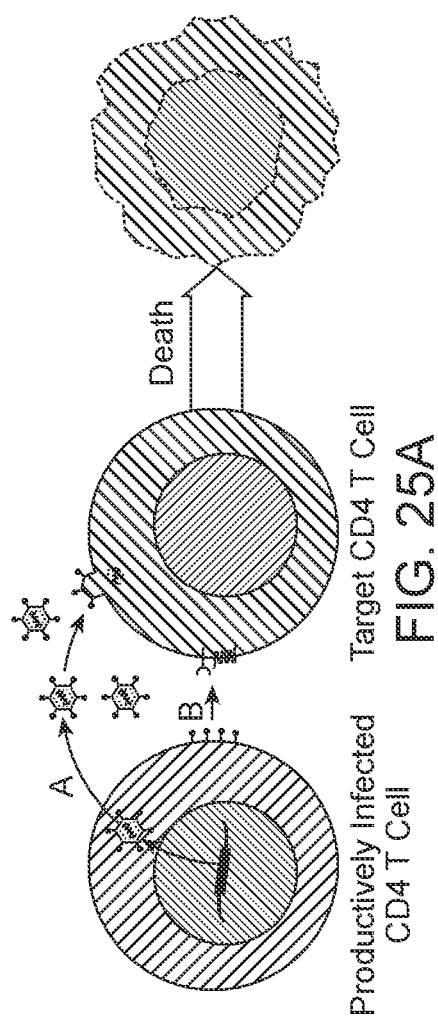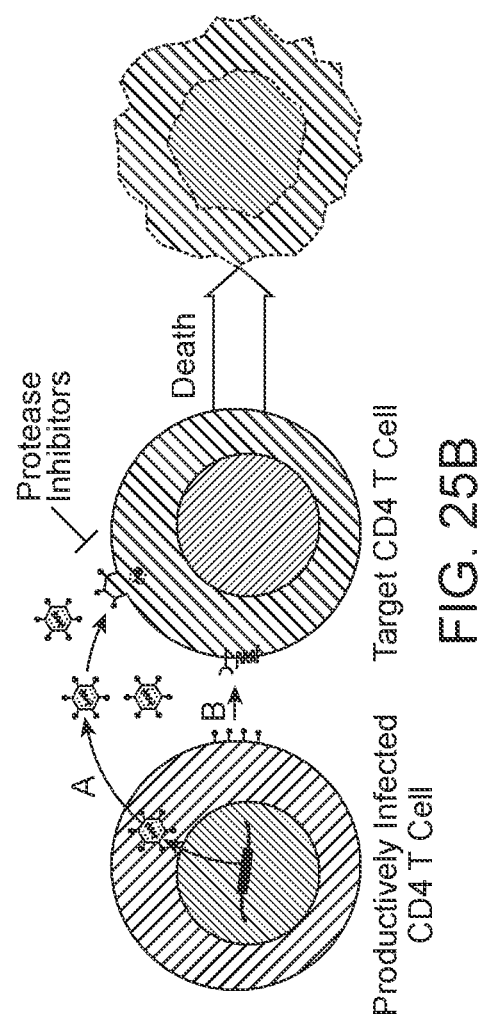

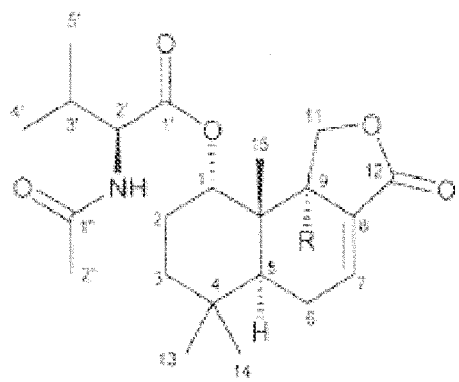
1  R=H
2  R=OH
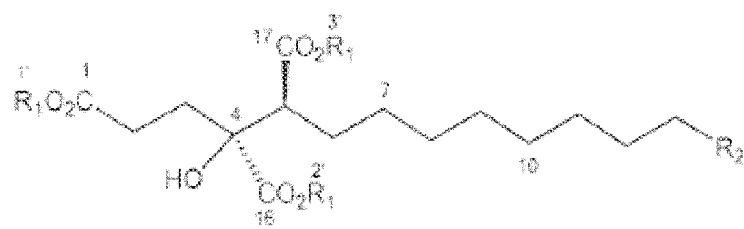
3  $R_1$ = H   $R_2$ = $CH_2CH_3$     4  $R_1$ = $CH_3$   $R_2$ = $CH_2CH_3$
7  $R_1$ = H   $R_2$ = $CH=CH_2$     8  $R_1$ = $CH_3$   $R_2$ = $CH=CH_2$
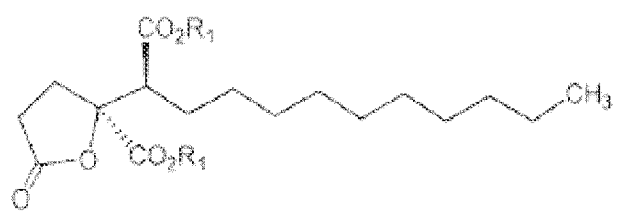
5  $R_1$ = H   6  $R_1$ = $CH_3$
FIG. 30B fmk = fluoromethyl ketone

| Compound | Formula |
|---|---|
| 1 | 1-naphthylOAc-E-Asp-aldehyde |
| 2 | z-E-Asp-aldehyde |
| 3 | z-E-D-Asp-fmk |
| 4 | (1-Naphthyl)OAc-E-Asp-fmk |
| 5 | z-Glu(tetrazolyl)-Glu-D-CH2O(F2-Ph) |
| 6 | z-G-Asp-aldehyde |
| 7 | acetyl-G-Asp-aldehyde |
| 8 | z-Asp-G-aldehyde |
| 9 | z-G-Asp-fmk |
| 10 | z-G-Asp-CH2OPOPh2 |
| 11 | z-G-Asp-CH2O(2,3,5,6-F4Ph) |

9

G (n=1)

R-G-Asp-tfpmk analogues (tfpmk = tetra fluoro phenoxy methyl ketone)

| Compound | "R" group |
|---|---|
| 12 | (1-Naphthyl)CH2CO |
| 13 | PhCH2CO |
| 14 | PropargylOCO |
| 15 | 3,4,5-(MeO)3PhOCO |
| 16 | 3,4-MethylenedioxyPhOCO |
| 17 | 4-CH3OPHOCO |
| 18 | 4-CH3OBenzylNCO |
| 19 | PhSCO |
| 20 | F3COPhSO2 |
| 21 | Me2NSO2 |
| 22 | Ph2PO |

```
                        SEQUENCE LISTING

<160> NUMBER OF SEQ ID NOS: 49

<210> SEQ ID NO 1
<211> LENGTH: 4
<212> TYPE: PRT
<213> ORGANISM: Homo sapiens

<400> SEQUENCE: 1

Trp Glu His Asp
1

<210> SEQ ID NO 2
<211> LENGTH: 4
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa = Val or Leu
<220> FEATURE:
<221> NAME/KEY: misc_feature
<222> LOCATION: (3)..(3)
<223> OTHER INFORMATION: Xaa can be any naturally occurring amino acid

<400> SEQUENCE: 2

Xaa Glu Xaa Asp
1

<210> SEQ ID NO 3
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Asp = Ac-Asp
<220> FEATURE:
<221> NAME/KEY: misc_feature
<222> LOCATION: 4
<223> OTHER INFORMATION: Modified amino acid Asp = Asp-CHO

<400> SEQUENCE: 3

Asp Met Gln Asp
1

<210> SEQ ID NO 4
```

```
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Tyr = Ac-Tyr
<220> FEATURE:
<221> NAME/KEY: misc_feature
<222> LOCATION: 4
<223> OTHER INFORMATION: Modified amino acid Asp = Asp-CMK

<400> SEQUENCE: 4

Tyr Val Ala Asp
1

<210> SEQ ID NO 5
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Asp = Z-Asp
<220> FEATURE:
<221> NAME/KEY: misc_feature
<222> LOCATION: 4
<223> OTHER INFORMATION: Modified amino acid Asp =Asp-CMK

<400> SEQUENCE: 5

Asp Glu Val Asp
1

<210> SEQ ID NO 6
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Asp = Z-Asp

<400> SEQUENCE: 6

Asp Glu Val Asp
1

<210> SEQ ID NO 7
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Tyr = Ac-Tyr
<220> FEATURE:
<221> NAME/KEY: misc_feature
<222> LOCATION: 4
<223> OTHER INFORMATION: Modified amino acid Asp =Asp-FMK

<400> SEQUENCE: 7
```

Tyr Val Ala Asp
1

<210> SEQ ID NO 8
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Ile = Ac-Ile

<400> SEQUENCE: 8

Ile Glu Thr Asp
1

<210> SEQ ID NO 9
<211> LENGTH: 5
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Val = Ac-Val

<400> SEQUENCE: 9

Val Asp Val Ala Asp
1               5

<210> SEQ ID NO 10
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Asp = Ac-Asp

<400> SEQUENCE: 10

Asp Gln Met Asp
1

<210> SEQ ID NO 11
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Leu = Ac-Leu

<400> SEQUENCE: 11

Leu Glu His Asp
1

<210> SEQ ID NO 12
<211> LENGTH: 4
<212> TYPE: PRT

```
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Trp = Z-Trp

<400> SEQUENCE: 12

Trp Glu His Asp
1

<210> SEQ ID NO 13
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Trp = Z-Trp;
<220> FEATURE:
<221> NAME/KEY: misc_feature
<222> LOCATION: 4
<223> OTHER INFORMATION: Modified amino acid Asp = Asp-fmk

<400> SEQUENCE: 13

Trp Glu His Asp
1

<210> SEQ ID NO 14
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Trp = Z-Trp;
<220> FEATURE:
<221> NAME/KEY: misc_feature
<222> LOCATION: 2,3
<223> OTHER INFORMATION: OMe linker
<220> FEATURE:
<221> NAME/KEY: misc_feature
<222> LOCATION: 4
<223> OTHER INFORMATION: Modified amino acid Asp = Asp-(OMe)-fmk

<400> SEQUENCE: 14

Trp Glu His Asp
1

<210> SEQ ID NO 15
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Tyr = Z-Tyr

<400> SEQUENCE: 15

Tyr Val Ala Asp
1
```

```
<210> SEQ ID NO 16
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Tyr = Z-Tyr;
<220> FEATURE:
<221> NAME/KEY: misc_feature
<222> LOCATION: 4
<223> OTHER INFORMATION: Modified amino acid Asp = Asp-fmk

<400> SEQUENCE: 16

Tyr Val Ala Asp
1

<210> SEQ ID NO 17
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Tyr = Ac-Tyr;
<220> FEATURE:
<221> NAME/KEY: misc_feature
<222> LOCATION: 4
<223> OTHER INFORMATION: Modified amino acid Asp = Asp-cmk

<400> SEQUENCE: 17

Tyr Val Ala Asp
1

<210> SEQ ID NO 18
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Val = Ac-Val

<400> SEQUENCE: 18

Val Glu Ile Asp
1

<210> SEQ ID NO 19
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Val = Z-Val

<400> SEQUENCE: 19

Val Glu Ile Asp
```

```
<210> SEQ ID NO 20
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Tyr = Z-Tyr;
<220> FEATURE:
<221> NAME/KEY: misc_feature
<222> LOCATION: 4
<223> OTHER INFORMATION: Modified amino acid Asp = Asp-(OMe)-fmk

<400> SEQUENCE: 20

Tyr Val Ala Asp
1

<210> SEQ ID NO 21
<211> LENGTH: 30
<212> TYPE: DNA
<213> ORGANISM: Artificial
<220> FEATURE:
<223> OTHER INFORMATION: Description of Artificial Sequence: Primer

<400> SEQUENCE: 21
cagtacaggc aaaaagcagc tgcttatatg                                    30

<210> SEQ ID NO 22
<211> LENGTH: 29
<212> TYPE: DNA
<213> ORGANISM: Artificial
<220> FEATURE:
<223> OTHER INFORMATION: Description of Artificial Sequence: Primer

<400> SEQUENCE: 22
gcatccggag tacttcaaga actgctgac                                     29

<210> SEQ ID NO 23
<211> LENGTH: 22
<212> TYPE: DNA
<213> ORGANISM: Artificial
<220> FEATURE:
<223> OTHER INFORMATION: Description of Artificial Sequence: Primer

<400> SEQUENCE: 23
aaggcagctg tagatcttag cc                                            22

<210> SEQ ID NO 24
<211> LENGTH: 29
<212> TYPE: DNA
<213> ORGANISM: Artificial
<220> FEATURE:
<223> OTHER INFORMATION: Description of Artificial Sequence: Primer

<400> SEQUENCE: 24
actgctgtgc cttggaatgc tagttggag                                     29

<210> SEQ ID NO 25
<211> LENGTH: 33
<212> TYPE: DNA
<213> ORGANISM: Artificial
<220> FEATURE:
<223> OTHER INFORMATION: Description of Artificial Sequence: Primer
```

<400> SEQUENCE: 25
atgagagtga aggagaagta tcagcacttg tgg                               33

<210> SEQ ID NO 26
<211> LENGTH: 100
<212> TYPE: DNA
<213> ORGANISM: Artificial
<220> FEATURE:
<223> OTHER INFORMATION: Description of Artificial Sequence: Construct

<400> SEQUENCE: 26
ctgctagaga ttttccacac tgactaaaag ggtctgaggg atctctagtt accagagtac    60
cacaacagac gggcagagac tactttgagc actcaaggca                        100

<210> SEQ ID NO 27
<211> LENGTH: 81
<212> TYPE: DNA
<213> ORGANISM: Artificial
<220> FEATURE:
<223> OTHER INFORMATION: Description of Artificial Sequence: Construct

<400> SEQUENCE: 27
agctttattg aggcttaagc agtgggttcc ctagttagcc agagagctcc caggctcaga    60
tctggtctaa ccagagagac c                                            81

<210> SEQ ID NO 28
<211> LENGTH: 50
<212> TYPE: DNA
<213> ORGANISM: Artificial
<220> FEATURE:
<223> OTHER INFORMATION: Description of Artificial Sequence: Primer

<400> SEQUENCE: 28
gggctcgcca ctccccagtc ccgcccaggc cacgcctccc tggaaagtcc              50

<210> SEQ ID NO 29
<211> LENGTH: 55
<212> TYPE: DNA
<213> ORGANISM: Artificial
<220> FEATURE:
<223> OTHER INFORMATION: Description of Artificial Sequence: Primer

<400> SEQUENCE: 29
cctccactct aacacttctc tctcagggtc atccattcca tgcaggctca caggg         55

<210> SEQ ID NO 30
<211> LENGTH: 55
<212> TYPE: PRT
<213> ORGANISM: Artificial
<220> FEATURE:
<223> OTHER INFORMATION: Description of Artificial Sequence: Primer

<400> SEQUENCE: 30

Gly Gly Cys Thr Cys Ala Ala Cys Thr Gly Gly Thr Ala Cys Thr Ala
1               5                   10                  15

Gly Cys Thr Thr Gly Thr Ala Gly Cys Ala Cys Cys Ala Thr Cys Cys
            20                  25                  30

Ala Ala Ala Gly Gly Thr Cys Ala Gly Thr Gly Gly Ala Thr Ala Thr
        35                  40                  45

Cys Thr Gly Ala Cys Cys Cys
    50                  55

```
<210> SEQ ID NO 31
<211> LENGTH: 47
<212> TYPE: DNA
<213> ORGANISM: Artificial
<220> FEATURE:
<223> OTHER INFORMATION: Description of Artificial Sequence: Primer

<400> SEQUENCE: 31
gccaatcagg gaagtagcct tgtgtgtggt agatccacag atcaagg          47

<210> SEQ ID NO 32
<211> LENGTH: 52
<212> TYPE: DNA
<213> ORGANISM: Artificial
<220> FEATURE:
<223> OTHER INFORMATION: Description of Artificial Sequence: Primer

<400> SEQUENCE: 32
gggagtgaat tagcccttcc agtccccct tttcttttaa aaagtggcta ag      52

<210> SEQ ID NO 33
<211> LENGTH: 50
<212> TYPE: DNA
<213> ORGANISM: Artificial
<220> FEATURE:
<223> OTHER INFORMATION: Description of Artificial Sequence: primer

<400> SEQUENCE: 33
ggtgtgactg gaaaacccac ctcttcctcc tcttgtgctt ctagccaggc          50

<210> SEQ ID NO 34
<211> LENGTH: 106
<212> TYPE: DNA
<213> ORGANISM: Artificial
<220> FEATURE:
<223> OTHER INFORMATION: Description of Artificial Sequence: Primer

<400> SEQUENCE: 34
gcattgttag ctgctgtatt gctacttgtg attgctccat gttttctag gccccatctg   60 ctgctggctc agctcgtctc attctttccc ttacagcagg ccatcc              106

<210> SEQ ID NO 35
<211> LENGTH: 51
<212> TYPE: DNA
<213> ORGANISM: Artificial
<220> FEATURE:
<223> OTHER INFORMATION: Description of Artificial Sequence: Primer

<400> SEQUENCE: 35
ccacttgcca cccatcttat agcaaaatcc tttccaagcc ctgtcttatt c         51

<210> SEQ ID NO 36
<211> LENGTH: 54
<212> TYPE: DNA
<213> ORGANISM: Artificial
<220> FEATURE:
<223> OTHER INFORMATION: Description of Artificial Sequence: Primer

<400> SEQUENCE: 36
ggcgaatagc tctataagct gcttgtaata cttctataac cctatactgt cccc       54

<210> SEQ ID NO 37
<211> LENGTH: 4
<212> TYPE: PRT
<213> ORGANISM: Artificial
```

```
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Tyr = Acetyl-Tyr
<220> FEATURE:
<221> NAME/KEY: misc_feature
<222> LOCATION: 4
<223> OTHER INFORMATION: Modified amino acid Asp = Asp-amino-4-
      methylcoumarin

<400> SEQUENCE: 37

Tyr Val Ala Asp
1

<210> SEQ ID NO 38
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Asp = Acetyl-Asp
<220> FEATURE:
<221> NAME/KEY: misc_feature
<222> LOCATION: 4
<223> OTHER INFORMATION: Modified amino acid Asp = Asp-amino-4-
      methylcoumarin

<400> SEQUENCE: 38

Asp Glu Val Asp
1

<210> SEQ ID NO 39
<211> LENGTH: 22
<212> TYPE: DNA
<213> ORGANISM: Artificial
<220> FEATURE:
<223> OTHER INFORMATION: Description of Artificial Sequence: Primer

<400> SEQUENCE: 39
ggctaactag ggaacccact gc                                           22

<210> SEQ ID NO 40
<211> LENGTH: 22
<212> TYPE: DNA
<213> ORGANISM: Artificial
<220> FEATURE:
<223> OTHER INFORMATION: Description of Artificial Sequence: Primer

<400> SEQUENCE: 40
caacagacgg gcacacacta ct                                           22

<210> SEQ ID NO 41
<211> LENGTH: 31
<212> TYPE: DNA
<213> ORGANISM: Artificial
<220> FEATURE:
<223> OTHER INFORMATION: Description of Artificial Sequence: Primer
<220> FEATURE:
<221> NAME/KEY: misc_feature
<222> LOCATION: 1
<223> OTHER INFORMATION: Modified base: 6~FAM bound thymine
<220> FEATURE:
<221> NAME/KEY: misc_feature
<222> LOCATION: 31
```

<223> OTHER INFORMATION: Modified base: Cytosine bound to MGBNFQ

<400> SEQUENCE: 41
taagcctcaa taaagcttgc cttgagtgct c                          31

<210> SEQ ID NO 42
<211> LENGTH: 19
<212> TYPE: DNA
<213> ORGANISM: Artificial
<220> FEATURE:
<223> OTHER INFORMATION: Description of Artificial Sequence: Primer

<400> SEQUENCE: 42
ttgacagccg cctagcatt                                        19

<210> SEQ ID NO 43
<211> LENGTH: 21
<212> TYPE: DNA
<213> ORGANISM: Artificial
<220> FEATURE:
<223> OTHER INFORMATION: Description of Artificial Sequence:  Primer

<400> SEQUENCE: 43
ttgaagtact ccggatgcag c                                     21

<210> SEQ ID NO 44
<211> LENGTH: 16
<212> TYPE: DNA
<213> ORGANISM: Artificial
<220> FEATURE:
<223> OTHER INFORMATION: Description of Artificial Sequence:  Primer
<220> FEATURE:
<221> NAME/KEY: misc_feature
<222> LOCATION: 1
<223> OTHER INFORMATION: Cytosine bound to 6-FAM,
<220> FEATURE:
<221> NAME/KEY: misc_feature
<222> LOCATION: 16
<223> OTHER INFORMATION: Guanine bond to MGB

<400> SEQUENCE: 44
catcacgtgg cccgag                                           16

<210> SEQ ID NO 45
<211> LENGTH: 25
<212> TYPE: DNA
<213> ORGANISM: Artificial
<220> FEATURE:
<223> OTHER INFORMATION: Description of Artificial Sequence: Primer

<400> SEQUENCE: 45
tggacaaatg acatggtaga acaga                                 25

<210> SEQ ID NO 46
<211> LENGTH: 24
<212> TYPE: DNA
<213> ORGANISM: Artificial
<220> FEATURE:
<223> OTHER INFORMATION: Description of Artificial Sequence: Primer

<400> SEQUENCE: 46
tttacacatg gctttaggct ttga                                  24

<210> SEQ ID NO 47
<211> LENGTH: 24
<212> TYPE: DNA
<213> ORGANISM: Artificial

```
<220> FEATURE:
<223> OTHER INFORMATION: Description of Artificial Sequence: Primer
<220> FEATURE:
<221> NAME/KEY: misc_feature
<222> LOCATION: 1
<223> OTHER INFORMATION: Cytosine bound to 6-FAM
<220> FEATURE:
<221> NAME/KEY: misc_feature
<222> LOCATION: 24
<223> OTHER INFORMATION: Guanine bound to MGB

<400> SEQUENCE: 47
catgaggata taatcagttt atgg                                          24

<210> SEQ ID NO 48
<211> LENGTH: 4
<212> TYPE: PRT
<213> ORGANISM: Artificial
<220> FEATURE:
<223> OTHER INFORMATION: Description of Artificial Sequence: caspase
      binding site
<220> FEATURE:
<221> NAME/KEY: misc_feature
<222> LOCATION: 1
<223> OTHER INFORMATION: Modified amino acid Asp = Z-Asp;
<220> FEATURE:
<221> NAME/KEY: misc_feature
<222> LOCATION: 4
<223> OTHER INFORMATION: Modified amino acid Asp = Asp-fmk

<400> SEQUENCE: 48

Asp Glu Val Asp
1

<210> SEQ ID NO 49
<211> LENGTH: 51
<212> TYPE: DNA
<213> ORGANISM: Artificial
<220> FEATURE:
<223> OTHER INFORMATION: Description of Artificial Sequence: primer

<400> SEQUENCE: 49
gcattgttag ctgctgtatt gctacttgtg attgctccat gttttctag g              51
```

TREATMENT OF HIV-1 INFECTION AND AIDS

CROSS-REFERENCE TO RELATED APPLICATIONS

This application is a continuation of U.S. application Ser. No. 14/731,259, filed Jun. 4, 2015, entitled "Treatment of HIV-1 Infection and AIDS," which is a continuation of U.S. application Ser. No. 13/556,054, filed Jul. 23, 2012, entitled "Treatment of HIV-1 Infection and AIDS," claiming the benefit of U.S. Appl. Ser. No. 61/572,883, filed Jul. 22, 2011, U.S. Appl. Ser. No. 61/511,023, filed Jul. 23, 2011, and U.S. Appl. Ser. No. 61/575,324, filed Aug. 17, 2011, each entitled "Treatment of HIV-1 Infection and AIDS," the disclosures of which are incorporated herewith and herein by reference in their entireties for all purposes.

FIELD OF INVENTION

The present invention relates generally to the treatment of HIV-1 infection and AIDS. More specifically this invention provides treatment of HIV-1 infection and AIDS using compounds that prevent the death of CD4 T-cells in HIV-1 infected patients. The invention also relates to compositions and methods that prevent the death of CD4 T-cells in a population of CD4 T-cells comprising HIV-1 infected CD4 T-cells and uninfected CD4 T-cells.

BACKGROUND OF THE INVENTION

Human Immunodeficiency Virus-Type 1 (HIV-1) is the etiologic agent that is responsible for Acquired Immunodeficiency Syndrome (AIDS), a syndrome characterized by depletion of $CD4^+$ T-lymphocytes and collapse of the immune system. HIV infection is pandemic and HIV-associated diseases have become a world-wide health problem. At present, the number of persons infected with the pathogenic virus, HIV, has exceeded 33,000,000 all over the world, and about 2,500,000 persons are being newly infected every year.

Helper CD4 T-cells are the most important cells in maintaining the body's powerful immunity and they are required for almost all our immune responses. As dramatically demonstrated in acquired immunodeficiency syndrome (AIDS) patients, a person lacking CD4 T-cells cannot fend off even microbes that are normally harmless. AIDS is caused by the human immunodeficiency virus (HIV), which infects and kills CD4 T-cells.

When the disease progresses from HIV-1 infection to full-blown AIDS, it is because the number of T-cells has dropped to dangerous levels. AIDS is heralded by a total lymphocyte count of less than $500/mm^3$ and a dangerously low T-cell count of below $200/mm^3$. With the immune system so depleted, the body becomes highly vulnerable to opportunistic diseases. As the term suggests, these are infections and other diseases that seize the opportunity presented by a weakened defense system. They commonly include herpes simplex infection and other herpes conditions such as shingles and the oral yeast infection, thrush; Kaposi's sarcoma, characterized by the dark lesions; CKV retinitis, a herpes virus that can bring blindness; meningitis, an infection of the spinal cord and brain; cervical cancer; tuberculosis, and a formerly rare type of pneumonia.

Despite extensive efforts over the past quarter century, the precise mechanism by which HIV-1 causes progressive depletion of CD4 T-cells remains debated. Both direct and indirect cytopathic effects have been proposed. When immortalized T-cell lines are infected with laboratory-adapted HIV-1 strains, direct CD4 T-cell killing predominates. Conversely, in more physiological systems, such as infection of lymphoid tissue with primary HIV-1 isolates, the majority of dying cells appear as uninfected "bystander" CD4 T-cells (Finkel et al., 1995, Nat Med 1:129-134; Jekle et al., 2003, J Virol 77:5846-5854).

Various mechanisms have been proposed to contribute to the death of these bystander CD4 T-cells including the action of host-derived factors like tumor necrosis factor-α, Fas ligand and TRAIL (Gandhi et al., 1998, J Exp Med 187:1113-1122; Herbeuval et al., 2005, Blood 106:3524-3531), and viral factors like HIV-1 Tat, Vpr, and Nef released from infected cells (Schindler et al., 2006, Cell 125:1055-1067; Westendorp et al., 1995, Nature 375:497-500). Considerable interest has also focused on the role of gp120 and gp41 Env protein in indirect cell death, although it is not clear whether death signaling involves gp120 binding to its chemokine receptor or gp41-mediated fusion. It is also unclear whether such killing is caused by HIV-1 virions or by infected cells expressing Env.

Most studies have focused on death mechanisms acting prior to viral entry. Less is known about the fate of HIV-1-infected CD4 T-cells that do not express viral genes, in particular naive CD4 T-cells in tissues that are refractory to productive HIV infection (Glushakova et al., 1995, Nat Med 1:1320-1322; Kreisberg et al., 2006, J Exp Med 203:865-870). In these cells, infection is aborted after viral entry, as reverse transcription is initiated but fails to reach completion (Kamata et al., 2009, PLoS Pathog 5, e1000342; Epub 100209 March 1000320; Swiggard et al., 2004, AIDS Res Hum Retroviruses 20:285-295; Zack et al., 1990, Cell 61:213-222; Zhou et al., 2005, J Virol 79:2199-2210).

Human lymphoid aggregate cultures (HLACs) prepared from tonsillar tissue closely replicate the conditions encountered by HIV in vivo and thus form an attractive, biologically relevant system for studying HIV-1 infection (Eckstein et al., 2001, Immunity 15:671-682). Lymphoid organs are the primary sites of HIV replication and contain more than 98% of the body's CD4 T-cells. Moreover, events critical to HIV disease progression occur in lymphoid tissues, where the network of cell-cell interactions mediating the immune response deteriorates and ultimately collapses. Primary cultures of peripheral blood cells do not fully mimic the cytokine milieu, the cellular composition of lymphoid tissue, nor the functional relationships that are undoubtedly important in HIV pathogenesis. Finally, HLACs can be infected with a low number of viral particles in the absence of artificial mitogens, allowing analysis of HIV cytopathicity in a natural and preserved environment.

In studies described more fully herein (e.g., see, Examples), it was discovered that the death of so-called uninfected "bystander" T-cells involves abortive HIV-1 infection. More specifically, it was discovered that after viral entry, incomplete HIV-1 reverse transcriptase products activate a host defense program that elicits a coordinated proapoptotic and proinflammatory response involving activation of the enzymes caspase-1 and caspase-3.

Caspases are a family of at least fourteen cysteine-dependent aspartate-directed proteases that are key mediators in the signaling pathways for apoptosis and cell disassembly (Thornberry, 1998, Chem Biol 5:R97-R103). These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

Caspase-1, the first identified caspase, is also known as interleukin converting enzyme or "ICE." Caspase-1 exists as an inactive proenzyme, which undergoes proteolytic processing at conserved aspartic residues to produce two subunits, large (caspase-1 p20 subunit) and small, (caspase-1 p10 subunit) that dimerize to form the active enzyme. Caspase-1 polypeptides are derived from various caspase-1 isoform precursors. Caspase-1 converts the inactive precursor of interleukin-1-beta (pIL-1β) to the pro-inflammatory active form by specific cleavage of pIL-1β between Asp-116 and Ala-117. Besides caspase-1 there are also eleven other known human caspases, all of which cleave specifically at aspartyl residues. They are also observed to have stringent requirements for at least four amino acid residues on the N-terminal side of the cleavage site.

The caspases have been classified into three groups depending on the amino acid sequence that is preferred or primarily recognized. The group of caspases, which includes caspases 1, 4, 5 and 11, have been shown to prefer hydrophobic aromatic amino acids at position 4 on the N-terminal side of the cleavage site (preferred sequence Trp-Glu-His-Asp (SEQ ID NO: 1)). Another group, which includes caspases 2, 3 and 7, recognize aspartyl residues at both positions 1 and 4 on the N-terminal side of the cleavage site, and preferably a sequence of Asp-Glu-X-Asp. A third group, which includes caspases 6, 8, 9 and 10, tolerate many amino acids in the primary recognition sequence, but seem to prefer residues with branched, aliphatic side chains such as valine and leucine at position 1 (Leu/Val-Glu-X-Asp (SEQ ID NO: 2)).

The caspases have also been grouped according to their perceived function. The first subfamily consists of caspases-1 (ICE), 4, 5, 11 and 12. These caspases have been shown to be involved in pro-inflammatory cytokine processing and therefore play an important role in inflammation. Caspase-1, the most studied enzyme of this class, activates the IL-1β precursor by proteolytic cleavage. This enzyme therefore plays a key role in the inflammatory response. Applicants, however, are unaware of anything in the art suggesting the use of caspase-1 inhibitors in methods for the treatment of an HIV-1 infection and AIDS and for use in related methods described herein.

The remaining caspases make up the second and third subfamilies. These enzymes are of central importance in the intracellular signaling pathways leading to apoptosis. One subfamily consists of the enzymes involved in initiating events in the apoptotic pathway, including transduction of signals from the plasma membrane. Members of this subfamily include caspases-2, 8, 9 and 10. The other subfamily, consisting of the effector caspases 3, 6 and 7, are involved in the final downstream cleavage events that result in the systematic breakdown and death of the cell by apoptosis. Caspases involved in the upstream signal transduction activate the downstream caspases, which then disable the DNA repair mechanisms, fragment the nuclear DNA, dismantle the cell cytoskeleton and finally fragment the cell.

Caspase-3 (also known as apopain, CPP-32, and YAMA) is responsible for proteolytic cleavage of a variety of fundamental proteins including cytoskeletal proteins, kinases and DNA-repair enzymes. It is a critical mediator of apoptosis in neurons. Caspase-3 exists as an inactive proenzyme, which undergoes proteolytic processing at conserved aspartic residues to produce two subunits, large (caspase-3 p17 subunit) and small, (caspase-3 p12 subunit) that dimerize to form the active enzyme. Caspase-3 polypeptides are derived from various caspase-3 isoform precursors. Inhibition of caspase-3 has shown efficacy in models, such as stroke, traumatic brain spinal cord injury, hypoxic brain damage, cardiac ischemia and reperfusion injury. Inhibition of caspase-1 has been shown to be beneficial in models of, e.g., rheumatoid arthritis, osteoarthritis, inflammatory bowel disease and asthma. However, as much as Applicants are aware, hitherto, nothing in the art suggested the use of caspase-1 or caspase-3 inhibitors in methods for the treatment of an HIV-1 infection and AIDS and for use in related methods described herein.

The present treatments available for HIV-1 infection and AIDS seek to block one or more steps involved in the production of viral particles and often are based on a combination of several drugs, a so-called cocktail of inhibitors of reverse transcriptase and protease inhibitors. Treatment options involve administration of reverse transcriptase inhibitors, inhibitors of viral protease, fusion, entry, or integration inhibitors in different combinations to block multiple steps in the viral life cycle. This approach, termed highly active antiviral therapy (HAART) has greatly decreased morbidity and mortality in people infected with HIV (Palella et al., 1998, *N Engl J Med* 338(13):855-860). While HAART is quite effective and can reduce the virus back to undetectable levels in patient's blood, it is not a cure for the patient, because the virus is still present in the immune cells, and the disease can reappear at any time due to emergence of drug-resistant viruses; upon discontinuation of therapy viremia peaks and rapid progression to AIDS is frequently observed. Furthermore, the immunodeficiency and the HIV-1 specific T-cell dysfunction persist during HAART. This therapy requires life-long treatment and the treatment is very expensive. The cost of the drugs alone often exceeds USD 15,000. There are, in addition, several other problems associated with this therapy; difficulties with patient compliance (complicated drug regimens), development of resistant viruses, non-ideal pharmacokinetics and side effects such as, for example, suppression of bone-marrow and long-term metabolic effects.

The global health crisis caused by HIV-1 is unquestioned, and while recent advances in drug therapies have been successful in slowing the progression of AIDS, there is still a need to find a safer, more efficient, less expensive way to control the virus, to treat patients having an HIV-1 infection or AIDS. Applicants herein provide novel methods for the treatment of HIV-1 infection and AIDS that overcome the afore-mentioned problems.

BRIEF SUMMARY OF THE INVENTION

This application discloses the surprising finding that compounds that inhibit the activation and/or activity of caspase-1 are useful for the treatment of HIV-1 infection and AIDS, for slowing disease progression in HIV-1 infected patients, for treatment of patients being infected with HIV-1, for treatment of patients having AIDS, for preserving CD4 T-cells, for inhibition of pyroptosis, and for decreasing inflammation.

In one aspect, the invention provides a method for the treatment of a patient having an HIV-1 infection, of a patient suspected of having an HIV-1 infection, or of a patient having AIDS. In some embodiments, this method comprises the step of selecting a patient having an HIV-1 infection, suspected of having an HIV-1 infection or having AIDS. In some embodiments, this method comprises the step of administering to the patient in need of such treatment a therapeutically effective amount of a caspase-1 inhibitor.

The patient being treated according to a method of the present invention may have cells comprising incomplete HIV-1 nucleic acids. The incomplete HIV-1 nucleic acids may be the product of an abortive HIV-1 reverse transcription reaction.

In some embodiments, the patient being treated according to a method of the present invention may have developed a resistance against an anti-HIV-1 compound.

In some embodiments of the method for the treatment of a patient having an HIV-1 infection, of a patient suspected of having an HIV-1 infection, or of a patient having AIDS, the caspase-1 inhibitor administered to the patient in need of such treatment, is a caspase-1 inhibitor selected from the group of caspase-1 inhibitors having Formula 1a, 1b, 2, 3, 4, 4.1, 4.2, 4.3, 5, 6, 7, 8, 8.1, 8.2, 9, 9.1, 10, 11, 12, 13, 14, 15, 16, 16.1, 16.2, 16.3, 16.4, 16.5, 16.6, 16.7, 17, 17.1, 17.2, 17.3, 17.4, 17.5, 17.6, 17.7, 17.8, 17.9, 17.10, 17.11, 17.12, 17.13, 17.14, 17.15, 17.16, 17.17, 17.18, 17.19, 17.20, 17.21, 17.22, 18A, 18B, 18.1, 18.2, 19, 19A, 19B, 20, 20A, 21, 21A, 22, 22A, 23(I), 23(II), 23(III), 24, 25, 26, 27, a caspase-1 inhibitor depicted in FIGS. 30 and 31 and combinations thereof.

In some embodiments of the method for the treatment of a patient having an HIV-1 infection, of a patient suspected of having an HIV-1 infection, or of a patient having AIDS, the caspase-1 inhibitor is selected from the group of caspase-1 inhibitors consisting of BACMK (Boc-Asp(Obzl)-CMK, z-VAD (Z-Val-Ala-Asp), BocD, LY333531, casputin, Ac-DQMD-CHO (Ac-Asp-Met-Gln-Asp-CHO) (SEQ ID NO: 3), CV-1013, VX-740, VX-765, VX-799, Ac-YVAD-CMK (SEQ ID NO: 4), IDN-5370, IDN-6556, IDN-6734, IDN-1965, IDN-1529, z-VAD-fmk (Z-Val-Ala-Asp(OMe)-Fluoro methyl ester), z-DEVD-cmk (SEQ ID NO: 5), Z-DEVD (SEQ ID NO: 6), Ac-YVAD-fmk (SEQ ID NO: 7), z-Asp-Ch2-DCB, Ac-IETD (SEQ ID NO: 8), Ac-VDVAD (SEQ ID NO: 9), Ac-DQMD (SEQ ID NO: 10), Ac-LEHD (SEQ ID NO: 11), Z-WEHD (SEQ ID NO: 12), Z-WEHD-fmk (SEQ ID NO: 13), Z-WE(OMe)HD(OMe)-fmk (SEQ ID NO: 14), Z-YVAD (SEQ ID NO: 15), Z-YVAD-fmk (SEQ ID NO: 16), Ac-YVAD-cmk (SEQ ID NO: 17), Ac-VEID (SEQ ID NO: 18) and single stereoisomers, mixtures of stereoisomers, pharmaceutically acceptable salts or prodrugs thereof. A preferred caspase-1 inhibitor is VX-765.

In some embodiments of the method for the treatment of a patient having an HIV-1 infection or of a patient suspected of having an HIV-1 infection, or of a patient having AIDS, the caspase-1 inhibitor is selected from the group of caspase-1 inhibitors consisting of Boc-Phg-Asp-fmk, Boc-(2-F-Phg)-Asp-fmk, Boc-($F_3$-Val)-Asp-fmk, Boc-(3-F-Val)-Asp-fmk, Ac-Phg-Asp-fmk, Ac-(2-F-Phg)-Asp-fmk, Ac-($F_3$-Val)-Asp-fmk, Ac-(3-F-Val)Asp-fmk, Z-Phg-Asp-fmk Z-(2-F-Phg)-Asp-fmk, Z-($F_3$-Val)-Asp-fmk, Z-Chg-Asp-fmk, Z-(2-Fug)-Asp-fmk, Z-(4-F-Phg)-Asp-fmk, Z-(4-Cl-Phg)-Asp-fmk, Z-3-Thg)-Asp-fmk, Z-(2-Fua)-Asp-fmk, Z-(2-Tha)-Asp-fmk, Z-3-Fua)-Asp-fmk, Z-(3-Tha)-Asp-fmk, Z-(3-Cl-Ala)-Asp-fmk, Z-(3-F-Ala)-Asp-fmk, Z-($F_3$-Ala)-Asp-fmk, Z-(3-F-3-Me-Ala)-Asp-fmk, Z-(3-$C_{1-3}$-F-Ala)-Asp-fmk, Z-(2-Me-Val)Asp-ink, Z-(2-Me-Ala)-Asp-fmk, Z-(2-i-Pr-β-Ala)-Asp-fmk, Z-(3-Ph-β-Ala)-Asp-fmk, Z-(3-CN-Ala)-Asp-fmk, Z-(1-Nal)-Asp-fmk, Z-Cha-Asp-fmk, Z-3-$CF_3$-Ala)Asp-fmk, Z-(4-$CF_3$-Phg)-Asp-fmk, Z-(3-$Me_2$N-Ala)-Asp-fmk, Z-(2-Abu)-Asp-ink, Z-Tle-Asp-fmk, Z-Cpg-Asp-fmk, Z-Cbg-Asp-fmk, Z-Thz-Asp-fmk, Z-(3-F-Val)-Asp-fmk, Z-2-Thg)Asp-fmk and single stereoisomers, mixtures of stereoisomers, pharmaceutically acceptable salts or prodrugs thereof.

In some embodiments of the method for the treatment of a patient having an HIV-1 infection or of a patient suspected of having an HIV-1 infection, or of a patient having AIDS, the method comprises the step of administering to the patient an anti HIV-1 compound. In some embodiments, HAART is co-administered to the patient.

In some embodiments of the method for the treatment of a patient having an HIV-1 infection or of a patient suspected of having an HIV-1 infection, or of a patient having AIDS, the patient has a reduced T-cell count of less than 1,000/mm$^3$, less than 750/mm$^3$ or less than 500/mm$^3$.

The invention also provides a method for preventing the death of a CD4 T-cell in a population of CD4 T-cells comprising HIV-1 infected and uninfected CD4 T-cells. This method can be practiced in vitro and in vivo.

In some embodiments of the method for preventing the death of a CD4 T-cell in a population of CD4 T-cells comprising HIV-1 infected and uninfected CD4 T-cells, the method comprises the step of contacting the population of CD4 T-cells with a caspase-1 inhibitor, hereby preventing the death of the CD4 T-cell. When practiced in vivo, the method comprises the step of selecting a patient in need of having the CD4 T-cell contacted with a caspase-1 inhibitor.

In some embodiments of the method for preventing the death of a CD4 T-cell in a population of CD4 T-cells comprising HIV-1 infected and uninfected CD4 T-cells, the caspase-1 inhibitor is selected from the group of caspase-1 inhibitors having Formula 1a, 1b, 2, 3, 4, 4.1, 4.2, 4.3, 5, 6, 7, 8, 8.1, 8.2, 9, 9.1, 10, 11, 12, 13, 14, 15, 16, 16.1, 16.2, 16.3, 16.4, 16.5, 16.6, 16.7, 17, 17.1, 17.2, 17.3, 17.4, 17.5, 17.6, 17.7, 17.8, 17.9, 17.10, 17.11, 17.12, 17.13, 17.14, 17.15, 17.16, 17.17, 17.18, 17.19, 17.20, 17.21, 17.22, 18A, 18B, 18.1, 18.2, 19, 19A, 19B, 20, 20A, 21, 21A, 22, 22A, 23(I), 23(II), 23(III), 24, 25, 26, 27, 28, 29, 30, 31A, 31B, 32, 33, 34, 35, 36, 37, 38, 39, 40, 41, 42, 43, a caspase-1 inhibitor depicted in FIGS. 30 and 31 and combinations thereof.

In some embodiments of the method for preventing the death of a CD4 T-cell in a population of CD4 T-cells comprising HIV-1 infected and uninfected CD4 T-cells, the caspase-1 inhibitor is selected from the group of caspase-1 inhibitors consisting of BACMK (Boc-Asp(Obzl)-CMK, z-VAD (Z-Val-Ala-Asp), BocD, LY333531, casputin, Ac-DQMD-CHO (Ac-Asp-Met-Gln-Asp-CHO) (SEQ ID NO: 3), CV-1013, VX-740, VX-765, VX-799, Ac-YVAD-CMK (SEQ ID NO: 4), IDN-5370, IDN-6556, IDN-6734, IDN-1965, IDN-1529, z-VAD-fmk (Z-Val-Ala-Asp(OMe)-Fluoro methyl ester), z-DEVD-cmk (SEQ ID NO: 5), Z-DEVD (SEQ ID NO: 6), Ac-YVAD-fmk (SEQ ID NO: 7), z-Asp-Ch2-DCB, Ac-IETD (SEQ ID NO: 8), Ac-VDVAD (SEQ ID NO: 9), Ac-DQMD (SEQ ID NO: 10), Ac-LEHD (SEQ ID NO: 11), Z-WEHD (SEQ ID NO: 12), Z-WEHD-fmk (SEQ ID NO: 13), Z-WE(OMe)HD(OMe)-fmk (SEQ ID NO: 14), Z-YVAD (SEQ ID NO: 15), Z-YVAD-fmk (SEQ ID NO: 16), Ac-YVAD-cmk (SEQ ID NO: 17), Ac-VEID (SEQ ID NO: 18) and single stereoisomers, mixtures of stereoisomers, pharmaceutically acceptable salts or prodrugs thereof. A preferred caspase-1 inhibitor is VX-765.

In some embodiments of the method for preventing the death of a CD4 T-cell in a population of CD4 T-cells comprising HIV-1 infected and uninfected CD4 T-cells, the caspase-1 inhibitor is selected from the group of caspase-1 inhibitors consisting of Boc-Phg-Asp-fmk, Boc-(2-F-Phg)-Asp-fmk, Boc-($F_3$-Val)-Asp-fmk, Boc-(3-F-Val)-Asp-fmk, Ac-Phg-Asp-fmk, Ac-(2-F-Phg)-Asp-fmk, Ac-($F_3$-Val)-Asp-fmk, Ac-(3-F-Val)Asp-fmk, Z-Phg-Asp-fmk Z-(2-F-Phg)-Asp-fmk, Z-($F_3$-Val)-Asp-fmk, Z-Chg-Asp-fmk, Z-(2-Fug)-Asp-fmk, Z-(4-F-Phg)-Asp-fmk, Z-(4-Cl-Phg)-Asp-fmk, Z-3-Thg)-Asp-fmk, Z-(2-Fua)-Asp-fmk, Z-(2-Tha)-Asp-fmk, Z-3-Fua)-Asp-fmk, Z-(3-Tha)-Asp-fmk, Z-(3-Cl-Ala)-Asp-fmk, Z-(3-F-Ala)-Asp-fmk, Z-($F_3$-Ala)-Asp-fmk, Z-(3-F-3-Me-Ala)-Asp-fmk, Z-(3-$C_{1-3}$-F-Ala)-Asp-fmk, Z-(2-Me-Val)Asp-ink, Z-(2-Me-Ala)-Asp-fmk, Z-(2-i-Pr-β-Ala)-Asp-fmk, Z-(3-Ph-β-Ala)-Asp-fmk, Z-(3-CN-Ala)-Asp-fmk, Z-(1-Nal)-Asp-fmk, Z-Cha-Asp-fmk, Z-3-$CF_3$-Ala)Asp-fmk, Z-(4-$CF_3$-Phg)-Asp-fmk, Z-(3-$Me_2$N-Ala)-Asp-fmk, Z-(2-Abu)-Asp-ink, Z-Tle-Asp-fmk, Z-Cpg-Asp-fmk, Z-Cbg-Asp-fmk, Z-Thz-Asp-fmk, Z-(3-F-Val)-Asp-fmk, Z-2-Thg)Asp-fmk and single stereoisomers, mixtures of stereoisomers, pharmaceutically acceptable salts or prodrugs thereof.

The invention also provides a method for inhibiting pyroptosis. This method can be practiced in vitro and in vivo.

In some embodiments of the method for inhibiting pyroptosis, the method comprises the step of administering a caspase-1 inhibitor to a patient in need of inhibiting pyroptosis. In some embodiments, the method comprises the steps of selecting a patient having cells undergoing pyroptosis and administering to the patient a pharmaceutically effective amount of a caspase-1 inhibitor. Thereby pyroptosis is inhibited.

In some embodiments of the method for inhibiting pyroptosis, the caspase-1 inhibitor is selected from the group of caspase-1 inhibitors having Formula 1a, 1b, 2, 3, 4, 4.1, 4.2, 4.3, 5, 6, 7, 8, 8.1, 8.2, 9, 9.1, 10, 11, 12, 13, 14, 15, 16, 16.1, 16.2, 16.3, 16.4, 16.5, 16.6, 16.7, 17, 17.1, 17.2, 17.3, 17.4, 17.5, 17.6, 17.7, 17.8, 17.9, 17.10, 17.11, 17.12, 17.13, 17.14, 17.15, 17.16, 17.17, 17.18, 17.19, 17.20, 17.21, 17.22, 18A, 18B, 18.1, 18.2, 19, 19A, 19B, 20, 20A, 21, 21A, 22, 22A, 23(I), 23(II), 23(III), 24, 25, 26, 27, 28, 29, 30, 31A, 31B, 32, 33, 34, 35, 36, 37, 38, 39, 40, 41, 42, 43, a caspase-1 inhibitor depicted in FIGS. 30 and 31 and combinations thereof.

In some embodiments of the method for inhibiting pyroptosis the caspase-1 inhibitor is selected from the group of caspase-1 inhibitors consisting of BACMK (Boc-Asp(Obzl)-CMK, z-VAD (Z-Val-Ala-Asp), BocD, LY333531, casputin, Ac-DQMD-CHO (Ac-Asp-Met-Gln-Asp-CHO) (SEQ ID NO: 3), CV-1013, VX-740, VX-765, VX-799, Ac-YVAD-CMK (SEQ ID NO: 4), IDN-5370, IDN-6556, IDN-6734, IDN-1965, IDN-1529, z-VAD-fmk (Z-Val-Ala-Asp(OMe)-Fluoro methyl ester), z-DEVD-cmk (SEQ ID NO: 5), Z-DEVD (SEQ ID NO: 6), Ac-YVAD-fmk (SEQ ID NO: 7), z-Asp-Ch2-DCB, Ac-IETD (SEQ ID NO: 8), Ac-VDVAD (SEQ ID NO: 9), Ac-DQMD (SEQ ID NO: 10), Ac-LEHD (SEQ ID NO: 11), Z-WEHD (SEQ ID NO: 12), Z-WEHD-fmk (SEQ ID NO: 13), Z-WE(OMe)HD(OMe)-fmk (SEQ ID NO: 14), Z-YVAD (SEQ ID NO: 15), Z-YVAD-fmk (SEQ ID NO: 16), Ac-YVAD-cmk (SEQ ID NO: 17), Ac-VEID (SEQ ID NO: 18) and single stereoisomers, mixtures of stereoisomers, pharmaceutically acceptable salts or prodrugs thereof. A preferred caspase-1 inhibitor is VX-765.

In some embodiments of the method for inhibiting pyroptosis, the caspase-1 inhibitor is selected from the group of caspase-1 inhibitors consisting of Boc-Phg-Asp-fmk, Boc-(2-F-Phg)-Asp-fmk, Boc-($F_3$-Val)-Asp-fmk, Boc-(3-F-Val)-Asp-fmk, Ac-Phg-Asp-fmk, Ac-(2-F-Phg)-Asp-fmk, Ac-($F_3$-Val)-Asp-fmk, Ac-(3-F-Val)Asp-fmk, Z-Phg-Asp-fmk Z-(2-F-Phg)-Asp-fmk, Z-($F_3$-Val)-Asp-fmk, Z-Chg-Asp-fmk, Z-(2-Fug)-Asp-fmk, Z-(4-F-Phg)-Asp-fmk, Z-(4-Cl-Phg)-Asp-fmk, Z-3-Thg)-Asp-fmk, Z-(2-Fua)-Asp-fmk, Z-(2-Tha)-Asp-fmk, Z-3-Fua)-Asp-fmk, Z-(3-Tha)-Asp-fmk, Z-(3-Cl-Ala)-Asp-fmk, Z-(3-F-Ala)-Asp-fmk, Z-($F_3$-Ala)-Asp-fmk, Z-(3-F-3-Me-Ala)-Asp-fmk, Z-(3-$C_{1-3}$-F-Ala)-Asp-fmk, Z-(2-Me-Val)Asp-ink, Z-(2-Me-Ala)-Asp-fmk, Z-(2-i-Pr-β-Ala)-Asp-fmk, Z-(3-Ph-β-Ala)-Asp-fmk, Z-(3-CN-Ala)-Asp-fmk, Z-(1-Nal)-Asp-fmk, Z-Cha-Asp-fmk, Z-3-$CF_3$-Ala)Asp-fmk, Z-(4-$CF_3$-Phg)-Asp-fmk, Z-(3-$Me_2$N-Ala)-Asp-fmk, Z-(2-Abu)-Asp-ink, Z-Tle-Asp-fmk, Z-Cpg-Asp-fmk, Z-Cbg-Asp-fmk, Z-Thz-Asp-fmk, Z-(3-F-Val)-Asp-fmk, Z-2-Thg)Asp-fmk and single stereoisomers, mixtures of stereoisomers, pharmaceutically acceptable salts or prodrugs thereof.

Also contemplated is the use of a caspase-1 inhibitor for the preparation of a medicament for the treatment of HIV-1 infection and/or AIDS.

Also contemplated is the use of a caspase-1 inhibitor for the preparation of a medicament for preventing the death of a CD4 T-cell in a population of CD4 T-cells comprising HIV-1 infected and uninfected CD4 T-cells.

Minus-strand DNA synthesis is accompanied by partial degradation of the RNA in the resulting RNA-DNA hybrid by RNase H, exposing viral ssDNA intermediates in the host cytoplasm. Subsequently, fragments of RNA that were not removed by the RNase H at polypurine tract (ppt) sites, serve as primers for plus-strand DNA synthesis. Plus-strand DNA is formed before minus-strand DNA synthesis is completed, exposing "islands" of viral dsDNA intermediates in the host cytoplasm. DNA chain elongation depends on nucleotide supply and therefore occurs after uncoating, in the host cell cytoplasm. In non-permissive cells such as most CD4 T-cells in lymphoid tissues, elongation of DNA polymerization is inhibited (i.e. "Killing Zone") (Kamata et al., 2009, *PLos Pathog* 5:e1000342; Pierson et al., 2002, *J Virol* 76:8518-8531; Swiggard et al., 2004, *AIDS Res Hum Retroviruses* 20:285-295; Zack et al., 1990, *Cell* 61:213-222; Zhou et al., 2005, *J Virol* 79:2199-2210). In turn, viral ssDNA and dsDNA intermediates accumulating in the host cytoplasm are detected by an as-yet unidentified sensor(s), and elicit a multifaceted antiviral response involving apoptotic cell death and secretion of proinflammatory cytokines such as IL-1β. Because AZT and endogenous arrest of reverse transcript elongation occur at the same phase of viral life cycle (Arts and Wainberg, 1994, *Antimicrob Agents Chemother* 38:1008-1016), AZT is not required to elicit the abortive infection-associated cell death in the nonpermissive nave CD4 T-cells present in HLACs. Reverse transcription scheme is adapted from S. J. Flint et al., Principles Of Virology, 2000 ASM Press, Washington D.C., with permission.

Figure 2:
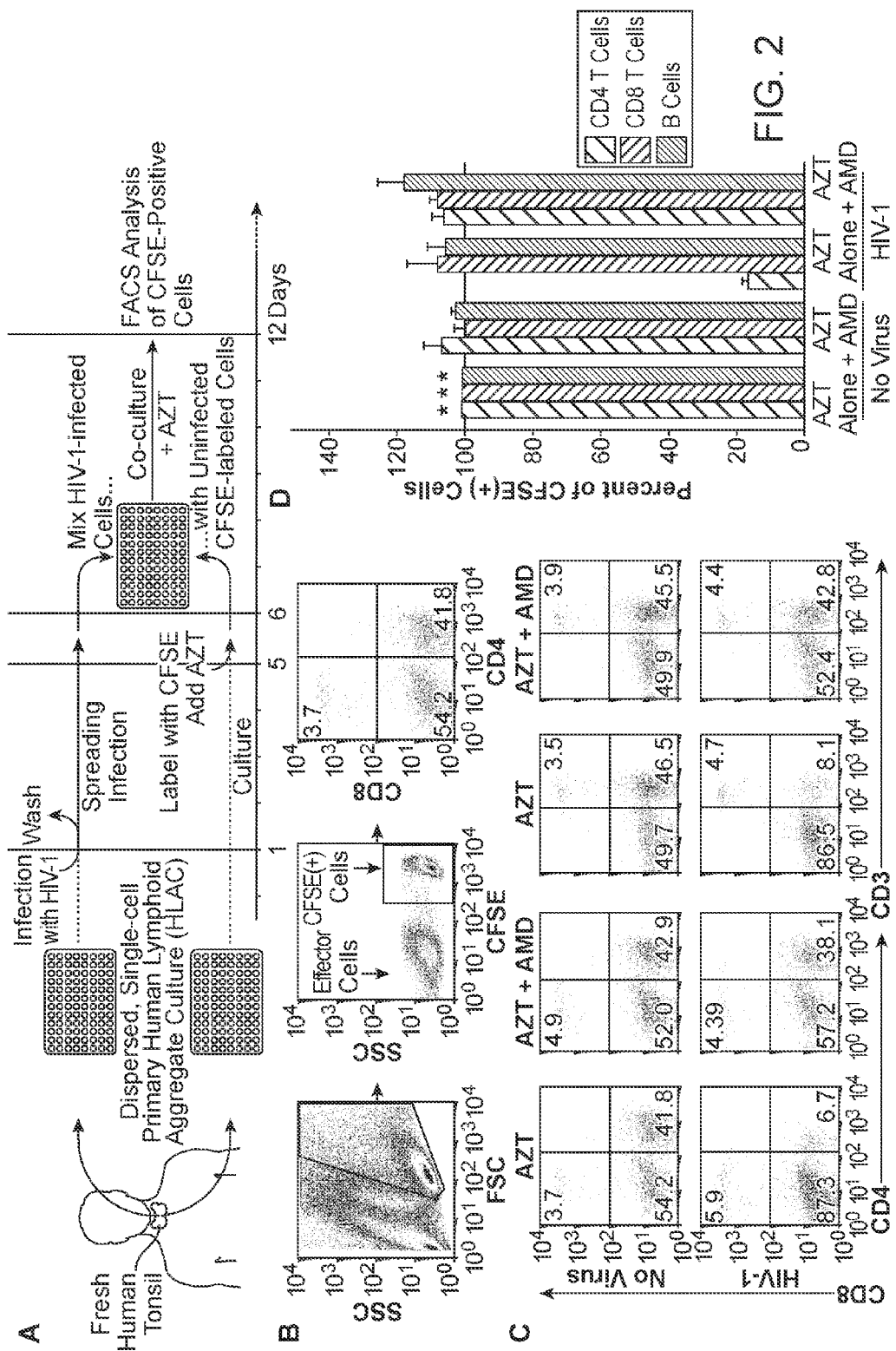
FIG. 2 depicts that CD4 T-cell depletion in HIV-1-infected HLACs predominantly involves non-productively infected cells. (A) Experimental strategy to assess indirect cell killing in HIV-1-infected human lymphoid cultures. Fresh human tonsil tissue from a single donor is processed into HLAC, and then separated into two fractions. One fraction is challenged with HIV-1 and cultured for 6 days, allowing viral spread. On day 5, the uninfected fraction is treated with AZT (5 μM) and labeled with CFSE (1 μM). On day 6, the infected and CFSE-labeled (i.e., uninfected) cultures are mixed and co-cultured in the presence of AZT. Because of its site of action, AZT does not block viral output from the HIV-infected cells but prevents productive infection of CFSE-labeled cells. After 6 days of co-culturing, the number of viable CFSE-positive cells is determined by flow cytometry. (B) Flow cytometry analysis of the mixed HLACs. Indirect killing is determined by gating on live CFSE-positive cells in the mixed cultures. Effector cells are either infected or uninfected cells. (C) Extensive depletion of non-productively infected CD4 T-cells by HIV-1. CFSE-labeled cells mixed with uninfected or infected cells were cultured in the presence of 5 μM AZT alone or together with 250 nM AMD3100. Data represent live CFSE-positive cells 6 days after co-culture with infected or uninfected effector cells. The absence of productive infection in the CFSE-positive cells was confirmed by internal p24 staining and monitoring GFP expression following infection with the NLENG1 HIV-1 reporter virus (not shown). (D) Preferential depletion of non-productively infected CD4 T-cells by HIV-1. The absolute numbers of viable CFSE-positive CD4 and CD8 T-cells and B cells were determined. Percentages are normalized to the number of viable CFSE-positive cells co-cultured with uninfected cells in the presence of AZT, as depicted by (*). Error bars represent standard deviations of three samples from the same donor. This experiment is the representative of more than 10 independent experiments with more than 10 donors of tonsillar tissues. See also FIG. 3.

(B and C) Fresh human spleen from a single donor were processed into HLAC and assessed in indirect cell killing assay as described in FIG. 2A. Effector spleen HLAC were stimulated with PHA and IL-2 48 hours before mixing, but not during co-culturing with CFSE-labeled cells. Non-activated resting CFSE-labeled spleen cells were co-cultured with NL4-3-infected or uninfected effector cells in the presence or absence of the following drugs, AZT (5 µM), AMD3100 (250 nM), Efavirenz (100 nM), or Raltegravir (30 µM), as indicated. Graft versus host toxicity was not observed during co-culture of spleen and tonsils even those these organs were obtained from different donors. Percentages were normalized to the number of viable CFSE-positive spleen CD4 T-cells co-cultured with uninfected effectors in the presence of AZT, as depicted by (*). Error bars represent standard error of the mean for three experiments performed with three different spleen and tonsil donors.

Figure 11:
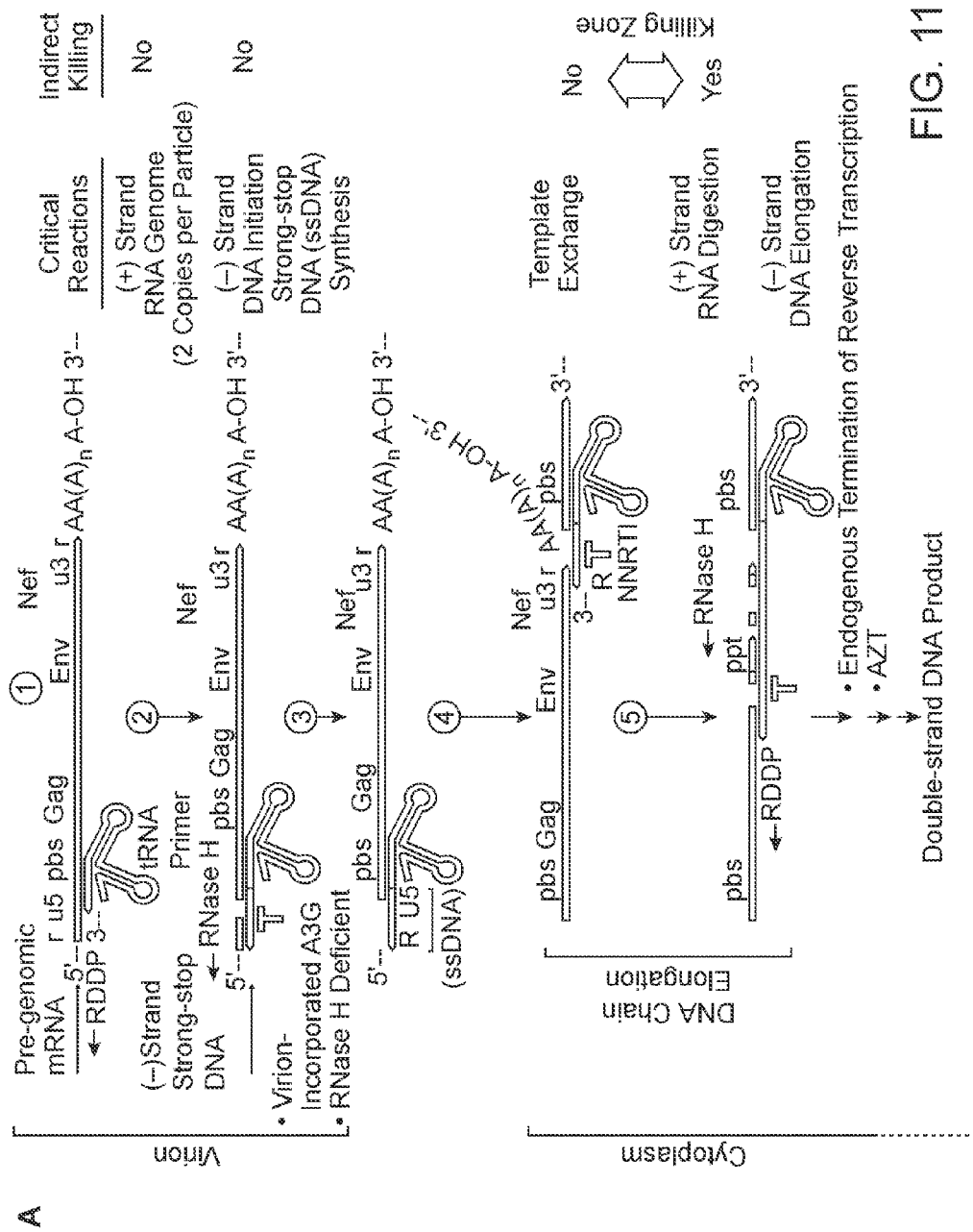
FIG. 11 depicts critical reactions in reverse transcription and their effect on abortive infection-mediated killing (A) and extensive depletion of abortively infected CD4 T-cells in human spleen (B, C). (A) (Step 1) Minus-strand DNA synthesis is initiated near the 5' end of the pregenomic mRNA from the 3'OH of the tRNA bound to the primer biding site (PBS.) This initial step occurs in the natural microenvironments of HIV-1 virions before infection, and was termed natural endogenous reverse transcription (nERT) (Zhang et al., 1996, *J Virol* 70:2809-2824). (Steps 2-3) DNA synthesis proceeds to the 5' end of the mRNA genome, while RNase H digests the RNA portion of the newly formed RNA-DNA hybrid, freeing the resulting short, single-stranded DNA fragment known as the minus-strand strong-stop DNA. In RNase H-defective HIV-1 (E478Q) the viral RNA is not degraded, and reverse transcription is paused after strong-stop DNA synthesis (Smith et al., 1999, *J Virol* 73:6573-6581). In vif-deficient HIV-1 (Δvif-HIV-1) cellular A3G is packaged into the virion and inhibits accumulation of strong-stop DNA products (Bishop et al., 2008, *PLoS Pathog* 4:e1000231). Interrupting reverse transcription at these steps prevents indirect killing, suggesting that strong-stop DNA products are not sufficient to induce a cytopathic response in CD4 T-cells. (Steps 4-5) The exposed minus-strand strong-stop DNA is transferred to the 3' end of the genome, where it hybridizes with the r region at the 3' end of the same or the second RNA genome, a reaction known as first template exchange, allowing the continuation of RNA-dependent DNA polymerization (RDDP) of the minus DNA stand. NNRTIs bind a small hydrophobic pocket near the RT active site, inducing a change in the structure of RT that blocks early RNA-dependent and DNA-dependent polymerase activities. Inhibition of DNA synthesis by NNRTIs prevents indirect killing, indicating that this step is key for initiating the cytopathic response.
Figure 11:
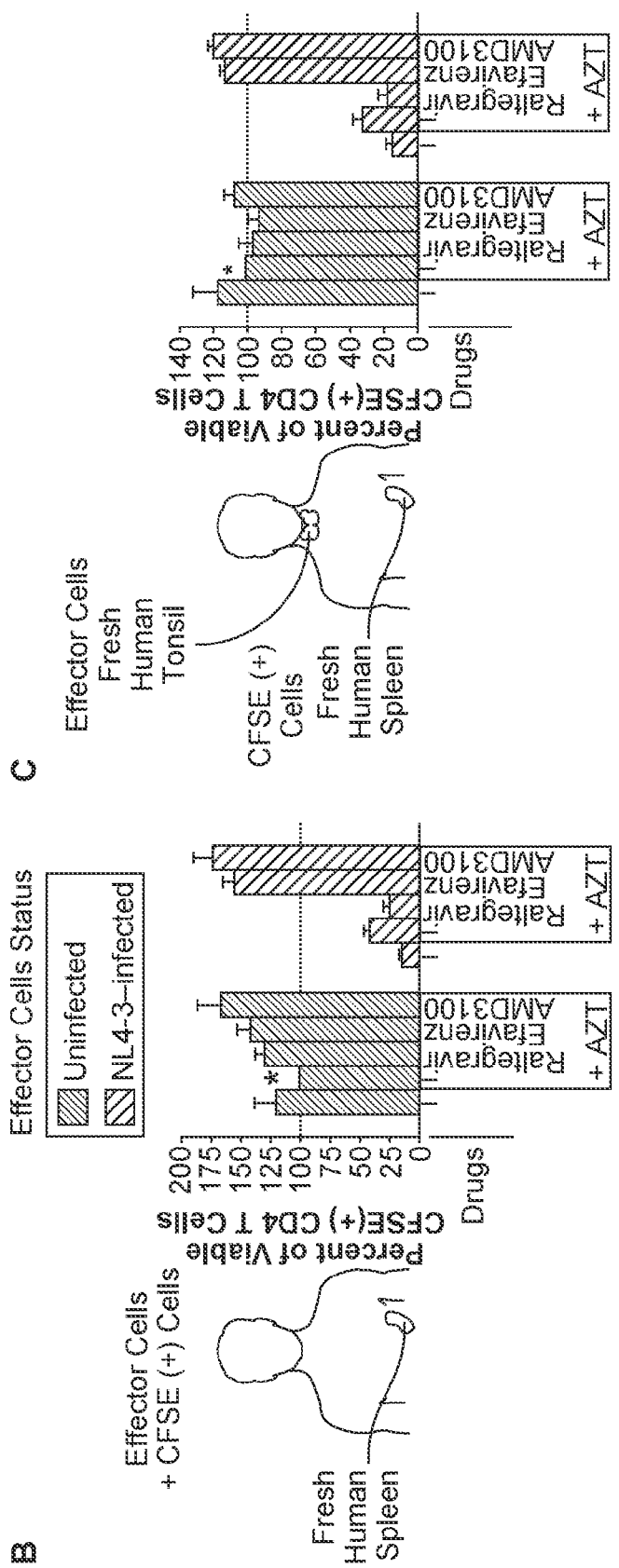
Figure 12:
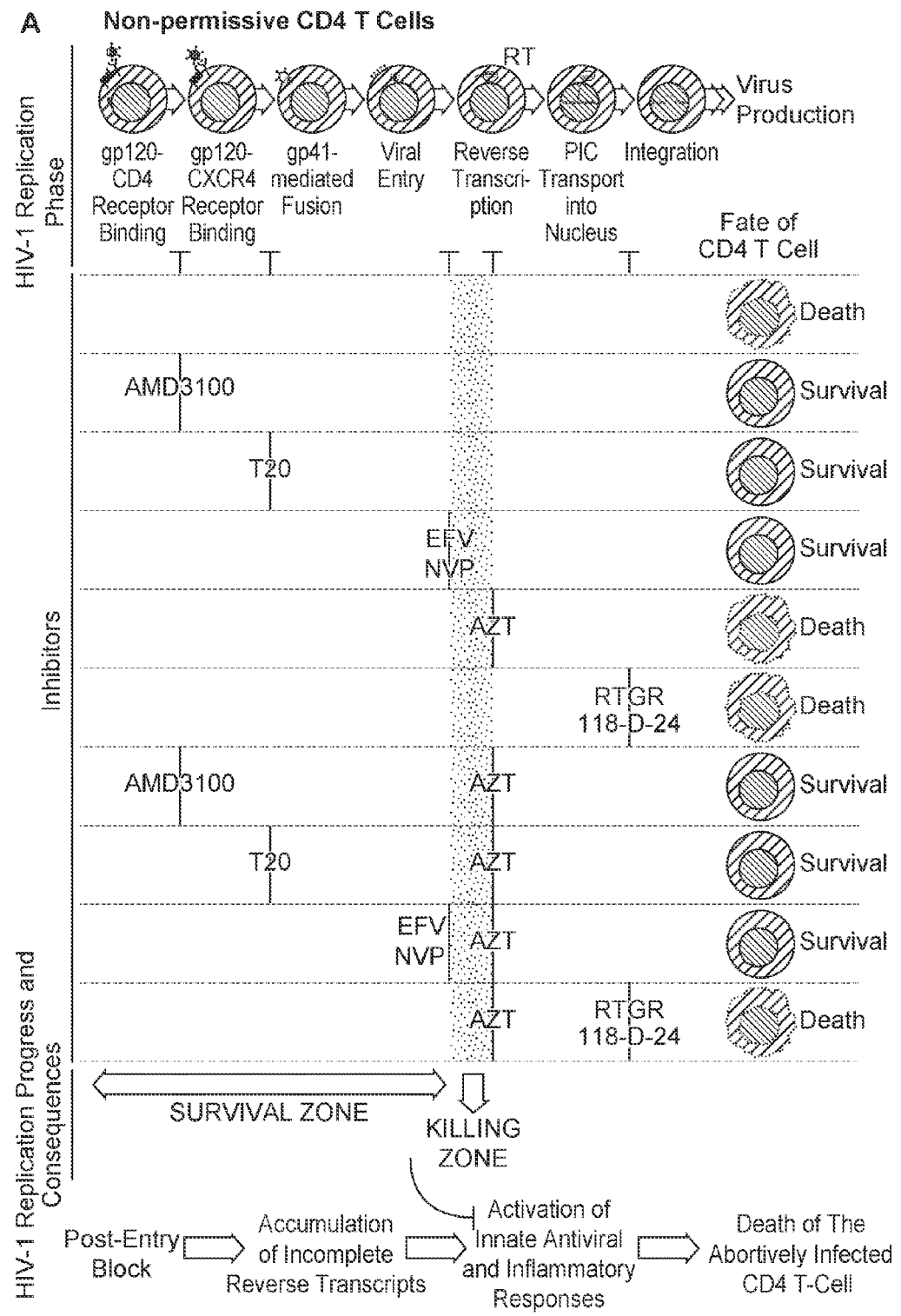
Figure 12:
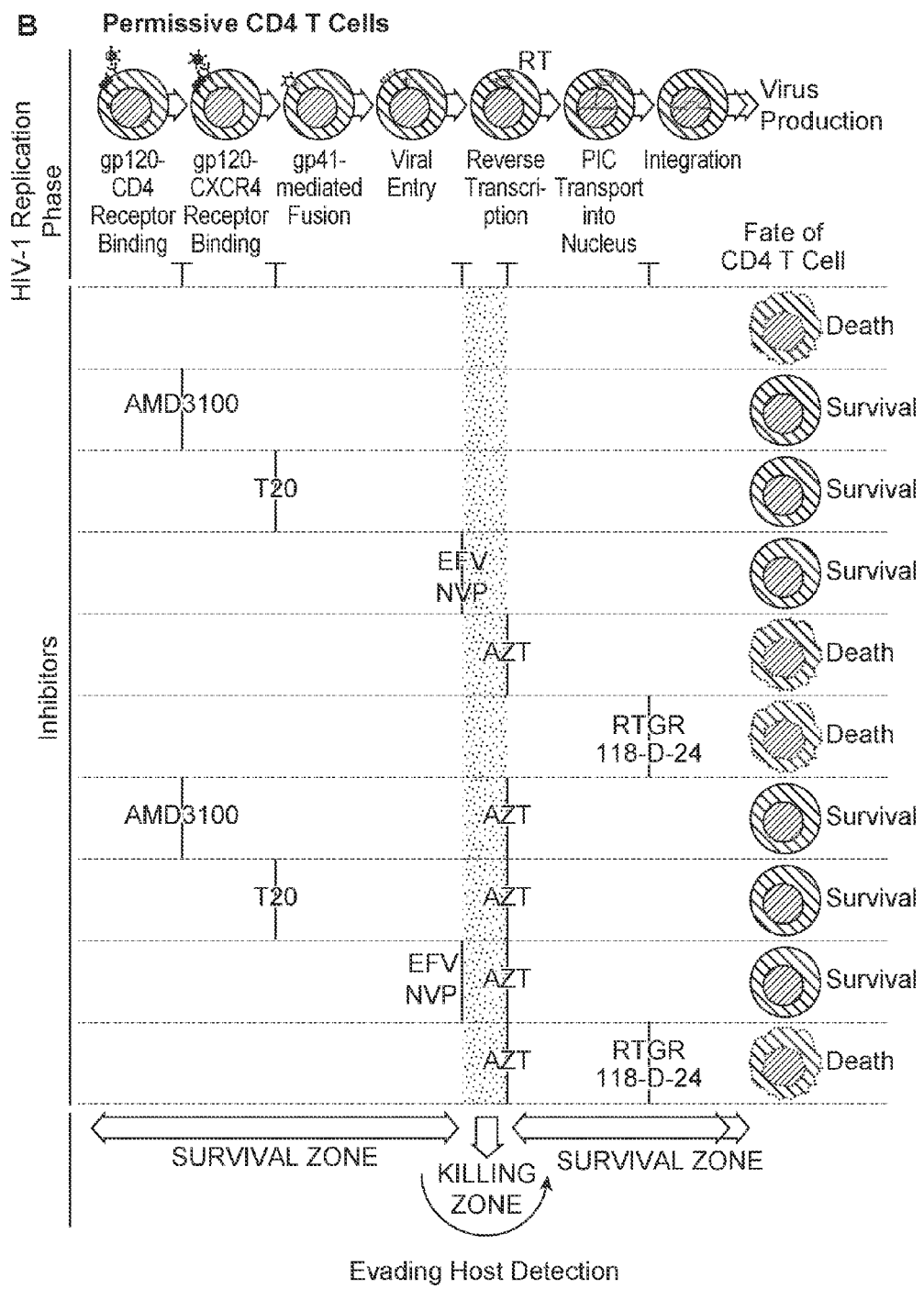

FIG. 12 depicts consequences of inhibiting early steps of HIV-1 infection on CD4 T-cell death. (A) The nonpermissive state of most CD4 T-cells in lymphoid tissue leads to endogenous termination of reverse transcription during DNA chain elongation (i.e. "killing zone"). As a result, DNA intermediates accumulate in the cytoplasm and elicit a multifaceted proapoptotic and proinflammatory innate immune defense program, coordinated by IFN-stimulatory DNA (ISD) response, Caspase-3, Caspase-1, and IL-1β, to restrict viral spread. Different classes of antiretroviral drugs act at different stages of the HIV life cycle. NNRTIs like efavirenz and nevirapine inhibit early steps of DNA synthesis and therefore prevent such response and the subsequent CD4 T-cell death. AZT is less efficient at blocking DNA synthesis and therefore unable to abrogate this response. (B) In permissive CD4 T-cells reverse transcription proceeds, allowing HIV-1 to bypass the "killing zone" and move on to productive (or latent) infection. Interrupting reverse transcription by AZT traps the virus in the "killing zone" and induces cell death. EFV, Efavirenz; NVP, Nevirapine, RTGR, Raltegravir. See also FIG. 11.

FIG. 13, including FIGS. 13A, 13B, 13C, 13D, 13E, and 13F, depicts that drugs that inhibit ATP-sensitive potassium channel P2X7 receptor or caspase-1 activation and/or activity prevent CD4 T-cell depletion and inflammation in HIV-infected human lymphoid tissues.

FIGS. 13A and 13B depict that cell death is caused by suicidal innate immune responses against this viral DNA leading to caspase-1 and caspase-3 activation.

FIGS. 13C and 13D depict that caspase-1 activation leads to inflammasome assembly, cleavage of the pro-interleukin-1β to bioactive IL-1β and to a highly inflammatory form of cell death called pyroptosis.

FIG. 13E depicts that healthy lymphoid CD4 T-cells but not CD8 T-cells nor B cells present in tonsil and spleen are primed for inflammation as evidenced by constitutive expression of high levels of pro-IL-1β.

FIG. 13F depicts that caspase-1 inhibitors Z-WEHD (SEQ ID NO: 12) and Z-YVAD (SEQ ID NO: 15) inhibit inflammation and CD4 T-cell death in HIV-infected human lymphoid cultures.

Figure 14:
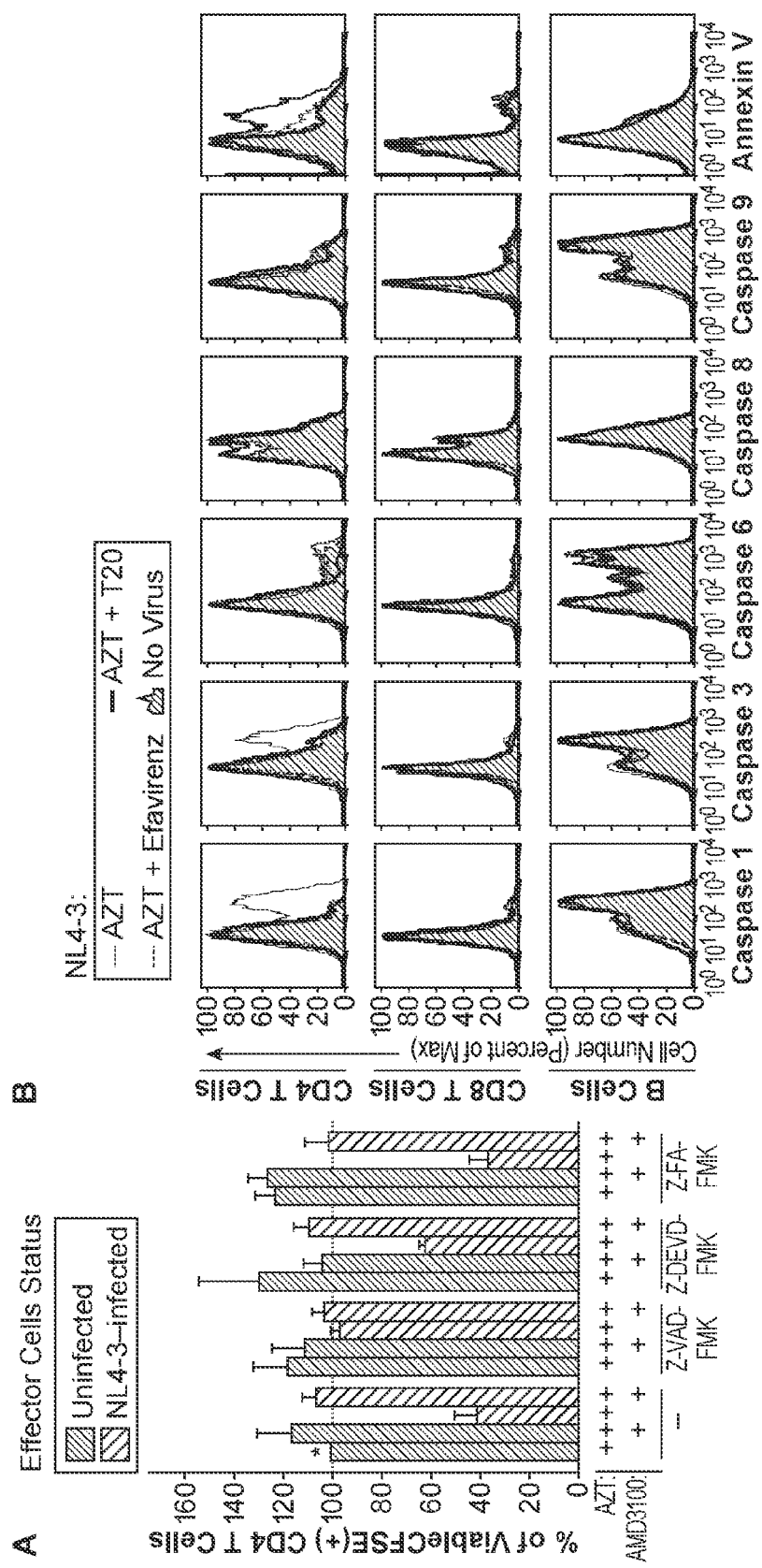

FIG. 14 depicts that death of abortively infected CD4 T-cells requires activation and/or activity of caspases. (A) CSFE-labeled cells were preincubated with 20 µM of Z-VAD-FMK, a general caspase inhibitor; Z-DEVD-FMK (SEQ ID NO: 18), a caspase-3 inhibitor; or Z-FA-FMK, a negative control for caspase inhibitors. After 2 hours, CFSE-labeled cells were co-cultured with NL4-3-infected or uninfected effector cells in the presence of 5 μM AZT or together with 250 nM AMD3100, as indicated. After 4 days of coculture the number of viable CSFE-positive CD4 T-cells was determined by flow cytometry. Percentages are normalized to the number of viable CFSE-positive CD4 T-cells co-cultured with uninfected effectors in the presence of AZT, as depicted by (*). Error bars represent standard error of the mean of three experiments from three different HLAC donors. (B and C) HLACs were spinoculated alone or with NL4-3 in the presence of AZT (5 μM), Efavirenz (100 nM), and T20 (10 μg/ml), as indicated (spinoculation is described in detail in FIG. 7 A, B). After 3 days, cells were assessed by flow cytometry for annexin V binding, and intracellular levels of activated caspases (Panel B), and for cytokine expression including TNF-α, IFN-β IL-1β and serine-37 phosphorylated forms of p53 indicative of DNA damage (Panel C). After spinoculation with NL4-3, HLAC CD4 T-cells displayed increased intracellular levels of activated caspase-1, caspase-3, IFN-β and IL-1β, together with the apoptotic marker annexin V. Efavirenz and T20 but not AZT prevented these responses, indicating they resulted from abortive HIV-1 infection. In contrast to CD4 T-cells, these intracellular markers in CD8 T and B cells were not altered following NL4-3 infection, indicating a selective CD4 T-cell response, and excluding non-specific toxicity of HIV-1. Ethidium monoazide staining was used to exclude dead and necrotic cells in annexin V binding analysis. Data are representative of three independent spinoculation experiments performed with cells from three different donors. (D) depicts representative fluorescence images of ISRE-GFP reporter H35 cell line. Depicted H35 cells were uninfected or infected with VSVg-pseudotyped NL4-3 in the presence of AZT (5 μM), Efavirenz (100 nM), and Raltegravir (30 μM) as indicated. (E) depicts a schematic illustration of the synthetic reverse transcription intermediates used in FIG. 10G. Uncapped or capped HIV-1 mRNA was produced by in vitro transcription. To generate the strong-stop and RNA-DNA heteroduplex reverse transcription intermediate (–) DNA primers were annealed to the uncapped or capped HIV-1 mRNA in the indicated sites. To generate the 150-, 500-, 1500-, and 3300 bp dsDNA reverse transcription products (step 5), PCR products corresponding to the indicated HIV-1 pregenomic mRNA were generated using specific primers. To generate ssDNA, the PCR products were heated at 95° C. for 5-10 minutes followed by 10 minutes on ice. The detailed protocol and sequences are provided in the Examples.

Figure 15:
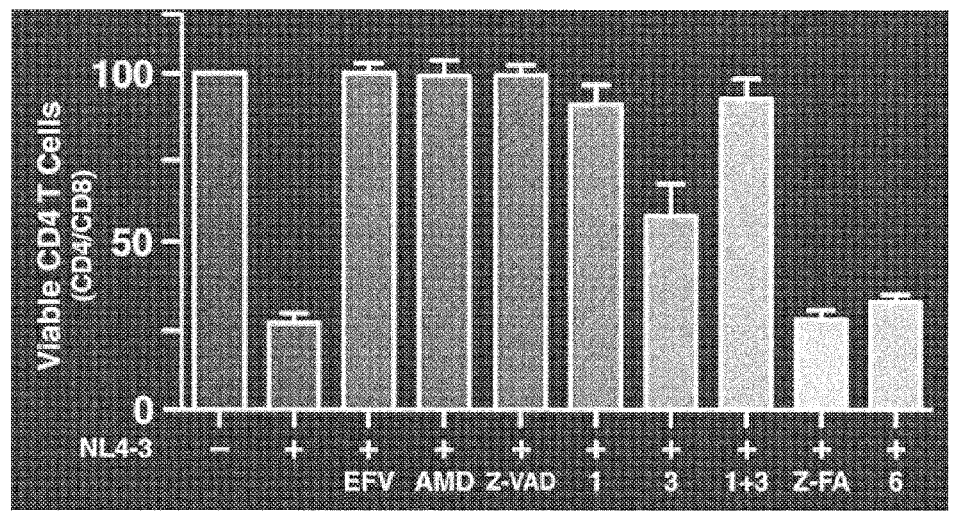

FIG. 15 depicts that inhibition of caspase-1 is sufficient to prevent depletion of HIV-1 CD4 T-cells in human lymphoid tissues. Pan-caspase inhibitor Z-VAD, caspase-1 inhibitor Z-WEHD ("1") (SEQ ID NO: 12), evafirenz (EFV), AND AMD3100 (AMD), but not caspase-6 inhibitor Z-VEID ("6") (SEQ ID NO: 19) or control compound Z-FA, inhibit the death of infected CD4 T-cells. Caspase-3 inhibitor Z-DEVD ("3") (SEQ ID NO: 6) also inhibits death of infected CD4 T cells, however, not as efficient as caspase-1 inhibitors. Data shown represent 4 different donors (SEM).

Figure 16:
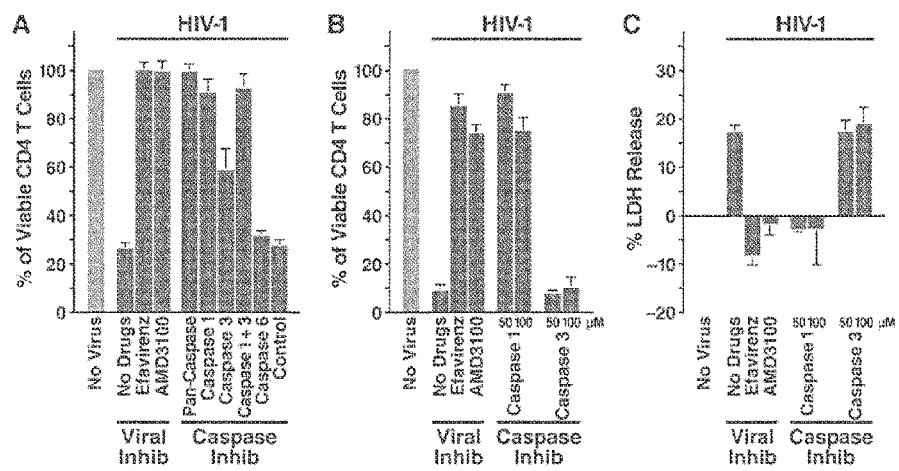

FIG. 16 depicts that caspase-1 inhibitors efficiently inhibit CD4 T-cell death in HIV-1-infected human lymphoid tissues. (A). CD4 T-cell death in HIV-1-infected cultures was prevented by the pan-caspase inhibitor Z-VAD ("Pan-Caspase") and by the caspase-1 inhibitor (Z-WEHD, "Caspase 1") (SEQ ID NO: 12) as efficient as by efavirenz and AMD3100, but not by the Z-FA-FM (commercial negative control; "Control") and caspase-6 inhibitor. Treatment with caspase-3 inhibitor (Z-DEVD; "Caspase 3") (SEQ ID NO: 6) prevented the death of only 50% CD4 T-cell population. Error bars represent standard error of the mean of three experiments from three different HLAC donors. (B). CD4 T-cell death in HIV-infected cultures was prevented by the caspase-1 inhibitor (Caspase-II inhibitor, Calbiochem; "Caspase 1") as efficient as by efavirenz and AMD3100. In these experiments, treatment with caspase-3 inhibitor (Z-DEVD; "Caspase 3") (SEQ ID NO: 6) did not prevent the death of HIV-infected CD4 T cells. Error bars represent standard error of the mean of three experiments from three different HLAC donors. (C). LDH was not released form infected cells treated with efavirenz. AMD3100, or caspase-1 inhibitor (Caspase-II inhibitor, Calbiochem; "Caspase 1"). Treatment with caspase-3 inhibitor (Z-DEVD; "Caspase 3") (SEQ ID NO: 6) did not prevent the LDH release from HIV-1 infected cells. Error bars represent standard error of the mean of three experiments from three different HLAC donors. Details are described in Example 23.

Figure 17:
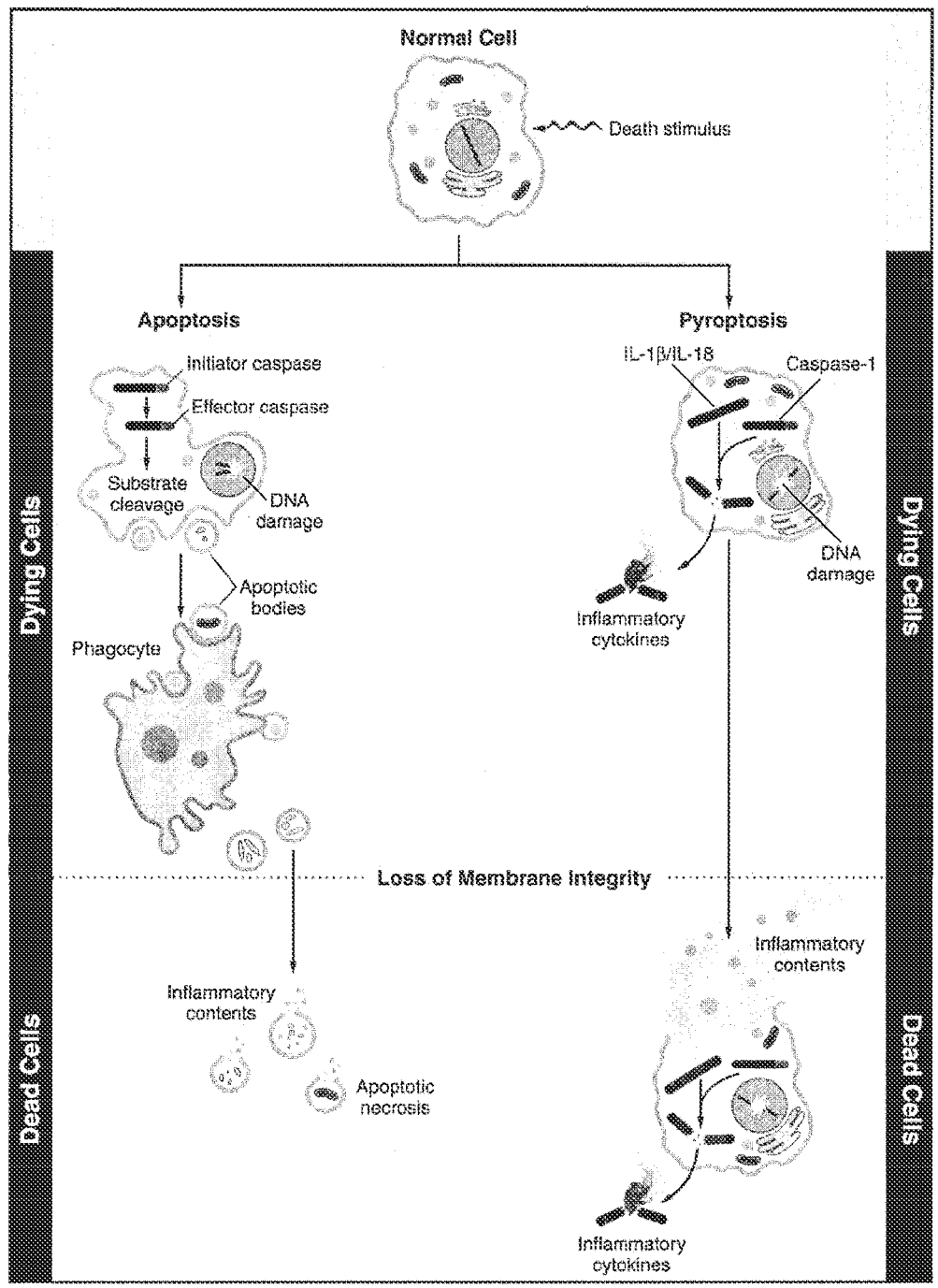

FIG. 17 schematically depicts cellular changes occurring during apoptosis and pyroptosis leading to cell death. Apoptosis is an active, programmed process of autonomous cellular dismantling that avoids eliciting inflammation. Pyroptosis, a pathway of cell death mediated by the activation and/or activity of caspase-1 includes caspase-1 cleavage of the inflammatory cytokines IL-1β and IL-18 to their bioactive forms. Pyroptotic cells are not removed by phagocytosis but undergo cell lysis and release of inflammatory cellular contents. Adapted from Fink and Cookson, 2005, *Infection and Immunity*.

Figure 18:
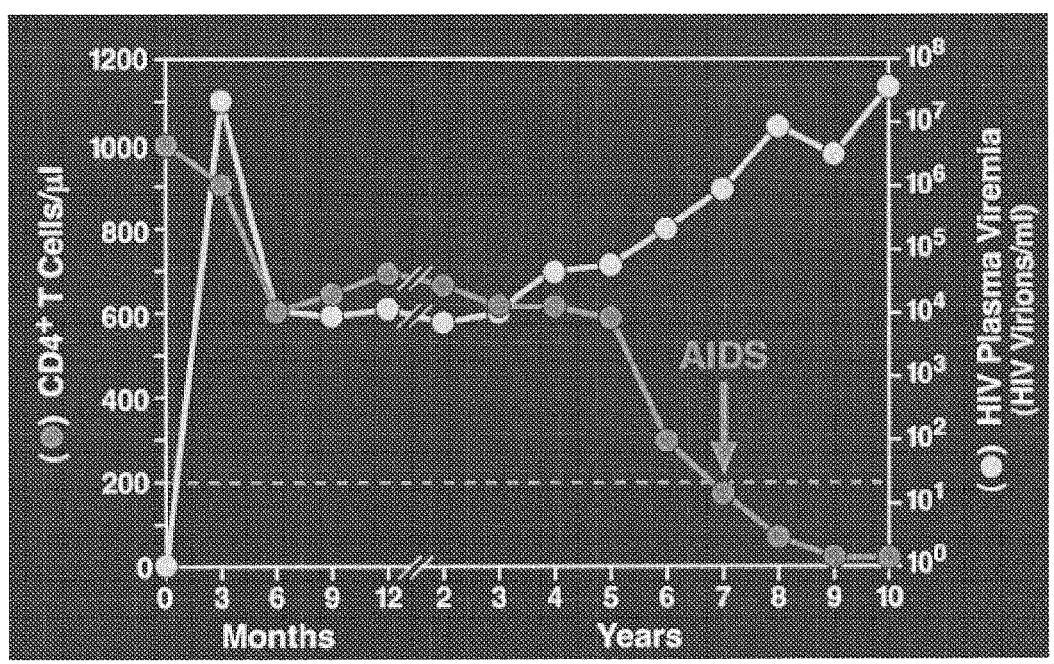

FIG. 18 depicts that AIDS is associated with a progressive loss of CD4 T-cells. Details are described in the Examples.

Figure 20:
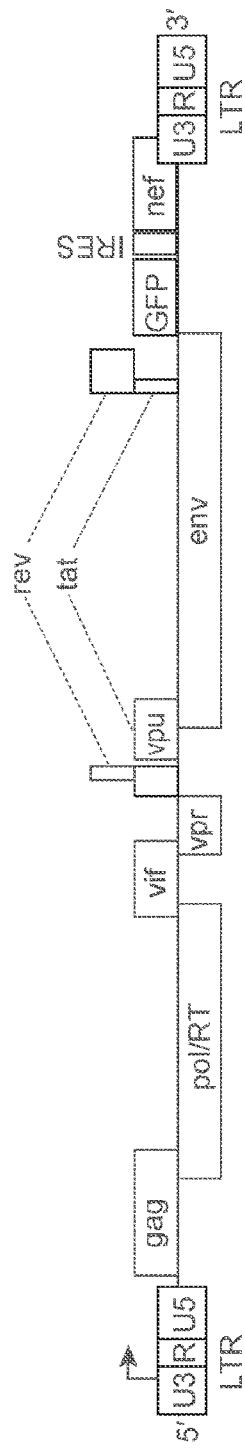

FIG. 19 depicts an ex vivo human lymphoid culture system as a model to study cell death in HIV-1 infection. Details are described in the Examples FIG. 20 depicts an HIV-1 reporter system used herein. Insertion of an IRES in the Nef gene supports GFP expression and preserves wild-type levels of Nef. A fully replication-competent virus is produced. The HIV-1 reporter system allows simultaneous quantification of the dynamics of HIV-1 infection and T-cell depletion. Details are described in the Examples.

Figure 21:
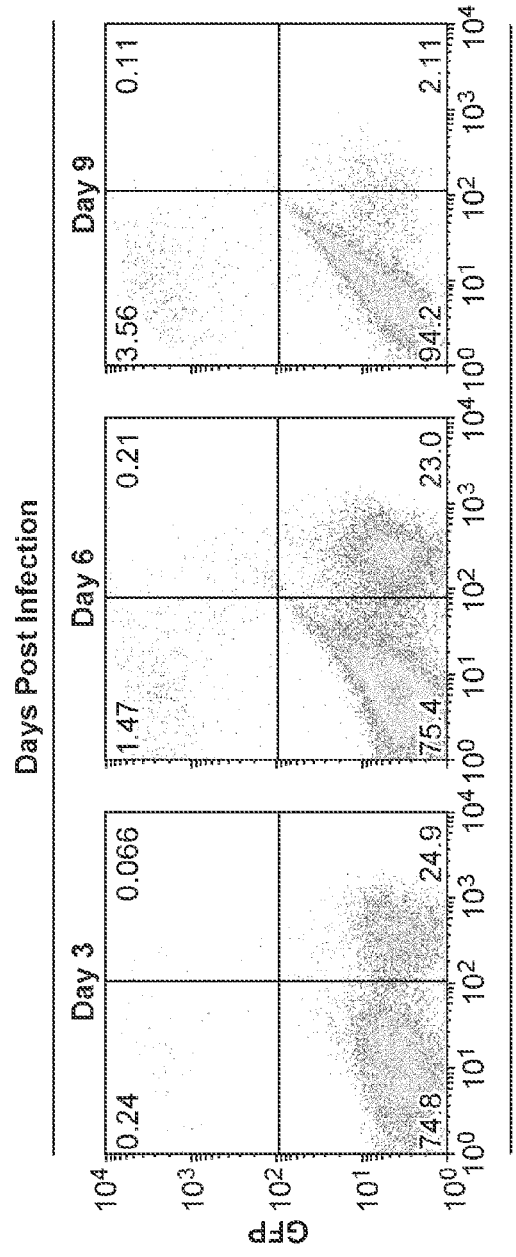

FIG. 21 depicts massive depletion of CD4 T-cells after infection of tonsillar tissue with HIV-1. Details are described in the Examples.

Figure 22:
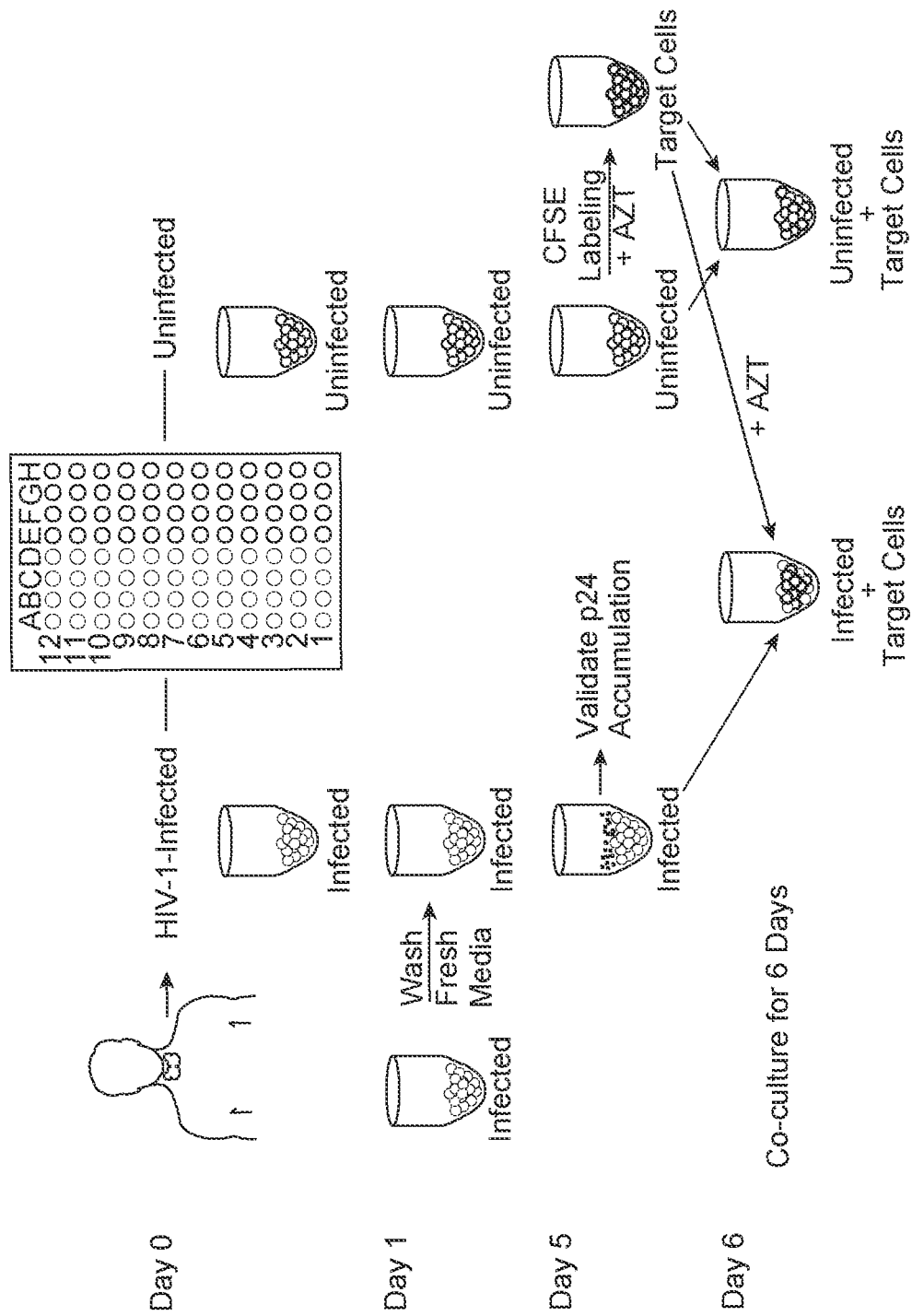

FIG. 22 depicts an experimental strategy to explore indirect cell killing in HIV-1-infected human lymphoid cultures. Details are described in the Examples.

Figure 23:
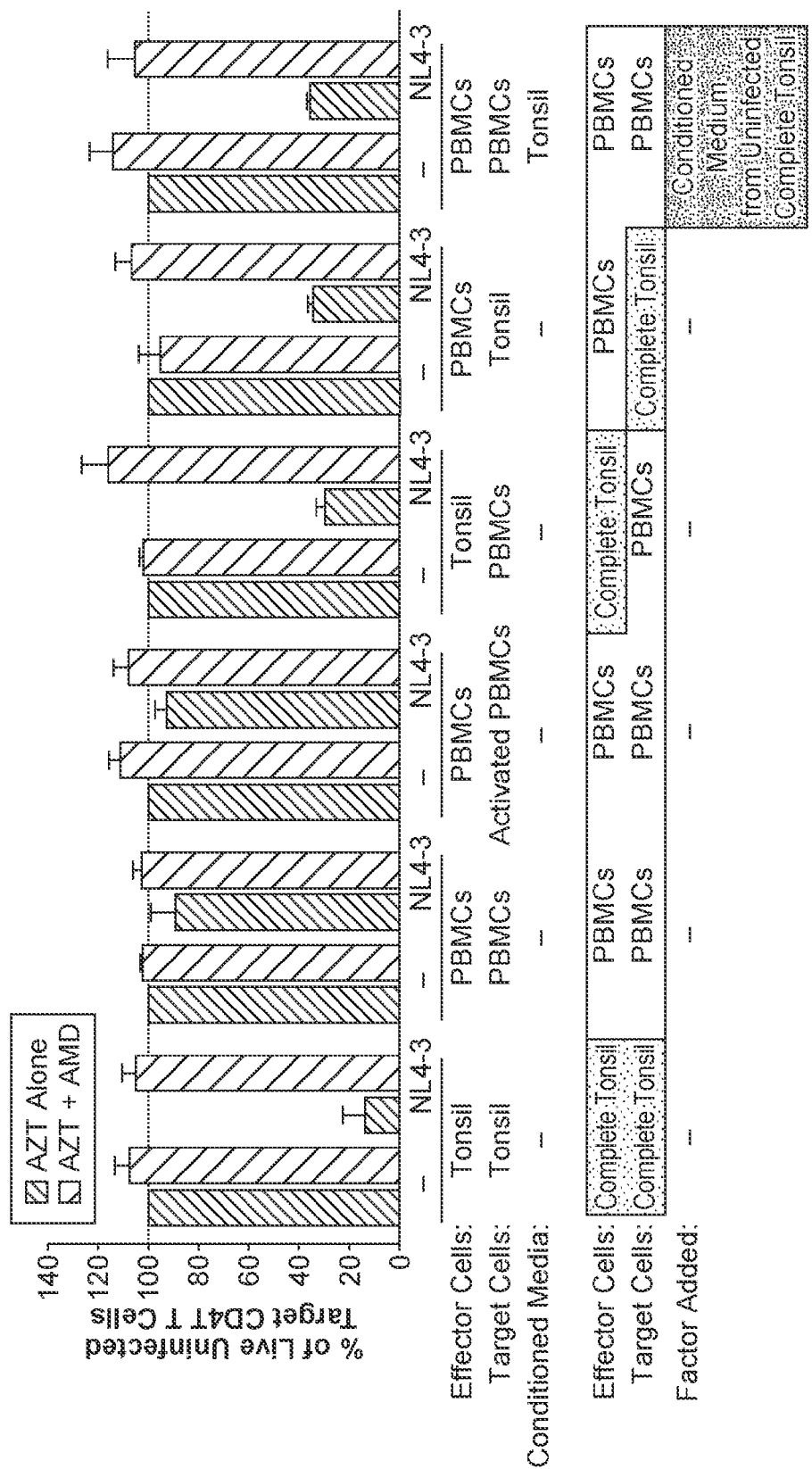

FIG. 23 depicts that soluble factors in tonsil render CD4 T-cells sensitive to indirect killing. Details are described in the Examples.

Figure 24A:
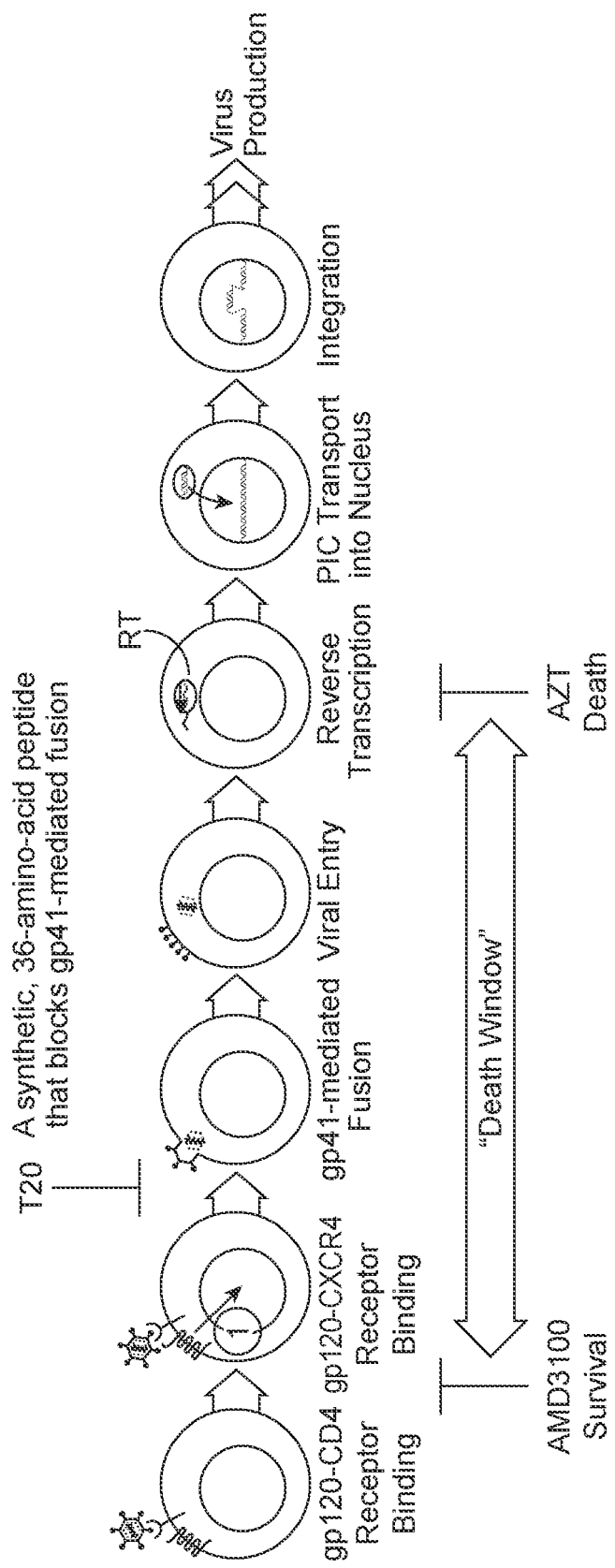
Figure 24B:
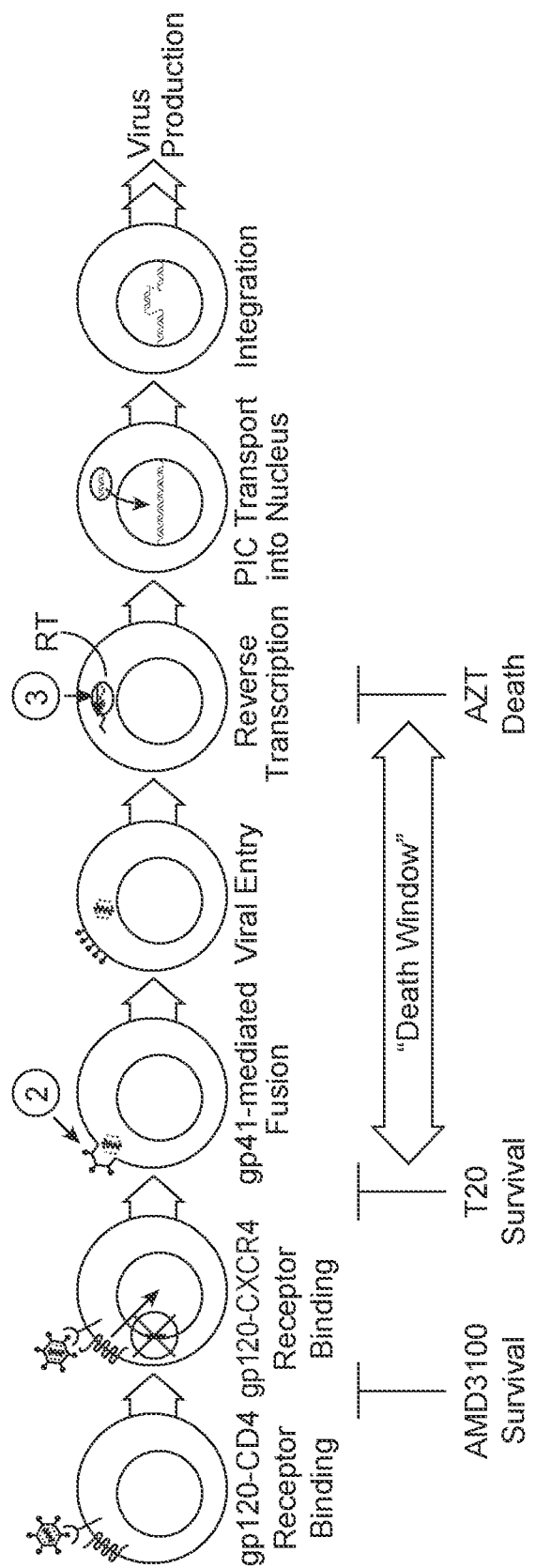

FIG. 24A depicts an experimental design to address whether HIV-1 gp41-mediated fusion is necessary for depletion of non-productively infected CD4 T-cells. FIG. 24B depicts that CXCR4 signaling is not sufficient to elicit indirect T-cell killing and that HIV-1 gp41-mediated fusion is necessary for depletion of non-productively infected CD4 T-cells. Details are described in the Examples.

FIG. 25A depicts two possible death-induced mechanisms that were examined herein based on the findings that indirect killing of CD4 T-cells requires both gp41-mediated fusion and close interaction with HIV-1-infected cells. "A" examines whether virions are the killing units and if cell death is caused by fusion of HIV-1 virions to nearby CD4 T-cells. "B" examines whether productively infected CD4 T-cells are the killing units and if cell death is caused by engagement of cell-associated Env on HIV-1-infected cells with neighboring CD4 T-cells. FIG. 25B depicts the conclusion of the experimental data described herein that the killing signal is delivered by virions not by productively infected cells. Details are described in the Examples.

Figure 26:
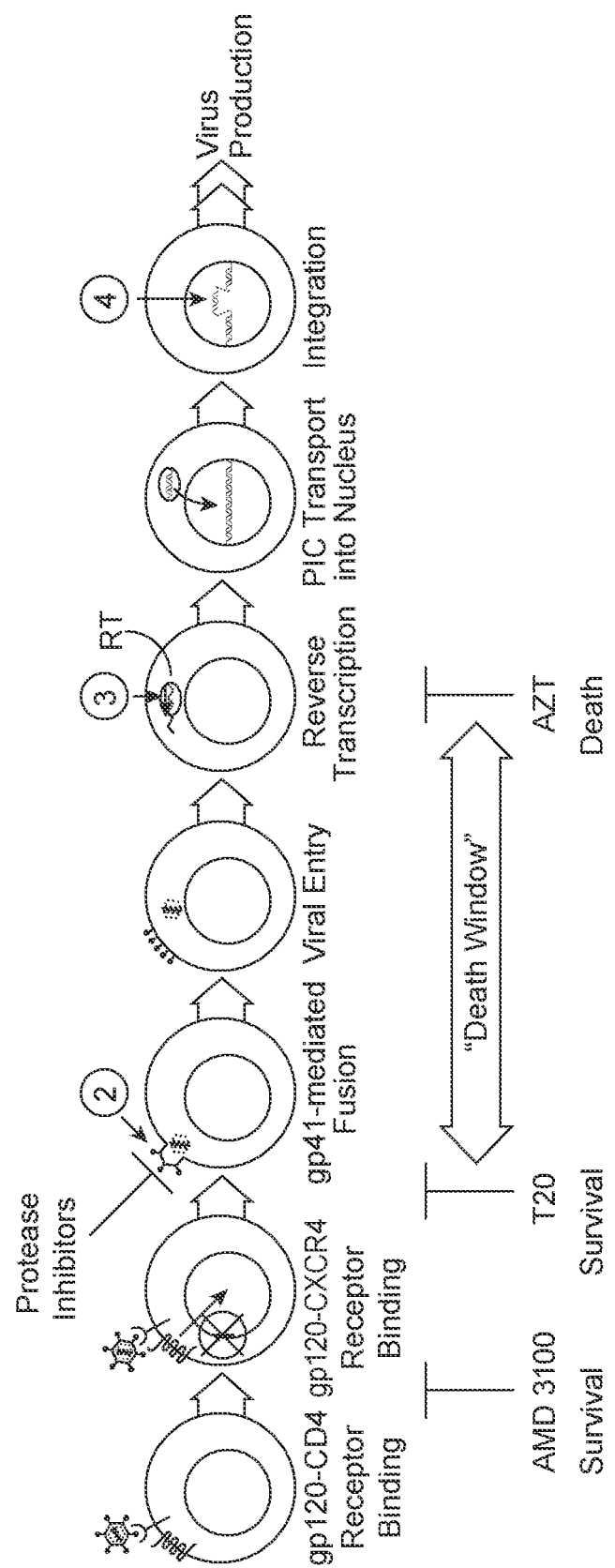

FIG. 26 depicts possible mechanism of HIV-1-induced indirect CD4 T-cell death in human lymphoid tissue that were examined herein, including (1) gp120-mediated signaling through the CXCR4 receptor, (2) gp41-mediated fusion of virus-cell or cell-cell (syncytia), (3) impaired reverse transcription, and (4) integration. Details are described in the Examples.

Figure 27:
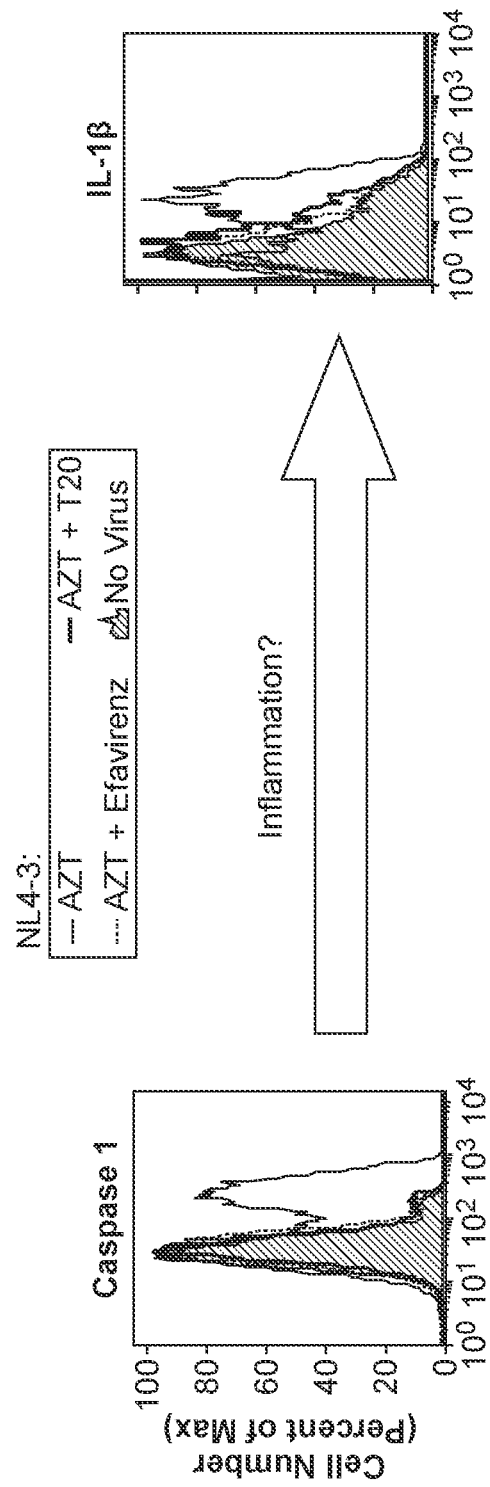

FIG. 27 depicts experimental findings and set-up to address whether HIV-1 signals for maturation and release of bioactive IL-1β in abortively infected CD4 T-cells. Details are described in the Examples.

Figure 28:
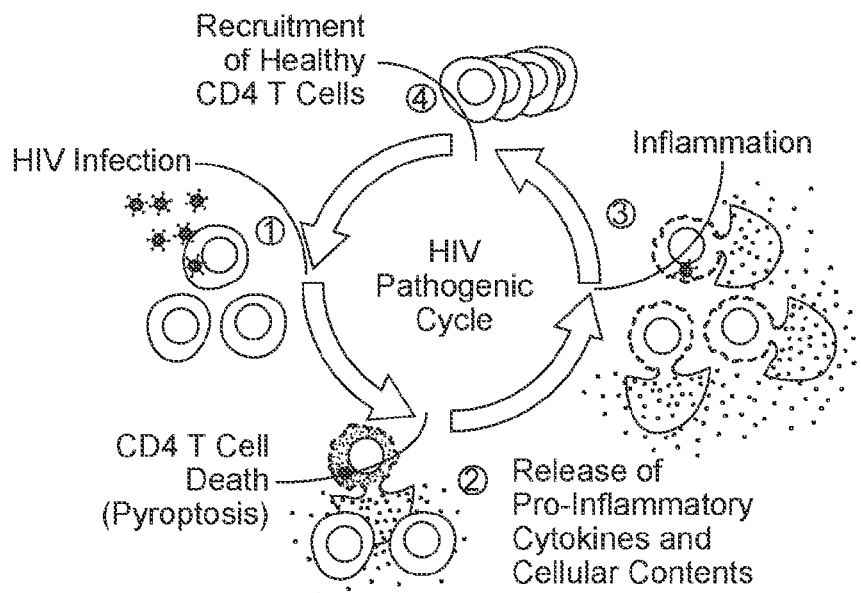
Figure 29:
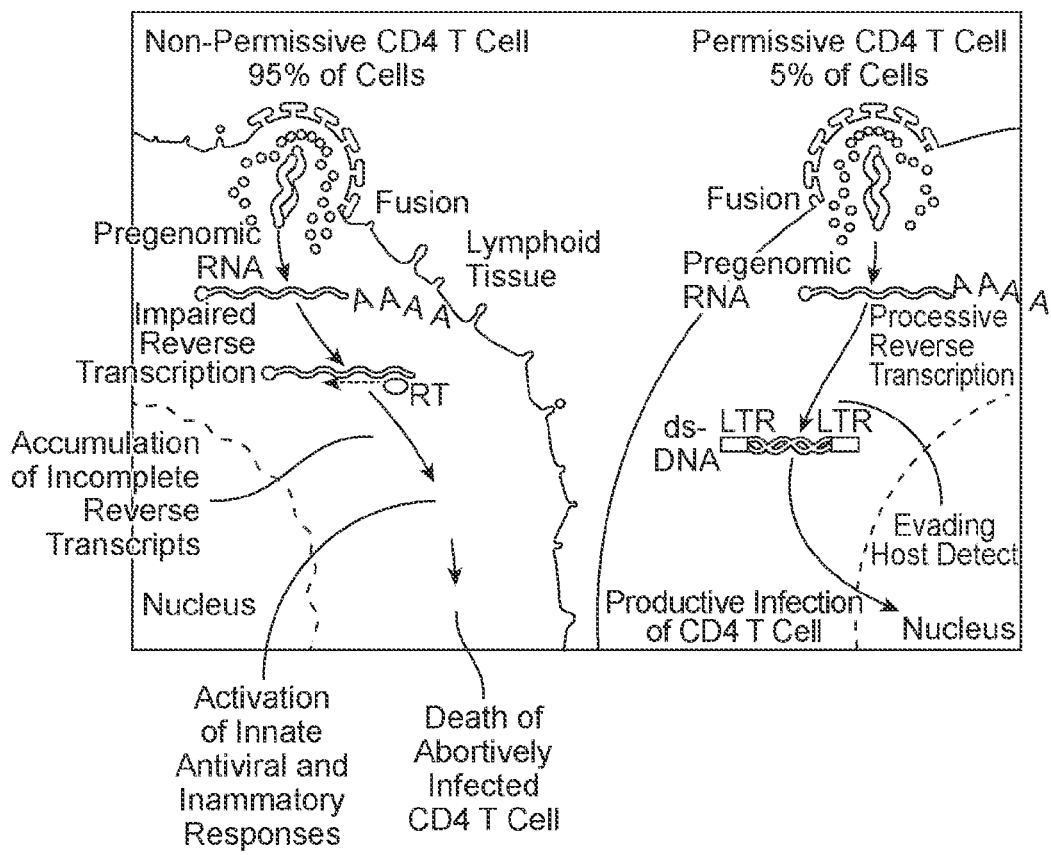

FIGS. 28 and 29 depict that HIV-1 infection causes repeating cycles of cell death and inflammation. The surprising and unexpected findings described in the Examples leading to this conclusion include that (i) dying bystander CD4 T-cells are abortively infected with HIV-1, (ii) cell death is not caused by HIV-1 products but rather by an innate immune response to the cytosolic viral DNA that accumulates in resting CD4 T-cells, (iii) the death of CD4 T-cells is associated with intense inflammation (pyroptosis), (iv) tissue-based CD4 T-cells are primed for inflammation-increased pro-IL-1β, (v) resting CD4 T-cells from lymphoid tissue die following HIV-1 infection in the absence or presence of AZT, and (vi) activated CD4 T-cells are killed by HIV-1 when AZT is present.

Figure 30A:
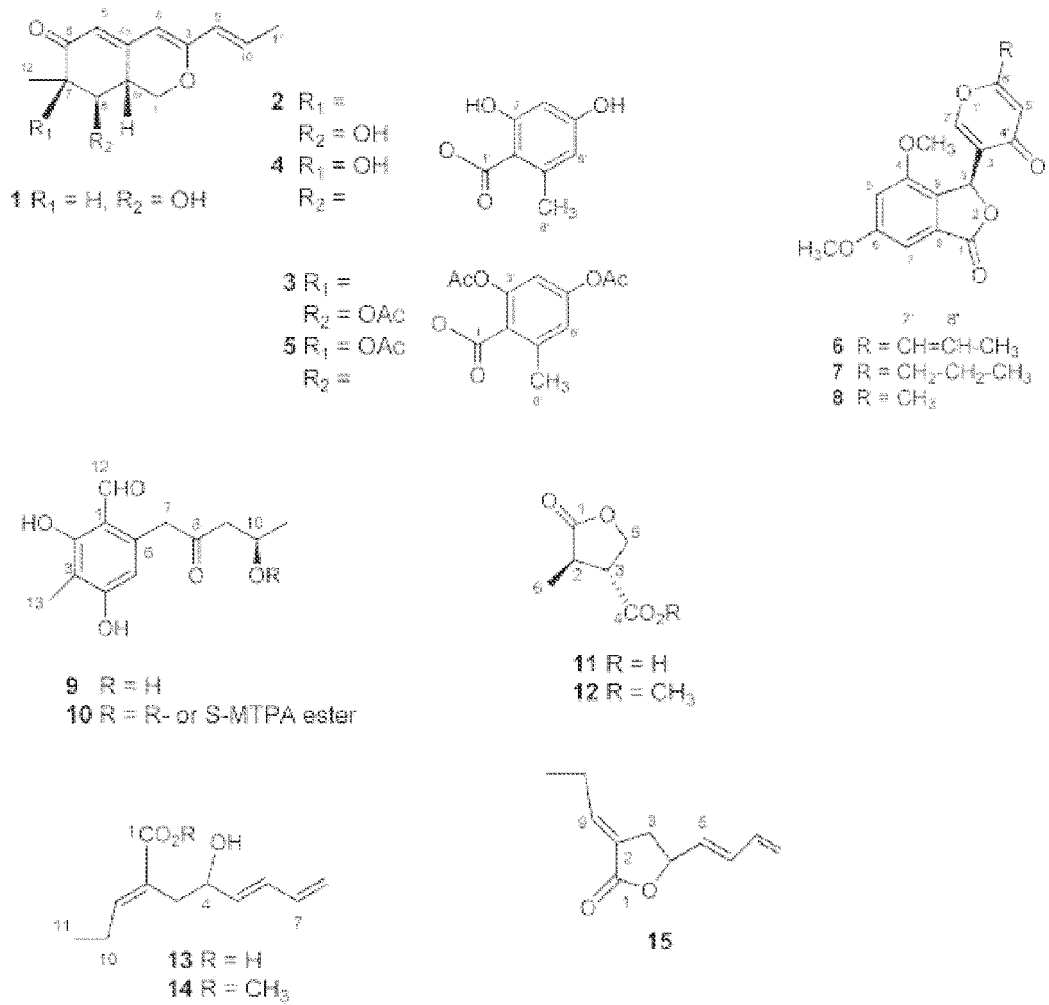

FIGS. 30A and 30B depict compounds useful for practicing the present invention, in particular, methods of the present invention using a caspase-1 inhibitor. Details of those compounds and compositions are described by Stierle et al. (Stierle et al., *J Nat Prod* (2012) 75:344-350; Stierle et al., *J Nat Prod* (2012) 75:262-266).

Figure 31A:
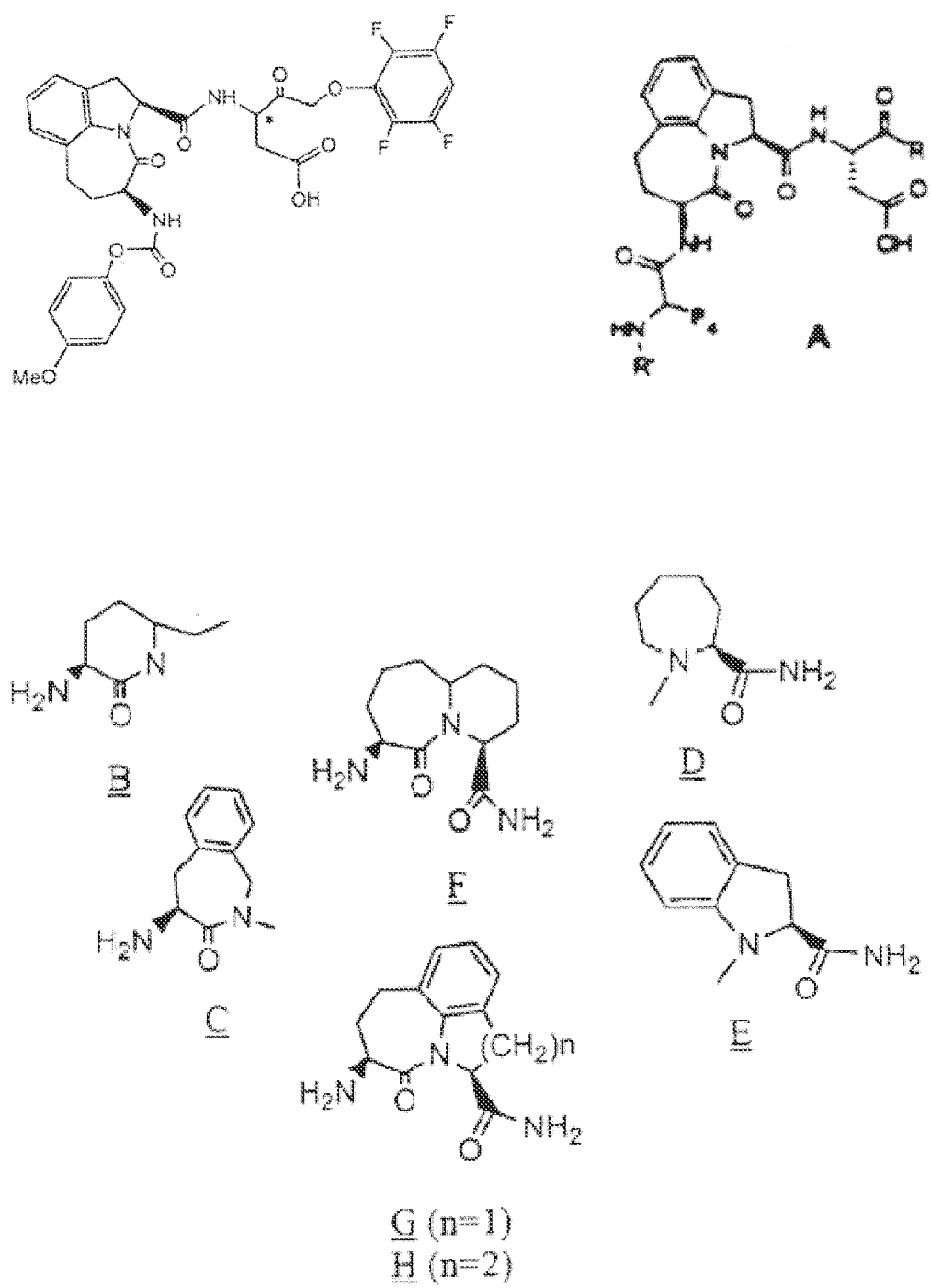
Figure 31B:
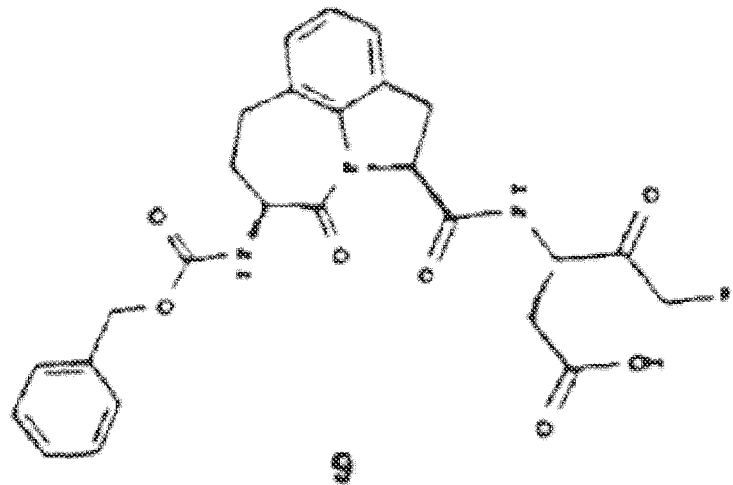
Figure 31C:
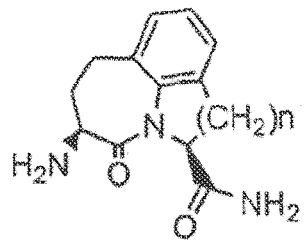

FIGS. 31A, 31B, and 31C depict compounds useful for practicing the present invention, in particular, methods of the present invention using a caspase-1 inhibitor. Details of those compounds and compositions were described at the April 2001 American Chemical Society (ACS) meeting in San Diego, Calif., USA.

DETAILED DESCRIPTION OF THE INVENTION

I. Definitions

Throughout the present specification and the accompanying claims the words "comprise" and "include" and variations thereof such as "comprises", "comprising", "includes" and "including" are to be interpreted inclusively. That is, these words are intended to convey the possible inclusion of other elements or integers not specifically recited, where the context allows. No language in the specification should be construed as indicating any non-claimed element essential to the practice of the invention.

The terms "a" and "an" and "the" and similar referents used in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximate") one particular value, and/or to "about" (or "approximate") another particular value. When such a range is expressed, another embodiment includes from the one particular value and/or to the other particular value. Similarly, when values are expressed as approximations, by use of the antecedent "about" or "approximate" it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that is "less than or equal to the value" or "greater than or equal to the value" possible ranges between these values are also disclosed, as appropriately understood by the skilled artisan. For example, if the value "10" is disclosed the "less than or equal to 10" as well as "greater than or equal to 10" is also disclosed.

All methods described herein can be performed in any suitable order unless otherwise indicated herein or otherwise clearly contradicted by context. The use of any and all examples, or exemplary language (e. g. "such as") provided herein is intended merely to better illuminate the invention and does not pose a limitation on the scope of the invention otherwise claimed.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); The Glossary of Genetics, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, the term "about" refers to a range of values of plus or minus 10% of a specified value. For example, the phrase "about 200" includes plus or minus 10% of 200, or from 180 to 220, unless clearly contradicted by context.

As used herein, the term "administering" means the actual physical introduction of a composition into or onto (as appropriate) a host or cell. Any and all methods of introducing the composition into the host or cell are contemplated according to the invention; the method is not dependent on any particular means of introduction and is not to be so construed. Means of introduction are well-known to those skilled in the art, and also are exemplified herein.

As used herein, the term "administration in combination," "combination therapy" or similar grammatical equivalents refers to both simultaneous and sequential administration of compounds. One or more caspase-1 antagonist can be delivered or administered at the same site or a different site and can be administered at the same time or after a delay, preferably not exceeding 48 hours. Concurrent or combined administration, as used herein, means that one or more caspase-1 antagonists are administered to a subject either (a) simultaneously, or (b) at different times during the course of a common treatment schedule. In the latter case, the compounds are administered sufficiently close in time to achieve the intended effect. Concurrent or combined administration, as used herein, also means that one or more caspase-1 antagonists can be administered in combination with another compound useful for the treatment of HIV-1 infection and AIDS.

As used herein, an "agent" or "compound" can be any chemical compound, for example, a macromolecule or a small molecule disclosed herein. The agent can have a formula weight of less than about 10,000 grams per mole, less than 5,000 grams per mole, less than 1,000 grams per mole, or less than about 500 grams per mole. The agent can be naturally occurring (e.g., a herb or a nature product), synthetic, or both. Examples of macromolecules are proteins, protein complexes, and glycoproteins, nucleic acids, e.g., DNA, RNA and PNA (peptide nucleic acid). Examples of small molecules are peptides, peptidomimetics (e.g., peptoids), amino acids, amino acid analogs, polynucleotides, polynucleotide analogs, nucleotides, nucleotide analogs, organic or inorganic compounds e.g., heteroorganic or organometallic compounds. An agent can be the only substance used by the method described herein. Alternatively, a collection of agents can be used either consecutively or concurrently by the methods described herein.

As used herein, the term "aliphatic" means straight chained, branched or cyclic $C_1$-$C_{12}$ hydrocarbons which are completely saturated or which contain one or more units of unsaturation. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl.

As used herein, the term "alkenyl" refers to a straight or branched chain unsaturated hydrocarbyl moiety having one or more double bonds. Examples of alkenyl groups include vinyl, allyl, 2-propenyl, crotyl, 2-isopentenyl, 2-(butadienyl), 2,4-pentadienyl and 3-(1,4-pentadienyl). The term "lower alkenyl" refers to alkenyl groups having from 2 to 4 carbon atoms.

As used herein, the term "alkenylene" refers to a divalent group derived from an alkenyl group and includes, for example, ethenylene, —CH═CH—, propenylene, —CH═C═CH—, and the like.

As used herein, the term "alkoxy" refers to —OR$^d$ wherein R$^d$ is alkyl as defined herein. Representative examples of alkoxy groups include methoxy, ethoxy, butoxy, trifluoromethoxy, and the like.

As used herein, the term "alkyl," by itself or as part of another substituent, means, unless otherwise stated, a straight (i.e. unbranched) or branched chain, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "lower alkyl" refers to alkyl groups having from 1 to 4 carbon atoms.

As used herein, the term "alkylene" by itself or as part of another substituent means a divalent radical derived from an alkyl, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

As used herein, the term "alkynyl" refers to an unsaturated alkyl group one having one or more triple bonds. Examples of alkynyl groups include ethynyl (acetylenyl), 1-propynyl, 1- and 2-butynyl, and the higher homologs and isomers.

As used herein, the terms "alkylsulfonyl" and "haloalkylsulfonyl" refer to sulfonyl (—SO$_2$—) moieties substituted by an alkyl or haloalkyl group, respectively.

As used herein, the term "alkylthio" refer to sulfur atoms substituted by alkyl groups of the indicated number of carbon atoms.

As used herein, the terms "altering the immune response" or "regulating the immune response" or grammatical equivalents thereof, refer to any alteration in any cell type involved in the immune response. The definition is meant to include an increase or decrease in the number of cells, such as CD4 T-cells, an increase or decrease in the activity of the cells, such as CD4 T-cells, or any other changes that can occur within the immune system. The cells may be, but are not limited to, T lymphocytes, B lymphocytes, natural killer (NK) cells, macrophages, eosinophils, mast cells, dendritic cells, or neutrophils. The definition encompasses both a stimulation or enhancement of the immune system to develop a sufficiently potent response to a caspase-1 antagonist as described herein, as well as a suppression of the immune system to avoid a destructive response to a desirable target. In the case of stimulation of the immune system, the definition includes future protection against subsequent HIV-1 infection.

As used herein, the term "amount sufficient", an "effective amount" or "therapeutically effective amount" or grammatical equivalents is that amount of a given compound to ameliorate, or in some manner, reduce a symptom or stop or reverse progression of a disease, disorder, or condition. In some embodiments, the desired activity of interest is diminishing, abolishing or interfering with the physiological action of a caspase-1 polypeptide, which provides either a subjective relief of a symptom(s) or an objectively identifiable improvement as noted by a clinician or other qualified observer. In some embodiments, the desired activity of interest is decreasing the amount or activity of biologically active IL-1β. The dosing range varies with the compound used, the route of administration and the potency of the particular compound. Amelioration of a symptom(s) of a particular condition by administration of a pharmaceutical composition described herein refers to any lessening, whether permanent or temporary, lasting or transient that can be associated with the administration of the pharmaceutical composition. An "effective amount" can be administered in vivo and in vitro.

As used herein, the terms "antagonist" or "inhibitor" (used interchangeably herein) mean a chemical substance that diminishes, abolishes or interferes with the physiological action of a polypeptide. The antagonist may be, for example, a chemical antagonist, a pharmacokinetic antagonist, a non-competitive antagonist, or a physiological antagonist, such as a biomolecule, e.g., a polypeptide, a peptide antagonist or a non-peptide antagonist. A preferred antagonist diminishes, abolishes or interferes with the physiological action of a caspase-1 polypeptide. As used herein, a "cytokine antagonist is a compound that inhibits or blocks the expression and/or activity of a cytokine, e.g. an interleukin (IL), such as IL-1β, or interferon or another cytokine.

As used herein, the term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described herein. "Substituted heteroaryl" refers to a unsubstituted heteroaryl group as defined above in which one or more of the ring members is bonded to a non-hydrogen atom such as described above with respect to substituted alkyl groups and substituted aryl groups. Representative substituents include straight and branched chain alkyl groups —$CH_3$, —$C_2H_5$, —$CH_2OH$, —OH, —$OCH_3$, —$OC_2H_5$, —$OCF_3$, —OC(=O)$CH_3$, —OC(=O)$NH_2$, —OC(=O)N($CH_3$)$_2$, —CN, —$NO_2$, —C(=O)$CH_3$, —$CO_2H$, —$CO_2CH_3$, —$CONH_2$, —$NH_2$, —N($CH_3$)$_2$, —$NHSO_2CH_3$, —$NHCOCH_3$, —NHC(=O)$OCH_3$, —$NHSO_2CH_3$, —$SO_2CH_3$, —$SO_2NH_2$ and halo. "Arylene" and "heteroarylene" refers to a divalent radical derived from a aryl and heteroaryl, respectively.

As used herein, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like.

As used herein, the term "biaryl" (when used as a group or as part of a group) refers to a group containing the specified number of atoms and containing two aromatic rings which have two atoms in common. Examples of biaryl as used herein include, but are not limited to naphthyl. Said biaryl groups may be optionally substituted—where not otherwise specified, the substitutions may be one or more groups selected from $C_1$-$C_3$alkyl, $C_1$-$C_3$alkoxy, —C(O)Me, $CO_2H$, $CO_2$Me and =O.

As used herein, the term "biologically active" when referring to an agent or compound is art-recognized and refers to a form of an agent or compound that allows for it, or a portion of the amount of agent or compound administered, to be absorbed by, incorporated into, or otherwise physiologically available to a subject or patient to whom it is administered.

As used herein, the terms "caspase antagonist", "caspase inhibitor" or "inhibitor of caspase activity" refer to a compound that is capable of preventing, whether fully or partially, activity of a caspase polypeptide, as measured by any suitable assay, such as those described and referenced herein. Preferred caspases are caspase-1 and caspase-3. Most preferred is a caspase-1.

As used herein, the term "caspase-1" refers to nucleic acids, polypeptides and polymorphic variants, alleles, mutants, and interspecies homologues thereof and as further described herein, that: (1) have an amino acid sequence that has greater than about 85%, 90%, preferably 91%, 92%, 93%, 94%, 95%, 96%, 97%, 98% or 99% or greater amino acid sequence identity, preferably over a region of at least about 25, 50, 75, 100, 150, 200, 250, 300, 350, or more amino acids, to a sequence as deposited under GenBank Accession Nos., e.g., NP_150634, NP_001214, AAT72297, or NP_150635; (2) bind to antibodies, e.g., monoclonal and/or polyclonal antibodies, raised against an immunogen comprising an amino acid sequence as deposited under GenBank Accession Nos., e.g., NP_150634, NP_001214, AAT72297, or NP_150635, or conservatively modified variants thereof or a fragment thereof; (3) modulate at least partially, indirectly or directly the production of bioactive IL-1β; (4) specifically hybridize under stringent hybridization conditions to a nucleic acid sequence as deposited under GenBank Accession Nos., e.g., NM_033292, NM_001223, AY660536, or NM_033293, or conservatively modified variants thereof; (5) have a nucleic acid sequence that has greater than about 90%, preferably greater than about 96%, 97%, 98%, 99%, or higher nucleotide sequence identity, preferably over a region of at least about 30, 50, 100, 200, 500, 1000, 1,200 or more nucleotides, to a nucleic acid sequences as deposited under GenBank Accession Nos., e.g., NM_033292, NM_001223, AY660536, or NM_033293; (6) have at least 25, often 50, 75, 100, 150, 200, 250, 300, 350, or more contiguous amino acid residues of a polypeptide the sequence of which is deposited under GenBank Accession Nos., e.g., NP_150634, NP_001214, AAT72297, or NP_150635; and/or (7) have at least 25, often 50, 75, 100, 150, 200, 250, 300, 350, 400, 500, 600, 700, 800, 900, 1,000, 1,200, or more contiguous nucleotides of a nucleic acid sequences as deposited under GenBank Accession Nos., e.g., NM_033292, NM_001223, AY660536, or NM_033293. Preferred is a mammalian caspase-1. A preferred mammalian caspase-1 is a human caspase-1. Also preferred is a simian caspase-1.

As used herein, the terms "caspase-1 antagonist" or "caspase-1 inhibitor" or "inhibitor of caspase-1 activity" refer to a compound that is capable of preventing, whether fully or partially, activation and/or activity of a caspase-1 polypeptide, as measured by any suitable assay such as those described and referenced herein. A "peptide caspase-1 inhibitor" comprises at least one natural amino acid or at least one non-natural amino acid.

As used herein, the term "caspase-3" refers to nucleic acids, polypeptides and polymorphic variants, alleles, mutants, and interspecies homologues thereof and as further described herein, that: (1) have an amino acid sequence that has greater than about 85%, 90%, preferably 91%, 92%, 93%, 94%, 95%, 96%, 97%, 98% or 99% or greater amino acid sequence identity, preferably over a region of at least about 25, 50, 75, 100, 150, 200, 250, or more amino acids, to a sequence as deposited under GenBank Accession Nos., e.g., NP_004337, NP_116786, or CAC88866; (2) bind to antibodies, e.g., polyclonal and/or monoclonal antibodies, raised against an immunogen comprising an amino acid sequence as deposited under GenBank Accession Nos. e.g., NP_004337, NP_116786, or CAC88866, or conservatively modified variants thereof or a fragment thereof; (3) modulate at least partially, indirectly or directly the activation of caspases 6, 7, and 9 or cleavage of amyloid-beta 4A precursor protein; (4) specifically hybridize under stringent hybridization conditions to a nucleic acid sequence as deposited under GenBank Accession Nos., e.g., NM_004346, NM_032991, or AJ413269, or conservatively modified variants thereof; (5) have a nucleic acid sequence that has greater than about 90%, preferably greater than about 96%, 97%, 98%, 99%, or higher nucleotide sequence identity, preferably over a region of at least about 30, 50, 100, 200, 500, 1000, 1,500 or more nucleotides, to a nucleic acid sequences as deposited under GenBank Accession Nos., e.g., NM_004346, NM_032991, or AJ413269; (6) have at least 25, often 50, 75, 100, 150, 200, 250, or more contiguous amino acid residues of a polypeptide the sequence of which is deposited under GenBank Accession Nos. e.g., NP_004337, NP_116786, or CAC88866; and/or (7) have at least 25, often 50, 75, 100, 150, 200, 250, 300, 350, 400, 500, 600, 700, 800, 900, 1,000, 1,200, 1,500, or more contiguous nucleotides of a nucleic acid sequences as deposited under GenBank Accession Nos., e.g., NM_004346, NM_032991, or AJ413269. Preferred is a mammalian caspase-3. A preferred mammalian caspase-3 is a human caspase-3. Also preferred is a simian caspase-3.

As used herein, the terms "caspase-3 antagonist" or "caspase-3 inhibitor" or "inhibitor of caspase-3 activity" refer to a compound that is capable of preventing, whether fully or partially, activation and/or activity of a caspase-3 polypeptide, as measured by any suitable assay such as those described and referenced herein. Some caspase-1 antagonists described herein also diminish, abolish or interfere with the physiological action of a caspase-3 polypeptide.

Throughout the present specification and the accompanying claims the words "comprise" and "include" and variations such as "comprises", "comprising", "includes" and "including" are to be interpreted inclusively. That is, these words are intended to convey the possible inclusion of other additives, elements, components, integers or steps not specifically recited, where the context allows.

By "contacting" is meant an instance of exposure of at least one substance to another substance. For example, contacting can include contacting a substance, such as a cell or a polypeptide to an agent described herein. A cell can be contacted with the agent, for example, by adding the agent to the culture medium (by continuous infusion, by bolus delivery, or by changing the medium to a medium that contains the agent) or by adding the agent to the extracellular fluid in vivo (by local delivery, systemic delivery, intravenous injection, bolus delivery, or continuous infusion). The duration of contact with a cell or group of cells is determined by the time the agent is present at physiologically effective (biologically active) levels or at presumed physiologically effective (biologically active) levels in the medium or extracellular fluid bathing the cell. In the present invention, for example, a virally infected cell (e. g. an HIV-1 infected cell) or a cell at risk for viral infection (e. g., before, at about the same time, or shortly after HIV-1 infection of the cell) is contacted with an agent. The term "contacting" is used herein interchangeably with the following: combined with, added to, mixed with, passed over, incubated with, flowed over, place in direct physical association with another substance, etc.

As used herein, the terms "cycloalkyl" and "heterocycloalkyl", by themselves or in combination with other terms, represent, unless otherwise stated, cyclic versions of "alkyl" and "heteroalkyl", respectively. The term "cycloalkyl" refers to a saturated cyclic hydrocarbon having 3 to 8 carbon atoms, and 1 to 3 rings that can be fused or linked covalently. Additionally, for heterocycloalkyl, a heteroatom can occupy the position at which the heterocycle is attached to the remainder of the molecule. Cycloalkyl groups useful in the present invention include, but are not limited to, cyclopentyl, cyclohexyl, cycloheptyl and cyclooctyl, and the like. Bicycloalkyl groups useful in the present invention include, but are not limited to, [3.3.0]bicyclooctanyl, [2.2.2]bicyclooctanyl, [4.3.0]bicyclononane, [4.4.0]bicyclodecane (decalin), spiro[3.4]octanyl, spiro[2.5]octanyl, and so forth. Examples of heterocycloalkyl include, but are not limited to, 1 (1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and "heterocycloalkylene" refer to a divalent radical derived from cycloalkyl and heterocycloalkyl, respectively.

As used herein, the term "cycloalkenyl" refers to an unsaturated cyclic hydrocarbon having 3 to 15 carbons, and 1 to 3 rings that can be fused or linked covalently. Cycloalkenyl groups useful in the present invention include, but are not limited to, cyclopentenyl, cyclohexenyl, cycloheptenyl and cyclooctenyl. Bicycloalkenyl groups are also useful in the present invention.

As used herein, the term "decreased expression" refers to the level of a gene expression product that is lower and/or the activity of the gene expression product is lowered. Preferably, the decrease is at least 20%, more preferably, the decrease is at least 30%, at least 40%, at least 50%, at least 60%, at least 70%, at least 80%, or at least 90% and most preferably, the decrease is at least 100%, relative to a control. A preferred gene expression product for decreasing its expression is interleukin-1 beta (IL-1β).

As used herein, the terms "derivative" or "derivatized" or "modified" refer to a compound that is produced from another compound of similar structure by the replacement of substitution of one atom, molecule or group by another. For example, a hydrogen atom of a compound may be substituted by alkyl, acyl, amino, hydroxyl, halo, haloalkyl, etc. to produce a derivative of that compound or a derivatized compound. The derivative of a compound preferably retains at least one function of the compound from which it is produced, such as diminishing, abolishing or interfering with the physiological action of a caspase-1 polypeptide. The activity of derivative compounds is tested as described herein.

By "determining the functional effect" is meant assaying for a compound that decreases a parameter that is indirectly or directly under the influence of a caspase-1 polypeptide, e.g., functional, enzymatic, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties for the polypeptide, measuring inducible markers or activation and/or activity of the caspase-1 polypeptide; measuring binding activity, e.g., binding of a compound to the caspase-1 polypeptide, measuring cellular proliferation, measuring apoptosis, pyroptosis, or the like. The functional effects can be evaluated by many means known to those skilled in the art, e.g., microscopy for quantitative or qualitative measures of alterations in morphological features, measurement of changes in caspase-1 RNA or protein levels, measurement of RNA stability, identification of downstream or reporter gene expression (CAT, luciferase, β-gal, GFP and the like), e.g., via chemiluminescence, fluorescence, colorimetric reactions, antibody binding, inducible markers, and ligand binding assays. "Functional effects" include in vitro, in vivo, and ex vivo activities.

As used herein, the term "different" means not the same, not of the same identity.

As used herein, "disorder", "disease" or "pathological condition" are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information. Disease specifically includes HIV-1 infection, AIDS and pathological conditions associated with or developing in a subject as a consequence of HIV-1 infection and AIDS.

As used herein, "HAART" refers to a treatment for HIV-1 infection, which is a cocktail of anti-viral drugs known as Highly Active Anti-Retroviral Therapy. HAART includes two reverse transcriptase inhibitors and a protease inhibitor. HAART reduces the viral load in many patients to levels below the current limits of detection, but the rapid mutation rate of this virus limits the efficacy of this therapy (Perrin and Telenti, 1998, Science 280:1871-1873).

As used herein, the term "haloalkyl" refers to alkyl groups substituted by one or more halogen atoms, which may be the same or different. Exemplary, non-limiting, haloalkyl groups include $CF_3$, $CCl_3$, $CHF_2$, $CHCl_2$, $C_2F_5$, $C_2Cl_5$, and the like.

As used herein, the terms "halo" or "halogen," by themselves or as part of another substituent, mean, unless otherwise stated, a fluorine (F), chlorine (Cl), bromine (Br), or iodine (I) atom.

As used herein, the term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, CH=CH—N($CH_3$)—$CH_3$, O—$CH_3$, —O—$CH_2$—$CH_3$, and —CN. Up to two heteroatoms may be consecutive, such as, for example, —$CH_2$—NH—$OCH_3$ and —$CH_2$—O—Si($CH3$)$_3$. Similarly, the term "heteroalkylene" by itself or as part of another substituent means a divalent radical derived from heteroalkyl, as exemplified, but not limited by, —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R' represents both —C(O)$_2$R' and —R'C(O)$_2$. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

As used herein, the term "heteroatom" or "ring heteroatom" is meant to include oxygen (O), nitrogen (N), sulfur (S), phosphorus (P), and silicon (Si).

As used herein, the term "hetero-biaryl" (when used as a group or as part of a group) refers to a biaryl group containing the specified number of atoms and which contains one or more nitrogen, sulphur, or oxygen heteroatoms. Examples of hetero-biaryl as used herein include, but are not limited to; quinoline, isoquinoline, quinoxaline, and benzotriazine groups. Said hetero-biaryl groups may be optionally substituted. In some embodiments, the substitutions may be one or more groups selected from $C_1$-$C_3$alkyl, $C_1$-$C_3$alkoxy, —C(O)Me, $CO_2H$, $CO_2Me$ and =O.

As used herein, the term "heterocyclyl" (Hetcy) unless otherwise specified, means mono- and bicyclic saturated rings and ring systems containing at least one heteroatom selected from N, S and O, each of said ring having from 3 to 10 atoms in which the point of attachment may be carbon or nitrogen. Examples of "heterocyclyl" include, but are not limited to, azetidinyl, pyrrolidinyl, piperidinyl, piperazinyl, imidazolidinyl, tetrahydrofuranyl, 1,4-dioxanyl, morpholinyl, thiomorpholinyl, tetrahydrothienyl and the like. Heterocyclys can also exist in tautomeric forms, e.g., 2- and 4-pyridones. Heterocyclyl moreover includes such moieties in charged form, e.g., piperidinium.

In each of the above embodiments designating a number of atoms e.g. "$C_{1-8}$" is meant to include all possible embodiments that have one fewer atom. Non-limiting examples include $C_{1-7}$, $C_{2-8}$, $C_{2-7}$, $C_{3-8}$, $C_{3-7}$ and the like.

As used herein, "HIV" is used herein to refer to the human immunodeficiency virus. It is recognized that the HIV virus is an example of a hyper-mutable retrovirus, having diverged into two major subtypes (HIV-1 and HIV-2), each of which has many subtypes.

As used herein, the term "HIV-1 infection" refers to indications of the presence of the Human Immunodeficiency Virus type-1 (HIV-1) in an individual and includes asymptomatic seropositivity, aids-related complex (arc), and acquired immunodeficiency syndrome (AIDS).

As used herein, the term "HIV-1 viral load" refers to the number of HIV-1 viral particles in a sample of blood plasma. HIV-1 viral load is increasingly employed as a surrogate marker for disease progression. It is measured by PCR and bDNA tests and is expressed in number of HIV-1 copies or equivalents per milliliter.

As used herein, the term "immune response" means any physiological change resulting in activation and/or expansion of a "B" cell population with production of antibodies, and/or activation and/or expansion of a "T" cell population.

As used herein, the term "incomplete HIV-1 nucleic acid" refers to a not full-length HIV-1 nucleic acid. Full-length HIV-1 nucleic acids have about 9,700-9,800 nt (single-stranded) or about 9,700-9,800 bps (double-stranded). Thus, an "incomplete HIV-1 nucleic acid" is an HIV-1 nucleic acid of less than about 9,000 nt (single-stranded) or less than about 9,000 bps (double-stranded). Incomplete HIV-1 nucleic acids in a cell can be the result of an abortive HIV-1 reverse transcription reaction.

As used herein, the terms "individual," "subject," "host," and "patient" (used interchangeably herein), refer to a mammal, including, but not limited to, humans and non-human mammals, such as simians. Preferred is a human. As used herein, "subject" or "patient" to be treated for a pathological condition, disorder, or disease by a subject method means either a human or non-human mammal in need of treatment for a pathological condition, disorder, or disease. The term "non-human mammal" includes non-human primates (particularly higher primates), sheep, dog, rodent (e.g., mouse or rat), guinea pig, goat, pig, cat, rabbits, cow, etc. In some embodiments, the subject is a human. In other embodiments, the subject is an experimental animal or an animal suitable as a disease model.

As used herein, the terms "inhibition" or "inhibits" mean to reduce an activity as compared to a control (e. g. an activity in the absence of such inhibition). It is understood that inhibition can mean a slight reduction in activity to the complete ablation of all activity. An "inhibitor" can be anything that reduces activity. For example, an inhibition of caspase-1 activity by a disclosed composition can be determined by assaying the amount of IL-1β in the presence of the composition to the amount of IL-1β in the absence of the composition. In this example, if the amount of IL-1β is reduced in the presence of the composition as compared to the amount of IL-1β in the absence of the composition, the composition can be said to inhibit the activity of caspase-1. Inhibition of caspase-1 polypeptide activity is achieved when the level or activity value relative to a control is reduced by about 10%, preferably about 20%, preferably about 30%, preferably about 40%, preferably about 50%, preferably about 60%, preferably about 70%, preferably about 80%, or preferably about 90-100%. Likewise, inhibition of cell death is achieved when the cell death relative to a control is reduced by about 10%, preferably about 20%, preferably about 30%, preferably about 40%, preferably about 50%, preferably about 60%, preferably about 70%, preferably about 80%, or preferably about 90-100%. Likewise, inhibition of pyroptosis is achieved when pyroptosis relative to a control is reduced by about 10%, preferably about 20%, preferably about 30%, preferably about 40%, preferably about 50%, preferably about 60%, preferably about 70%, preferably about 80%, or preferably about 90-100%.

As used herein, the term "in vitro" means outside the body of the organism from which a cell or cells is obtained or from which a cell line is isolated.

As used herein, the term "in vivo" means within the body of the organism from which a cell or cells is obtained or from which a cell line is isolated.

Compounds that have the same molecular formula but differ in the nature or sequence of bonding of their atoms or the arrangement of their atoms in space are termed "isomers." Isomers that differ in the arrangement of their atoms in space are termed "stereoisomers." "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the scope of the present invention includes individual enantiomers, racemates, diastereomers, tautomers, geometric isomers, and stereoisomers as well as mixtures of the compounds. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992) differ in the chirality of one or more stereocenters.

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or di-substituted with an alkyl group and situations where the heterocyclo group is not substituted with the alkyl group. The terms also refer to a subsequently described composition that may but need not be present, and that the description includes instances where the composition is present and instances in which the composition is nor present.

As used herein, the term "pharmaceutically acceptable" refers to compositions that are physiologically tolerable and do not typically produce an allergic or similar untoward reaction when administered to a subject, preferably a human subject. Preferably, as used herein, the term "pharmaceutically acceptable" means approved by a regulatory agency of a Federal or state government or listed in the U.S. Pharmacopeia or other generally recognized pharmacopeia for use in animals, and more particularly in humans.

As used herein, the term "physiologically functional derivative" refers to any pharmaceutically acceptable derivative of a compound of the present invention, for example an ester or an amide thereof, and includes any pharmaceutically acceptable salt, ester, or salt of such ester of a compound of the present invention which, upon administration to a mammal, such as a human, is capable of providing (directly or indirectly) a compound of the present invention or an active metabolite or residue thereof. It will be appreciated by those skilled in the art that the compounds of the present invention may be modified to provide physiologically functional derivatives thereof at any of the functional groups in the compounds, and that the compounds of the present invention may be so modified at more than one position.

As used herein, the terms "polypeptide" and "protein" (used interchangeably herein) refer to a polymer of amino acid residues. Preferred polypeptides are caspase-1 polypeptides, in particular human caspase-1 polypeptides.

As used herein, the term "population of cells" refers to cells, preferably mammalian cells, more preferably human cells, grown in vitro or in vivo. The term also refers to cells within a host and may comprise a mixture of cells, such as virally infected cells and uninfected cells. A preferred population of cells is a population of CD4 T-cells. A more preferred population of cells is a population of CD4 T-cells within a host. An even more preferred population of cells is a population of CD4 T-cells within a host comprising HIV-1 infected CD4 T-cells and uninfected CD4 T-cells.

As used herein, the term "preventing death of a cell in a population of cells" or grammatical equivalents thereof means that in a population of cells more cells survive when contacted with a compound of the invention as compared to a cells in a population of cells not contacted with the compound, but otherwise treated comparably (control). As such, the death of a cell is prevented, when at least 5%, at least 10%, at least 20%, at least 30%, at least 40%, at least 50%, at least 60%, at least 70%, at least 80%, at least 90-100% of cells in a population of cells survive when contacted with a compound of the invention as compared to cells in a population of cells not contacted with the compound, but otherwise treated comparably (control).

As used herein, the term "prodrug" refers to a precursor or derivative form of a pharmaceutically active substance that is less cytotoxic to cells compared to the parent drug and is capable of being enzymatically activated or converted into the more active parent form. See, e.g., Wihnan, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al, (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, (β-lactam-containing prodrugs, optionally substituted phenoxyacetamide-containing prodrugs or optionally substituted phenylacetamide-containing prodrugs, 5 fluorocytosine and other 5-fluorouridine prodrugs which can be converted into the more active cytotoxic free drug.

As used herein, the term "protease inhibitor" ("PI") refers to inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 Daltons) and substantial peptide character, e.g. CRIXIVAN® (available from Merck) as well as non-peptide protease inhibitors e.g., VIRACEPT® (available from Agouron.

As used herein, the terms "salt" and "pharmaceutically acceptable salt" refer to salts of a compound which is prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., 1977, "Pharmaceutical Salts", Journal of Pharmaceutical Science, 66:1-19). Certain specific compounds of the present invention contain both basic and acidic functionalities that allow the compounds to be converted into either base or acid addition salts. The neutral forms of a compound may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "solvate" refers to a compound that is complexed to a solvent. Solvents that can form solvates with the compounds of the present invention include common organic solvents such as alcohols (methanol, ethanol, etc.), ethers, acetone, ethyl acetate, halogenated solvents (methylene chloride, chloroform, etc.), hexane and pentane. Additional solvents include water. When water is the complexing solvent, the complex is termed a "hydrate."

Each of the chemical terms herein (e.g., "alkyl," "heteroalkyl," "aryl" and "heteroaryl") is meant to include both "unsubstituted" and optionally "substituted" forms of the indicated radical, unless otherwise indicated. Typically each radical is substituted with 0, 1, 2 3 4 or 5 substituents, unless otherwise indicated. Examples of substituents for each type of radical are provided herein.

"Substituted" refers to a group as defined herein in which one or more bonds to a carbon(s) or hydrogen(s) are replaced by a bond to non-hydrogen and non-carbon atom "substituents" such as, but not limited to, a halogen atom such as F, Cl, Br, and I; an oxygen atom in groups such as hydroxyl groups, alkoxy groups, aryloxy, and acyloxy groups; a sulfur atom in groups such as thiol groups, alkyl and aryl sulfide groups, sulfone groups, sulfonyl groups, and sulfoxide groups; a nitrogen atom in groups such as amino, alkylamines, dialkylamines, arylamines, alkylarylamines, diarylamines, alkoxyamino, hydroxyamino, acylamino, sulfonylamino, N-oxides, imides, and enamines; and other heteroatoms in various other groups. "Substituents" also include groups in which one or more bonds to a carbon(s) or hydrogen(s) atom is replaced by a higher-order bond (e.g., a double or triple-bond) to a heteroatom such as oxygen in oxo, acyl, amido, alkoxycarbonyl, aminocarbonyl, carboxyl, and ester groups; nitrogen in groups such as imines, oximes, hydrazones, and nitriles. "Substituents" further include groups in which one or more bonds to a carbon(s) or hydrogen(s) atoms is replaced by a bond to a cycloalkyl, heterocyclyl, aryl, and heteroaryl groups. Representative "substituents" include, among others, groups in which one or more bonds to a carbon or hydrogen atom is/are replaced by one or more bonds to fluoro, chloro, or bromo group. Another representative "substituent" is the trifluoromethyl group and other groups that contain the trifluoromethyl group. Other representative "substituents" include those in which one or more bonds to a carbon or hydrogen atom is replaced by a bond to an oxygen atom such that the substituted alkyl group contains a hydroxyl, alkoxy, or aryloxy group. Other representative "substituents" include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group. Still other representative "substituents" include those in which one or more bonds to a carbon(s) or hydrogen(s) atoms is replaced by a bond to an alkyl, cycloalkyl, aryl, heteroaryl, or heterocyclyl group.

As used herein, the terms "treatment", "treating" or grammatical equivalents thereof refer to both therapeutic treatment and prophylactic or preventative measures. Those in need of treatment include those already with the disease or disorder as well as those in which the disease or disorder is to be prevented. Hence, a subject may have been diagnosed as having the disease or disorder or may be predisposed or susceptible to the disease. As such, the terms include: (1) preventing a pathological condition, disorder, or disease, i.e. causing the clinical symptoms of a pathological condition, disorder, or disease not to develop in a subject that may be predisposed to the pathological condition, disorder, or disease but does not yet experience any symptoms of the pathological condition, disorder, or disease; (2) inhibiting the pathological condition, disorder, or disease, i.e. arresting or reducing the development of the pathological condition, disorder, or disease or its clinical symptoms; or (3) relieving the pathological condition, disorder, or disease, i.e. causing regression of the pathological condition, disorder, or disease or its clinical symptoms. These terms encompass also prophylaxis, therapy and cure. Treatment means any manner in which the symptoms of a pathological condition, disorder, or disease are ameliorated or otherwise beneficially altered. Preferably, the subject in need of such treatment is a mammal, more preferable a human.

II. Treatment of HIV-1 Infection and AIDs

Applicants have studied the mechanisms by which HIV kills helper CD4 T-cells—the fundamental problem in AIDS. Using a physiologically relevant system formed of human lymphoid tissues, it was demonstrated that killing of CD4 T-cells by HIV can be efficiently prevented by inhibitors of caspase-1. Applicants' finding forms a new strategy for preserving CD4 T-cells in AIDS patients.

Despite the vigorous research over the last 30 years, the cause of CD4 T-cell death in AIDS remains poorly understood, and is cited as one of the top unsolved problems in HIV research. Applicants explored the mechanisms by which HIV depletes CD4 T-cells using a unique, physiologically relevant experimental system formed of fresh human lymphoid cultures. In many regards, this system is one of the most powerful experimental approaches to modeling molecular and cellular events during HIV infection in human patients. Surprisingly, using this system Applicants discovered that the overwhelming majority of the cells die not from HIV, but rather from the cell's own defensive response to HIV before the virus can make copies of itself. After HIV-1 infection, >95% of lymphoid CD4 T-cells that die are not productively infected, and accumulate cytoplasmic viral DNA due to incomplete reverse transcription It appears that HIV enters the CD4 T-cells that are destined to die and starts to make a DNA copy of its RNA, a process called reverse transcription. However, during this process, the cells sense the incomplete DNA intermediates (incomplete HIV nucleic acids) that accumulate in the cells are sensed and trigger the cell to 'commit suicide' in an attempt to protect the body (Doitsh et al., 2010, Cell, 143(5): 789-801; incorporated herewith by reference). While this response is likely designed to be protective, HIV subverts and amplifies it so effectively that it becomes a central driver of HIV pathogenesis.

A second surprise was finding that the mechanism of cell death was not a silent one. These infected cells die a fiery death known as pyroptosis, causing significant inflammation as they erupt their cellular contents and release chemical signals, which recruit healthy CD4 T-cells to the site of infection. This establishes a vicious cycle, whereby the dying CD4 T-cells release inflammatory signals that attract more cells to die (Doitsh et al., 2010, Cell, 143(5):789-801; incorporated herewith by reference).

Figure 1:
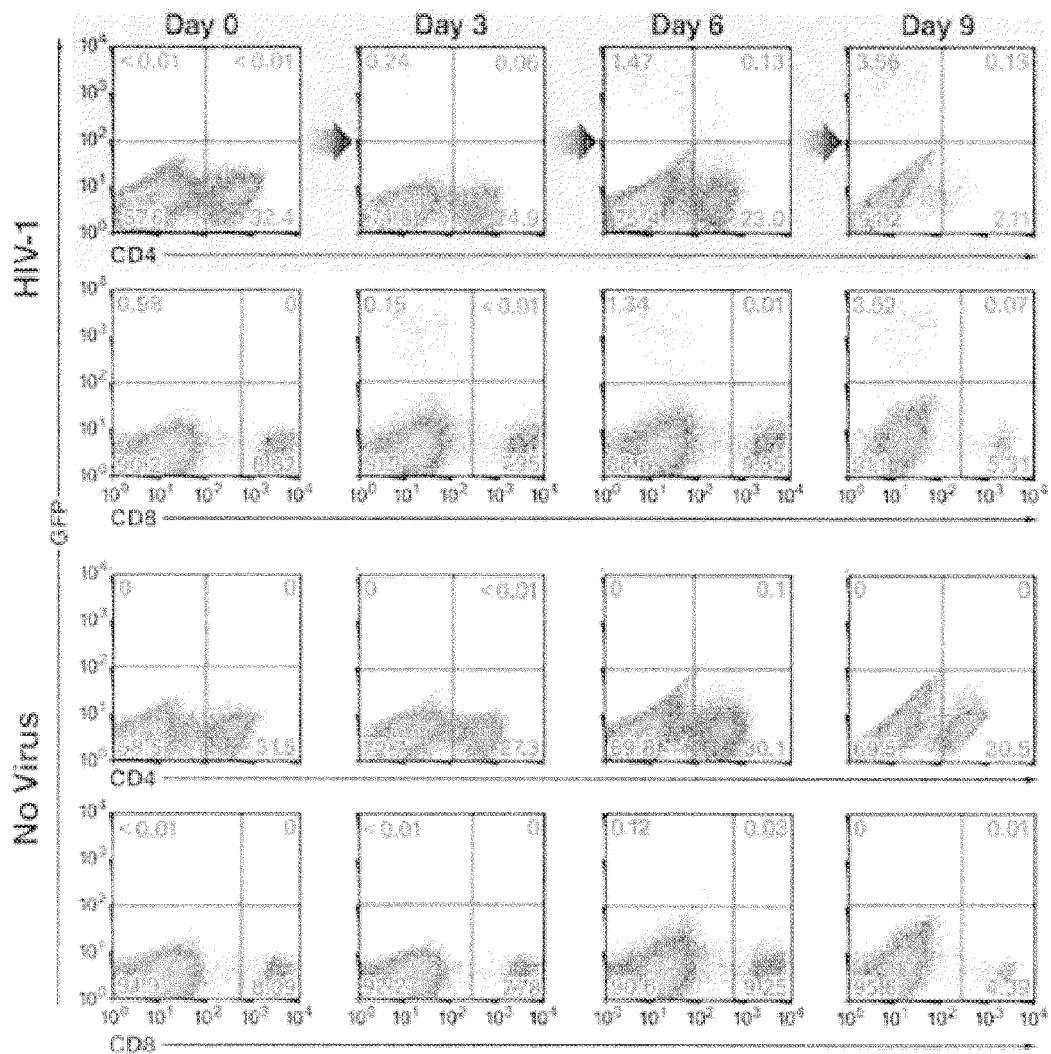
FIG. 1 depicts massive depletion of CD4 T-cells in HLACs containing a small number of productively infected cells. (A) Kinetics of spreading viral infection versus depletion of CD4 T-cells after infection of HLACs with a replication-competent HIV reporter virus encoding GFP. CD4 downregulation in GFP-positive cells likely represents the combined action of the HIV Nef, Vpu, and Env proteins expressed by this virus. Ratios of viable CD4 versus CD8 T-cells in HIV-infected and uninfected cultures are also shown. Flow cytometry plots represent live-gated cells, based on the forward-scatter versus side-scatter profile of the complete culture. These data are the representative results of six independent experiments utilizing tonsil cells from six different donors.

Destruction of cells by pyroptosis also releases high levels of an intracellular component called adenosine-5'-triphosphate (5'ATP) into the extracellular space. Extracellular ATP binds to membrane channels termed P2X7 purinergic receptors and acts as an inflammatory stimulus to induce pyroptosis in nearby cells. Thus, pyroptosis activated initially by HIV infection may result in an avalanche of new rounds of pyroptosis in healthy CD4 T-cells by the repeated release of intracellular ATP in a virus-independent manner (FIG. 1).

Lymphoid tissues serve as home to more than 98% of the body's CD4 T-cells and form the primary sites of HIV replication and spread. Applicants' experimental system, built on these tissues, closely recapitulates these conditions and thus provides a compelling experimental platform for studying HIV pathogenesis and exploring new strategies aimed at blocking CD4 T-cell death thereby curbing AIDS progression (Doitsh et al., 2010, Cell, 143(5):789-801; incorporated herewith by reference).

The data provided herein suggest that CD4 T-cell depletion in AIDS is not triggered by HIV-1 toxicity, but is mediated by a cellular antiviral innate immune response against the virus. This response involves intense inflammation associated with the pyroptotic death of CD4 T-cells, and was likely designed to protect the host. However, the ensuing inflammation that results during this process may spin out of control with inflammation attracting new CD4 T-cells to undergo new rounds of infection and cell death.

The finding that CD4 T-cell death is associated with inflammation provides an unexpected and exciting nexus between the virus and host with strong implications for the role of inflammation in HIV pathogenesis and disease progression. It is striking that Simian Immunodeficiency Virus (SIV) infection of its natural monkey hosts does not result in AIDS. While the SIV virus is cytopathic for CD4 T-cells like HIV-1 (i.e., it also kills monkeys' CD4 T-cells), monkeys do not mount an inflammatory response when SIV infection occurs, as it does in humans. Thus, from an evolutionary point of view, the threat of AIDS has been neutralized not by controlling the virus but by negating an inflammatory response by the host against the virus. The discovery described herein, namely that peptide and non-peptide caspase-1 antagonists can be used to block the inflammation occurring during CD4 T-cell pyroptosis and thus interrupt the generation of inflammatory signals is surprising and unexpected. Thus, the peptide and non-peptide caspase-1 antagonists described herein or related drugs open the door to use of an entirely new class of "anti-AIDS" agents that curb CD4 T-cell loss by suppressing pyroptosis and the associated inflammatory response that is pivotal in HIV-1 pathogenesis.

III. Compounds

Applicants discovered that small molecule compounds (peptide and non-peptide small molecules compounds), that inhibit activation and/or activity of caspase-1 are useful in the methods of the present invention, in particular, in methods for the treatment of a patient having an HIV-1 infection or suspected of having an HIV-1 infection or having AIDS and in methods for preventing the death of a CD4 T-cell in a population of CD4 T-cells comprising HIV-1 infected and uninfected CD4 T-cells.

A. Caspase-1 Inhibitors

The present invention describes a variety of caspase-1 inhibitors for use in the methods of the present invention. More specifically, the present invention describes a variety of caspase-1 inhibitors for use as compositions and practicing methods of the present invention.

Caspase-1 inhibitors are currently commercially available from a number of sources, including Calbiochem (La Jolla, Calif.), Biomol (Plymouth, Mass.), Sigma-Aldrich (St. Louis, Mo.), and A.G. Scientific, Inc. (caspases.com division) (San Diego, Calif.). In addition, a number of experimental caspase inhibitors are under development at a number of pharmaceutical companies. The most commonly employed caspase inhibitors are short-chain peptides (typically 3-6 amino acids), either per se or modified with, for example, ester or carbonyl-containing groups. Typical derivatives include aldehydes, chloromethyl ketones, fluoromethyl ketones, trifluoroacetates, benzoyloxymethyl ketones, nitroanilides, and various substituted coumarins. Lists of these are found, for example, in the catalogs of the commercial sources mentioned above. These caspase inhibitors are useful for practicing the present invention.

In some embodiments of the present invention, a caspase-1 inhibitor is a peptide caspase-1 inhibitor or single stereoisomers, mixtures of stereoisomers, pharmaceutically acceptable salts or prodrugs thereof.

It is possible to generate reversible or irreversible inhibitors of caspase-1 activation by coupling caspase-1-specific peptides to certain aldehyde, nitrile or ketone compounds. These caspase inhibitors can successfully inhibit the induction of apoptosis in various tumor cell lines (Schlegel et al., *J Biol Chem* (1996) 271:1841; Martins et al., *J Biol Chem* (1997) 272:7421; Huang et al., *Mol Cell Biol* (1999) 19:2986; Guo and Kyprianou, *Cancer Res* (1999) 59:1366) as well as normal cells (Zaks et al., *J Immunol* (1999) 162:3273; Gastman et al., *Cancer Res* (1999) 59:1422). Peptide caspase-1 inhibitors described herein can be derivatized and act as effective irreversible inhibitors with no apparent added cytotoxic effect. Peptide caspase-1 inhibitors can be derivatized to include fluoromethyl ketone (fmk), tetra fluoro phenoxy methyl ketone (tfpmk) or an aldehyde group at the C-terminus. Peptide caspase-1 inhibitors can also be synthesized with a benzyloxycarbonyl group (known as BOC or Z) or an acetyl group at the N-terminus and with O-methyl side chains. They exhibit enhanced cellular permeability, thus greatly facilitating their use in both in vitro cell culture as well as in vivo animal and human studies.

In some embodiments of the present invention, a peptide caspase-1 inhibitor is selected from the group consisting of BACMK (Boc-Asp(Obzl)-CMK, z-VAD (Z-Val-Ala-Asp), BocD, LY333531, casputin, Ac-DQMD-CHO (Ac-Asp-Met-Gln-Asp-CHO) (SEQ ID NO: 3), CV-1013, VX-740, VX-765, VX-799, Ac-YVAD-CMK (SEQ ID NO: 4), IDN-5370, IDN-6556, IDN-6734, IDN-1965, IDN-1529, z-VAD-fmk (Z-Val-Ala-Asp(OMe)-Fluoro methyl ester), z-DEVD-cmk (SEQ ID NO: 5), Z-DEVD (SEQ ID NO: 6), Ac-YVAD-fmk (SEQ ID NO: 7), z-Asp-Ch2-DCB, Ac-IETD (SEQ ID NO: 8), Ac-VDVAD (SEQ ID NO: 9), Ac-DQMD (SEQ ID NO: 10), Ac-LEHD (SEQ ID NO: 11), Z-WEHD (SEQ ID NO: 12), Z-WEHD-fmk (SEQ ID NO: 13), Z-WE(OMe)HD(OMe)-fmk (SEQ ID NO: 14), Z-YVAD (SEQ ID NO: 15), Z-YVAD-fmk (SEQ ID NO: 16), Ac-YVAD-cmk (SEQ ID NO: 17), Ac-VEID (SEQ ID NO: 18) and single stereoisomers, mixtures of stereoisomers, pharmaceutically acceptable salts or prodrugs thereof.

In some embodiments of the present invention, a peptide caspase-1 inhibitor is selected from the group consisting of Boc-Phg-Asp-fmk, Boc-(2-F-Phg)-Asp-fmk, Boc-($F_3$-Val)-Asp-fmk, Boc-(3-F-Val)-Asp-fmk, Ac-Phg-Asp-fmk, Ac-(2-F-Phg)-Asp-fmk, Ac-($F_3$-Val)-Asp-fmk, Ac-(3-F-Val)Asp-fmk, Z-Phg-Asp-fmk Z-(2-F-Phg)-Asp-fmk, Z-($F_3$-Val)-Asp-fmk, Z-Chg-Asp-fmk, Z-(2-Fug)-Asp-fmk, Z-(4-F-Phg)-Asp-fmk, Z-(4-Cl-Phg)-Asp-fmk, Z-3-Thg)-Asp-fmk, Z-(2-Fua)-Asp-fmk, Z-(2-Tha)-Asp-fmk, Z-3-Fua)-Asp-fmk, Z-(3-Tha)-Asp-fmk, Z-(3-Cl-Ala)-Asp-fmk, Z-(3-F-Ala)-Asp-fmk, Z-($F_3$-Ala)-Asp-fmk, Z-(3-F-3-Me-Ala)-Asp-fmk, Z-(3-$C_{1-3}$-F-Ala)-Asp-fmk, Z-(2-Me-Val)Asp-ink, Z-(2-Me-Ala)-Asp-fmk, Z-(2-i-Pr-β-Ala)-Asp-fmk, Z-(3-Ph-β-Ala)-Asp-fmk, Z-(3-CN-Ala)-Asp-fmk, Z-(1-Nal)-Asp-fmk, Z-Cha-Asp-fmk, Z-3-$CF_3$-Ala)Asp-fmk, Z-(4-$CF_3$-Phg)-Asp-fmk, Z-(3-$Me_2$N-Ala)-Asp-fmk, Z-(2-Abu)-Asp-ink, Z-Tle-Asp-fmk, Z-Cpg-Asp-fmk, Z-Cbg-Asp-fmk, Z-Thz-Asp-fmk, Z-(3-F-Val)-Asp-fmk, Z-2-Thg)Asp-fmk, and single stereoisomers, mixtures of stereoisomers, pharmaceutically acceptable salts or prodrugs thereof.

In some embodiments of the present invention, a peptide caspase-1 inhibitor is Z-VAD or Z-VAD-fmk or single stereoisomers, mixtures of stereoisomers, pharmaceutically acceptable salts or prodrugs thereof.

In some embodiments of the present invention, a peptide caspase-1 inhibitor is Z-WEHD (SEQ ID NO: 12), Z-WEHD fmk (SEQ ID NO: 13), or Z-WE(OMe)HD(OMe)-fmk (SEQ ID NO: 14), or single stereoisomers, mixtures of stereoisomers, pharmaceutically acceptable salts or prodrugs thereof. This caspase-1 inhibitor is available, e.g., from R&D Systems (catalog number FMK002).

In some embodiments of the present invention, a peptide caspase-1 inhibitor is Z-YVAD (SEQ ID NO: 15), Z-YVAD-fmk (SEQ ID NO: 16) or Z-YVAD(OMe)-fmk (SEQ ID NO: 20) or single stereoisomers, mixtures of stereoisomers, pharmaceutically acceptable salts or prodrugs thereof. This caspase-1 inhibitor is available, e.g., by Enzyme Systems (Livermore, Calif., USA) and R&D Systems (catalog number FMK005).

In some embodiments of the present invention, a peptide caspase-1 inhibitor is Z-DEVD (SEQ ID NO: 6) or Z-DEVD-fmk (SEQ ID NO: 18) or single stereoisomers, mixtures of stereoisomers, pharmaceutically acceptable salts or prodrugs thereof. This caspase-1 inhibitor is available, e.g., by Enzyme Systems, Livermore, Calif., USA).

In some embodiments of the present invention, a caspase-1 inhibitor is Ac-YVAD-CMK (SEQ ID NO: 17) or single stereoisomers, mixtures of stereoisomers, pharmaceutically acceptable salts or prodrugs thereof. This caspase-1 inhibitor can be obtained, e.g., from Calbiochem (Prod. No. 400012).

Other caspase-1 inhibitors that can be used in the practice of the invention include without limitation those described in WO93/05071, WO93/09135, WO93/14777, WO95/26958, WO95/29672, WO95/33751, WO95/35308, WO96/03982, WO96/30395, WO97/07805, WO97/08174, WO97/22618, WO97/22619, WO97/27220, WO98/11109, WO98/11129, WO98/16502, WO98/16504, WO98/16505, WO98/24804, WO98/24805, WO99/47545, WO01/90063, EP 519748 (U.S. equivalents are U.S. Pat. Nos. 5,430,128 and 5,434,248), EP 547699, EP 618223, EP 623592 (U.S. equivalents are U.S. Pat. Nos. 5,985,838, and 6,576,614), EP 623606 (U.S. equivalents are U.S. Pat. Nos. 5,462,939 and 5,585,486), EP 628550 (U.S. equivalents are U.S. Pat. Nos. 5,585,357 and 5,677,283), EP 644198, U.S. Pat. No. 5,430,128, U.S. Pat. No. 5,434,248, U.S. Pat. No. 5,462,939, U.S. Pat. No. 5,552,400, U.S. Pat. No. 5,565,430, U.S. Pat. No. 5,585,357, U.S. Pat. No. 5,585,486, U.S. Pat. No. 5,622,967, U.S. Pat. No. 5,639,745, U.S. Pat. No. 5,656,627, U.S. Pat. No. 5,670,494, U.S. Pat. No. 5,677,283, U.S. Pat. No. 5,716,929, U.S. Pat. No. 5,739,279, U.S. Pat. No. 5,756,465, U.S. Pat. No. 5,756,466, U.S. Pat. No. 5,798,247, U.S. Pat. No. 5,798,442, U.S. Pat. No. 5,834,514, U.S. Pat. No. 5,843,904, U.S. Pat. No. 5,843,905, U.S. Pat. No. 5,847,135, U.S. Pat. No. 5,866,545, U.S. Pat. No. 5,843,904, U.S. Pat. No. 5,843,905, U.S. Pat. No. 5,847,135, U.S. Pat. No. 5,866,545, U.S. Pat. No. 5,869,519, U.S. Pat. No. 5,874,424, U.S. Pat. No. 5,932,549, U.S. Pat. No. 7,417,029, US 2006/0128696, Mjalli et al., 1993, *Bioorg Med Chem Lett* 3:2689-2693, Mjalli et al., 1994, *Bioorg Med Chem Lett* 4:1965-1968, Mjalli et al., 1995 *Bioorg Med Chem Lett* 5:1405-1408, Mjalli et al., 1995, *Bioorg Med Chem Lett* 5:1409-1414, Thornberry et al., 1994, *Biochem* 33:3934-3940, Dolle et al., 1994, *J Med Chem* 37:563-564, Dolle et al., 1994, *J Med Chem* 37: 3863-3866, Dolle et al., 1995, *J Med Chem* 38: 220-222, Graybill et al., 1997 *Bioorg Med Chem Lett* 7:41-46, Semple et al., 1998, *Bioorg Med Chem Lett* 8:959-964, and Okamoto et al., 1999, *Chem Pharm Bull* 47:11-21, herewith incorporated by reference in their entireties for all purposes.

1. Caspase-1 Inhibitor Having Formula 1a or 1b

In some embodiments of the present invention a caspase-1 inhibitor for use in a method of the present invention is a compound described in published US2011/0144074, US2009/0215736, US2008/0015172, and US2003/0092703 (herewith incorporated by reference in their entireties). Preferred compounds described in published US2011/0144074, US2009/0215736, US2008/0015172, and US2003/0092703 for use in the methods of the present invention are referred to herein as caspase-1 inhibitor having Formula 1a or 1b:

Formula Ia and Ib

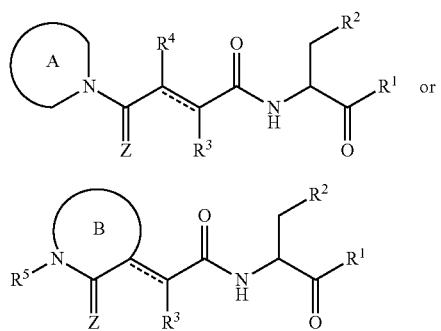

or single stereoisomers, mixtures of stereoisomers, pharmaceutically acceptable salts or prodrugs thereof, wherein: next to $R^3$ represents a single or double bond; Z is oxygen or sulfur; $R^1$ is hydrogen, —$CHN_2$, —R, —$CH_2OR$, —$CH_2SR$, or —$CH_2Y$; R is a $C_{1-12}$ aliphatic, aryl, heterocyclyl, or heterocyclylalkyl; Y is an electronegative leaving group; $R^2$ is $CO_2H$, $CH_2CO_2H$, or esters, amides or isosteres thereof; $R^3$ is a group capable of fitting into the S2 sub-site of a caspase; $R^4$ is hydrogen or a $C_{1-6}$ aliphatic group that is optionally interrupted by —O—, —S—, —$SO_2$—, —CO—, —NH—, or —N($C_{1-4}$ alkyl)-, or $R^3$ and $R^4$ taken together with their intervening atoms optionally form a 3-7 membered ring having 0-2 heteroatoms selected from nitrogen, oxygen or sulfur; Ring A is a nitrogen-containing mono-, bi- or tricyclic ring system having 0-5 additional ring heteroatoms selected from nitrogen, oxygen or sulfur; Ring B is a nitrogen-containing 5-7 membered ring having 0-2 additional ring heteroatoms selected from nitrogen, oxygen or sulfur; $R^5$ is $R^6$, $(CH_2)_nR^6$, $COR^E$, $CO_2R^6$, $SO_2R^6$, $CON(R^6)_2$, or $SO_2N(R^6)_2$; n is one to three; and each $R^6$ is independently selected from hydrogen, an optionally substituted $C_{1-4}$ aliphatic group, an optionally substituted $C_{6-10}$ aryl group, or a mono- or bicyclic heteroaryl group having 5-10 ring atoms.

2. Caspase-1 Inhibitor Having Formula 2

In some embodiments of the present invention a caspase-1 inhibitor for use in a method of the present invention is a compound described in published US2011/0137037 and US2007/0155718 (herewith incorporated by reference in their entireties). Preferred compounds described in published US2011/0137037 and US2007/0155718 for use in the methods of the present invention are referred to herein as caspase-1 inhibitor having Formula 2:

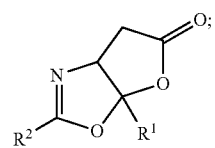

Formula 2 or single stereoisomers, mixtures of stereoisomers, pharmaceutically acceptable salts or prodrugs thereof, wherein $R^1$ is H, $R^4$, haloalkyl, $CHN_2$, $CH_2Cl$, $CH_2F$, —$CH_2OPO(R^4)_2$, —$CH_2OPO(OR^4)_2$, or —$C_{1-2}$alkyl-$R^3$—$R^4$; $R^2$ is a $P_4$—$P_3$—$P_2$, $P_3$—$P_2$, or $P_2$ moiety of a caspase-1 inhibitor; $R^3$ is —O—, —NH—, —$NR^4$—, —S—, or —O(C=O)—; $R^4$ is $C_{1-12}$aliphatic, $C_{6-10}$aryl, 5-10 membered heterocyclyl, 5-10 membered heteroaryl, $C_{3-10}$cycloaliphatic, —($C_{1-6}$alkyl)-$C_{6-10}$aryl, —($C_{1-6}$alkyl)-(5-10 membered heteroaryl), —($C_{1-6}$alkyl)-(5-10 membered heterocyclyl), or —($C_{1-6}$alkyl)-$C_{3-10}$cycloaliphatic; wherein said $R^4$ group is optionally substituted with 0-5 J and 0-2 $J^2$; or two $R^4$ groups, together with the atom to which they are attached, form a 3-8 membered monocyclic or 8-12 membered bicyclic ring optionally substituted with 0-5 J and 0-2 $J^2$; J is halogen, —OR', —$NO_2$, —CN, —$CF_3$, —$OCF_3$, —R', 1,2-methylenedioxy, 1,2-ethylenedioxy, —N(R')$_2$, —SR', —SOR', —$SO_2$R', —$SO_2$N(R')$_2$, —$SO_3$R', C(O)R', —C(O)C(O)R', —C(O)C(O)OR', —C(O)C(O)N(R')$_2$, —C(O)$CH_2$C(O)R', —C(S)R', —C(S)OR', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')$SO_2$R', —N(R')$SO_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —CN, —C(=NR')N(R')$_2$, —C(O)N(OR')R', —C(=NOR')R', —OP(O)(OR')$_2$, —P(O)(R')$_2$, —P(O)(OR')$_2$, or —P(O)(H)(OR'); $J_2$ is =NR', =N(OR'), =O, or =S; R' is H, $C_{1-12}$aliphatic, $C_{6-10}$aryl, 5-10 membered heterocyclyl, 5-10 membered heteroaryl, $C_{3-10}$cycloaliphatic, —($C_{1-6}$alkyl)-$C_{6-10}$aryl, —($C_{1-6}$alkyl)-(5-10 membered heteroaryl), —($C_{1-6}$alkyl)-(5-10 membered heterocyclyl), or —($C_{1-6}$alkyl)-$C_{3-10}$cycloaliphatic; each R' is independently and optionally substituted with 0-5 occurrences of H, $C_{1-6}$alkyl, $CF_3$, halogen, $NO_2$, $OCF_3$, CN, OH, O($C_{1-6}$alkyl), $NH_2$, N($C_{1-6}$alkyl), N($C_{1-6}$alkyl)$_2$, C(=O)$CH_3$, or $C_{1-6}$alkyl optionally interrupted 1 time with a heteroatom selected from O, N, and S; wherein each $C_{1-6}$alkyl is unsubstituted; unless otherwise indicated, any group with suitable valence is optionally substituted with 0-5 J and 0-2 $J^2$.

3. Caspase-1 Inhibitor Having Formula 3

In some embodiments of the present invention a caspase-1 inhibitor for use in a method of the present invention is a compound described in published US2011/0130436 and US2009/0131456 (herewith incorporated by reference in their entireties). Preferred compounds described in published US2011/0130436 and US2009/0131456 for use in the methods of the present invention are referred to herein as caspase-1 inhibitor having Formula 3:

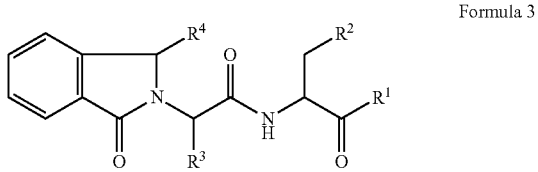

Formula 3 or single stereoisomers, mixtures of stereoisomers, pharmaceutically acceptable salts or prodrugs thereof, wherein $R^1$ is hydrogen, CN, $CHN_2$, R, or $-CH_2Y$; R is an aliphatic group, a substituted aliphatic group, an aryl group, a substituted aryl group, an aralkyl group, a substituted aralkyl group, a non-aromatic heterocyclic group or a substituted non-aromatic heterocyclic group; Y is an electronegative leaving group or $-OR$, $-SR$, $-OC=O(R)$, or $-OPO(R^8)(R^9)$; $R^8$ and $R^9$ are independently selected from R or OR; $R^2$ is $CO_2H$, $CH_2CO_2H$, or esters, amides or isosteres thereof; $R^3$ is hydrogen or a $C_{1-6}$ straight chained or branched alkyl; and $R^4$ is independently selected from hydrogen, halo, R, OR, SR, aryl, substituted aryl, OH, $NO_2$, CN, $NH_2$, NHR, $N(R)_2$, NHCOR, NHCONHR, $NHCON(R)_2$, NRCOR, $NHCO_2R$, $CO_2R$, $CO_2H$, COR, CONHR, $CON(R)_2$, $S(O)_2R$, $SONH_2$, $S(O)R$, $SO_2NHR$, or $NHS(O)_2R$.

4. Caspase-1 Inhibitor Having Formula 4, 4.1, 4.2, or 4.3

In some embodiments of the present invention a caspase-1 inhibitor for use in a method of the present invention is a compound described in published US2011/0077190 (herewith incorporated by reference in its entirety). Preferred compounds described in published US2011/0077190 for use in the methods of the present invention are referred to herein as caspase-1 inhibitor having 4:

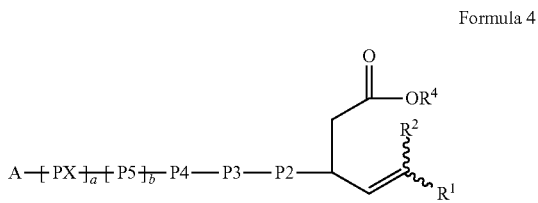

Formula 4 or single stereoisomers, mixtures of stereoisomers, pharmaceutically acceptable salts or prodrugs thereof, wherein a is 0 or 1; b is 0 or 1 provided that when b is 0, a is 0; A is 1) H, 2) $C_1$-$C_6$ alkyl, 3) aryl, 4) heteroaryl, 5) heterocyclyl, 6) $R^3$—C(O)—, 7) $R^3$—OC(O)—; 8) $R^3$—C(O)O—, or 9) $R^3$—S(O)_2—; P2, P3, P4 and, when present, P5 and PX, are any (D) or (L) amino acid residue; the line "-" when located between P2, P3, P4, P5 or PX represents a peptide bond or a peptidomimetic bond; the wavy line represents either cis or trans orientation of $R^1$ and $R^2$; $R^1$ is 1) aryl, 2) heteroaryl, 3) heterocyclyl, 4) $C_2$-$C_6$ alkene-$R^{20}$, 5) $SO_2R^5$, 6) $SO_3R^5$, 7) $SOR^5$, 8) $SONHR^5$, 9) $SO_2NHR^5$, 10) CN, 11) $CO_2R^5$, 12) $COR^5$, 13) $PO_3R^5$, 14) $PO(OR^5)_2$, or 15) $PO(OR^5)$, wherein the aryl, the heteroaryl, or the heterocyclyl are optionally substituted with one or more $R^{30}$; $R^2$ is 1) $R^1$; or 2) H, 3) halogen, 4) haloalkyl, 5) $C_1$-$C_6$ alkyl, 6) $C_2$-$C_6$ alkene, 7) $C_3$-$C_7$ cycloalkyl, 8) $OR^9$; 9) $OCOR^6$, 10) $OCO_2R^6$, 11) $NR^7R^8$, 12) $NHSO_2R^6$, 13) $NHCOR^6$, 14) aryl, 15) heteroaryl, or 16) heterocyclyl; $R^3$ is 1) $C_1$-$C_6$ alkyl, 2) aryl, 3) heteroaryl, or 4) heterocyclyl; $R^4$ is 1) H, or 2) $C_1$-$C_6$ alkyl; $R^5$ is 1) H, 2) $C_1$-$C_6$ alkyl, 3) $C_2$-$C_6$ alkene, 4) $C_3$-$C_7$ cycloalkyl, 5) aryl, 6) heteroaryl, 7) heterocyclyl, or 8) any optionally protected (D) or (L) amino acid residue, or non-natural amino acid residue; $R^6$ is 1) any (D) or (L) amino acid residue or non-natural amino acid residue, 2) $C_1$-$C_6$ alkyl, 3) $C_3$-$C_7$ cycloalkyl, 4) aryl, 5) heteroaryl, or 6) heterocyclyl, in which the alkyl or the cycloalkyl are optionally substituted with one or more $R^{10}$ substituents; and in which the aryl, heteroaryl or heterocyclyl are optionally substituted with one or more $R^{20}$ substituents; $R^7$ and $R^8$ are independently selected from: 1) H, 2) $C_1$-$C_6$ alkyl, 3) $C_3$-$C_7$ cycloalkyl, 4) haloalkyl, 5) aryl, 6) heteroaryl, or 7) heterocyclyl, wherein the alkyl and the cycloalkyl are optionally substituted with one or more $R^{10}$ substituents, and the aryl, the heteroaryl and the heterocyclyl are optionally substituted with one or more $R^{20}$ substituents; $R^9$ is 1) H, 2) $C_1$-$C_6$ alkyl, 3) $C_3$-$C_7$ cycloalkyl, 4) aryl, 5) heteroaryl, or 6) heterocyclyl, in which the alkyl or the cycloalkyl are optionally substituted with one or more $R^{10}$ substituents; and in which the aryl, heteroaryl or heterocyclyl are optionally substituted with one or more $R^{20}$ substituents; $R^{10}$ is independently selected from: 1) halogen, 2) $C_1$-$C_6$ alkyl, 3) $C_3$-$C_7$ cycloalkyl, 4) haloalkyl, 5) aryl, 6) heteroaryl, 7) heterocyclyl, 8) $OR^9$, 9) $S(O)_mR^9$, 10) $NR^7R^8$, 11) $COR^9$, 12) $C(O)OR^9$, 13) $OC(O)R^9$, 14) $SC(O)R^9$, 15) $CONR^7R^8$, or 16) $S(O)_2NR^7R^8$; $R^{20}$ is independently selected from: 1) halogen, 2) $NO_2$, 3) CN, 4) $C_1$-$C_6$ alkyl, 5) haloalkyl, 6) $C_3$-$C_7$ cycloalkyl, 7) $OR^7$, 8) $NR^7R^8$, 9) $SR^7$, 10) aryl, 11) heteroaryl, 12) heterocyclyl, 13) $SO_2R^5$, 14) $SO_3R^5$, 15) $SOR^5$, 16) $SONHR^5$, 17) $SO_2NHR^5$, 18) $PO_3R^5$, 19) $PO(OR^5)_2$, 20) $PO(OR^5)$, 21) $COR^7$, 22) $CO_2R^7$, 23) $S(O)_mR^7$, 24) $CONR^7R^8$, or 25) $S(O)_2NR^7R^8$, wherein the alkyl and the cycloalkyl are optionally substituted with one or more $R^6$ substituents; and wherein the aryl, the heteroaryl, or the heterocyclyl are optionally substituted with one or more $R^{30}$; $R^{30}$ is 1) $NO_2$, 2) $C_2$-$C_6$ alkene-$R^{20}$, 3) $SO_2R^5$, 4) $SOR^5$, 5) $SONHR^5$, 6) $SO_2NHR^5$, 7) CN, 8) $CO_2R^5$, 9) $COR^5$, 10) $PO_3R^5$, 11) $PO(OR^5)_2$, or 12) $PO(OR^5)$;

or the compound is labeled with a detectable label or an affinity tag thereof, of Formula 4.1 (referred to herein as caspase-1 inhibitor having Formula 4.1):

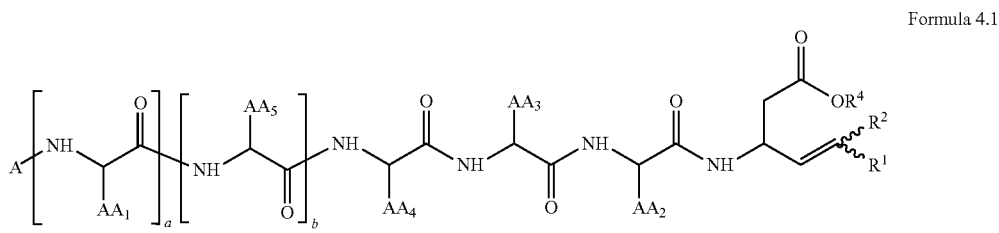

Formula 4.1 wherein a is 0 or 1; b is 0 or 1 provided that when b is 0, a is 0; A is 1) H, 2) $C_1$-$C_6$ alkyl, 3) aryl, 4) heteroaryl, 5) heterocyclyl, 6) $R^3$—OC(O)—; 7) $R^3$—C(O)O—, or 8) $R^3$—$S(O)_2$—; $AA_2$ is the (R) or (S) amino acid side chain of Val, Leu, Pro, Met, Ala, Thr, His, Ser, Lys, or Ile; $AA_3$ is the (R) or (S) amino acid side chain of Trp, Tyr, Ala, Asp, Gln, Glu, Phe, Ser, Thr, Val, Tyr, Gly, Leu, His, or Ile; or $AA_3$ is phenylglycine, indanylglycine, or Ala-(2'-quinolyl); $AA_4$ is the (R) or (S) amino acid side chain of Asp, Ile, Leu, Glu, Ala, Val, Tyr, Trp, Phe, or Pro; $AA_5$, when present, is the (R) or (S) amino acid side chain of Val or Leu; $AA_x$, when present, is the (R) or (S) amino acid side chain of any D or L amino acid residue or the amino acid side chain of the non-natural amino acid residue; the wavy line represents either cis or trans orientation of $R^1$ and $R^2$; $R^1$ is 1) aryl, 2) heteroaryl, 3) heterocyclyl, 4) $C_2$-$C_6$ alkene-$R^{20}$, 5) $SO_2R^5$, 6) $SO_3R^5$, 7) $SOR^5$, 8) $SONHR^5$, 9) $SO_2NHR^5$, 10) CN, 11) $CO_2R^5$, 12) $COR^5$, 13) $PO_3R^5$, 14) $PO(OR^5)_2$, or 15) $PO(OR^5)$, wherein the aryl, the heteroaryl, or the heterocyclyl are optionally substituted with one or more $R^{30}$; $R^2$ is 1) $R^1$; or 2) H, 3) halogen, 4) haloalkyl, 5) $C_1$-$C_6$ alkyl, 6) $C_2$-$C_6$ alkene, 7) $C_3$-$C_7$ cycloalkyl, 8) $OR^9$; 9) $OCOR^6$, 10) $OCO_2R^6$, 11) $NR^7R^8$, 12) $NHSO_2R^6$, 13) $NHCOR^6$, 14) aryl, 15) heteroaryl, or 16) heterocyclyl; $R^3$ is 1) $C_1$-$C_6$ alkyl, 2) aryl, 3) heteroaryl, or 4) heterocyclyl; $R^4$ is 1) H, or 2) $C_1$-$C_6$ alkyl; $R^5$ is 1) H, 2) $C_1$-$C_6$ alkyl, 3) $C_2$-$C_6$ alkene, 4) $C_3$-$C_7$ cycloalkyl, 5) aryl, 6) heteroaryl, 7) heterocyclyl, or 8) any optionally protected (D) or (L) amino acid residue; $R^6$ is 1) any (D) or (L) amino acid residue, 2) $C_1$-$C_6$ alkyl, 3) $C_3$-$C_7$ cycloalkyl, 4) aryl, 5) heteroaryl, or 6) heterocyclyl, in which the alkyl or the cycloalkyl are optionally substituted with one or more $R^{10}$ substituents; and in which the aryl, heteroaryl or heterocyclyl are optionally substituted with one or more $R^{20}$ substituents; $R^7$ and $R^8$ are independently selected from: 1) H, 2) $C_1$-$C_6$ alkyl, 3) $C_3$-$C_7$ cycloalkyl, 4) haloalkyl, 5) aryl, 6) heteroaryl, or 7) heterocyclyl, wherein the alkyl and the cycloalkyl are optionally substituted with one or more $R^{10}$ substituents, and the aryl, the heteroaryl and the heterocyclyl are optionally substituted with one or more $R^{20}$ substituents; $R^9$ is 1) H, 2) $C_1$-$C_6$ alkyl, 3) $C_3$-$C_7$ cycloalkyl, 4) aryl, 5) heteroaryl, or 6) heterocyclyl, in which the alkyl or the cycloalkyl are optionally substituted with one or more $R^{10}$ substituents; and in which the aryl, heteroaryl or heterocyclyl are optionally substituted with one or more $R^{20}$ substituents; $R^{10}$ is independently selected from: 1) halogen, 2) $C_1$-$C_6$ alkyl, 3) $C_3$-$C_7$ cycloalkyl, 4) haloalkyl, 5) aryl, 6) heteroaryl, 7) heterocyclyl, 8) $OR^9$, 9) $S(O)mR^9$, 10) $NR^7R^8$, 11) $COR^5$, 12) $C(O)OR^9$, 13) $OC(O)R^9$, 14) $SC(O)R^9$, 15) $CONR^7R^8$, or 16) $S(O)_2NR^7R^8$; $R^{20}$ is independently selected from: 1) halogen, 2) $NO_2$, 3) CN, 4) $C_1$-$C_6$ alkyl, 5) haloalkyl, 6) $C_3$-$C_7$ cycloalkyl, 7) $OR^7$, 8) $NR^7R^8$, 9) $SR^7$, 10) aryl, 11) heteroaryl, 12) heterocyclyl, 13) $SO_2R^5$, 14) $SO_3R^5$, 15) $SOR^5$, 16) $SONHR^5$, 17) $SO_2NHR^5$, 18) $PO_3R^5$, 19) $PO(OR^5)_2$, 20) $PO(OR^5)$, 21) $COR^7$, 22) $CO_2R^7$, 23) $S(O)mR^7$, 24) $CONR^7R^8$, or 25) $S(O)_2NR^7R^8$, wherein the alkyl and the cycloalkyl are optionally substituted with one or more $R^6$ substituents; and wherein the aryl, the heteroaryl, or the heterocyclyl are optionally substituted with one or more $R^{30}$; $R^{30}$ is 1) $NO_2$, 2) $C_2$-$C_6$ alkene-$R^{20}$, 3) $SO_2R^5$, 4) $SOR^5$, 5) $SONHR^5$, 6) $SO_2NHR^5$, 7) CN, 8) $CO_2R^5$, 9) $COR^5$, 10) $PO_3R^5$, 11) $PO(OR^5)_2$, or 12) $PO(OR^5)$; or the compound is labeled with a detectable label or an affinity tag thereof;

a compound of Formula 4.2 (referred to herein as caspase-1 inhibitor having Formula 4.2):

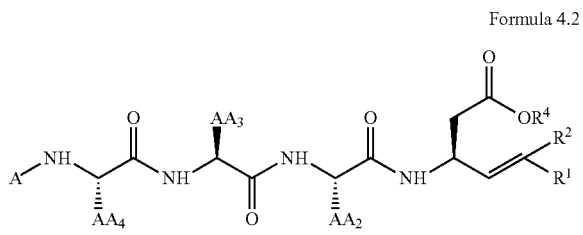

Formula 4.2 wherein $AA_2$ is the amino acid side chain of Val, Leu, Pro, Met, Ala, Thr, His, Ser, Lys, or Ile; $AA_3$ is the amino acid side chain of Trp, Tyr, Ala, Asp, Gln, Phe, Ser, Thr, Val, Tyr, Gly, Leu; or $AA_3$ is phenylglycine, indanylglycine, or Ala-(2'-quinolyl); $AA_4$ is the amino acid side chain of Asp or Trp; or wherein $AA_2$ is the amino acid side chain of Thr, His, Val, Trp, Ile, or Ala $AA_3$ is the amino acid side chain of Glu or $AA_3$ is Ala-(2'-quinolyl); $AA_4$ is the amino acid side chain of Ile, Leu, Glu, Asp, Ala, Pro or Val; or wherein $AA_2$ is the amino acid side chain of Val, Ala, Thr, or His; $AA_3$ is the amino acid side chain of Glu, Gln, Asp, Ala, Gly, Thr, Val, Trp; or $AA_3$ is phenylglycine or indanylglycine; $AA_4$ is the amino acid side chain of Tyr, Trp, Phe, or Asp;

or a compound of Formula 4.3 (referred to herein as caspase-1 inhibitor having Formula 4.3):

Formula 4.3 wherein $AA_2$ is the amino acid side chain of Ala, Ser, Lys or Val; $AA_3$ is the amino acid side chain of Val, Glu, Thr, or Gln; $AA_4$ is the amino acid side chain of Asp, or Leu; $AA_5$ is the amino acid side chain of Val or Leu.

5. Caspase-1 Inhibitor Having Formula 5

In some embodiments of the present invention a caspase-1 inhibitor for use in a method of the present invention is a compound described in published US2011/0003824 (herewith incorporated by reference in its entirety). Preferred compounds described in published US2011/0003824 for use in the methods of the present invention are referred to herein as caspase-1 inhibitor having Formula 5:

Formula 5 or single stereoisomers, mixtures of stereoisomers, pharmaceutically acceptable salts or prodrugs thereof, wherein: $R^1$ is hydrogen, $CHN_2$, R, or —$CH_2Y$; R is an aliphatic group, an aryl group, an aralkyl group, a heterocyclic group, or a heterocyclylalkyl group; Y is group halogen, arylsulfonyloxy, alkylsulfonyloxy, trifluoromethanesulfonyloxy, OR, SR, —OC=O(R), or —OPO($R^3$)($R^4$); $R^2$ is $CO_2H$, $CH_2CO_2H$, or an ester of $CO_2H$ or $CH_2CO_2H$ selected from the group consisting of $C_{1-12}$aliphatic esters, aryl esters, aralkyl esters, heterocyclyl esters, heteroclyclylalkyl esters; $C_{1-12}$aliphatic amides, aryl amides, aralkyl amides, keterocyclyl amides, and heterocyclylalkyl amides; or $R^2$ is an isostere of $CO_2H$ or $CH_2CO_2H$ selected from the group consisting of $CONHSO_2$(alkyl) and $CH_2CONHSO_2$(alkyl); $X_2$-$X_1$ is $C(R^3)_2$—$C(R^3)$, $C(R^3)$=C, C(=O)—$C(R^3)$; each $R^3$ is independently selected from hydrogen or $C_{1-6}$ aliphatic, Ring C is a fused aryl ring; n is 0, 1 or 2; and each methylene carbon in Ring A is optionally and independently substituted by =O, or by one or more halogen, $C_{1-4}$ alkyl, or $C_{1-4}$ alkoxy.

6. Caspase-1 Inhibitor Having Formula 6

In some embodiments of the present invention a caspase-1 inhibitor for use in a method of the present invention is a compound described in published US2010/0137359 and US2004/0192612 (herewith incorporated by reference in their entireties). Preferred compounds described in published US2010/0137359 and US2004/0192612 for use in the methods of the present invention are referred to herein as caspase-1 inhibitor having Formula 6:

Formula 6

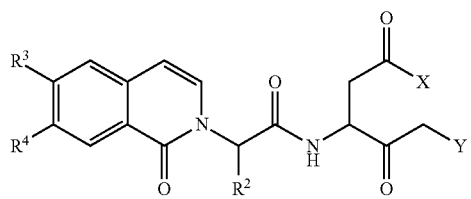

or single stereoisomers, mixtures of stereoisomers, pharmaceutically acceptable salts or prodrugs thereof, wherein: X is —$OR^1$ or —$N(R^5)_2$, Y is halo, trifluorophenoxy, or tetrafluorophenoxy; $R^1$ is: $C_{1-6}$ straight chained or branched alkyl, or $C_{2-6}$ straight chained or branched alkenyl or alkynyl, wherein the alkyl, alkenyl, or alkynyl is optionally substituted with optionally substituted phenyl, $CF_3$, Cl, F, OMe, OEt, $OCF_3$, CN, or $NMe_2$; $C_{3-6}$ cycloalkyl, wherein 1-2 carbon atoms in the cycloalkyl is optionally replaced with —O— or —$NR^5$—; $R^2$ is $C_{1-6}$ straight chained or branched alkyl; $R^3$ is hydrogen, halo, $OCF_3$, CN, or $CF_3$; $R^4$ is hydrogen, halo, $OCF_3$, CN, or $CF_3$; and each $R^5$ is independently H, $C_{1-6}$ straight chained or branched alkyl, aryl, —O—$C_{1-6}$ straight chained or branched alkyl, or —O-aryl.

7. Caspase-1 Inhibitor Having Formula 7

In some embodiments of the present invention a caspase-1 inhibitor for use in a method of the present invention is a compound described in published US2010/0105914 and US2005/0233979 (herewith incorporated by reference in their entireties). Preferred compounds described in published US2010/0105914 and US2005/0233979 for use in the methods of the present invention are referred to herein as caspase-1 inhibitor having Formula 7:

Formula 7

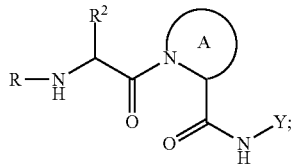

or single stereoisomers, mixtures of stereoisomers, pharmaceutically acceptable salts or prodrugs thereof, wherein Y is

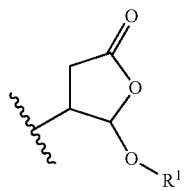

$R^1$ is H, $C_{1-12}$aliphatic, $C_{3-10}$cycloaliphatic, $C_{6-10}$aryl, 5-10 membered heterocyclyl, 5-10 membered heteroaryl, ($C_{3-10}$cycloalkyl)-($C_{1-12}$aliphatic)-, cycloalkenyl-($C_{1-12}$aliphatic)-, ($C_{6-10}$aryl)-($C_{1-12}$aliphatic)-, (5-10 membered heterocyclyl)-($C_{1-12}$ aliphatic)-, or (5-10 membered heteroaryl)-($C_{1-12}$aliphatic)-, wherein any hydrogen atom is optionally and independently replaced by $R^8$ and any set of two hydrogen atoms bound to the same atom is optionally and independently replaced by carbonyl; Ring A is

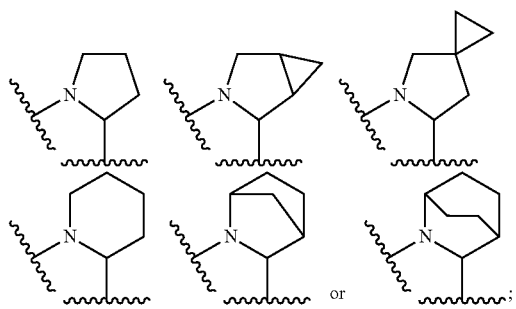

wherein, in each ring, any hydrogen atom is optionally and independently replaced by $R^4$ and any set of two hydrogen atoms bound to the same atom is optionally and independently replaced by carbonyl; when Ring A is

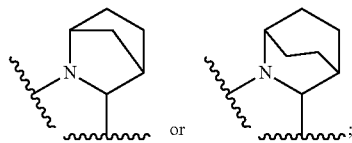 [SMILES: *C1C2CCC(C2)N1* ; *C1C2CCC(CC2)N1*]

then R is $R^3C(O)$—, HC(O), $R^3SO_2$—, $R^3OC(O)$, ($R^3)_2$NC(O), ($R^3$)(H)NC(O), $R^3C(O)C(O)$—, $R^3$—, ($R^3)_2$NC(O)C(O), ($R^3$)(H)NC(O)C(O), or $R^3OC(O)C(O)$—; and $R^3$ is $C_{1-12}$aliphatic, $C_{3-10}$cycloaliphatic, $C_{6-10}$aryl, 5-10 membered heterocyclyl, 5-10 membered heteroaryl, ($C_{3-10}$cycloaliphatic)-($C_{1-12}$aliphatic)-, ($C_{6-10}$aryl)-($C_{1-12}$aliphatic)-, (5-10 membered heterocyclyl)-($C_{1-12}$aliphatic)-, or (5-10 membered heteroaryl)-($C_{1-12}$aliphatic)-; or two $R^3$ groups bound to the same atom form together with that atom a 3-10 membered aromatic or nonaromatic ring; wherein any ring is optionally fused to an $C_{6-10}$aryl, 5-10 membered heteroaryl, $C_{3-10}$cycloalkyl, or 5-10 membered heterocyclyl; wherein up to 3 aliphatic carbon atoms may be replaced by a group selected from O, N, $NR^9$, S, SO, and $SO_2$, wherein $R^3$ is substituted with up to 6 substituents independently selected from $R^8$; when Ring A is

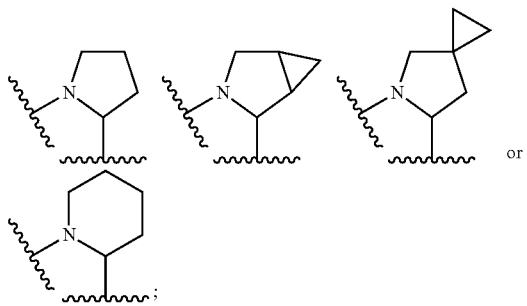

then R is $R^3C(O)$—, as shown below:

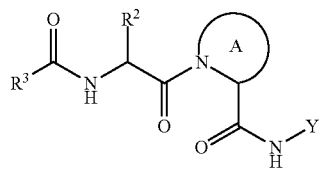

and $R^3$ is phenyl, thiophene, or pyridine, wherein each ring is optionally substituted with up to 5 groups independently selected from $R^{8'}$, and wherein at least one position on the phenyl, thiophene, or pyridine adjacent to bond x is substituted by $R^{12}$, wherein $R^{12}$ has no more than 5 straight-chained atoms; $R^4$ is halogen, —$OR^9$, —$NO_2$—CN—$CF_3$, —$OCF_1$, —$R^9$, 1,2-methylenedioxy, 1,2-ethylenedioxy, —$N(R^9)_2$, —$SR^9$, —$SOR^9$, —$SO_2R^9$—$SO_2N(R^9)_2$, —$SO_3R^9$, —$C(O)R^9$, —$C(O)C(O)R^9$, —$C(O)C(O)OR^9$, —$C(O)C(O)N(R^9)_2$, —$C(O)CH_2C(O)R^9$, —$C(S)R^9$, —$C(S)OR^9$, —$C(O)OR^9$, —$OC(O)R^9$, —$C(O)N(R^9)_2$, —$OC(O)N(R^9)_2$, —$C(S)N(R^9)_2$, —$(CH_2)_{0-2}NHC(O)R^9$, —$N(R^9)N(R^9)COR^9$, —$N(R^9)N(R^9)C(O)OR^9$, —$N(R^9)N(R^9)CON(R^9)_2$, —$N(R^9)SO_2R^9$, —$N(R^9)SO_2N(R^9)_2$, —$N(R^9)C(O)OR^9$, —$N(R^9)C(O)R^9$, —$N(R^9)C(S)R^9$, —$N(R^9)C(O)N(R^9)_2$, —$N(R^9)C(S)N(R^9)_2$—$N(COR^9)COR^9$, —$N(OR^9)R^9$, —$C(=NH)N(R^9)_2$, —$C(O)N(OR^9)R^9$, —$C(=NOR^9)R^9$, —$OP(O)(OR^9)_2$, —$P(O)(R^9)_2$,—$P(O)(OR^9)_2$, or —$P(O)(H)(OR^9)$; $R^2$ is —$C(R^5)(R^6)(R^7)$, $C_{6-10}$aryl, 5-10 membered heteroaryl, or $C_{3-7}$ cycloalkyl; $R^5$ is H or a $C_{1-6}$ straight-chained or branched alkyl; $R^6$ is H or a $C_{1-6}$ straight-chained or branched alkyl; $R^7$ is —$CF_3$, —$C_{3-7}$cycloalkyl, $C_{6-10}$aryl, 5-10 membered heteroaryl, heterocycle, or a $C_{1-6}$ straight-chained or branched alkyl, wherein each carbon atom of the alkyl is optionally and independently substituted with $R^{10}$; or $R^5$ and $R^7$ taken together with the carbon atom to which they are attached form a 3-10 membered cycloaliphatic; $R^8$ and $R^{8'}$ are each independently halogen, —$OR^9$, —$NO_2$, —CN, —$CF_3$, —$OCF_3$, —$R^9$, 1,2-methylenedioxy, 1,2-ethylenedioxy, —$N(R^9)_2$, —$SR^9$, —$SOR^9$, —$SO_2R^9$, —$SO_2N(R^9)_2$—$SO_3R^9$, —$C(O)R^9$, —$C(O)C(O)R^9$, —$C(O)OR^9$, —$C(O)C(O)N(R^9)_2$, —$C(O)CH_2C(O)R^9$, —$C(S)R^9$, —$C(S)OR^9$, —$C(O)OR^9$, —$OC(O)R^9$, —$C(O)N(R^9)_2$, —$OC(O)N(R^9)_2$, —$C(S)N(R^9)_2$, —$(CH_2)_{0-2}NHC(O)R^9$, —$N(R^9)N(R^9)COR^9$, —$N(R^9)N(R^9)C(O)OR^9$, —$N(R^9)N(R^9)CON(R^9)_2$, —$N(R^9)SO_2R^9$, —$N(R^9)SO_2N(R^9)_2$, —$N(R^9)C(O)OR^9$, —$N(R^9)C(O)R^9$, —$N(R^9)C(S)R^9$, —$N(R^9)C(O)N(R^9)_2$, —$N(R^9)C(S)N(R^9)_2$, —$N(COR^9)COR^9$, —$N(OR^9)R^9$, —$C(=NH)N(R^9)_2$,—$C(O)N(OR^9)R^9$, —$C(=NOR^9)R^9$, —$OP(O)(OR^9)_2$, —$P(O)(R^9)_2$, —$P(O)(OR^9)_2$, and —$P(O)(H)(OR^9)$; $R^9$ is hydrogen, $C_{1-12}$aliphatic, $C_{3-10}$cycloaliphatic, $C_{6-10}$aryl, 5-10 membered heterocyclyl, 5-10 membered heteroaryl, ($C_{3-10}$cycloaliphatic)-($C_{1-12}$aliphatic)-, ($C_{6-10}$aryl)-($C_{1-12}$aliphatic)-, (5-10 membered heterocyclyl)-($C_{1-12}$aliphatic)-, or heteroaryl-($C_{1-12}$aliphatic)-; wherein any hydrogen atom is optionally and independently replaced by $R^{13}$ and any set of two hydrogen atoms bound to the same atom is optionally and independently replaced by carbonyl; $R^{10}$ is halogen, —$OR^{11}$, —$NO_2$, —CN, —$CF_3$—$OCF_3$, —$R^{11}$, or —$SR^{11}$; wherein $R^{11}$ is $C_{1-4}$-aliphatic-; $R^{11}$ is $C_{1-4}$-aliphatic-; $R^{12}$ is halogen, —$OR^{11}$, —$NO_2$—CN—$CF_3$—$OCF_3$, —$R^{11}$, or —$SR^9$; $R^{13}$ is —$OR^{11}$, —$NO_2$, —CN, —$CF_3$,—$OCF_3$,—$R^{11}$, 1,2-methylenedioxy, 1,2-ethylenedioxy, —$N(R^{11})_2$, —$SR^{11}$, —$SOR^{11}$, —$SO_7R^{11}$—$SO_2N(R^{11})_2$—$SO_3R^{11}$, —$C(O)R^{11}$, —$C(O)C(O)R^{11}$, —$C(O)C(O)OR^{11}$, —$C(O)C(O)N(R^{11})_2$, —$C(O)CH_2C(O)R^{11}$—$C(S)R^{11}$, —$C(S)OR^{11}$, —$C(O)OR^{11}$, —$OC(O)R^{11}$, —$C(O)N(R^{11})_2$, —$OC(O)N(R^{11})_2$, —$C(S)N(R^{11})_2$, —$(CH_2)_{0-2}NHC(O)R^{11}$, —$N(R^{11})N(R^{11})COR^{11}$, —$N(R^{11})N(R^{11})C(O)OR^{11}$, —$N(R^{11})N(R^{11})CON(R^{11})_2$, —$N(R^{11})SO_2R^{11}$, —$N(R^{11})SO_2N(R^{11})_2$, —$N(R^{11})C(O)OR^{11}$, —$N(R^{11})C(O)R^{11}$, —$N(R^{11})C(S)R^{11}$, —$N(R^{11})C(O)N(R^{11})_2$, —$N(R^{11})C(S)N(R^{11})_2$, —$N(COR^{11})COR^{11}$, —$N(OR^{11})R^{11}$, —$C(=NH)N(R^{11})_2$, —$C(O)N(OR^{11})R^{11}$, —$C(=NOR^{11})R^{11}$, —$OP(O)(OR^{11})_2$, —$P(O)(R^{11})_2$, —$P(O)(OR^{11})_2$, and —$P(O)(H)(OR^{11})$; $R^{11}$ is hydrogen, $C_{1-12}$aliphatic, $C_{3-10}$cycloaliphatic, $C_{6-10}$aryl, 5-10 membered heterocyclyl, 5-10 membered heteroaryl, ($C_{3-10}$cycloaliphatic)-($C_{1-12}$aliphatic), ($C_{6-10}$aryl)-($C_{1-12}$aliphatic)-, (5-10 membered heterocyclyl)-($C_{1-12}$aliphatic)-, or heteroaryl-($C_{1-12}$aliphatic)-; comprising reacting a compound shown below:

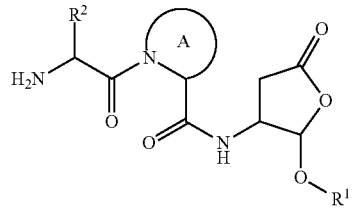

wherein $R^1$, $R^2$, and Ring A are as defined above; and a compound of Formula RX, wherein R is as defined above and X is OH or an appropriate derivative or leaving group, in the presence of conditions for coupling an amine and an acid (when X is OH) or appropriate acid derivative (when X is an appropriate leaving group) to provide the compound of Formula 7.

8. Caspase-1 Inhibitor Having Formula 8, 8.1, or 8.2

In some embodiments of the present invention a caspase-1 inhibitor for use in a method of the present invention is a compound described in published US2009/0281128 and US2004/0072850 (herewith incorporated by reference in their entireties). Preferred compounds described in published US2009/0281128 and US2004/0072850 for use in the methods of the present invention are referred to herein as caspase-1 inhibitor having Formula 8:

Formula 8

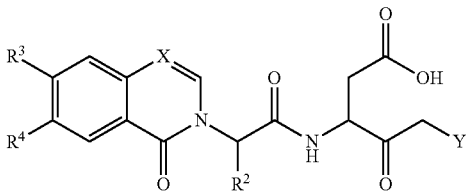

or single stereoisomers, mixtures of stereoisomers, pharmaceutically acceptable salts or prodrugs thereof, wherein X is N; Y is halo, trifluorophenoxy, or tetrafluorophenoxy; $R^2$ is $C_{1-6}$ straight chained or branched alkyl; $R^3$ is hydrogen, halo, $OCF_3$, CN, or $CF_3$; and $R^4$ is hydrogen, halo, $OCF_3$, SR, CN, $CF_3$, Ar, or T-Ar; wherein: T is O or S; R is a $C_{1-6}$ straight chained or branched alkyl; Ar is a phenyl ring optionally substituted with 1-3 groups selected from halo, $CH_3$, $CF_3$, CN, OMe, $OCF_3$, and $NR^5R^6$; and $R^5$ and $R^6$ each is independently H or $C_{1-6}$ straight chained or branched alkyl, or $R^5$ and $R^6$, taken together, form a 5-7 membered ring optionally containing up to 3 heteroatoms selected from O, S, NH, and $N(C_{1-6}$-straight chained or branched alkyl); provided that when Y is halo, then both, $R^3$ and $R^4$, are not simultaneously hydrogen;

a compound of Formula 8.1 (referred to herein as caspase-1 inhibitor having Formula 8.1):

Formula 8.1

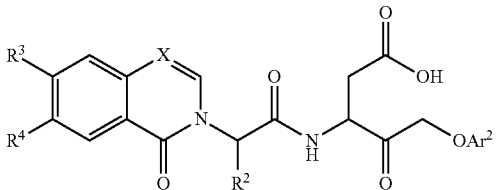

or single stereoisomers, mixtures of stereoisomers, pharmaceutically acceptable salts or prodrugs thereof, wherein: X is N; $R^2$ is ethyl, n-propyl, or isopropyl; $R^3$ and $R^4$ are each independently hydrogen, halo, $OCF_3$, CN, or $CF_3$; and $Ar^2$ is trifluorophenyl or tetrafluorophenyl;

or a compound of Formula 8.2 (referred to herein as caspase-1 inhibitor having Formula 8.2):

Formula 8.2

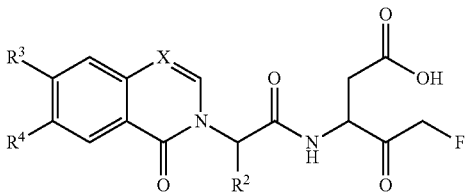

or single stereoisomers, mixtures of stereoisomers, pharmaceutically acceptable salts or prodrugs thereof, wherein: $R^2$ is ethyl, n-propyl, or isopropyl; $R^3$ is hydrogen, halo, $OCF_3$, CN, or $CF_3$; $R^4$ is halo, $OCF_3$, CN, $CF_3$, SR, or T-Ar; T is O or S; R is a $C_{1-6}$ straight chained or branched alkyl; Ar is a phenyl ring optionally substituted with 1-3 groups selected from halo, $CH_3$, $CF_3$, CN, OMe, $OCF_3$, and $NR^5R^6$; and $R^5$ and $R^6$ each is independently H or $C_{1-6}$ straight chained or branched alkyl, or $R^5$ and $R^6$, taken together, form a 5-7 membered ring optionally containing up to 3 heteroatoms selected from O, S, NH, and $N(C_{1-6}$-straight chained or branched alkyl), 9. Caspase-1 Inhibitor Having Formula 9 or 9.1

In some embodiments of the present invention a caspase-1 inhibitor for use in a method of the present invention is a compound described in published US2009/0093416 (herewith incorporated by reference in its entirety). Preferred compounds described in published US2009/0093416 for use in the methods of the present invention are referred to herein as caspase-1 inhibitor having Formula 9:

Formula 9

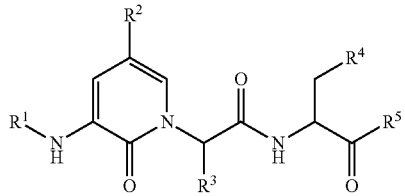

or single stereoisomers, mixtures of stereoisomers, pharmaceutically acceptable salts or prodrugs thereof, wherein: $R^1$ is $R^6C(O)$—, HC(O)—, $R^6SO_2$—, $R^6OC(O)$—, $(R^6)_2NC(O)$—, $(R^6)(H)NC(O)$—, $R^6C(O)C(O)$—, $R^6$—, $(R^6)_2NC(O)C(O)$—, $(R^6)(H)NC(O)C(O)$—, or $R^6OC(O)C(O)$—; $R^2$ is hydrogen, —$CF_3$, -halo, —$OR^7$, —$NO_2$, —$OCF_3$, —CN, or $R^8$; $R^3$ is hydrogen or (C1-C4)-aliphatic-; $R^4$ is —COOH or —$COOR^8$; $R^5$ is —$CH_2F$ or —$CH_2O$-2,3,5,6-tetrafluorophenyl; $R^6$ is (C1-C12)-aliphatic-(C3-C10)-cycloaliphatic-, (C6-C10)-aryl-, (C3-C10)-heterocyclyl-, (C5-C10)-heteroaryl-, (C3-C10)-cycloaliphatic-(C1-C12)-aliphatic-, (C6-C10)-aryl-(C1-C12)-aliphatic-, (C3-C10)-heterocyclyl-(C1-C12)-aliphatic-, (C5-C10)-heteroaryl(C1-C12)-aliphatic-, or two $R^6$ groups bound to the same atom form together with that atom a 3- to 10-membered aromatic or nonaromatic ring; wherein any ring is optionally fused to a (C6-C10)aryl, (C5-C10)heteroaryl, (C3-C10)cycloalkyl, or a (C3-C10)heterocyclyl; wherein up to 3 aliphatic carbon atoms may be replaced by a group selected from O, N, N(R), S, SO, and $SO_2$; and wherein $R^6$ is substituted with up to 6 substituents independently selected from R; R is halogen, —$OR^7$, —OC(O)$N(R^7)_2$, —$NO_2$, —CN, —$CF_3$, —$OCF_3$, —$R^7$, oxo, thioxo, =$NR^7$, =$N(OR^7)$, 1,2-methylenedioxy, 1,2-ethylenedioxy, —$N(R^7)_2$, —$SR^7$, —$SOR^7$, —$SO_2R^7$, —$SO_2N(R^7)_2$, —$SO_3R^7$, —$C(O)R^7$, —$C(O)C(O)R^7$, —$C(O)C(O)OR^7$, —$C(O)C(O)N(R^7)_2$, —$C(O)CH_2C(O)R^7$, —$C(S)R^7$, —$C(S)OR^7$, —$C(O)OR^7$, —$OC(O)R^7$, —$C(O)N(R^7)_2$, —$OC(O)N(R^7)_2$, —$C(S)N(R^7)_2$, —$(CH_2)_{0-2}NHC(O)R^7$, —$N(R^7)N(R^7)COR^7$, —$N(R^7)N(R^7)C(O)OR^7$, —$N(R^7)N(R^7)CON(R^7)_2$, —$N(R^7)SO_2R^7$, —$N(R^7)SO_2N(R^7)_2$, —$N(R^7)C(O)OR^7$, —$N(R^7)C(O)R^7$, —$N(R^7)C(S)R^7$, —$N(R^7)C(O)N(R^7)_2$, —$N(R^7)C(S)N(R^7)_2$, —$N(COR^7)COR^7$, —$N(OR^7)R^7$, —C(=NH)$N(R^7)_2$, —$C(O)N(OR^7)R^7$, —C(=$NOR^7)R^7$, —$OP(O)(OR^7)_2$, —$P(O)(R^7)_2$, —$P(O)(OR^7)_2$, or —$P(O)(H)(OR^7)$; two $R^7$ groups together with the atoms to which they are bound form a 3- to 10-membered aromatic or non-aromatic ring having up to 3 heteroatoms independently selected from N, N(R), O, S, SO, or $SO_2$, wherein the ring is optionally fused to a (C6-C10)aryl, (C5-C10)heteroaryl, (C3-C10)cycloalkyl, or a (C3-C10)heterocyclyl, and wherein any ring has up to 3 substituents selected independently from $J_2$; or each $R^7$ is independently selected from: hydrogen-, (C1-C12)-aliphatic-, (C3-C10)-cycloaliphatic-, (C3-C10)-cycloaliphatic-(C1-C12)-aliphatic-, (C6-C10)-aryl-, (C6-C10)-aryl-(C1-C12)aliphatic-, (C3-C10)-heterocyclyl-, (C6-C10)-heterocyclyl-(C1-C12)aliphatic-, (C5-C10)-heteroaryl-, or (C5-C10)-heteroaryl-(C1-C12)-aliphatic-; wherein $R^7$ has up to 3 substituents selected independently from $J_2$; and $J_2$ is halogen, —$OR^7$, —$OC(O)N(R^7)_2$, —$NO_2$, —CN, —$CF_3$, —$OCF_3$, —$R^7$, oxo, thioxo, =$N(R^7)$, =$NO(R^7)$, 1,2-methylenedioxy, 1,2-ethylenedioxy, —$N(R^7)_2$, —$SR^7$, —$SOR^7$, —$SO_2R^7$, —$SO_2N(R^7)_2$, —$SO_3R^7$, —$C(O)R^7$, —$C(O)C(O)R^7$, —$C(O)C(O)OR^7$, —$C(O)C(O)N(R^7)_2$, —$C(O)CH_2C(O)R^7$, —$C(S)R^7$, —$C(S)OR^7$, —$C(O)R^7$, —$OC(O)R^7$, —$C(O)N(R^7)_2$, —$OC(O)N(R^7)_2$, —$C(S)N(R^7)_2$, —$(CH_2)_{0-2}NHC(O)R^7$, —$N(R^7)N(R^7)COR^7$, —$N(R^7)N(R^7)C(O)OR^7$, —$N(R^7)N(R^7)CON(R^7)_2$, —$N(R^7)SO_2R^7$—$N(R^7)SO_2N(R^7)_2$, —$N(R^7)C(O)OR^7$, —$N(R^7)C(O)R^7$, —$N(R^7)C(S)R^7$—$N(R^7)C(O)N(R^7)_2$, —$N(R^7)C(S)N(R^7)_2$, —$N(COR^7)COR^7$, —$N(OR^7)R^7$, —CN, —$C(=NH)N(R^7)_2$, —$C(O)N(OR^7)R^7$, —$C(=NOR^7)R^7$, —$OP(O)(OR^7)_2$, —$P(O)(R^7)_2$, —$P(O)(OR^7)_2$, or —$P(O)(H)(OR^7)$; and $R^8$ is (C1-C12)-aliphatic-, (C3-C10)-cycloaliphatic-, (C6-C10)-aryl-, (C3-C10)-heterocyclyl-, (C5-C10)-heteroaryl-, (C3-C10)-cycloaliphatic-(C1-C12)-aliphatic-, (C6-C10)-aryl-(C1-C12)-aliphatic-, (C3-C10)-heterocyclyl-(C1-C12)-aliphatic-, or (C5-C10)-heteroaryl(C1-C12)-aliphatic-, wherein up to 3 aliphatic carbon atoms may be replaced with a group selected from O, N, N(R), S, SO, and $SO_2$; and wherein $R^8$ is optionally substituted with up to 6 substituents independently selected from R; or a compound of Formula 9.1 (referred to herein as caspase-1 inhibitor having Formula 9.1):

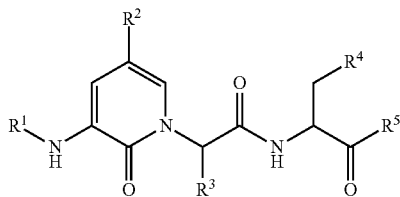

Formula 9.1 wherein: $R^1$ is $R^6C(O)$—, $R^6SO_2$—, $R^6OC(O)$—, $(R^6)_2NC(O)$—, $R^6C(O)C(O)$—, $R^6$—, $(R^6)_2NC(O)C(O)$—, or $R^6OC(O)C(O)$—; $R^2$ is hydrogen, —$CF_3$, -halo, —$OR^7$, —$NO_2$, —$OCF_3$, —CN, or $R^8$; $R^3$ is hydrogen or (C1-C4)-aliphatic-; $R^4$ is —COOH or —$COOR^8$; $R^5$ is —$CH_2F$ or —$CH_2O$-2,3,5,6-tetrafluorophenyl; $R^6$ is (C1-C12)-aliphatic-(C3-C10)-cycloaliphatic-, (C6-C10)-aryl-, (C3-C10)-heterocyclyl-, (C5-C10)-heteroaryl-, (C3-C10)-cycloaliphatic-(C1-C12)-aliphatic-, (C6-C10)-aryl-(C1-C12)-aliphatic-, (C3-C10)-heterocyclyl-(C1-C12)-aliphatic-, (C5-C10)-heteroaryl(C1-C12)-aliphatic-, or two $R^6$ groups bound to the same atom form together with that atom a 3- to 10-membered aromatic or nonaromatic ring; wherein any ring is optionally fused to a (C6-C10)aryl, (C5-C10)heteroaryl, (C3-C10)cycloalkyl, or a (C3-C10)heterocyclyl; wherein up to 3 aliphatic carbon atoms may be replaced by a group selected from O, N, N(R), S, SO, and $SO_2$; and wherein $R^6$ is substituted with up to 6 substituents independently selected from R; R is halogen, —$OR^7$, —$OC(O)N(R^7)_2$, —$NO_2$, —CN, —$CF_3$, —$OCF_3$, —$R^7$, oxo, thioxo, 1,2-methylenedioxy, 1,2-ethylenedioxy, —$N(R^7)_2$, —$SR^7$, —$SOR^7$, —$SO_2R^7$, —$SO_2N(R^7)_2$, —$SO_3R^7$, —$C(O)R^7$, —$C(O)C(O)R^7$, —$C(O)CH_2C(O)R^7$, —$C(S)R^7$, —$C(O)OR^7$, —$OC(O)R^7$, —$C(O)N(R^7)_2$, —$OC(O)N(R^7)_2$, —$C(S)N(R^7)_2$, —$(CH_2)_{0-2}NHC(O)R^7$, —$N(R^7)N(R^7)COR^7$, —$N(R^7)N(R^7)C(O)OR^7$—$N(R^7)N(R^7)CON(R^7)_2$—, —$N(R^7)SO_2R^7$, —$N(R^7)SO_2N(R^7)_2$, —$N(R^7)C(O)OR^7$, —$N(R^7)C(O)R^7$, —$N(R^7)C(S)R^7$—$N(R^7)C(O)N(R^7)_2$, —$N(R^7)C(S)N(R^7)_2$, —$N(COR^7)COR^7$, —$N(OR^7)R^7$, —$R^7$, —CN, —$C(=NH)N(R^7)_2$, —$C(O)N(OR^7)R^7$, —$C(=NOR^7)R^7$, —$OP(O)(OR^7)_2$, —$P(O)(R^7)_2$, —$P(O)(OR^7)_2$, or —$P(O)(H)(OR^7)$; two $R^7$ groups together with the atoms to which they are bound form a 3- to 10-membered aromatic or non-aromatic ring having up to 3 heteroatoms independently selected from N, N(R), O, S, SO, or $SO_2$, wherein the ring is optionally fused to a (C6-C10)aryl, (C5-C10)heteroaryl, (C3-C10)cycloalkyl, or a (C3-C10)heterocyclyl, and wherein any ring has up to 3 substituents selected independently from $J_2$; or each $R^7$ is independently selected from: hydrogen-, (C1-C12)-aliphatic-, (C3-C10)-cycloaliphatic-, (C3-C10)-cycloaliphatic-(C1-C12)-aliphatic-, (C6-C10)-aryl-, (C6-C10)-aryl-(C1-C12)aliphatic-, (C3-C10)-heterocyclyl-, (C6-C10)-heterocyclyl-(C1-C12)aliphatic-, (C5-C10)-heteroaryl-, or (C5-C10)-heteroaryl-(C1-C12)-aliphatic-; wherein $R^7$ has up to 3 substituents selected independently from $J_2$; and $J_2$ is halogen, —$OR^7$, —$OC(O)N(R^7)_2$, —$NO_2$, —CN, —$CF_3$, —$OCF_3$, —$R^7$, oxo, thioxo, 1,2-methylenedioxy, 1,2-ethylenedioxy, —$N(R^7)_2$, —$SR^7$, —$SOR^7$, —$SO_2R^7$, —$SO_2N(R^7)_2$, —$SO_3R^7$, —$C(O)R^7$, —$C(O)C(O)R^7$, —$C(O)CH_2C(O)R^7$, —$C(S)R^7$, —$C(O)OR^7$, —$OC(O)R^7$, —$C(O)N(R^7)_2$, —$OC(O)N(R^7)_2$, —$C(S)N(R^7)_2$, —$(CH_2)_{0-2}NHC(O)R^7$, —$N(R^7)N(R^7)COR^7$, —$N(R^7)N(R^7)C(O)OR^7$, —$N(R^7)N(R^7)CON(R^7)_2$, —$N(R^7)SO_2R^7$, —$N(R^7)SO_2N(R^7)_2$, —$N(R^7)C(O)OR^7$7-$N(R^7)C(O)R^7$, —$N(R^7)C(S)R^7$, —$N(R^7)C(O)N(R^7)_2$, —$N(R^7)C(S)N(R)_2$, —$N(COR^7)COR^7$, —$N(OR^7)R^7$, —CN, —$C(=NH)N(R^7)_2$, —$C(O)N(OR^7)R^7$—$C(=NOR^7)R^7$, —$OP(O)(OR^7)_2$, —$P(O)(R^7)_2$, —$P(O)(OR^7)_2$, or —$P(O)(H)(OR^7)$; and $R^8$ is (C1-C12)-aliphatic-(C3-C10)-cycloaliphatic-, (C6-C10)-aryl-, (C3-C10)-heterocyclyl-, (C5-C10)-heteroaryl-, (C3-C10)-cycloaliphatic-(C1-C12)-aliphatic-, (C6-C10)-aryl-(C1-C12)-aliphatic-, (C3-C10)-heterocyclyl-(C1-C12)-aliphatic-, or (C5-C10)-heteroaryl(C1-C12)-aliphatic-, wherein up to 3 aliphatic carbon atoms may be replaced with a group selected from O, N, N(R), S, SO, and $SO_2$.

10. Caspase-1 Inhibitor Having Formula 10

In some embodiments of the present invention a caspase-1 inhibitor for use in a method of the present invention is a compound described in published US2008/0286201 (herewith incorporated by reference in its entirety). Preferred compounds described in published US2008/0286201 for use in the methods of the present invention are referred to herein as caspase-1 inhibitor having Formula 10:

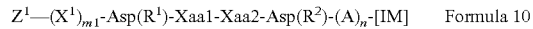

Formula 10 or single stereoisomers, mixtures of stereoisomers, pharmaceutically acceptable salts or prodrugs thereof, wherein: $Z^1$ is attached to the N-terminus of $X^1$ or the Asp residue, and is H or a metabolism inhibiting group; $X^1$ is a cell membrane permeable leader sequence peptide of 4 to 20 amino acids which facilitates cell membrane transport from the outside to the inside of a mammalian cell in vivo; Xaa1 is Glu($R^3$) or Met; Xaa2 is Val or is Gln when Xaa1 is Met; Asp is aspartic acid; $-(A)_n$- is a linker group wherein each A is independently —$CR_2$—, —CR=CR—, —C≡C—, —$CR_2CO_2$—, —$CO_2CR_2$—, —NRCO—, —CONR—, —NR(C=O)NR—, —NR(C=S)NR—, —$SO_2NR$—, —$NRSO_2$—, —$CR_2OCR_2$—, —$CR_2SCR_2$—, —$CR_2NRCR_2$—, a $C_{4-8}$ cycloheteroalkylene group, a $C_{4-8}$ cycloalkylene group, a $C_{5-12}$ arylene group, or a $C_{3-12}$ heteroarylene group, an amino acid, a sugar or a monodisperse polyethyleneglycol (PEG) building block; each R is independently chosen from H, $C_{1-4}$ alkyl, $C_{2-4}$ alkenyl, $C_{2-4}$ alkynyl, $C_{1-4}$ alkoxyalkyl or $C_{1-4}$ hydroxyalkyl; $R^1$, $R^2$ and $R^3$ are independently R' groups which are attached at the carboxy side chain of the Asp or Glu amino acid residue, where each R' is chosen from H, $C_{1-8}$ alkyl, $C_{2-8}$ alkoxyalkyl, $C_{5-12}$ aryl or $C_{5-16}$ aralkyl; $m_1$ is 0 or 1; n is an integer of value 0 to 10; IM is an optional imaging moiety which comprises a gamma-emitting radioactive halogen or a positron-emitting radioactive non-metal.

11. Caspase-1 Inhibitor Having Formula 11

In some embodiments of the present invention a caspase-1 inhibitor for use in a method of the present invention is a compound described in published US2007/0010457 and US2003/0096737 (herewith incorporated by reference in their entireties). Preferred compounds described in published US2007/0010457 and US2003/0096737 for use in the methods of the present invention are referred to herein as caspase-1 inhibitor having Formula 11:

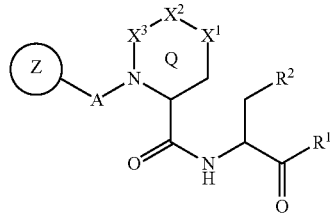

Formula 11 or single stereoisomers, mixtures of stereoisomers, pharmaceutically acceptable salts or prodrugs thereof, wherein: $R^1$ is hydrogen, CN, $CHN_2$, R, or —$CH_2Y$; R is an aliphatic group, a substituted aliphatic group, an aryl group, a substituted aryl group, an aralkyl group, a substituted aralkyl group, a non-aromatic heterocyclic group, or a substituted non-aromatic heterocyclic group; Y is an electronegative leaving group, —OR, —SR, —OC=O(R), or —OPO($R^3$)($R^4$); $R^3$ and $R^4$ are independently R or OR; $R^2$ is $CO_2H$, $CH_2CO_2H$, or optionally substituted esters, amides or isosteres thereof; A is C=O or $SO_2$; $X^1$ is oxygen, sulfur, —NH, or —$CH_2$, wherein —NH is optionally substituted by an alkyl group, a cycloalkyl group, a (cycloalkyl)alkyl group, an amino acid N-terminal protecting group, or COR and —$CH_2$ is optionally substituted by fluorine, an alkyl group, a cycloalkyl group, a (cycloalkyl) alkyl group, an aralkyl group, an aryl group, an alkyloxy group, an alkylthioxy group, an aryloxy group, an arylthioxy group, an oxo group (i.e., =O), or a NHCOR group; $X^2$ is oxygen, sulfur, —NH, or —$CH_2$, wherein —NH is optionally substituted by an alkyl group, or an amino acid N-terminal protecting group and —$CH_2$ is optionally substituted by an alkyl group, an aryl group, an alkyloxy group, an alkylthioxy group, an aryloxy group, an arylthioxy group, or an oxo (i.e., =O) group, a NHCOR group; $X^1$ and $X^2$ optionally form part of a phenyl ring that is fused to the adjoining ring Q; $X^3$ is $CH_2$ or $X^2$ and $X^3$ optionally form part of a phenyl ring that is fused to the adjoining ring Q, provided that when $X^2$ forms a ring with $X^3$, then $X^2$ does not form a ring with $X^1$; any two hydrogens attached to adjacent positions in ring Q are optionally replaced by a double bond; and Z is an optionally substituted ring selected from the group consisting of a carbocyclic, an aryl, a saturated heterocycle, a partially saturated heterocycle, and a heteroaryl wherein the ring is connected to A at a ring carbon.

12. Caspase-1 Inhibitor Having Formula 12

In some embodiments of the present invention a caspase-1 inhibitor for use in a method of the present invention is a compound described in published US2006/0160862 (herewith incorporated by reference in its entirety). Preferred compounds described in published US2006/0160862 for use in the methods of the present invention are referred to herein as caspase-1 inhibitor having Formula 12:

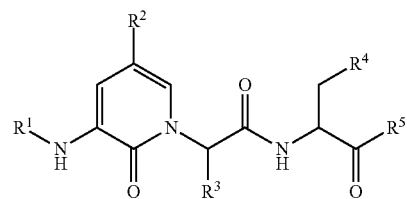

Formula 12 or single stereoisomers, mixtures of stereoisomers, pharmaceutically acceptable salts or prodrugs thereof, wherein: $R^1$ is $R^6C(O)$—, HC(O)—, $R^6SO_2$—, $R^6OC(O)$—, $(R^6)_2NC(O)$—, $(R^6)(H)NC(O)$—, $R^6C(O)C(O)$—, $(R^6)_2NC(O)C(O)$—, $(R^6)(H)NC(O)C(O)$—, or $R^6OC(O)C(O)$—; $R^2$ is hydrogen, —$CF_3$, halo, —$OR^7$, —$NO_2$, —$OCF_3$, —CN, or R; $R^3$ is -T-$R^9$; $R^4$ is —COOH or —$COOR^8$; $R^5$ is —$CH_2F$ or —$CH_2O$-2,3,5,6-tetrafluorophenyl; $R^6$ is $R^{6a}$ or $R^{6b}$; two $R^6$ groups, together with the same atom to which they are bound, optionally form a 3- to 10-membered aromatic or nonaromatic ring; wherein the ring is optionally fused to a (C6-C10) aryl, (C5-C10)heteroaryl, (C3-C10)cycloalkyl, or a (C3-C10)heterocyclyl; wherein up to 3 aliphatic carbon atoms may be replaced by a group selected from O, N, N($R^7$), S, SO, and $SO_2$; and wherein each $R^6$ is independently substituted with up to 6 substituents independently selected from R; $R^{6a}$ and $R^{6b}$ are each independently (C1-C3)-aliphatic-, (C4-C12)-aliphatic-, (C3-C10)-cycloaliphatic-, (C6-C10)-aryl-, (C3-C10)-heterocyclyl-, (C5-C10)-heteroaryl-, (C3-C10)-cycloaliphatic-(C1-C12)-aliphatic-, (C6-C10)-aryl-(C1-C12)-aliphatic-, (C3-C10)-heterocyclyl-(C1-C12)-aliphatic-, (C5-C10)-heteroaryl(C1-C12)-aliphatic-; R is halogen, —$OR^7$, —OC(O)N($R^7$)$_2$, —$NO_2$, —CN, —$CF_3$, —$OCF_3$, —$R^7$, oxo, thioxo, =$NR^7$, =N($OR^7$), 1,2-methylenedioxy, 1,2-ethylenedioxy, —N($R^7$)$_2$, —$SR^7$, —$SOR^7$, —$SO_2R^7$, —$SO_2N(R^7)_2$, —$SO_3R^7$, —C(O)$R^7$, —C(O)C(O)$R^7$, —C(O)C(O)$OR^7$, —C(O)C(O)N($R^7$)$_2$, —C(O)$CH_2$C(O)$R^7$, —C(S)$R^7$, —C(S)$OR^7$, —C(O)$OR^7$, —OC(O)$R^7$, —C(O)N($R^7$)$_2$, —OC(O)N($R^7$)$_2$, —C(S)N($R^7$)$_2$, —$(CH_2)_{0-2}$NHC(O)$R^7$, —N($R^7$)N($R^7$)COR$^7$, —N($R^7$)N($R^7$)C(O)$OR^7$, —N($R^7$)N($R^7$)CON($R^7$)$_2$, —N($R^7$)$SO_2R^7$, —N($R^7$)$SO_2N(R^7)_2$, —N($R^7$)C(O)$OR^7$, —N($R^7$)C(O)$R^7$, —N($R^7$)C(S)$R^7$, —N($R^7$)C(O)N($R^7$)$_2$, —N($R^7$)C(S)N($R^7$)$_2$, —N(COR$^7$)COR$^7$, —N($OR^7$)$R^7$, —C(=$NR^7$)N($R^7$)$_2$, —C(O)N($OR^7$)$R^7$, —C(=$NOR^7$)$R^7$, —OP(O)($OR^7$)$_2$, —P(O)($R^7$)$_2$, —P(O)($OR^7$)$_2$, or —P(O)(H)($OR^7$); two $R^7$ groups together with the atoms to which they are bound optionally form a 3- to 10-membered aromatic or non-aromatic ring having up to 3 heteroatoms independently selected from N, N($R^7$), O, S, SO, or $SO_2$, wherein the ring is optionally fused to a (C6-C10)aryl, (C5-C10)heteroaryl, (C3-C10) cycloalkyl, or a (C3-C10)heterocyclyl, and wherein any ring has up to 3 substituents selected independently from $J_2$; or each $R^7$ is independently selected from: hydrogen-, (C1-C12)-aliphatic-, (C3-C10)-cycloaliphatic-, (C3-C10)-cycloaliphatic-(C1-C12)-aliphatic-, (C6-C10)-aryl-, (C6-C10)-aryl-(C1-C12)aliphatic-, (C3-C10)-heterocyclyl-, (C6-C10)-heterocyclyl-(C1-C12)aliphatic-, (C5-C10)-heteroaryl-, or (C5-C10)-heteroaryl-(C1-C12)-aliphatic-; wherein $R^7$ has up to 3 substituents selected independently from $J_2$; and $J_2$ is halogen, —OR⁷, —OC(O)N(R⁷)₂, —NO₂, —CN, —CF₃, —OCF₃, —R⁷, oxo, thioxo, =NR⁷, =NO(R⁷), 1,2-methylenedioxy, 1,2-ethylenedioxy, —N(R⁷)₂, —SR⁷, —SOR⁷, —SO₂R⁷, —SO₂N(R⁷)₂, —SO₃R⁷, —C(O)R⁷, —C(O)C(O)R⁷, —C(O)C(O)OR⁷, —C(O)C(O)N(R⁷)₂, —C(O)CH₂C(O)R⁷, —C(S)R⁷, —C(S)OR⁷, —C(O)OR⁷, —OC(O)R⁷, —C(O)N(R⁷)₂, —OC(O)N(R⁷)₂, —C(S)N(R⁷)₂, —(CH₂)₀₋₂NHC(O)R⁷, —N(R⁷)N(R⁷)COR⁷, —N(R⁷)N (R⁷)C(O)OR⁷, —N(R⁷)N(R⁷)CON(R⁷)₂, —N(R⁷)SO₂R⁷, —N(R⁷)SO₂N(R⁷)₂, —N(R⁷)C(O)OR⁷, —N(R⁷)C(O)R⁷, —N(R⁷)C(S)R⁷, —N(R⁷)C(O)N(R⁷)₂, —N(R⁷)C(S)N(R⁷)₂, —N(COR⁷)COR₇, —N(OR⁷)R⁷, —CN, —C(=NR⁷) N(R⁷)₂, —C(O)N(OR⁷)R⁷, —C(=NOR⁷)R⁷, —OP(O) (OR⁷)₂, —P(O)(R⁷)₂, —P(O)(OR⁷)₂, or —P(O)(H)(OR⁷); and R⁸ is (C1-C12)-aliphatic-, (C3-C10)-cycloaliphatic-, (C6-C10)-aryl-, (C3-C10)-heterocyclyl-, (C5-C10)-heteroaryl-, (C3-C10)-cycloaliphatic-(C1-C12)-aliphatic-, (C6-C10)-aryl-(C1-C12)-aliphatic-, (C3-C10)-heterocyclyl-(C1-C12)-aliphatic-, or (C5-C10)-heteroaryl-(C1-C12)-aliphatic-, wherein up to 3 aliphatic carbon atoms may be replaced with a group selected from O, N, N(R⁷), S, SO, and SO₂; and wherein R⁸ is optionally substituted with up to 6 substituents independently selected from R; T is a direct bond or (C1-C6)aliphatic wherein up to 2 aliphatic carbon atoms in T may be optionally replaced with S, —SO—, SO₂, O, N(R⁷), or N in a chemically stable arrangement; wherein each T may be optionally substituted with up to 3 R substituents; R⁹ is optionally substituted (C6-C10)-aryl or (C5-C10)-heteroaryl.

13. Caspase-1 Inhibitor Having Formula 13

In some embodiments of the present invention a caspase-1 inhibitor for use in a method of the present invention is a compound described in published US2004/0116355 (herewith incorporated by reference in its entirety). Preferred compounds described in published US2004/0116355 for use in the methods of the present invention are referred to herein as caspase-1 inhibitor having Formula 13:

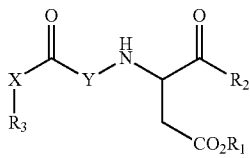

Formula 13 or single stereoisomers, mixtures of stereoisomers, pharmaceutically acceptable salts or prodrugs thereof, wherein: R₁ is an optionally substituted alkyl or hydrogen; R₂ is hydrogen or optionally substituted alkyl; R₃ is an alkyl, saturated carbocyclic, partially saturated carbocyclic, aryl, saturated heterocyclic, partially saturated heterocyclic or heteroaryl group, wherein said group is optionally substituted; X is O, S, NR₄ or (CR₄R₅)ₙ, where R₄ and R₅ are, at each occurrence, independently selected from the group consisting of hydrogen, alkyl and cycloalkyl, and n is 0, 1, 2 or 3; or X is NR₄, and R₃ and R₄ are taken together with the nitrogen atom to which they are attached to form a saturated heterocyclic, partially saturated heterocyclic or heteroaryl group, wherein said group is optionally substituted; or X is CR₄R₅, and R₃ and R₄ are taken together with the carbon atom to which they are attached to form a saturated carbocyclic, partially saturated carbocyclic, aryl, saturated heterocyclic, partially saturated heterocyclic or oxygen-containing heteroaryl group, wherein said group is optionally substituted; and Y is a residue of a natural or non-natural amino acid; provided that when X is O, then R₃ is not unsubstituted benzyl or t-butyl; and when X is CH₂, then R₃ is not hydrogen.

14. Caspase-1 Inhibitor Having Formula 14

In some embodiments of the present invention a caspase-1 inhibitor for use in a method of the present invention is a compound described in published US2004/0048895 (herewith incorporated by reference in its entirety). Preferred compounds described in published US2004/0048895 for use in the methods of the present invention are referred to herein as caspase-1 inhibitor having Formula 14:

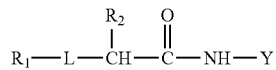

Formula 14 or single stereoisomers, mixtures of stereoisomers, pharmaceutically acceptable salts or prodrugs thereof, wherein R₁ is chosen from optionally substituted aryl, optionally substituted aralkyl, optionally substituted heteroaryl, and optionally substituted heteroaralkyl; L is a linker; R₂ is chosen from optionally substituted aryl, optionally substituted aralkyl, optionally substituted heteroaryl, and optionally substituted heteroaralkyl; and a compound of Formula 14, wherein Y is

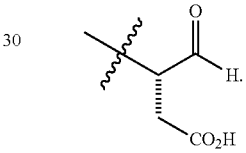

15. Caspase-1 Inhibitor Having Formula 15

In some embodiments of the present invention a caspase-1 inhibitor for use in a method of the present invention is a compound described in published US2004/0019017 (herewith incorporated by reference in its entirety). Preferred compounds described in published US2004/0019017 for use in the methods of the present invention are referred to herein as caspase-1 inhibitor having Formula 15:

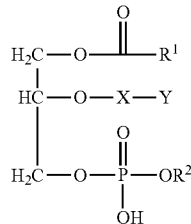

Formula 15 or single stereoisomers, mixtures of stereoisomers, pharmaceutically acceptable salts or prodrugs thereof, wherein R¹ is a saturated or unsaturated, straight-chain or branched, substituted or unsubstituted hydrocarbon chain; R² is H or a phospholipid head group; X is a direct covalent bond or a group C(O)LR³; wherein L is a saturated or unsaturated, straight-chain or branched, substituted or unsubstituted hydrocarbon chain having from 2 to 15 carbon atoms, which optionally includes cyclic elements, and is optionally interrupted by one or more atoms selected from the group consisting of oxygen, sulfur and N(R⁴), R³ is selected from the group consisting of O, S and N(R$^4$); wherein R$^4$ is a saturated or unsaturated hydrocarbon chain having 1 to 6 carbon atoms; and Y is a residue of a caspase-1 inhibitor.

16. Caspase-1 Inhibitor Having Formula 16, 16.1, 16.2, 16.3, 16.4, 16.5, 16.6, or 16.7

In some embodiments of the present invention a caspase-1 inhibitor for use in a method of the present invention is a compound described in published US2003/0232846 (herewith incorporated by reference in its entirety). Preferred compounds described in published US2003/0232846 for use in the methods of the present invention are referred to herein as caspase-1 inhibitor having Formula 16:

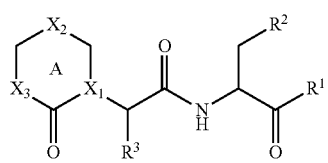

Formula 16 or single stereoisomers, mixtures of stereoisomers, pharmaceutically acceptable salts or prodrugs thereof, wherein R$^1$ is hydrogen, CN, CHN$_2$, R, or —CH$_2$Y; R is an aliphatic group, a substituted aliphatic group, an aryl group, a substituted aryl group, an aralkyl group, a substituted aralkyl group, a non-aromatic heterocyclic group or a substituted non-aromatic heterocyclic group; Y is an electronegative leaving group or —OR, —SR, —OC=O(R), or —OPO(R$^8$)(R$^9$); R$^8$ and R$^9$ are independently selected from R or OR; R$^2$ is CO$_2$H, CH$_2$CO$_2$H, or esters, amides or isosteres thereof; R$^3$ is hydrogen or a C$_{1-6}$ straight chained or branched alkyl; Ring A contains zero to two double bonds, and is optionally fused to a saturated or unsaturated five to seven membered ring containing zero to three heteroatoms; X$_1$ and X$_3$ in Ring A are independently selected from nitrogen or carbon, and X$_2$ is selected from a valence bond, oxygen, sulfur, nitrogen or carbon, wherein any X with suitable valence may bear a substituent; each carbon with suitable valence in Ring A, including the fused ring if present, is independently substituted by hydrogen, halo, R, OR, SR, OH, NO$_2$, CN, NH$_2$, NHR, N(R)$_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR, NHS(O)$_2$R, =O, =S, =NNHR, =NNR$_2$, =N—OR, =NNHCOR, =NNHCO$_2$R, =NNHSO$_2$R, or =NR; each substitutable nitrogen in Ring A is substituted by hydrogen, R, COR, S(O)$_2$R, or CO$_2$R; provided that when X$_3$ is a carbon, a substituent on X$_3$ is attached by an atom other than nitrogen; and further provided that at least one X in Ring A is a nitrogen;

a compound having Formula 16.1 (referred to herein as caspase-1 inhibitor having Formula 16.1):

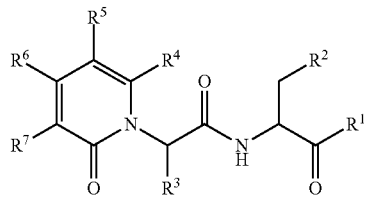

Formula 16.1 or single stereoisomers, mixtures of stereoisomers, pharmaceutically acceptable salts or prodrugs thereof, wherein R$^1$ is hydrogen, CN, CHN$_2$, R, —CH$_2$Y; R is an aliphatic group, a substituted aliphatic group, an aryl group, a substituted aryl group, an aralkyl group, a substituted aralkyl group, a non-aromatic heterocyclic group or a substituted non-aromatic heterocyclic group; Y is an electronegative leaving group, —OR, —SR, —OC=O(R), or —OPO(R$^8$)(R$^9$); R$^8$ and R$^9$ are each independently selected from R or OR; R$^2$ is CO$_2$H, CH$_2$CO$_2$H, or esters, amides or isosteres thereof; R$^3$ is hydrogen or a C$_{1-6}$ straight chained or branched alkyl; each of R$^4$-R$^6$ is independently selected from hydrogen, halo, R, OR, SR, aryl, substituted aryl, OH, NO$_2$, CN, NH$_2$, NHR, N(R)$_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR, or NHS(O)$_2$R; and R$^7$ is selected from hydrogen, halo, R, OR, SR, aryl, substituted aryl, OH, CN, CO$_2$R, CO$_2$H, COR, CONHR, CON(R)$_2$, S(O)$_2$R, SONH$_2$, S(O)R, or SO$_2$NHR;

a compound having Formula 16.2 (referred to herein as caspase-1 inhibitor having Formula 16.2):

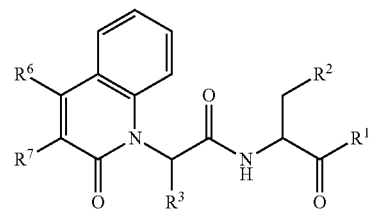

Formula 16.2 or single stereoisomers, mixtures of stereoisomers, pharmaceutically acceptable salts or prodrugs thereof, wherein R$^1$ is hydrogen, CN, CHN$_2$, R, or —CH$_2$Y; R is an aliphatic group, a substituted aliphatic group, an aryl group, a substituted aryl group, an aralkyl group, a substituted aralkyl group, a non-aromatic heterocyclic group or a substituted non-aromatic heterocyclic group; Y is an electronegative leaving group or —OR, —SR, —OC=O(R), or —OPO(R$^8$)(R$^9$); R$^8$ and R$^9$ are each independently selected from R or OR; R$^2$ is CO$_2$H, CH$_2$CO$_2$H, or esters, amides or isosteres thereof; R$^3$ is hydrogen or a C$_{1-6}$ straight chained or branched alkyl; R$^6$ is selected from hydrogen, halo, R, OR, SR, aryl, substituted aryl, OH, NO$_2$, CN, NH$_2$, NHR, N(R)$_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR, or NHS(O)$_2$R; and R$^7$ is selected from hydrogen, halo, R, OR, SR, aryl, substituted aryl, OH, CN, CO$_2$R, CO$_2$H, COR, CONHR, CON(R)$_2$, S(O)$_2$R, SONH$_2$, S(O)R, or SO$_2$NHR;

a compound having Formula 16.3 (referred to herein as caspase-1 inhibitor having Formula 16.3):

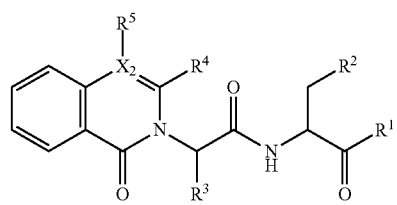

Formula 16.3 or single stereoisomers, mixtures of stereoisomers, pharmaceutically acceptable salts or prodrugs thereof, wherein R$^1$ is hydrogen, CN, CHN$_2$, R, or —CH$_2$Y; R is an aliphatic group, a substituted aliphatic group, an aryl group, a substituted aryl group, an aralkyl group, a substituted aralkyl group, a non-aromatic heterocyclic group or a substituted non-aromatic heterocyclic group; Y is an electronegative leaving group or —OR, —SR; —OC=O(R), or —OPO($R^8$)($R^9$); $R^8$ and $R^9$ are independently selected from R or OR; $R^2$ is $CO_2H$, $CH_2CO_2H$, or esters, amides or isosteres thereof; $R^3$ is hydrogen or a $C_{1-6}$ straight chained or branched alkyl; $R^4$ and $R^5$ are each independently selected from hydrogen, halo, R, OR, SR, aryl, substituted aryl, OH, $NO_2$, CN, $NH_2$, NHR, $N(R)_2$, NHCOR, NHCONHR, NHCON($R)_2$, NRCOR, $NHCO_2R$, $CO_2R$, $CO_2H$, COR, CONHR, CON$(R)_2$, S(O)$_2$R, SONH$_2$, S(O)R, SO$_2$NHR, NHS(O)$_2$R, =O, =S, =NNHR, =NNR$_2$, =N—OR, =NNHCOR, =NNHCO$_2$R, =NNHSO$_2$R, or =NR;

a compound having Formula 16.4 (referred to herein as caspase-1 inhibitor having Formula 16.4):

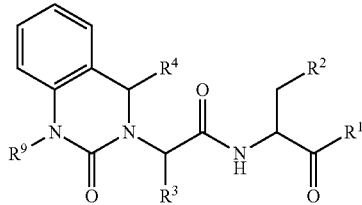

Formula 16.4 or single stereoisomers, mixtures of stereoisomers, pharmaceutically acceptable salts or prodrugs thereof, wherein $R^1$ is hydrogen, CN, CHN$_2$, R, —CH$_2$Y; R is an aliphatic group, a substituted aliphatic group, an aryl group, a substituted aryl group, an aralkyl group, a substituted aralkyl group, a non-aromatic heterocyclic group or a substituted non-aromatic heterocyclic group; Y is an electronegative leaving group or —OR, —SR, —OC=O(R), or —OPO($R^8$)($R^9$); $R^8$ and $R^9$ are independently selected from R or OR; $R^2$ is CO$_2$H, CH$_2$CO$_2$H, or esters, amides or isosteres thereof; $R^3$ is hydrogen or a $C_{1-6}$ straight chained or branched alkyl; $R^4$ is independently selected from hydrogen, halo, R, OR, SR, aryl, substituted aryl, OH, NO$_2$, CN, NH$_2$, NHR, N(R)$_2$, NHCOR, NHCONHR, NHCON(R)2, NRCOR, NHCO$_2$R, CO$_2$R, CO$_2$H, COR, CONHR$_2$, CON(R)$_2$, S(O)$_2$R, SONH$_2$, S(O)R, SO$_2$NHR, or NHS(O)$_2$R; $R^7$ is selected from hydrogen, halo, R, OR, SR, aryl, substituted aryl, OH, CN, CO$_2$R, CO$_2$H, COR, CONHR, CON(R)$_2$, S(O)$_2$R, SONH$_2$, S(O)R, or SO$_2$NHR;

a compound having Formula 16.5 (referred to herein as caspase-1 inhibitor having Formula 16.5):

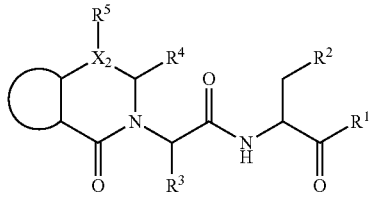

Formula 16.5 or single stereoisomers, mixtures of stereoisomers, pharmaceutically acceptable salts or prodrugs thereof, wherein $R^1$ is hydrogen, CN, CHN$_2$, R, —CH$_2$Y; R is an aliphatic group, a substituted aliphatic group, an aryl group, a substituted aryl group, an aralkyl group, a substituted aralkyl group, a non-aromatic heterocyclic group or a substituted non-aromatic heterocyclic group; Y is an electronegative leaving group or —OR, —SR, —OC=O(R), or —OPO($R^8$)($R^9$); $R^8$ and $R^9$ are independently selected from R or OR; $R^2$ is CO$_2$H, CH$_2$CO$_2$H, or esters or isosteres thereof; $R^3$ is hydrogen or a $C_{1-6}$ straight chained or branched alkyl; $R^4$ and $R^5$ are each independently selected from hydrogen, halo, R, OR, SR, aryl, substituted aryl, OH, NO$_2$, CN, NH$_2$, NHR, N(R)$_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR, or NHS(O)$_2$R; and the fused ring is an aromatic or non-aromatic heterocyclic ring;

a compound having Formula 16.6 (referred to herein as caspase-1 inhibitor having Formula 16.6):

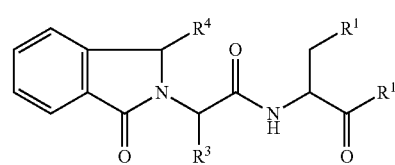

Formula 16.6 or single stereoisomers, mixtures of stereoisomers, pharmaceutically acceptable salts or prodrugs thereof, wherein $R^1$ is hydrogen, CN, CHN$_2$, R, or —CH$_2$Y; R is an aliphatic group, a substituted aliphatic group, an aryl group, a substituted aryl group, an aralkyl group, a substituted aralkyl group, a non-aromatic heterocyclic group or a substituted non-aromatic heterocyclic group; Y is an electronegative leaving group or —OR, —SR, —OC=O(R), or —OPO($R^8$)($R^9$); $R^8$ and $R^9$ are independently selected from R or OR; $R^2$ is CO$_2$H, CH$_2$CO$_2$H, or esters, amides or isosteres thereof; $R^3$ is hydrogen or a $C_{1-6}$ straight chained or branched alkyl; and $R^4$ is independently selected from hydrogen, halo, R, OR, SR, aryl, substituted aryl, OH, NO$_2$, CN, NH$_2$, NHR, N(R)$_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR, or NHS(O)$_2$R;

or a compound having Formula 16.7 (referred to herein as caspase-1 inhibitor having Formula 16.7):

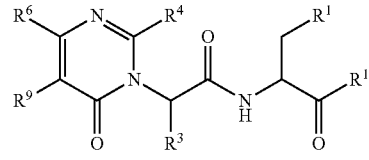

Formula 16.7 or single stereoisomers, mixtures of stereoisomers, pharmaceutically acceptable salts or prodrugs thereof, wherein $R^1$ is hydrogen, CN, CHN$_2$, R, or —CH$_2$Y; R is an aliphatic group, a substituted aliphatic group, an aryl group, a substituted aryl group, an aralkyl group, a substituted aralkyl group, a non-aromatic heterocyclic group or a substituted non-aromatic heterocyclic group; Y is an electronegative leaving group or —OR, —SR, —OC=O(R), or —OPO($R^8$)($R^9$); $R^8$ and $R^9$ are independently selected from R or OR; $R^2$ is CO$_2$H, CH$_2$CO$_2$H, or esters, amides or isosteres thereof; $R^3$ is hydrogen or a $C_{1-6}$ straight chained or branched alkyl; each of $R^4$ and $R^6$ is independently selected from hydrogen, halo, R, OR, SR, aryl, substituted aryl, OH, NO$_2$, CN, NH$_2$, NHR, N(R)$_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR, or NHS(O)$_2$R; and $R^7$ is selected from hydrogen, halo, R, OR, SR, aryl, substituted aryl, OH, CN, CO$_2$R, CO$_2$H, COR, CONHR, CON(R)$_2$, S(O)$_2$R, SONH$_2$, S(O)R, or SO$_2$NHR.

17. Caspase-1 Inhibitor Having Formula 17, 17.1, 17.2, 17.3, 17.4, 17.5, 17.6, 17.7, 17.8, 17.9, 17.10, 17.11, 17.12, 17.13, 17.14, 17.15, 17.16, 17.17, 417.18, 17.19, 17.20. 17.21, and 17.22

In some embodiments of the present invention a caspase-1 inhibitor for use in a method of the present invention is a compound described in published US2010/0040607 (herewith incorporated by reference in its entirety). Preferred compounds described in published US2010/0040607 for use in the methods of the present invention are referred to herein as caspase-1 inhibitor having Formula 17:

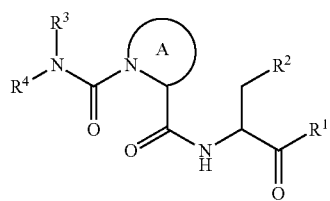

Formula 17 or single stereoisomers, mixtures of stereoisomers, pharmaceutically acceptable salts or prodrugs thereof, wherein Ring A is an optionally substituted piperidine, tetrahydroquinoline or tetrahydroisoquinoline ring, $R^1$ is hydrogen, CN, CHN$_2$, R, or CH$_2$Y, R is an optionally substituted group selected from an aliphatic group, an aryl group, or an aralkyl group, Y is an electronegative leaving group, $R^2$ is CO$_2$H, CH$_2$CO$_2$H, or esters, amides or isosteres thereof, $R^3$ is hydrogen, an optionally substituted aryl group, an optionally substituted aralkyl group, or an optionally substituted C$_{1-6}$ aliphatic group, $R^4$ is an optionally substituted group selected from an aryl group or a heterocyclyl group, or $R^3$ and $R^4$ taken together with the nitrogen to which they are attached optionally form is a substituted or unsubstituted monocyclic, bicyclic or, tricyclic ring;

a compound having Formula 17.1 (referred to herein as caspase-1 inhibitor having Formula 17.1):

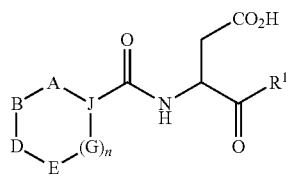

Formula 17.1 or single stereoisomers, mixtures of stereoisomers, pharmaceutically acceptable salts or prodrugs thereof, wherein $R^1$ is H, an aliphatic, heteroaliphatic, aryl, heteroaryl, alkylaryl, alkylheteroaryl, heteroalkylaryl, or heteroalkylheteroaryl moiety; n is 0 or 1; A is CR$^A$, C(R$^A$)$_2$, C=O, S, NR$^A$, N(R$^A$)$_2$, or O; B is CR$^B$, C(R$^B$)$_2$, C=O, S, NR$^B$, N(R$^B$)$_2$, or O; D is CR$^D$, C(R$^D$)$_2$, C=O, S, NR$^D$, N(R$^D$)$_2$, or O; E is CR$^E$, C(R$^E$)$_2$, C=O, S, NR$^E$, N(R$^E$)$_2$, or O; G is CR$^G$, C(R$^G$)$_2$, C=O, S, NR$^G$, N(R$^G$)$_2$, or O; J is CR$^J$; each of A-B, B-D, D-E, E-G, G-J and A-J are connected by a single or double bond as valency and stability permits; each occurrence of R$^A$, R$^B$, R$^D$, R$^E$, R$^G$ and R$^J$ is independently hydrogen, halogen, —OR$^2$, —N(R$^2$)$_2$, —SR$^2$, —CN, —COOR$^2$, —COR$^2$, —CON(R$^2$, —SOR$^2$, —SO$_2$R$^2$, —SO$_2$N(R$^2$)$_2$, —NR$^2$SO$_2$R$^2$, —O(C=O)N(R$^2$)$_2$, —NR$^2$(C=O)N(R$^2$)$_2$, —NR$^2$(C=S)N(R$^2$)$_2$, —NR$^2$SO$_2$N(R$^2$)$_2$, or an aliphatic, heteroaliphatic, aryl, heteroaryl, alkylaryl, alkylheteroaryl, heteroalkylaryl, or heteroalkylheteroaryl moiety optionally independently substituted with one or more occurrences of R$^2$, wherein each occurrence of R$^2$ is independently hydrogen, halogen, —OR$^3$, —N(R$^3$)$_2$, —SR$^3$, —CN, —COOR$^3$, —COR$^3$, —CON(R$^3$)$_2$, —SOR$^3$, —SO$_2$R$^3$, —SO$_2$N(R$^3$)$_2$, —NR$^3$SO$_2$R$^3$, —O(C=O)N(R$^3$)$_2$, —NR$^3$(CO)N(R$^3$)$_2$, —NR$^3$(C=S)N(R$^3$)$_2$, —NR$^3$SO$_2$N(R$^2$)$_2$, or an aliphatic, heteroaliphatic, aryl, heteroaryl, alkylaryl, alkylheteroaryl, heteroalkylaryl, or heteroalkylheteroaryl moiety; wherein each occurrence of R$^3$ is independently hydrogen, or an aliphatic, heteroaliphatic, aryl, heteroaryl, alkylaryl, alkylheteroaryl, heteroalkylaryl, or heteroalkylheteroaryl moiety, and wherein at least one of R$^B$ or R$^D$ comprises —SR$^2$, —SOR$^2$, —SO$_2$R$^2$, —SO$_2$N(R$^2$)$_2$, —NR$^2$SO$_2$R$^2$, —N(R$^2$)$_2$, —(C=O)N(R$^2$)$_2$, —NR$^2$(C=O)R$^2$, —O(C=O)N(R$^2$)$_2$, —NR$^2$ (C=O)N(R$^2$)$_2$, —NR$^2$ (C=S)N(R$^2$)$_2$, —NR$^2$SO$_2$N (R$^2$)$_2$, or is an alkyl or heteroalkyl group substituted with one or more occurrences of R$^2$, wherein R$^2$ is —SR$^3$, —SOR$^3$, —SO$_2$R$^3$, —SO$_2$N(R$^3$, —NR$^3$SO$_2$R$^3$, —N(R$^3$)$_2$, —C=O)N (R$^3$)$_2$, —NR$^3$ (C=O)R$^3$, —O(C=O)N(R$^3$)$_2$, —NR$^3$ (C=O) N(R$^3$)$_2$, —NR$^3$(C=S)N(R$^3$)$_2$, —NR$^3$SO$_2$N(R$^3$)$_2$, wherein R$^3$ is an aliphatic, heteroaliphatic, aryl, heteroaryl, alkylaryl, alkylheteroaryl, heteroalkylaryl, or heteroalkylheteroaryl moiety, whereby each of the foregoing aliphatic, heteroaliphatic, alkyl and heteroalkyl moieties may be independently substituted or unsubstituted, cyclic or acyclic, linear or branched, and each of the foregoing aryl, heteroaryl, alkylaryl, alkylheteroaryl, heteroalkylaryl and heteroalkylheteroaryl moieties may be independently substituted or unsubstituted;

a compound having Formula 17.2 (referred to herein as caspase-1 inhibitor having Formula 17.2):

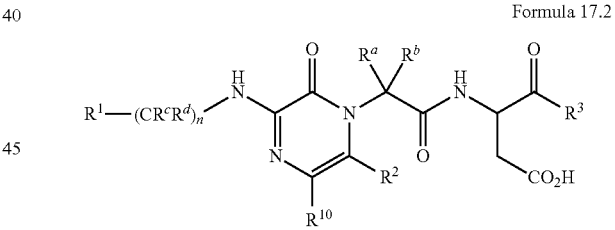

Formula 17.2 or single stereoisomers, mixtures of stereoisomers, pharmaceutically acceptable salts or prodrugs thereof, wherein $R^1$ is selected from the group consisting of: OH, C$_{1-4}$ alkyl, HET, Aryl, C$_{1-6}$ alkoxy, NH$_2$, NHC$_{1-6}$ alkyl, N(C$_{1-6}$ alkyl)$_2$, C$_{1-6}$ alkylC(O), C$_{1-6}$ alkylS(O)$_y$, Aryl-S(O)$_y$, HET-S(O)$_y$, wherein y is 0, 1 or 2, Aryl-C(O) and HET-C(O), the alkyl and alkyl portions of which being optionally substituted with 1-2 members selected from the group consisting of: OH, Aryl$^1$, HET, halo, NH$_2$, NHCH$_3$, N(CH$_3$)$_2$, CO$_2$H, CF$_3$ and C$_{1-4}$-acyl; Aryl represents a C$_{6-14}$ aromatic 1-3 ring system optionally substituted with 1-3 members selected from OH, C$_{1-6}$ alkyl, OC$_{1-6}$alkyl, Aryl$^1$, HET, halo, NH$_2$, NHCH$_3$, N(CH$_3$)$_2$, CF$_3$, CO$_2$H and C$_{1-4}$ acyl; Aryl$^1$ represents a C$_{6-14}$ membered aromatic ring system having 1-3 rings and optionally substituted with 1-3 members selected from the group consisting of: OH, HET, halo, NH$_2$, NHCH$_3$, N(CH$_3$)$_2$, CO$_2$H and C$_{1-4}$-acyl; HET represents a 5 to 15 membered aromatic, partially aromatic or non-aromatic ring system, containing 1-4 heteroatoms selected from O, S and N, and optionally substituted with 1-2 oxo groups and 1-3 groups selected from halo, $C_{1-4}$ alkyl, $C_{1-4}$alkoxy, $CF_3$ and $C_{1-4}$ acyl; $R^a$ and $R^b$ independently represent a member selected from the group consisting of: H, Aryl, $C_{1-6}$alkyl optionally substituted by 1-3 of halo, $OR^4$, $SR^4$ and $C_{5-7}$ cycloalkyl optionally containing one heteroatom selected from O, S and $NR^5$, or in the alternative, $R^a$ and $R^b$ are taken in combination and represent a non-aromatic carbocyclic 4-7 membered ring, optionally containing one heteroatom selected from O, S and $NR^5$; $R^4$ is selected from the group consisting of: H, $C_{1-5}$ alkyl, Aryl and Aryl-CIA alkyl optionally substituted with 1-2 groups selected from halo and $C_{1-4}$ alkyl; $R^5$ is H, $C_{1-4}$ alkyl or $C_{1-4}$ acyl; $R^c$ and $R^d$ each independently represents a member selected from the group consisting of: H, $C_{1-6}$ alkyl and Aryl, or in the alternative, $R^c$ and $R^d$ are taken in combination and represent a non-aromatic carbocyclic ring of 3-7 members, optionally containing one heteroatom selected from O, S and $NR^5$; n is an integer from 0-6 inclusive; $R^2$ represents H, halo or $C_{1-6}$ alkyl; $R^3$ represents H, $C_{1-6}$ alkyl, Aryl, HET, $C_{1-6}$ alkyl$SR^6$, $C_{1-6}$ alkyl$OR^6$, $C_{1-6}$ alkyl$OC(O)R^7$ or $C_{1-6}$alkyl$NR^8R^9$; $R^6$ represents $C_{1-6}$ alkyl, Aryl, HET or Aryl-$C_{1-6}$ alkyl, said alkyl and the alkyl portions being optionally substituted with 1-3 members selected from the group consisting of: OH, halo, $NH_2$, $NHCH_3$, $N(CH_3)_2$, $CO_2H$, $CF_3$ and $C_{1-4}$ acyl; $R^7$ represents $C_{1-8}$ alkyl, Aryl or HET; $R^8$ and $R^9$ independently represent H, $C_{1-10}$ alkyl, Aryl, HET, $C_{6-4}$ alkyl$N(C_{1-6}$ alkyl$)_{0-2}$, Aryl-$C_{1-6}$ alkyl, $C_{1-6}$ alkyl$OH$, or $C_{1-4}$ alkyl$OC_{1-6}$ alkyl, or $R^8$ and $R^9$ are taken in combination with the nitrogen atom to which they are attached and represent a 3-10 membered ring system containing 1-4 heteroatoms selected from O, S, N and optionally substituted with 1-2 oxo groups, and 1-3 groups selected from $C_{1-4}$ alkyl, HET, $CO_2R^c$ and $C(O)N(R)_2$, said alkyl and alkyl portions being optionally substituted with 1-3 groups selected from halo, $C_{1-3}$ alkyl, hydroxyl $C_{1-3}$ alkyl, $C_{1-3}$ alkoxy, $C_{1-3}$ alkoxy $C_{1-3}$ alkyl and Aryl$^1$, and $R^{10}$ represents H, $C_{1-20}$ alkyl, aryl or HU, with aryl and HET as previously described;

a compound having Formula 17.3 (referred to herein as caspase-1 inhibitor having Formula 17.3):

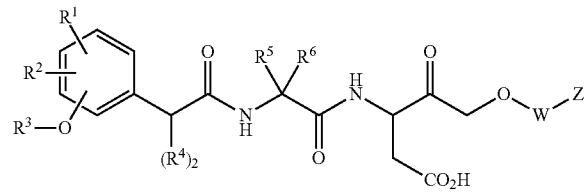

Formula 17.3 or single stereoisomers, mixtures of stereoisomers, pharmaceutically acceptable salts or prodrugs thereof, wherein W is a bond, —$CH_2$—; —$C(O)$— or —$C(O)CH_2$—; Z is selected from the group consisting of: (1) H, (2) $C_{1-11}$alkyl, (3) $C_{3-11}$cycloalkyl or a benzofused analog thereof, (4) phenyl or naphthyl, and (5) $HET^1$, wherein $HET^1$ represents a 5- to 10-membered mono- or bicyclic, aromatic or non-aromatic ring, or a benzofused analog thereof, containing 1-3 heteroatoms selected from O, S and N, groups (2), (3) and (5) above are optionally substituted with 1-2 oxo groups, groups (2)-(5) above are further optionally substituted with 1-3 substituents independently selected from the group consisting of: (a) halo, (b) nitro, (c) hydroxy, (d) $C_{1-4}$alkyl, (e) $C_{1-4}$alkoxy, (f) $C_{1-4}$alkylthio, (g) $C_{3-6}$cycloalkyl, (h) phenyl or naphthyl, (i) phenoxy, (j) benzyl, (k) benzyloxy, and (l) a 5 or 6-membered aromatic or non-aromatic ring containing from 1-3 heteroatoms selected from O, S and N, groups (d)-(g) above are optionally substituted with oxo and 1-3 substituents independently selected from halo and $C_{1-4}$alkoxy, groups (h)-(l) above are optionally substituted with 1-3 substituents independently selected from halo and $C_{1-4}$alkyl, and group (4) is further optionally substituted up to its maximum with halo groups; $R^1$ and $R^2$ are independently selected from the group consisting of: (1) H, (2) halo, (3) hydroxy, (4) nitro, (5) cyano, (6) $C_{1-10}$alkyl, $C_{3-10}$cycloalkyl, $C_{1-10}$alkoxy, —$S(O)_{0-2}$ $C_{1-10}$alkyl or —$NHC_{1-10}$ alkyl, each optionally substituted with 1-2 oxo or carboxy groups and further optionally substituted with 1-3 substituents independently selected from the group consisting of: (a) halo, (b) hydroxy, (c) cyano, (d) $C_{1-4}$ alkoxy, (e) —$NHR^7$, wherein $R^7$ is H or $C_{1-5}$alkyl, said $C_{1-5}$alkyl optionally substituted with —$NHR^8$, wherein $R^8$ is $C_{1-5}$alkyl optionally substituted with oxo and further optionally substituted with a 5- to 10-membered mono- or bicyclic, aromatic or non-aromatic ring, or a benzofused analog thereof, containing 1-3 heteroatoms selected from O, S and N, and optionally substituted with oxo, (f) —$S(O)_{0-2}C_{1-4}$alkyl, and (g) $HET^2$, wherein $HET^2$ represents a 5- to 7-membered aromatic or non-aromatic ring containing 1-4 heteroatoms selected from O, S and $NR^7$, wherein $R^7$ is H or $C_{1-5}$alkyl, said $HET^2$ being optionally substituted with oxo and further optionally substituted with 1-2 substituents independently selected from halo and $C_{1-4}$alkyl, said $C_{1-4}$alkyl being optionally substituted with 1-3 halo groups, (7) phenoxy or —$S(O)_{0-2}$-phenyl, (8) benzyloxy or —$S(O)_{0-2}$-benzyl, (9) benzoyl, (10) phenyl or naphthyl, (11) —$O$-$HET^2$ or —$S$-$HET^2$, said $HET^2$ being optionally substituted with oxo and further optionally substituted as defined below, and (12) $HET^3$, wherein HET is a 5- or 6-membered aromatic or non-aromatic ring, or a benzofused analog thereof, containing from 1 to 4 heteroatoms selected from O, S and N, said $HET^3$ being optionally substituted with oxo and further optionally substituted as defined below, groups (7)-(12) above are each optionally substituted with 1-2 substituents independently selected from the group consisting of: halo, cyano, $C_{1-4}$alkyl and $C_{1-4}$alkoxy, said $C_{1-4}$alkyl and $C_{1-4}$alkoxy being optionally substituted with 1-3 halo groups; or $R^1$ and $R^2$ may be taken in combination and represent a fused ring as shown below:

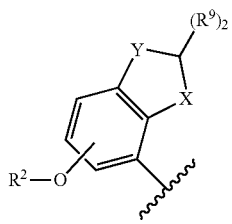

wherein Y and X are independently selected from the group consisting of —C(R$^{10}$)$_2$—, —C(R$^{10}$)$_2$C(R$^{10}$)$_2$—, NR$^{11}$—, —O— and —S—, R$^3$ is as defined below, each R$^9$ is independently selected from H and C$_{1-4}$alkyl, each R$^{10}$ is independently selected from H and C$_{1-4}$alkyl, and R$^{11}$ is H or C$_{1-4}$alkyl, or one R$^9$ may be joined with either one R$^{10}$ or R$^{11}$ on an adjacent atom to form a double bond; R$^3$ is C$_{1-10}$alkyl, optionally substituted with 1-2 oxo or carboxy groups and further optionally substituted with 1-3 substituents independently selected from the group consisting of: (a) halo, (b) hydroxy, (c) cyano, (d) C$_{1-4}$ alkoxy, (e) —NHR$^7$, wherein R$^7$ is H or C$_{1-5}$alkyl, said C$_{1-5}$alkyl optionally substituted with —NHR$^8$, wherein R$^8$ is C$_{1-5}$alkyl optionally substituted with oxo and further optionally substituted with a 5- to 10-membered mono- or bicyclic, aromatic or non-aromatic ring, or a benzofused analog thereof, containing 1-3 heteroatoms selected from O, S and N, and optionally substituted with oxo, (f) —S(O)$_{0-2}$ C$_{1-4}$alkyl, and (g) HET$^2$, wherein HET$^2$ represents a 5- to 7-membered aromatic or non-aromatic ring containing 1-4 heteroatoms selected from O, S and NR$^7$, wherein R$^7$ is H or C$_{1-5}$alkyl, said HET$^2$ being optionally substituted with oxo and further optionally substituted with 1-2 substituents independently selected from halo or C$_{1-4}$alkyl, said C$_{1-4}$alkyl being optionally substituted with 1-3 halo groups, each R$^4$ is independently selected from the group consisting of: H, halo, hydroxy, C$_{1-6}$alkyl and C$_{1-4}$alkoxy, said C$_{1-6}$alkyl and C$_{1-4}$alkoxy being optionally substituted with oxo and further optionally substituted with 1-3 halo groups; and R$^5$ is selected from the group consisting of: H, phenyl, naphthyl, C$_{1-6}$alkyl optionally substituted with OR$^{12}$ and 1-3 halo groups, and C$_{5-7}$cycloalkyl optionally containing one heteroatom selected from O, S and NR$^{13}$, wherein R$^{12}$ is selected from the group consisting of: H, C$_{1-5}$alkyl optionally substituted with 1-3 halo groups, and benzyl optionally substituted with 1-3 substituents independently selected from halo, C$_{1-4}$alkyl and C$_{1-4}$alkoxy, and R$^{13}$ is H or C$_{1-4}$alkyl optionally substituted with 1-3 halo groups; and R$^6$ represents H; or in the alternative, R$^5$ and R$^6$ are taken in combination and represent a ring of 4-7 members, said ring optionally containing one heteroatom selected from O, S and NR$^{13}$;

a compound (aspartic acid analog as caspase-1 (ICE) inhibitor) having Formula 17.4 (referred to herein as caspase-1 inhibitor having Formula 17.4):

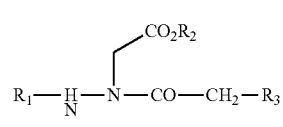

Formula 17.4 or single stereoisomers, mixtures of stereoisomers, pharmaceutically acceptable salts or prodrugs thereof, wherein, R$_2$ is H or alkyl; R$_3$ is a leaving group such as halogen; R$_1$ is heteroaryl-CO or an amino acid residue;

a compound (peptidic ketone as ICE inhibitor) having Formula 17.5 (referred to herein as caspase-1 inhibitor having Formula 17.5):

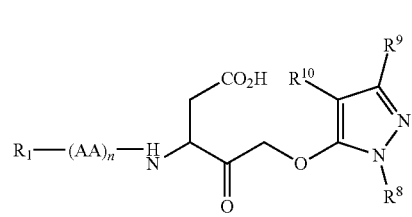

Formula 17.5 or single stereoisomers, mixtures of stereoisomers, pharmaceutically acceptable salts or prodrugs thereof, wherein n is 0-2; each AA is independently L-valine or L-alanine; R$_1$ is selected from the group consisting of N-benzyloxycarbonyl and other groups; R$_8$, R$_9$, R$_{10}$ are each independently hydrogen, lower alkyl and other groups;

a compound (peptide phenylalkyl ketone as reversible inhibitor of ICE) having Formula 17.6 (referred to herein as caspase-1 inhibitor having Formula 17.6):

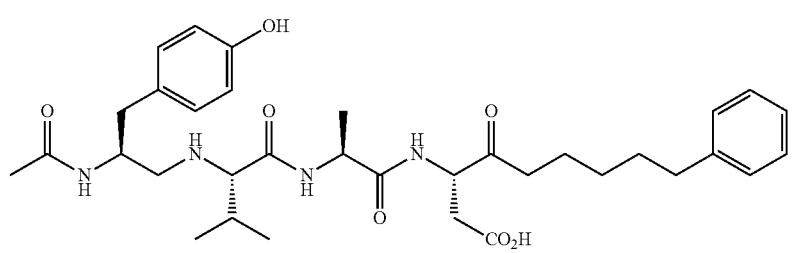

Formula 17.6 or single stereoisomers, mixtures of stereoisomers, pharmaceutically acceptable salts or prodrugs thereof;

a compound (peptide acyloxymethyl ketone) having Formula 17.7 (referred to herein as caspase-1 inhibitor having Formula 17.7):

Formula 17.7

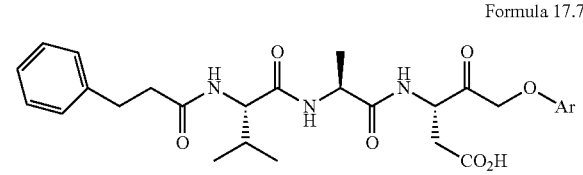

or single stereoisomers, mixtures of stereoisomers, pharmaceutically acceptable salts or prodrugs thereof; wherein Ar is COPh-2,6-(CF$_3$)$_2$, COPh-2,6-(CH$_3$)$_2$, Ph-F$_5$ and other groups;

a compound (PI aspartate-based peptide α-((2,6-dichlorobenzoyl)oxy)methyl ketone as a potent time-dependent inhibitor of ICE) having Formula 17.8 (referred to herein as caspase-1 inhibitor having Formula 17.8):

Formula 17.8

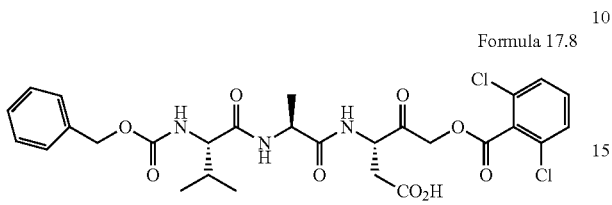

or single stereoisomers, mixtures of stereoisomers, pharmaceutically acceptable salts or prodrugs thereof;

a compound (activated ketone as a potent reversible inhibitor of ICE) having Formula 17.9 (referred to herein as caspase-1 inhibitor having Formula 17.9):

Formula 17.9

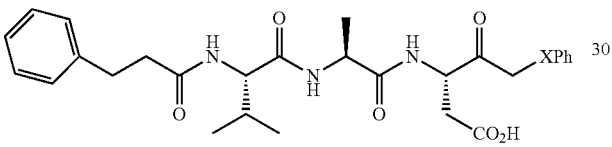

or single stereoisomers, mixtures of stereoisomers, pharmaceutically acceptable salts or prodrugs thereof; wherein X is NH(CH$_2$)$_2$, OCO(CH$_2$)$_2$, S(CH$_2$)$_3$ and other groups;

a compound ((1-phenyl-3-(trifluoromethyl)pyrazol-5-yl)oxy)methyl ketone as an irreversible inhibitor of ICE) having Formula 17.10 (referred to herein as caspase-1 inhibitor having Formula 17.10):

Formula 17.10

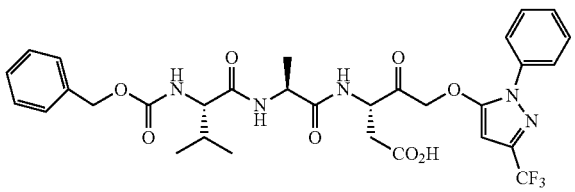

or single stereoisomers, mixtures of stereoisomers, pharmaceutically acceptable salts or prodrugs thereof;

a compound (N-acyl-aspartic acid ketone) having Formula 17.11 (referred to herein as caspase-1 inhibitor having Formula 17.11):

Formula 17.11

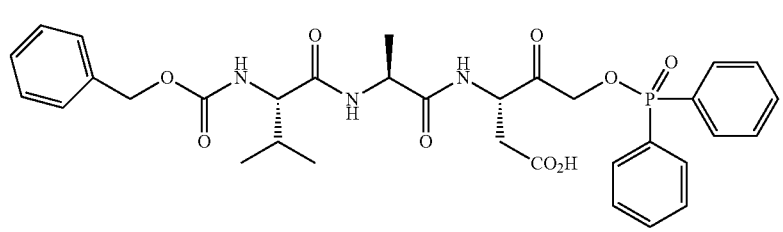

or single stereoisomers, mixtures of stereoisomers, pharmaceutically acceptable salts or prodrugs thereof; wherein XR$_2$ is NH(CH$_2$)$_2$Ph, OCO(CH$_2$)$_2$ cyclohexyl and other groups;

a compound (inhibitor of ICE exemplified by N-acyl-aspartyl aryloxymethyl ketone) having Formula 17.12 (referred to herein as caspase-1 inhibitor having Formula 17.12):

Formula 17.12 or single stereoisomers, mixtures of stereoisomers, pharmaceutically acceptable salts or prodrugs thereof;

a compound (aspartyl α-((diphenylphosphinyl)oxy)methyl ketone as an irreversible inhibitor of ICE) having Formula 17.13 (referred to herein as caspase-1 inhibitor having Formula 17.13):

Formula 17.13 or single stereoisomers, mixtures of stereoisomers, pharmaceutically acceptable salts or prodrugs thereof;

a compound (α-((tetronoyl)oxy)- and α-((tetramoyl)oxy)methyl ketones as inhibitors of ICE) having Formula 17.14 and 17.15, respectively (referred to herein as caspase-1 inhibitor having Formula 17.14 and 17.15, respectively):

Formula 17.14

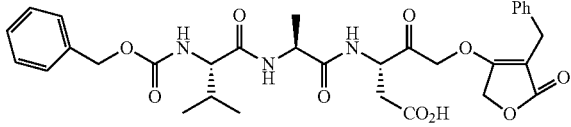

Formula 17.15

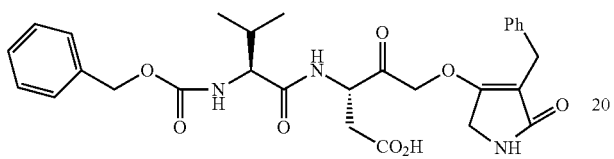

or single stereoisomers, mixtures of stereoisomers, pharmaceutically acceptable salts or prodrugs thereof;

a compound (peptidomimetic aminomethylene ketone as inhibitor of ICE) having Formula 17.16 (referred to herein as caspase-1 inhibitor having Formula 17.16):

Formula 17.16

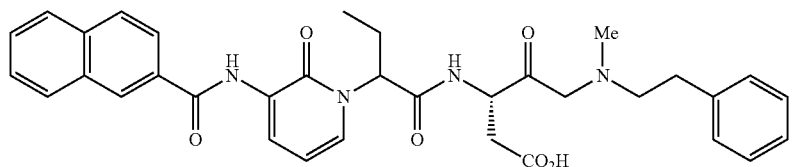

or single stereoisomers, mixtures of stereoisomers, pharmaceutically acceptable salts or prodrugs thereof;

a compound (peptide based ICE inhibitor with the P1 carboxyl group converted to an amide) having Formula 17.17 (referred to herein as caspase-1 inhibitor having Formula 17.17):

Formula 17.17

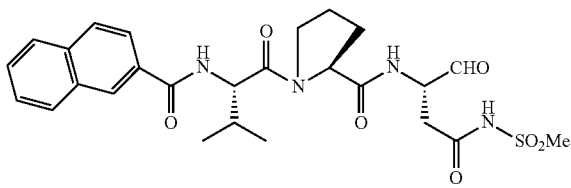

or single stereoisomers, mixtures of stereoisomers, pharmaceutically acceptable salts or prodrugs thereof;

a compound having Formula 17.18 (referred to herein as caspase-1 inhibitor having Formula 17.18):

R-A$_1$-A$_2$-X-A$_3$      Formula 17.18 or single stereoisomers, mixtures of stereoisomers, pharmaceutically acceptable salts or prodrugs thereof; wherein R is a protecting group or optionally substituted benzyloxy; A$_1$ is an α-hydroxy or α-amino acid residue or a radical shown below:

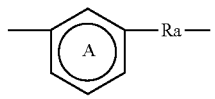

wherein ring A is optionally substituted by hydroxy or C$_{1-4}$ alkoxy and R$_a$ is CO or CS; A$_2$ is an α-hydroxy or .α-amino acid residue or A$_1$ and A$_2$ form together a pseudo-dipeptide or a dipeptide mimetic residue; X is a residue derived from Asp; A$_3$ is —CH$_2$—X$_1$—CO—Y$_1$, —CH$_2$—O—Y$_2$, —CH$_2$—S—Y$_3$, wherein X$_1$ is O or S; Y$_1$, Y$_2$ or Y$_3$ is cycloaliphatic residue, and optionally substituted aryl;

a compound (dipeptide) having Formula 17.19 (referred to herein as caspase-1 inhibitor having Formula 17.19):

Formula 17.19

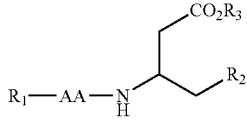

or single stereoisomers, mixtures of stereoisomers, pharmaceutically acceptable salts or prodrugs thereof; wherein R$_1$ is an N-terminal protecting group; AA is a residue of any natural or non-natural α-amino acid, β-amino acid, derivatives of an α-amino acid or β-amino acid; R$_2$ is H or CH$_2$R$_4$ where R$_4$ is an electronegative leaving group, and R$_3$ is alkyl or H, provided that AA is not His, Tyr, Pro or Phe;

a compound (dipeptide) having Formula 17.20 (referred to herein as caspase-1 inhibitor having Formula 17.20):

Formula 17.20

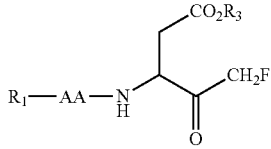

or single stereoisomers, mixtures of stereoisomers, pharmaceutically acceptable salts or prodrugs thereof; wherein R$_1$ is an N-terminal protecting group; AA is a residue of a non-natural α-amino acid or β-amino acid; R$_2$ is an optionally substituted alkyl or H. Exemplary inhibitors of caspases and apoptosis include Boc-Phg-Asp-fmk, Boc-(2-F-Phg)Asp-fmk, Boc-(F$_3$-Val)-Asp-fmk, Boc-(3-F-Val)Asp-fmk, Ac-Phg-Asp-fmk, Ac-(2-F-Phg)-Asp-fmk, Ac-(F$_3$-Val)-Asp-fmk, Ac-(3-F-Val)-Asp-fmk, Z-Phg-Asp-fmk, Z-(2-F-Phg)-Asp-fmk, Z-(F$_3$-Val)-Asp-fin, Z-Chg-Asp-fmk, Z-(2-Fug)-Asp-fmk, Z-(4-F-Phg)-Asp-fmk, Z-(4-Cl-Phg)-Asp-fmk, Z-(3-Thg)-Asp-fmk, Z-(2-Fua)-Asp-fmk, Z-(2-Tha)-Asp-fmk, Z-(3-Fua)-Asp-fmk, Z-(3-Tha)-Asp-fmk, Z-(3-Cl- Ala)-Asp-fmk, Z-(3-F-Ala)-Asp-fmk, Z-(3-Ala)Asp-fmk, Z-(3-F-3-Me-Ala)-Asp-fmk, Z-(3-C-3-F-Ala)-Asp-fmk, Z-(2-Me-Val)Asp-fmk, Z-(2-Me-Ala)-Asp-fmk, Z-(2-i-Pr-β-Ala)-Asp-fmk, Z-(3-Ph-β-Ala)-Asp-fmk, Z-(3-CN-Ala)-Asp-fmk, Z-(1-Nal)-Asp-fmk, Z-Cha-Asp-fmk, Z-(3-CF$_3$-Ala)-Asp-fmk, Z-(4-CF$_3$-Phg)-Asp-fmk, Z-(3-Me$_2$N-Ala)-Asp-fmk, Z-(2-Abu)-Asp-fmk, Z-Tle-Asp-fmk, Z-Cpg-Asp-fmk, Z-Cbg-Asp-fmk, Z-Thz-Asp-fmk, Z-(3-F-Val)-Asp-fmk, and Z-(2-Thg)-Asp-fmk; where Z is benzyloxycarbonyl, BOC is tert-butoxycarbonyl, Ac is acetyl, Phg is phenylglycine, 2-F-Phg is (2-fluorophenyl)glycine, F$_3$-Val is 4,4,4-trifluorovaline, 3-F-Val is 3-fluorovaline, 2-Thg is (2-thienyl)glycine, Chg is cyclohexylglycine, 2-Fug is (2-furyl)glycine, 4-F-Phg is (4-fluorophenyl)glycine, 4-Cl-Phg is (4-chlorophenyl)glycine, 3-Thg is (3-thienyl)glycine, 2-Fua is (2-furyl)alanine, 2-Tha is (2-thienyl)alanine, 3-Fua is (3-furyl)alanine, 3-Tha is (3-thienyl)alanine, 3-Cl-Ala is 3-chloroalanine, 3-F-Ala is 3-fluoroalanine, F$_3$-Ala is 3,3,3-trifluoroalanine, 3-F-3-Me-Ala is 3-fluoro-3-methylalanine, 3-C$_{1-3}$-F-Ala is 3-chloro-3-fluoroalanine, 2-Me-Val is 2-methylvaline, 2-Me-Ala is 2-methylalanine, 2-i-Pr-β-Ala is 3-amino-2-isopropylpropionic acid, 3-Ph-β-Ala is 3-amino-3-phenylpropionic acid, 3-CN-Ala is 3-cyanoalanine, 1-Nal is 3-(1-naphthyl)-alanine, Cha is cyclohexylalanine, 3-CF$_3$-Ala is 2-amino-4,4,4-trifluorobutyric acid, 4-CF$_3$-Phg is 4-trifluoromethylphenylglycine, 3-Me$_2$N-Ala is 3-dimethylamino-alanine, 2-Abu is 2-aminobutyric acid, Tle is tert-leucine, Cpg is cyclopentylglycine, Cbg is cyclobutylglycine, and Thz is thioproline;

compound having Formula 17.21 (referred to herein as caspase-1 inhibitor having Formula 17.21):

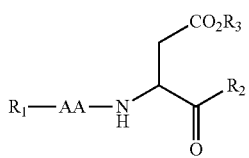

Formula 17.21 or single stereoisomers, mixtures of stereoisomers, pharmaceutically acceptable salts or prodrugs thereof; wherein R$_1$ is an N-terminal protecting group; AA is a residue of any natural or non-natural α-amino acid, β-amino acid, derivatives of an α-amino acid or β-amino acid; R$_2$ is H or CH$_2$R$_4$ where R$_4$ is an electronegative leaving group; and R$_3$ is alkyl or H; examples of such caspase-1 inhibitors include Boc-Ala-Asp-CH$_2$F, Boc-Val-Asp-CH$_2$F, Boc-Leu-Asp-CH$_2$F, Ac-Val-Asp-CH$_2$F, Ac-Ile-Asp-CH$_2$F, Ac-Met-Asp-CH$_2$F, Cbz-Val-Asp-CH$_2$F, Cbz-#-Ala-Asp-CH$_2$F, Cbz-Leu-Asp-CH$_2$F, Cbz-Ile-Asp-CH$_2$F, Boc-Ala-Asp(OMe)-CH$_2$F, Boc-Val-Asp(OMe)-CH$_2$F, Boc-Leu-Asp(OMe)-CH$_2$F, Ac-Val-Asp(OMe)-CH$_2$F, Ac-Ile-Asp(OMe)-CH$_2$F, Ac-Met-Asp(OMe)-CH$_2$F, Cbz-Val-Asp(OMe)-CH$_2$F, Cbz-g-Ala-Asp(OMe)-CH$_2$F, Cbz-Leu-Asp(OMe)CH$_2$F or Cbz-Ile-Asp(OMe)-CH$_2$F;

compound having Formula 17.22 (referred to herein as caspase-1 inhibitor having Formula 17.22):

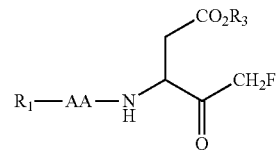

Formula 17.22 or single stereoisomers, mixtures of stereoisomers, pharmaceutically acceptable salts or prodrugs thereof; wherein R$_1$ is an N-terminal protecting group; AA is a residue of a non-natural α-amino acid or β-amino acid; and R$_2$ is an optionally substituted alkyl or H; examples of such caspase-1 inhibitors include Boc-Phg-Asp-fmk, Boc-(2-F-Phg)-Asp-fmk, Boc-(F$_3$-Val)-Asp-fmk, Boc-(3-F-Val)-Asp-fmk, Ac-Phg-Asp-fmk, Ac-(2-F-Phg)-Asp-fmk, Ac-(F$_3$-Val)-Asp-fmk, Ac-(3-F-Val)Asp-fmk, Z-Phg-Asp-fmk Z-(2-F-Phg)-Asp-fmk, Z-(F$_3$-Val)-Asp-fmk, Z-Chg-Asp-fmk, Z-(2-Fug)-Asp-fmk, Z-(4-F-Phg)-Asp-fmk, Z-(4-Cl-Phg)-Asp-fmk, Z-3-Thg)-Asp-fmk, Z-(2-Fua)-Asp-fmk, Z-(2-Tha)-Asp-fmk, Z-3-Fua)-Asp-fmk, Z-(3-Tha)-Asp-fmk, Z-(3-Cl-Ala)-Asp-fmk, Z-(3-F-Ala)-Asp-fmk, Z-(F$_3$-Ala)-Asp-fmk, Z-(3-F-3-Me-Ala)-Asp-fmk, Z-(3-C$_{1-3}$-F-Ala)-Asp-fmk, Z-(2-Me-Val)Asp-ink, Z-(2-Me-Ala)-Asp-fmk, Z-(2-i-Pr-β-Ala)-Asp-fmk, Z-(3-Ph-β-Ala)-Asp-fmk, Z-(3-CN-Ala)-Asp-fmk, Z-(1-Nal)-Asp-fmk, Z-Cha-Asp-fmk, Z-3-CF$_3$-Ala)Asp-fmk, Z-(4-CF$_3$-Phg)-Asp-fmk, Z-(3-Me$_2$N-Ala)-Asp-fmk, Z-(2-Abu)-Asp-ink, Z-Tle-Asp-fmk, Z-Cpg-Asp-fmk, Z-Cbg-Asp-fmk, Z-Thz-Asp-fmk, Z-(3-F-Val)-Asp-fmk, and Z-2-Thg)Asp-fmk.

18. Caspase-1 Inhibitor Having Formula 18

In some embodiments of the present invention a caspase-1 inhibitor for use in a method of the present invention is a compound described in published US2009/0149436 and US2004/0242494 (incorporated by reference in their entireties). Preferred compounds described in published US2009/0149436 and US2004/0242494 for use in the methods of the present invention are referred to herein as caspase-1 inhibitor having Formula 18A and 18B, respectively:

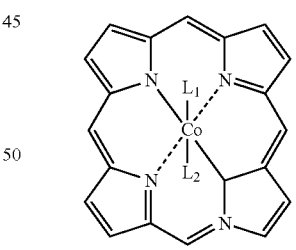

A

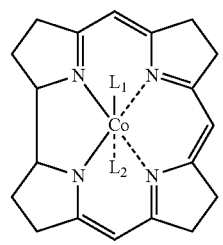

B

Formula 18A (top) and 18B (bottom)

or single stereoisomers, mixtures of stereoisomers, pharmaceutically acceptable salts or prodrugs thereof; wherein a porphyrin ring structure or a choline ring structure is coordinated to a cobalt atom, $L_1$ and $L_2$ are each independently, any ligand relative to cobalt, which may or may not be present, and when it is present, each independently, for example, $H_2O$, a cyano group, a hydroxyl group, a methyl group, an imidazolyl group or an adenosyl group;

a compound having Formula 18.1 (referred to herein as caspase-1 inhibitor having Formula 18.1):

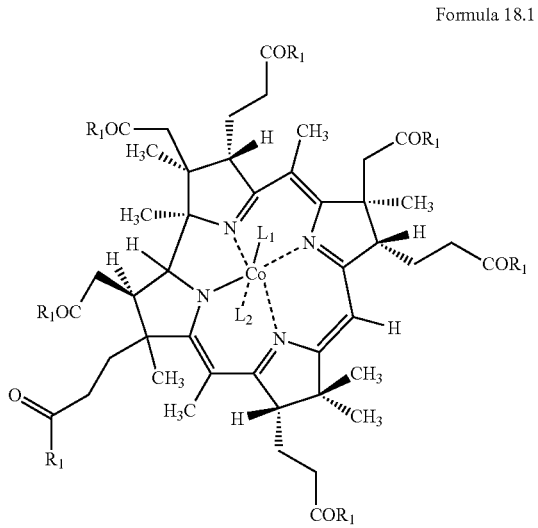

Formula 18.1 or single stereoisomers, mixtures of stereoisomers, pharmaceutically acceptable salts or prodrugs thereof; wherein the compound is a "cobyrinic acid derivative", each $R_1$ is independently, for example, a hydroxyl group, an amino group or a lower alkoxy group having 1 to 6 carbon atoms (e.g., methoxy, ethoxy, propoxy, isopropoxy, butoxy, isobutoxy, sec-butoxy, tert-butoxy, pentyloxy, isopentyloxy, neopentyloxy, hexyloxy etc.), $R_2$ is, for example, a hydroxyl group, an amino group, an optionally substituted alkylamino group or an optionally substituted or esterified hydroxyalkylamino group, and $L_1$ and $L_2$ are each independently any ligand relative to cobalt, which may or may not be present, and when it is present, each independently, for example, $H_2O$, a cyano group, a hydroxyl group, a methyl group, an imidazolyl group or an adenosyl group—the "alkylamino group" of the above-mentioned "optionally substituted alkylamino group" is an amino group having 1 or 2 lower alkyl groups having 1 to 6 carbon atoms (e.g., methyl, ethyl, propyl, isopropyl, butyl, isobutyl, sec-butyl, tert-butyl, pentyl, isopentyl, neopentyl, hexyl and the like) and, for example, methylamino, ethylamino, propylamino, isopropylamino, butylamino, isobutylamino, sec-butylamino, tert-butylamino, pentylamino, isopentylamino, neopentylamino, hexylamino and the like can be mentioned, the "hydroxyalkylamino group" of the above-mentioned "optionally substituted or esterified hydroxyalkylamino group" means the above-mentioned "alkylamino group" having a hydroxyl group at a substitutable position and, for example, hydroxymethylamino, 1-hydroxyethylamino, 2-hydroxyethylamino, 1-hydroxypropylamino, 2-hydroxypropylamino, 3-hydroxypropylamino and the like can be mentioned, the substituent and the number thereof that the hydroxyalkylamino group may have are not particularly limited, the hydroxy moiety of the hydroxyalkylamino group may further form an ester with α-D-ribofuranose 3-phosphoric acid, imidazolyl-α-D-ribofuranose 3-phosphoric acid, 5,6-dimethylbenzimidazolyl-α-D-ribofuranose 3-phosphoric acid and the like; examples of these cobyrinic acid derivatives include, but not limited to, cobinamide, cobamide, cobyrinamide, cobyrinic acid, cobyric acid, cobinic acid, cobamic acid and cobalamin, and cobyrinic acid derivatives having a ligand to the cobalt atom of these compounds, such as dicyanocobinamide, adenosylcobyrinamide, imidazolylcobalamin, cobalt protoporphyrin, cyanoimidazolylcobamide, cyanocobalamin and the like; a "cobyrinic acid derivative" wherein all $R_1$ in the above-mentioned formula are amino groups—examples of the cobyric acid derivatives include, but not limited to, cobyric acid derivatives such as cobinamide, cobamide, cobyrinamide, cobyric acid, cobalamin and the like;

a compound having Formula 18.2 (referred to herein as caspase-1 inhibitor having Formula 18.2):

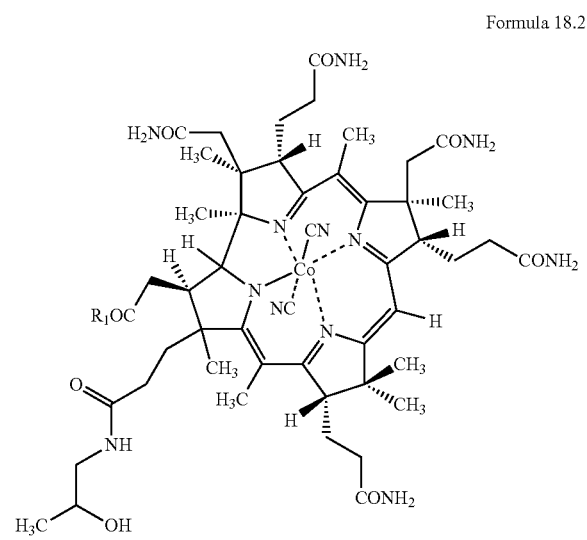

Formula 18.2 or single stereoisomers, mixtures of stereoisomers, pharmaceutically acceptable salts or prodrugs thereof; wherein the "cobyric acid derivative" to be used as the caspase-1 inhibitor is dicyanocobinamide.

19. Caspase-1 Inhibitor VX-765 and Related Compounds

In some embodiments of the present invention a caspase-1 inhibitor for use in a method of the present invention is VX-765 or single stereoisomers, mixtures of stereoisomers, pharmaceutically acceptable salts or prodrugs thereof. VX-765 is also known as is (S)-1-((S)-2-{[1-(4-Amino-3-chloro-phenyl)-methanoyl]-amino}-3,3-dimethyl-butanoyl)-pyrrolidine-2-carboxylic acid ((2R,3S)-2-ethoxy-5-oxo-tetrahydro-furan-3-yl)-amide. It is currently being considered as a treatment for epilepsy.

In some embodiments of the present invention a caspase-1 inhibitor for use in a method of the present invention is a compound described in published US2006/0128696 (herewith incorporated by reference in its entirety). Preferred compounds described in published US2006/0128696 for use in the methods of the present invention are referred to herein as caspase-1 inhibitor having Formula 19:

Formula 19

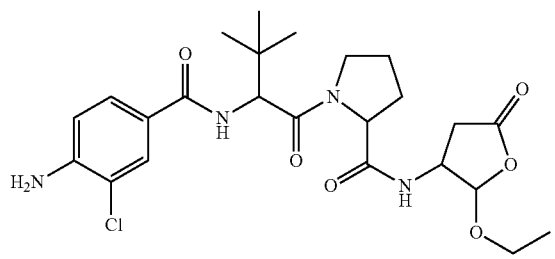

or single stereoisomers, mixtures of stereoisomers, pharmaceutically acceptable salts or prodrugs thereof.

The structure for caspase-1 inhibitor having Formula 19 is meant to include all stereochemical forms of the compound; i.e., the R and S configurations for each asymmetric center. Therefore, single stereochemical isomers as well as enantiomeric and diastereomeric mixtures of the present compound are within the scope of the invention. A preferred isomer is caspase-1 inhibitor having Formula 19A which has the "S" configuration at the carbon bearing the tert-butyl group, has the "S" configuration at the 2-position of the proline ring, has the "S" configuration at the 3-position of the furanone ring, and has the "R" configuration at the 2-ethoxy position of the furanone ring, as shown below.

Formula 19A

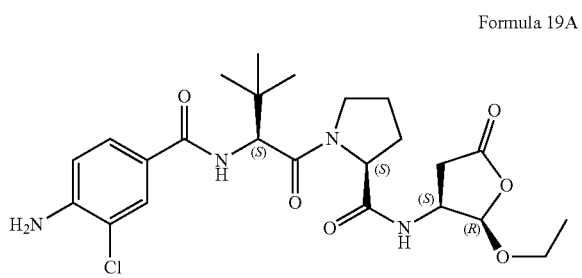

Another preferred isomer is caspase-1 inhibitor having Formula 19B.

Formula 19B

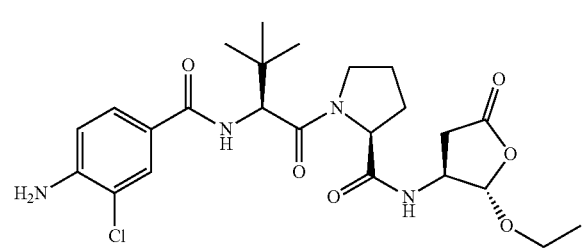

Preparation and purification of VX-765 has been described in U.S. Pat. No. 7,417,029 (herewith incorporated by reference in its entirety).

VX-765 is known as an orally active IL-converting enzyme/caspase-1 inhibitor. Recently, Stack et al. described that VX-765 blocked IL-1β secretion, however, did not disclose its use in a method of the present invention (Stack et al., J. Immunol (2005) 175:2630-2634; incorporated herein by reference)

VX-765 (synthesized by Vertex Pharmaceuticals) can be prepared as a DMSO stock solution and diluted to appropriate concentrations in medium, as described by Stack et al. VX-765 is a prodrug that is converted to its active metabolite, VRT-043198, both in vivo and in vitro by enzymatic and hydrolytic cleavage (Stack et al., J. Immunol (2005) 175: 2630-2634). VRT-043198 binds to the catalytic site and competitively inhibits ICE/caspase-1 with an inhibition constant $(K_i)$=0.8 nM. VX-765 inhibits the release of LPS-induced IL-1β and IL-18 by human PBMCs with an $IC_{50}$ of ~0.7 μM and reduces inflammatory response in murine models of inflammatory disease (Stack et al., J. Immunol (2005) 175: 2630-2634).

In some embodiments of the present invention a caspase-1 inhibitor for use in a method of the present invention is a compound described in published US2006/0128696 (herewith incorporated by reference in its entirety). Preferred compounds described in published US2006/0128696 for use in the methods of the present invention are referred to herein as caspase-1 inhibitor having Formula 20:

Formula 20

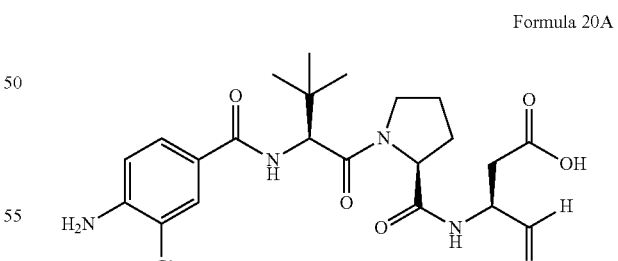

or single stereoisomers, mixtures of stereoisomers, pharmaceutically acceptable salts or prodrugs thereof, including Formula 20A 20. Caspase-1 Inhibitor Having Formula 21

In some embodiments of the present invention a caspase-1 inhibitor for use in a method of the present invention is a compound described in published US2006/0128696 (herewith incorporated by reference in its entirety). Preferred compounds described in published US2006/0128696 for use in the methods of the present invention are referred to herein as caspase-1 inhibitor having Formula 21:

Formula 21

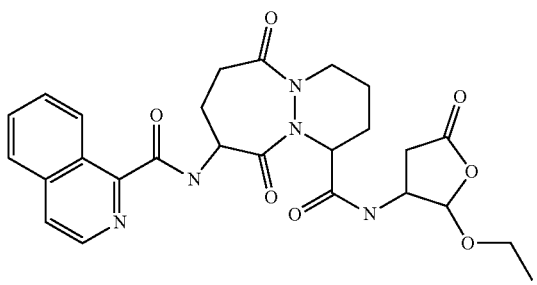

or single stereoisomers, mixtures of stereoisomers, pharmaceutically acceptable salts or prodrugs thereof, including Formula 21A

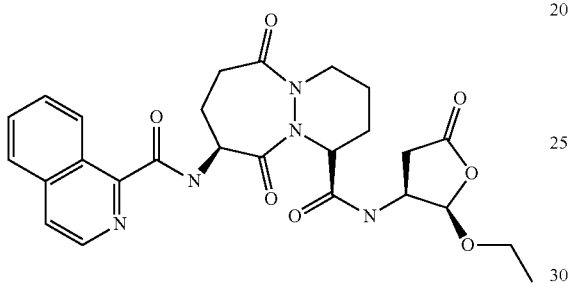

21. Caspase-1 Inhibitor Having Formula 22

In some embodiments of the present invention a caspase-1 inhibitor for use in a method of the present invention is a compound described in published US 2006/0128696 A1 (incorporated by reference in its entirety) and referred to herein as caspase-1 inhibitor having Formula 22:

Formula 22

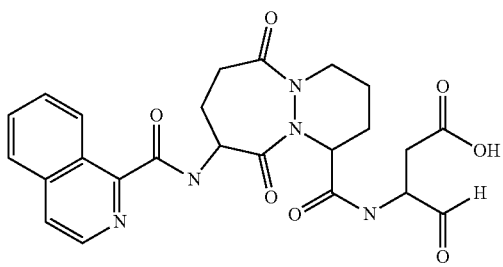

or single stereoisomers, mixtures of stereoisomers, pharmaceutically acceptable salts or prodrugs thereof, including Formula 22A

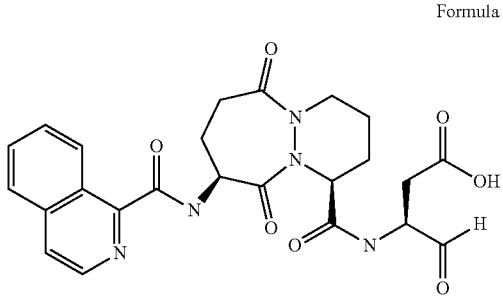

22. Caspase-1 Inhibitor Having Formula 23 (I), 23 (II) or 23 (III)

In some embodiments of the present invention a caspase-1 inhibitor for use in a method of the present invention is a compound described in published PCT application WO00/55114 (PCT/US00/06398; herewith incorporated by reference in its entirety). Preferred compounds described in published PCT application WO00/55114 for use in the methods of the present invention are referred to herein as caspase-1 inhibitor having Formula 23(I), 23(II) or 23(III):

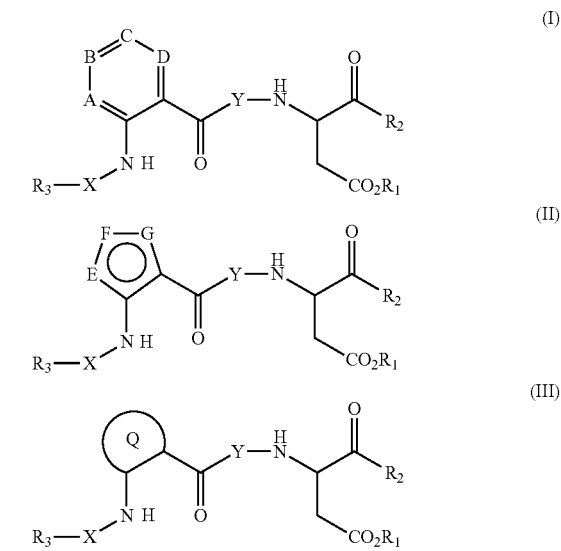

Formula 23(I), 23(II), 23(III)

or single stereoisomers, mixtures of stereoisomers, pharmaceutically acceptable salts or prodrugs thereof, wherein $R_1$, is an optionally substituted alkyl or hydrogen; $R_3$ is an N-protecting group; $R_2$ is hydrogen or optionally substituted alkyl; Q is an optionally substituted saturated or partially saturated carbocycle or heterocycle; X is a peptide of 1-4 amino acids or a bond; Y is a peptide of 1-4 amino acids or a bond; A is $CR_6$ or nitrogen; B is $CR_7$ or nitrogen; C is $CR_8$ or nitrogen; D is $CR_9$, or nitrogen; provided that not more than two of A, B, C or D is nitrogen; and $R_6$-$R_9$, independently are hydrogen, halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$) alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, cyano, $C_1$-$C_6$ acylamino, hydroxy, $C_1$-$C_6$ acyloxy, $C_1$-$C_6$ alkoxy, alkylthio, or carboxy; or one of $R_6$ and $R_7$, or $R_7$ and $R_8$, or $R_8$ and $R_9$ are taken together with the carbon atoms to which they are attached to form a carbocycle or heterocycle; E is $R_{14}$, nitrogen, oxygen or sulfur; F is $R_{15}$, nitrogen, oxygen or sulfur; G is $R_{16}$, nitrogen, oxygen or sulfur; provided that only one of E, F, G is nitrogen, oxygen or sulfur and $R_{14}$-$R_{16}$ are independently hydrogen, halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, cyano, $C_1$-$C_6$ acylamino, hydroxy, $C_1$-$C_6$ acyloxy, $C_1$-$C_6$ alkoxy, alkylthio, or carboxy; or one of $R_{14}$ and $R_{15}$, or $R_{15}$ and $R_{16}$, are taken together with the carbon atoms to which they are attached to form a carbocycle or heterocycle.

23. Caspase-1 Inhibitor Having Formula 24

In some embodiments of the present invention a caspase-1 inhibitor for use in a method of the present invention is a compound described in published PCT application WO00/61542 (PCT/US00/09319; herewith incorporated by reference in its entirety). Preferred compounds described in published PCT application WO00/61542 for use in the methods of the present invention are referred to herein as caspase-1 inhibitor having Formula 24:

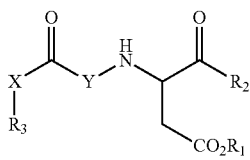

Formula 24 or single stereoisomers, mixtures of stereoisomers, pharmaceutically acceptable salts or prodrugs thereof, wherein $R_1$ is an optionally substituted alkyl or hydrogen; $R_2$ is hydrogen or optionally substituted alkyl; $R_3$ is an alkyl, saturated carbocyclic, partially saturated carbocyclic, aryl, saturated heterocyclic, partially saturated heterocyclic or heteroaryl group, wherein said group is optionally substituted; X is O, S, $NR_4$ or $(CR_4R_5)$ where $R_4$ and $R_5$ are, at each occurrence, independently selected from the group consisting of hydrogen, alkyl and cycloalkyl, and n is 0, 1, 2 or 3; or X is $NR_4$, and $R_3$ and $R_4$ are taken together with the nitrogen atom to which they are attached to form a saturated heterocyclic, partially saturated heterocyclic or heteroaryl group, wherein said group is optionally substituted; or X is $CR_4R_5$, and $R_3$ and $R_4$ are taken together with the carbon atom to which they are attached to form a saturated carbocyclic, partially saturated carbocyclic, aryl, saturated heterocyclic, partially saturated heterocyclic or oxygen-containing heteroaryl group, wherein said group is optionally substituted; and Y is a residue of a natural or non-natural amino acid; provided that when X is O, then $R_3$ is not unsubstituted benzyl or t-butyl; and when X is $CH_2$, then $R_3$ is not hydrogen.

24. Caspase-1 Inhibitor Having Formula 25

In some embodiments of the present invention a caspase-1 inhibitor for use in a method of the present invention is a compound described in U.S. Pat. No. 6,632,962 (herewith incorporated by reference in its entirety). Preferred compounds described in U.S. Pat. No. 6,632,962 for use in the methods of the present invention are referred to herein as caspase-1 inhibitor having Formula 25:

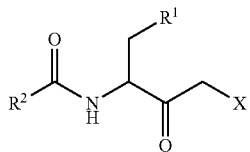

Formula 25 or single stereoisomers, mixtures of stereoisomers, pharmaceutically acceptable salts or prodrugs thereof, wherein X is F or Cl; $R^1$ is COOH, COO(alkyl), or an isostere thereof; and $R^2$ is an aryl group.

25. Caspase-1 Inhibitor Having Formula 26

In some embodiments of the present invention a caspase-1 inhibitor for use in a method of the present invention is a compound described in published PCT application WO01/16093 (PCT/US00/23566; herewith incorporated by reference in its entirety). Preferred compounds described in published PCT application WO01/16093 for use in the methods of the present invention are referred to herein as caspase-1 inhibitor having Formula 26:

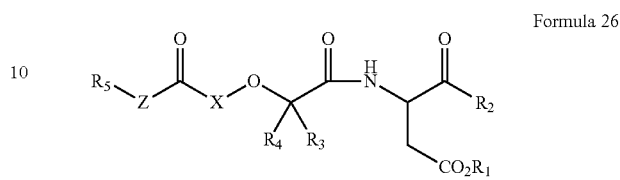

Formula 26 or single stereoisomers, mixtures of stereoisomers, pharmaceutically acceptable salts or prodrugs thereof, wherein $R_1$ is an optionally substituted alkyl or hydrogen; $R_2$ is hydrogen or optionally substituted alkyl; $R_3$ and $R_4$ independently are hydrogen, optionally substituted aryl, optionally substituted heterocycle, optionally substituted heteroaryl, optionally substituted carbocyclic, optionally substituted alkyl, optionally substituted alkenyl, or optionally substituted alkynyl; $R_5$ is an optionally substituted alkyl, optionally substituted carbocyclic, optionally substituted heterocycle, optionally substituted aryl or optionally substituted heteroaryl; Z is O, S, $NR_8$, or $(CR_9R_{10})_n$, where $R_8$, $R_9$ and $R_{10}$ independently are hydrogen, alkyl or cycloalkyl, and n is 0, 1, 2, or 3; and X is a peptide of 1-2 amino acids or a bond.

26. Caspase-1 Inhibitor Having Formula 27

In some embodiments of the present invention a caspase-1 inhibitor for use in a method of the present invention is a compound described in U.S. Pat. No. 7,517,987 (herewith incorporated by reference in its entirety). Preferred compounds described in U.S. Pat. No. 7,517,987 for use in the methods of the present invention are referred to herein as caspase-1 inhibitor having Formula 27:

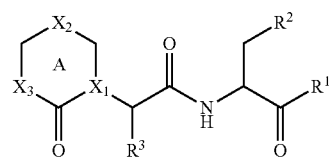

Formula 27 or single stereoisomers, mixtures of stereoisomers, pharmaceutically acceptable salts or prodrugs thereof, wherein where $R^1$ is hydrogen, CN, $CHN_2$, R, or $—CH_2Y$; R is an aliphatic group, a substituted aliphatic group, an aryl group, a substituted aryl group, an aralkyl group, a substituted aralkyl group, a non-aromatic heterocyclic group or a substituted non-aromatic heterocyclic group; Y is an electronegative leaving group or —OR, —SR, —OC=O(R), or —OPO($R^8$)($R^9$); $R^8$ and $R^9$ are independently selected from R or OR; $R^2$ is $CO_2H$, $CH_2CO_2H$, or esters, amides or isosteres thereof; $R^3$ is hydrogen or a $C_{1-6}$ straight chained or branched alkyl; Ring A contains zero to two double bonds, and is optionally fused to a saturated or unsaturated five to seven membered ring containing zero to three heteroatoms; $X_1$ and $X_3$ in Ring A are independently selected from nitrogen or carbon, and $X_2$ is selected from a valence bond, oxygen, sulfur, nitrogen or carbon, wherein any X with suitable valence may bear a substituent; each carbon with suitable valence in Ring A, including the fused ring if present, is independently substituted by hydrogen, halo, R, OR, SR, OH, $NO_2$, CN, $NH_2$, NHR, N(R)$_2$, NHCOR, NHCONHR, NHCON(R)$_2$, NRCOR, NHCO$_2$R, CO$_2$R, CO$_2$H, COR, CONHR, CON(R)$_2$, S(O)$_2$R, SONH$_2$, S(O)R, SO$_2$NHR, NHS(O)$_2$R, =O, =S, =NNHR, =NNR$_2$, =N—OR, =NNHCOR, =NNHCO$_2$R, =NNHSO$_2$R, or =NR; each substitutable nitrogen in Ring A is substituted by hydrogen, R, COR, S(O)$_2$R, or CO$_2$R; provided that when X$_3$ is a carbon, a substituent on X$_3$ is attached by an atom other than nitrogen, and further provided that at least one X in Ring A is a nitrogen.

27. Caspase-1 Inhibitor Having Formula 28

In some embodiments of the present invention a caspase-1 inhibitor for use in a method of the present invention is a compound described in U.S. Pat. Nos. 6,689,784 and 7,074,782 (herewith incorporated by reference in their entireties).). Preferred compounds described in U.S. Pat. Nos. 6,689,784 and 7,074,782 for use in the methods of the present invention are referred to herein as caspase-1 inhibitor having Formula 28:

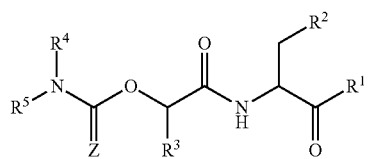

Formula 28 or single stereoisomers, mixtures of stereoisomers, pharmaceutically acceptable salts or prodrugs thereof, wherein Z is oxygen or sulfur; R$^1$ is hydrogen, —CHN$_2$, —R, —CH$_2$OR, —CH$_2$SR, or —CH$_2$Y; R is a C$_{1-12}$ aliphatic, aryl, aralkyl, heterocyclyl, or heterocyclylalkyl; Y is an electronegative leaving group; R$^2$ is CO$_2$H, CH$_2$CO$_2$H, or esters, amides or isosteres thereof; R$^3$ is a group capable of fitting into the S2 sub-site of a caspase; R$^4$ and R$^5$ taken together with the intervening nitrogen form a mono-, bi- or tricyclic hetero ring system having 1-6 heteroatoms selected from nitrogen, oxygen or sulfur.

28. Caspase-1 Inhibitor Having Formula 29

In some embodiments of the present invention a caspase-1 inhibitor for use in a method of the present invention is a compound described in U.S. Pat. No. 7,053,057 (herewith incorporated by reference in its entirety). Preferred compounds described in U.S. Pat. No. 7,053,057 for use in the methods of the present invention are referred to herein as caspase-1 inhibitor having Formula 29:

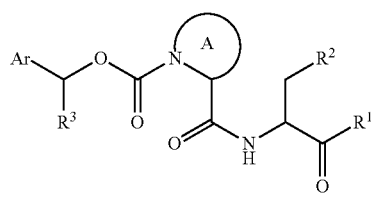

Formula 29 or single stereoisomers, mixtures of stereoisomers, pharmaceutically acceptable salts or prodrugs thereof, wherein Ring A is an optionally substituted piperidine, tetrahydroquinoline or tetrahydroisoquinoline ring; R$^1$ is hydrogen, CHN$_2$, R, or —CH$_2$Y; R is an optionally substituted group selected from an aliphatic group, an aryl group, an aralkyl group, a heterocyclic group, or an heterocyclylalkyl group; Y is an electronegative leaving group; R$^2$ is CO$_2$H, CH$_2$CO$_2$H, or esters, amides or isosteres thereof; Ar is an optionally substituted aryl group; and R$^3$ is hydrogen, an optionally substituted C$_{1-6}$ alkyl, F$_2$, CN, aryl or R$^3$ is attached to Ar to form an unsaturated or partially saturated five or six membered fused ring having 0-2 heteroatoms.

29. Caspase-1 Inhibitor Having Formula 30

In some embodiments of the present invention a caspase-1 inhibitor for use in a method of the present invention is a compound described in U.S. Pat. No. 7,205,327 (herewith incorporated by reference in its entirety). Preferred compounds described in U.S. Pat. No. 7,205,327 for use in the methods of the present invention are referred to herein as caspase-1 inhibitor having Formula 30:

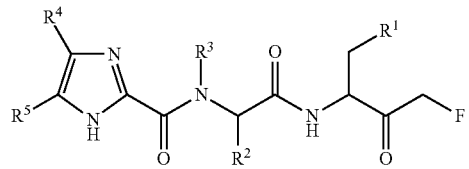

Formula 30 or single stereoisomers, mixtures of stereoisomers, pharmaceutically acceptable salts or prodrugs thereof, wherein R$^1$ is COH, CH$_2$CO$_2$H, or esters, amides or isosteres thereof; R$^2$ is hydrogen or an optionally substituted C$_1$-C$_6$ aliphatic group; R$^3$ is hydrogen or an optionally substituted C$_1$-C$_6$ aliphatic group; and R$^4$ and R$^5$ are each independently selected from hydrogen, an optionally substituted C$_1$-C$_6$ aliphatic group, or R$^4$ and R$^5$ taken together with the ring to which they are attached form an optionally substituted bicyclic ring, said bicyclic ring selected from the following:

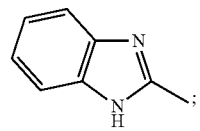

(a)

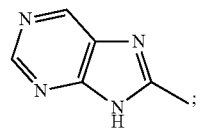

(b)

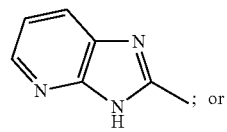

(c) ; or

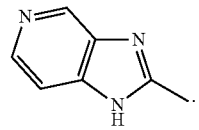

(d)

30. Caspase-1 Inhibitor Having Formula 31A or 31B

In some embodiments of the present invention a caspase-1 inhibitor for use in a method of the present invention is a compound described in U.S. Pat. No. 6,184,210 (herewith incorporated by reference in its entirety). Preferred compounds described in U.S. Pat. No. 6,184,210 for use in the methods of the present invention are referred to herein as caspase-1 inhibitor having Formula 31A:

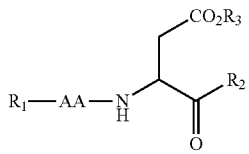

Formula 31A or single stereoisomers, mixtures of stereoisomers, pharmaceutically acceptable salts or prodrugs thereof, wherein $R_1$ is an N-terminal protecting group; AA is a residue of any natural or non-natural α-amino acid, β-amino acid, derivatives of an α-amino acid or β-amino acid; $R_2$ is H or $CH_2R_4$ where $R_4$ is an electronegative leaving group, and $R_3$ is alkyl or H, provided that AA is not His, Tyr, Pro or Phe.

In some embodiments of the present invention a caspase-1 inhibitor for use in a method of the present invention is a compound described in U.S. Pat. No. 6,184,210 (herewith incorporated by reference in its entirety). Preferred compounds described in U.S. Pat. No. 6,184,210 for use in the methods of the present invention are referred to herein as caspase-1 inhibitor having Formula 31B:

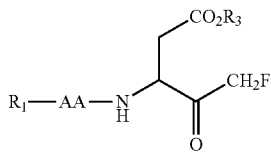

Formula 31B or single stereoisomers, mixtures of stereoisomers, pharmaceutically acceptable salts or prodrugs thereof, wherein $R_1$ is an N-terminal protecting group selected from the group consisting of t-butoxycarbonyl (Boc), acetyl (Ac) and benzyloxycarbonyl (Cbz); $R_3$ is alkyl or hydrogen; and AA is a residue of an amino acid selected from the group consisting of valine (Val), isoleucine (Ile) and leucine (Leu).

31. Caspase-1 Inhibitor Having Formula 32

In some embodiments of the present invention a caspase-1 inhibitor for use in a method of the present invention is a compound described in U.S. Pat. No. 6,184,244 (herewith incorporated by reference in its entirety). Preferred compounds described in U.S. Pat. No. 6,184,244 for use in the methods of the present invention are referred to herein as caspase-1 inhibitor having Formula 32:

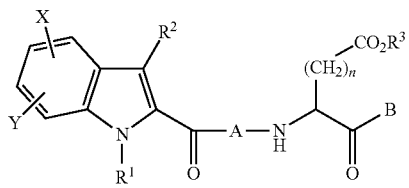

Formula 32 or single stereoisomers, mixtures of stereoisomers, pharmaceutically acceptable salts or prodrugs thereof, wherein n is 1 or 2; $R^1$ is alkyl, cycloalkyl, (cycloalkyl)alkyl, phenyl, (substituted)phenyl, phenylalkyl, (substituted)phenylalkyl, heteroaryl, (heteroaryl)alkyl or $(CH_2)_m CO_2R^4$, wherein m=1-4, and $R^4$ is as defined below; $R^2$ is a hydrogen atom, chloro, alkyl, cycloalkyl, cycloalkyl)alkyl, phenyl, (substituted)phenyl, phenylalkyl, (substituted)phenylalkyl, heteroaryl, (heteroaryl)alkyl or $(CH_2)_p CO_2R^5$, wherein p=0-4, and $R^5$ is as defined below; $R^3$ is a hydrogen atom, alkyl, cycloalkyl, (cycloalkyl)alkyl, phenylalkyl, or (substituted)phenylalkyl; $R^4$ is a hydrogen atom, alkyl, cycloalkyl, (cycloalkyl)alkyl, phenylalkyl, or (substituted)phenylalkyl; $R^5$ is a hydrogen atom, alkyl, cycloalkyl, (cycloalkyl)alkyl, phenylalkyl, or (substituted)phenylalkyl; A is a natural or unnatural amino acid; B is a hydrogen atom, a deuterium atom, alkyl, cycloalkyl, (cycloalkyl)alkyl, phenyl, (substituted)phenyl, phenylalkyl, (substituted)phenylalkyl, heteroaryl, (heteroaryl)alkyl, halomethyl, $CH_2ZR^6$, $CH_2OCO(aryl)$, or $CH_2OCO(heteroaryl)$, or $CH_2OPO(R^7)R^8$, where Z is an oxygen, $OC(=O)$ or a sulfur atom; $R^6$ is phenyl, substituted phenyl, phenylalkyl, (substituted phenyl)alkyl, heteroaryl or (heteroaryl)alkyl; $R^7$ and $R^8$ are independently selected from a group consistent of alkyl, cycloalkyl, phenyl, substituted phenyl, phenylalkyl, (substituted phenyl)alkyl and (cycloalkyl)alkyl; and X and Y are independently selected from the group consisting of a hydrogen atom, halo, trihalomethyl, amino, protected amino, an amino salt, mono-substituted amino, di-substituted amino, carboxy, protected carboxy, a carboxylate salt, hydroxy, protected hydroxy, a salt of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl.

32. Caspase-1 Inhibitor Having Formula 33

In some embodiments of the present invention a caspase-1 inhibitor for use in a method of the present invention is a compound described in U.S. Pat. No. 6,187,771 (herewith incorporated by reference in its entirety). Preferred compounds described in U.S. Pat. No. 6,187,771 for use in the methods of the present invention are referred to herein as caspase-1 inhibitor having Formula 33:

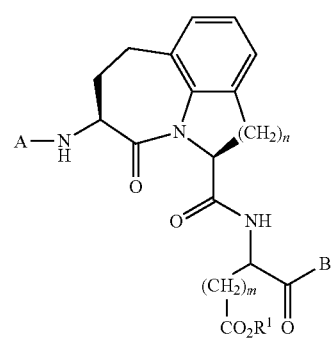

Formula 33 or single stereoisomers, mixtures of stereoisomers, pharmaceutically acceptable salts or prodrugs thereof, wherein n is 1 or 2; m is 1 or 2; A is $R^2CO—$, R3-O—CO—, or $R^4SO2-$; a group of the formula:

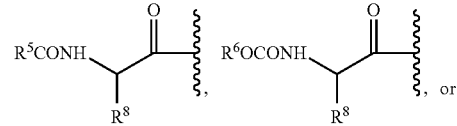

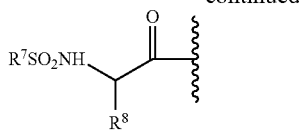

further wherein: $R^1$ is a hydrogen atom, alkyl or phenylalkyl; $R^2$ is alkyl, cycloalkyl, (cycloalkyl)alkyl, phenyl, phenylalkyl, substituted phenyl, (substituted phenyl)alkyl, heteroaryl, or (heteroaryl)alkyl; $R^3$ is alkyl, cycloalkyl, (cycloalkyl)alkyl, phenylalkyl or (substituted phenyl)alkyl; $R^4$ is alkyl, cycloalkyl, (cycloalkyl)alkyl, phenyl, phenylalkyl, substituted phenyl, (substituted phenyl)alkyl, heteroaryl, or (heteroaryl)alkyl; $R^5$ is alkyl, cycloalkyl, (cycloalkyl)alkyl, phenyl, phenylalkyl, substituted phenyl, (substituted phenyl)alkyl, heteroaryl, or (heteroaryl)alkyl; $R^6$ is alkyl, cycloalkyl, (cycloalkyl)alkyl, phenylalkyl, or (substituted phenyl)alkyl; $R^7$ is alkyl, cycloalkyl, (cycloalkyl)alkyl, phenyl, phenylalkyl, substituted phenyl, (substituted phenyl)alkyl, heteroaryl, or (heteroaryl)alkyl; $R^8$ is an amino acid side chain chosen from the group consisting of natural and unnatural amino acids; B is a hydrogen atom, a deuterium atom, alkyl, cycloalkyl, (cycloalkyl)alkyl, phenyl, phenylalkyl, substituted phenyl, (substituted phenyl)alkyl, heteroaryl, (heteroaryl)alkyl, or a halomethyl group; a group of the formula: wherein $R^9$ is phenyl, substituted phenyl, phenylalkyl, (substituted phenyl)alkyl, heteroaryl, or (heteroaryl)alkyl; and X is an oxygen or a sulfur atom;

a group of the formula: —$CH_2$—O—CO-(aryl);
a group of the formula: —$CH_2$—O—CO-(heteroaryl);
a group of the formula: —$CH_2$—O—PO—$(R^{10})R^{11}$;
wherein $R^{10}$ and $R^{11}$ are independently selected from a group consisting of alkyl, cycloalkyl, phenyl, substituted phenyl, phenylalkyl, and (substituted phenyl)alkyl.

33. Caspase-1 Inhibitor Having Formula 34

In some embodiments of the present invention a caspase-1 inhibitor for use in a method of the present invention is a compound described in U.S. Pat. No. 6,197,750 (herewith incorporated by reference in its entirety). Preferred compounds described in U.S. Pat. No. 6,197,750 for use in the methods of the present invention are referred to herein as caspase-1 inhibitor having Formula 34:

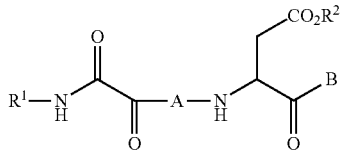

Formula 34 or single stereoisomers, mixtures of stereoisomers, pharmaceutically acceptable salts or prodrugs thereof, wherein A is a natural or unnatural amino acid of Formula IIa-i:

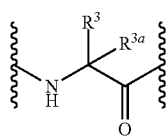

IIa

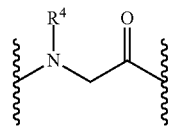

IIb

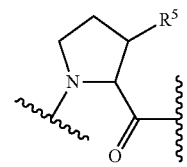

IIc

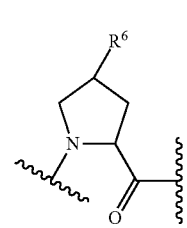

IId

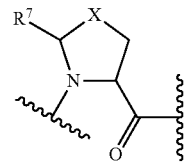

IIe

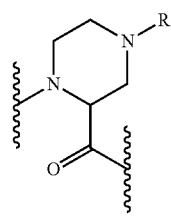

IIf

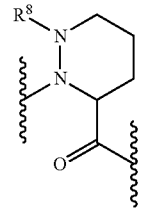

IIg

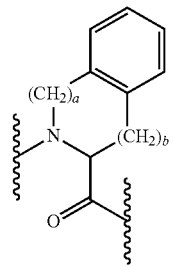

IIh

-continued

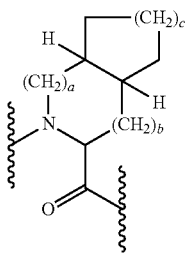

B is a hydrogen atom, a deuterium atom, alkyl, cycloalkyl, phenyl, substituted phenyl, naphthyl, substituted naphthyl, 2-benzoxazolyl, substituted 2-oxazolyl, (CH$_2$)cycloalkyl, (CH$_2$)$_n$phenyl, (CH$_2$)$_n$(substituted phenyl), (CH$_2$)$_n$(1 or 2-naphthyl), (CH$_2$)$_n$(heteroaryl), halomethyl, CO$_2$R$^{12}$, CONR$^{13}$R$^{14}$, CH$_2$ZR$^{15}$, CH$_2$OCO(aryl), CH$_2$OCO(heteroaryl), or CH$_2$OPO(R$^{16}$)R$^{17}$, where Z is an oxygen or a sulfur atom, or B is a group of the Formula IIIa-c:

IIIa

IIIb

IIIc

R$^1$ is alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, heteroaryl, (heteroaryl)alkyl, R$^{1a}$(R$^{1b}$)N, or R$^{1c}$O; and R$^2$ is hydrogen, lower alkyl, cycloalkyl, (cycloalkyl)alkyl, phenylalkyl, or substituted phenylalkyl; and wherein: R$^{1a}$ and R$^{1b}$ are independently hydrogen, alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, heteroaryl, or (heteroaryl)alkyl, with the proviso that R$^{1a}$ and R$^{1b}$ cannot both be hydrogen; R$^{1c}$ is alkyl, cycloalkyl, (cycloalkyl)alkyl, phenyl, substituted phenyl, phenylalkyl, substituted phenylalkyl, naphthyl, substituted naphthyl, (1 or 2 naphthyl)

IIi alkyl, heteroaryl, or (heteroaryl)alkyl; R$^3$ is C$_{1-6}$ lower alkyl, cycloalkyl, phenyl, substituted phenyl, (CH$_2$)$_n$NH$_2$, (CH$_2$)$_n$NHCOR$^9$, (CH$_2$)$_n$N(C=NH)NH$_2$, (CH$_2$)$_m$CO$_2$R$^2$, (CH$_2$)$_m$OR10, (CH$_2$)$_m$SR$^{11}$, (CH$_2$)$_n$cycloalkyl, (CH$_2$)$_n$phenyl, (CH$_2$)$_n$(substituted phenyl), (CH$_2$)$_n$(1 or 2-naphthyl) or (CH$_2$)$_n$(heteroaryl), wherein heteroaryl includes pyridyl, thienyl, furyl, thiazolyl, imidazolyl, pyrazolyl, isoxazolyl, pyrazinyl, pyrimidyl, triazinyl, tetrazolyl, and indolyl; R$^{3a}$ is hydrogen or methyl, or R$^3$ and R$^{3a}$ taken together are —(CH$_2$)$_d$— where d is an integer from 2 to 6; R$^4$ is phenyl, substituted phenyl, (CH$_2$)$_m$phenyl, (CH$_2$)$_m$(substituted phenyl), cycloalkyl, or benzofused cycloalkyl; R$^5$ is hydrogen, lower alkyl, cycloalkyl, phenyl, substituted phenyl, (CH$_2$)$_n$cycloalkyl, (CH$_2$)$_n$phenyl, (CH$_2$)$_n$(substituted phenyl), or (CH$_2$)$_n$(1 or 2-naphthyl); R$^6$ is hydrogen, fluorine, oxo, lower alkyl, cycloalkyl, phenyl, substituted phenyl, naphthyl, (CH$_2$)$_n$cycloalkyl, (CH$_2$)$_n$phenyl, (CH$_2$)$_n$(substituted phenyl), (CH$_2$)$_n$(1 or 2-naphthyl), OR$^{10}$, SR$^{11}$ or NHCOR$^9$; R$^7$ is hydrogen, oxo (i.e., =O), lower alkyl, cycloalkyl, phenyl, substituted phenyl, naphthyl, (CH$_2$)$_n$cycloalkyl, (CH$_2$)$_n$phenyl, (CH$_2$)$_n$(substituted phenyl), or (CH$_2$)$_n$(1 or 2-naphthyl); R$^8$ is lower alkyl, cycloalkyl, (CH$_2$)$_n$cycloalkyl, (CH$_2$)$_n$phenyl, (CH$_2$)$_n$(substituted phenyl), (CH$_2$)$_n$(1 or 2-naphthyl), or COR$^9$; R$^9$ is hydrogen, lower alkyl, cycloalkyl, phenyl, substituted phenyl, naphthyl, (CH$_2$)$_n$cycloalkyl, (CH$_2$)$_n$phenyl, (CH$_2$)$_n$(substituted phenyl), (CH$_2$)$_n$(1 or 2-naphthyl), OR$^{12}$, or NR$^{13}$R$^{14}$; R$^{10}$ is hydrogen, lower alkyl, cycloalkyl, phenyl, substituted phenyl, naphthyl, (CH$_2$)$_n$cycloalkyl, (CH$_2$)$_n$phenyl, (CH$_2$)$_n$(substituted phenyl), or (CH$_2$)$_n$(1 or 2-naphthyl); R$^{11}$ is lower alkyl, cycloalkyl, phenyl, substituted phenyl, naphthyl, (CH$_2$)$_n$cycloalkyl, (CH$_2$)$_n$phenyl, (CH$_2$)$_n$(substituted phenyl), or (CH$_2$)$_n$(1 or 2-naphthyl); R$^{12}$ is lower alkyl, cycloalkyl, (CH$_2$)$_n$cycloalkyl, (CH$_2$)$_n$phenyl, (CH$_2$)$_n$(substituted phenyl), or (CH$_2$)$_n$(1 or 2-naphthyl); R$^{13}$ is hydrogen, lower alkyl, cycloalkyl, phenyl, substituted phenyl, naphthyl, substituted naphthyl, (CH$_2$)$_n$cycloalkyl, (CH$_2$)$_n$phenyl, (CH$_2$)$_n$(substituted phenyl), or (CH$_2$)$_n$(1 or 2-naphthyl); R$^{14}$ is hydrogen or lower alkyl; or R$^{13}$ and R$^{14}$ taken together form a five to seven membered carbocyclic or heterocyclic ring, such as morpholine, or N-substituted piperazine; R$^{15}$ is phenyl, substituted phenyl, naphthyl, substituted naphthyl, heteroaryl, (CH$_2$)$_n$phenyl, (CH$_2$)$_n$(substituted phenyl), (CH$_2$)$_n$(1 or 2-naphthyl), or (CH$_2$)$_n$(heteroaryl); R$^{16}$ and R$^{17}$ are independently lower alkyl, cycloalkyl, phenyl, substituted phenyl, naphthyl, phenylalkyl, substituted phenylalkyl, or (cycloalkyl)alkyl; R$^{18}$ and R$^{19}$ are independently hydrogen, alkyl, phenyl, substituted phenyl, (CH$_2$)$_n$phenyl, (CH$_2$)$_n$(substituted phenyl), or R$^{18}$ and R$^{19}$ taken together are —(CH=CH)$_2$—; R$^{20}$ is hydrogen, alkyl, phenyl, substituted phenyl, (CH$_2$)$_n$phenyl, (CH$_2$)$_n$(substituted phenyl); R$^{21}$, R$^{22}$ and R$^{23}$ are independently hydrogen, or alkyl; X is CH$_2$, (CH$_2$)$_2$, (CH$_2$)$_3$, or S; Y$^1$ is O or NR$^{23}$; Y$^2$ is CH$_2$, O, or NR$^{23}$; a is 0 or 1 and b is 1 or 2, provided that when a is 1 then b is 1; c is 1 or 2, provided that when c is 1 then a is 0 and b is 1; m is 1 or 2; and n is 1, 2, 3 or 4.

34. Caspase-1 Inhibitor Having Formula 35

In some embodiments of the present invention a caspase-1 inhibitor for use in a method of the present invention is a compound described in U.S. Pat. No. 6,242,422 (herewith incorporated by reference in its entirety). Preferred compounds described in U.S. Pat. No. 6,242,422 for use in the methods of the present invention are referred to herein as caspase-1 inhibitor having Formula 35:

Formula 35

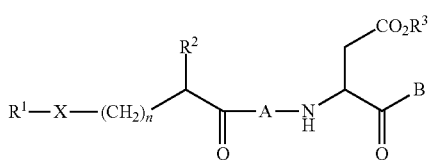

or single stereoisomers, mixtures of stereoisomers, pharmaceutically acceptable salts or prodrugs thereof, wherein n is 0, 1 or 2; X is $CH_2$, $C=O$, O, S or NH; A is a natural or unnatural amino acid of Formula IIa-i:

IIa

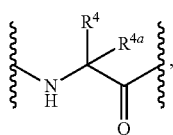

IIb

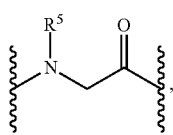

IIc

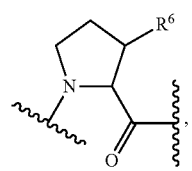

IId

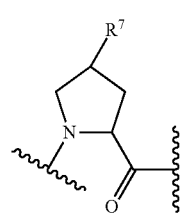

IIe

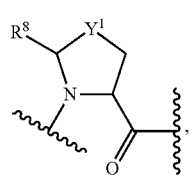

IIf

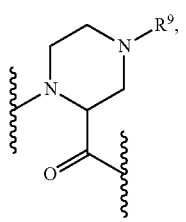

IIg

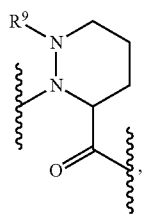

IIh

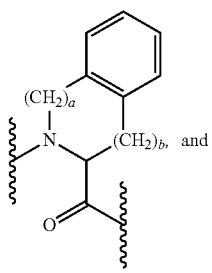

IIi

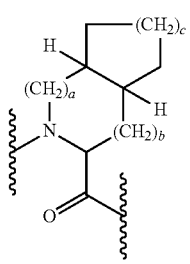

B is a hydrogen atom, a deuterium atom, $C_{1-10}$ straight chain or branched alkyl, cycloalkyl, phenyl, substituted phenyl, naphthyl, substituted naphthyl, 2-benzoxazolyl, substituted 2-oxazolyl, $(CH_2)_m$cycloalkyl, $(CH_2)_m$phenyl, $(CH_2)_m$(substituted phenyl), $(CH_2)_m$(1 or 2-naphthyl), $(CH_2)_m$heteroaryl, halomethyl, $CO_2R^{13}$, $CONR^{14}R^{15}$, $CH_2ZR^{16}$, $CH_2OCO$(aryl), $CH_2OCO$(heteroaryl), or $CH_2OPO(R^{17})R^{18}$, where Z is an oxygen or a sulfur atom, or B is a group of the Formula IIIa-c:

IIIa

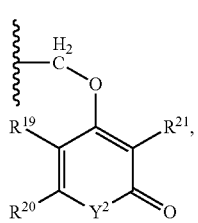

IIIb

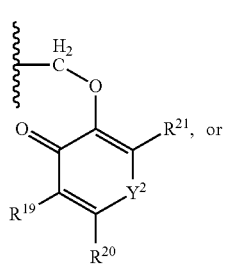

-continued

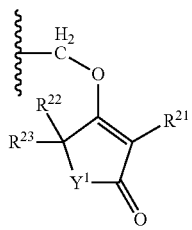
IIIc $R^1$ is phenyl, substituted phenyl, naphthyl, substituted naphthyl, heteroaryl, or substituted heteroaryl; $R^2$ is hydrogen, alkyl, cycloalkyl, phenyl, substituted phenyl, $(CH_2)_mNH_2$, $(CH_2)_m NHCOR^{10}$, $(CH_2)_mN(C=NH)NH_2$, $(CH_2)_pCO_2R^3$, $(CH_2)_pOR^{11}$, $(CH_2)_pSR^{12}$, $(CH_2)_m$cycloalkyl, $(CH_2)_m$phenyl, $(CH_2)_m$(substituted phenyl), $(CH_2)_m$(1 or 2-naphthyl), or $(CH_2)_m$heteroaryl, wherein heteroaryl includes (but is not limited to) pyridyl, thienyl, furyl, thiazolyl, imidazolyl, pyrazolyl, isoxazolyl, pyrazinyl, pyrimidyl, triazinyl, tetrazolyl, and indolyl; $R^3$ is hydrogen, alkyl, cycloalkyl, (cycloalkyl) alkyl, phenylalkyl, or substituted phenylalkyl; and wherein $R^4$ is alkyl, cycloalkyl, phenyl, substituted phenyl, $(CH_2)_mNH_2$, $(CH_2)_mNHCOR^{10}$, $(CH_2)_mN(C=NH)NH_2$, $(CH_2)_p CO_2R^3$, $(CH_2)_pOR^{11}$, $(CH_2)_pSR^{12}$, $(CH_2)_m$cycloalkyl, $(CH_2)_m$phenyl, $(CH_2)_m$(substituted phenyl), $(CH_2)_m$(1 or 2-naphthyl), or $(CH_2)_m$heteroaryl, wherein heteroaryl includes (but is not limited to) pyridyl, thienyl, furyl, thiazolyl, imidazolyl, pyrazolyl, isoxazolyl, pyrazinyl, pyrimidyl, triazinyl, tetrazolyl, and indolyl; $R^{4a}$ is hydrogen or methyl, or $R^4$ and $R^{4a}$ taken together are —$(CH_2)_d$— where d is an integer from 2 to 6; $R^5$ is phenyl, substituted phenyl, $(CH_2)_p$phenyl, $(CH_2)_p$(substituted phenyl), cycloalkyl, or benzofused cycloalkyl; $R^6$ is hydrogen, alkyl, cycloalkyl, phenyl, substituted phenyl, $(CH_2)_m$cycloalkyl, $(CH_2)_m$phenyl, $(CH_2)_m$(substituted phenyl), or $(CH_2)_m$(1 or 2-naphthyl); $R^7$ is hydrogen, fluorine, oxo (i.e., =O), alkyl, cycloalkyl, phenyl, substituted phenyl, naphthyl, $(CH_2)_m$cycloalkyl, $(CH_2)_m$phenyl, $(CH_2)_m$(substituted phenyl), $(CH_2)_m$(1 or 2-naphthyl), $OR^{11}$, $SR^{12}$, or $NHCOR^{10}$; $R^8$ is hydrogen, oxo, alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl); $R^9$ is alkyl, cycloalkyl, $(CH_2)_m$cycloalkyl, $(CH_2)_m$phenyl, $(CH_2)_m$(substituted phenyl), $(CH_2)_m$(1 or 2-naphthyl), or $COR^{10}$; $R^{10}$ is hydrogen, alkyl, cycloalkyl, phenyl, substituted phenyl, naphthyl, $(CH_2)_m$cycloalkyl, $(CH_2)_m$phenyl, $(CH_2)_m$(substituted phenyl), $(CH_2)_m$(1 or 2-naphthyl), $OR^{13}$, or $NR^{14}R^{15}$; $R^{11}$ is hydrogen, alkyl, cycloalkyl, phenyl, substituted phenyl, naphthyl, $(CH_2)_m$cycloalkyl, $(CH_2)_m$phenyl, $(CH_2)_m$(substituted phenyl), or $(CH_2)_m$(1 or 2-naphthyl); $R^{12}$ is alkyl, cycloalkyl, phenyl, substituted phenyl, naphthyl, $(CH_2)_m$cycloalkyl, $(CH_2)_m$ phenyl, $(CH_2)_m$(substituted phenyl), or $(CH_2)_m$(1 or 2-naphthyl); $R^{13}$ is alkyl, cycloalkyl, $(CH_2)_m$cycloalkyl, $(CH_2)_m$phenyl, $(CH_2)_m$(substituted phenyl), or $(CH_2)_m$(1 or 2-naphthyl); $R^{14}$ is hydrogen, alkyl, cycloalkyl, phenyl, substituted phenyl, naphthyl, substituted naphthyl, $(CH_2)_m$cycloalkyl, $(CH_2)_m$phenyl, $(CH_2)_m$(substituted phenyl), or $(CH_2)_m$(1 or 2-naphthyl); $R^{15}$ is hydrogen or alkyl; or $R^{14}$ and $R^{15}$ taken together form a five, six or seven membered carbocyclic or heterocyclic ring, such as morpholine or N-substituted piperazine; $R^{16}$ is phenyl, substituted phenyl, naphthyl, substituted naphthyl, heteroaryl, $(CH_2)_m$phenyl, $(CH_2)_m$(substituted phenyl), $(CH_2)_m$(1 or 2-naphthyl), or $(CH_2)_m$heteroaryl; $R^{17}$ and $R^{18}$ are independently alkyl, cycloalkyl, phenyl, substituted phenyl, naphthyl, or phenylalkyl, substituted phenylalkyl, or (cycloalkyl)alkyl; $R^{19}$ and $R^{20}$ are independently hydrogen, alkyl, phenyl, substituted phenyl, $(CH_2)$ phenyl, or $(CH_2)_m$(substituted phenyl), or $R^{19}$ and $R^{20}$ taken together are —$(CH=CH)^2$—; $R^{21}$ is hydrogen, alkyl, phenyl, substituted phenyl, $(CH_2)_m$phenyl, $(CH_2)_m$ (substituted phenyl); $R^{22}$, $R^{23}$ and $R^{24}$ are independently hydrogen or alkyl; $Y^1$ is $CH_2$, $(CH_2)_2$, $(CH_2)_3$, or S; $Y^2$ is O or $NR^{24}$; $Y^3$ is $CH_2$, O, or $NR^{24}$; a is 0 or 1 and b is 1 or 2, provided that when a is 1 then b is 1; c is 1 or 2, provided that when c is 1 then a is 0 and b is 1; m is 1, 2, 3 or 4; and p is 1 or 2.

35. Caspase-1 Inhibitor Having Formula 36

In some embodiments of the present invention a caspase-1 inhibitor for use in a method of the present invention is a compound described in published PCT application WO2002/22611 (herewith incorporated by reference in its entirety).). Preferred compounds described in published PCT application WO2002/22611 for use in the methods of the present invention are referred to herein as caspase-1 inhibitor having Formula 36:

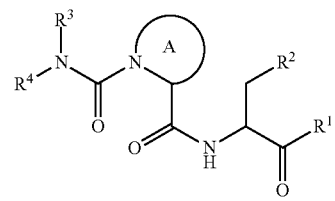
Formula 36 or single stereoisomers, mixtures of stereoisomers, pharmaceutically acceptable salts or prodrugs thereof, wherein Ring A is an optionally substituted piperidine, tetrahydroquinoline or tetrahydroisoquinoline ring; $R^1$ is hydrogen, CN, $CHN_2$, R, or $CH_2Y$; R is an optionally substituted group selected from an aliphatic group, an aryl group, or an aralkyl group; Y is an electronegative leaving group; $R^2$ is $CO_2H$, $CH_2CO_2H$, or esters, amides or isosteres thereof; and $R^3$ is hydrogen, an optionally substituted aryl group, an optionally substituted aralkyl group or an optionally substituted $C_{1-6}$ aliphatic group, $R^4$ is an optionally substituted group selected from an aryl group or a heterocyclyl group, or $R^3$ and $R^4$ taken together with the nitrogen to which they, are attached optionally form a substituted or unsubstituted monocyclic, bicyclic or tricyclic ring.

36. Caspase-1 Inhibitor Having Formula 37

In some embodiments of the present invention a caspase-1 inhibitor for use in a method of the present invention is a compound described in published PCT application WO02/085899 (PCT/US02/12638; herewith incorporated by reference in its entirety). Preferred compounds described in published PCT application WO02/085899 for use in the methods of the present invention are referred to herein as caspase-1 inhibitor having Formula 37:

Formula 37

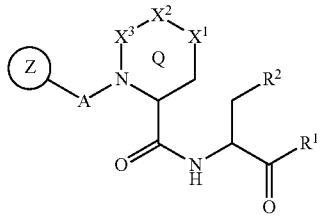

or single stereoisomers, mixtures of stereoisomers, pharmaceutically acceptable salts or prodrugs thereof, wherein $R^1$ is hydrogen, CN, $CHN_2$, R, or —$CH_2Y$; R is an aliphatic group, a substituted aliphatic group, an aryl group, a substituted aryl group, an aralkyl group, a substituted aralkyl group, a non-aromatic heterocyclic group, or a substituted non-aromatic heterocyclic group; Y is an electronegative leaving group, —OR, —SR, —OC=O(R), or —OPO($R^3$)($R^4$); $R^3$ and $R^4$ are independently R or OR; $R^2$ is $CO_2H$, $CH_2CO_2H$, or optionally substituted esters, amides or isosteres thereof; A is C=O or $SO_2$; $X^1$ is oxygen, sulfur, —NH, or —$CH_2$, wherein —NH is optionally substituted by an alkyl group, a cycloalkyl group, a (cycloalkyl)alkyl group, an amino acid N-terminal protecting group, or COR and —$CH_2$ is optionally substituted by fluorine, an alkyl group, a cycloalkyl group, a (cycloalkyl)alkyl group, an aralkyl group, an aryl group, an alkyloxy group, an alkylthioxy group, an aryloxy group, an arylthioxy group, an oxo group (i.e., =O), or a NHCOR group; $X^2$ is oxygen, sulfur, —NH, or —$CH_2$, wherein —NH is optionally substituted by an alkyl group, or an amino acid N-terminal protecting group and —$CH_2$ is optionally substituted by an alkyl group, an aryl group, an alkyloxy group, an alkylthioxy group, an aryloxy group, an arylthioxy group, or an oxo (i.e., =O) group, a NHCOR group; $X^1$ and $X^2$ optionally form part of a phenyl ring that is fused to the adjoining ring Q; $X^3$ is $CH_2$ or $X^2$ and $X^3$ optionally form part of a phenyl ring that is fused to the adjoining ring Q, provided that when $X^2$ forms a ring with $X^3$, then $X^2$ does not form a ring with $X^1$; any two hydrogens attached to adjacent positions in ring Q are optionally replaced by a double bond; and Z is an optionally substituted ring selected from the group consisting of a carbocyclic, an aryl, a saturated heterocycle, a partially saturated heterocycle, and a heteroaryl wherein the ring is connected to A at a ring carbon.

37. Caspase-1 Inhibitor from Extremophilic Fungus

In some embodiments of the present invention a caspase-1 inhibitor for use in a method of the present invention is a caspase-1 inhibitor from an extremophilic fungus or single stereoisomers, mixtures of stereoisomers, pharmaceutically acceptable salts or prodrugs thereof. Recently, Stierle et al. described caspase-1 inhibitors from an extremophilic fungus that specifically target leukemia cell lines, however, did not disclose its use in a method of the present invention (Stierle et al., *J Nat Prod* (2012) 75:344-350; Stierle et al., *J Nat Prod* (2011) 74(10):2273-2277; Stierle et al., *J Nat Prod* (2012) 75:262-266; incorporated herein by reference in their entireties).

Suitable caspase-1 inhibitors from an extremophilic fungus useful to practice a method of the present invention include those described in FIGS. 30A and 30B or single stereoisomers, mixtures of stereoisomers, pharmaceutically acceptable salts or prodrugs thereof.

In some embodiments of the present invention a caspase-1 inhibitor for use in a method of the present invention is Berkedrimane B or single stereoisomers, mixtures of stereoisomers, pharmaceutically acceptable salts or prodrugs thereof having Formula 38:

Formula 38

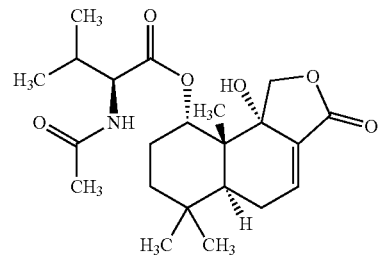

Compound of Formula 38 is known as 5aS,9S,9aR,9bS)-9b-Hydroxy-6,6,9a-trimethyl-3-oxo-1,3,5,5a,6,7,8,9,9a,9b-decahydronaphtho[1,2-c]furan-9-yl N-acetyl-L-valinate. (ChemSpider ID 26333271).

38. Caspase-1 Inhibitor VRT-018858

In some embodiments of the present invention a caspase-1 inhibitor for use in a method of the present invention is VRT-018858 or single stereoisomers, mixtures of stereoisomers, pharmaceutically acceptable salts or prodrugs thereof. Recently, Ross et al. described VRT-018858 as a selective, non-peptide caspase-1 inhibitor that markedly reduced brain damage induced by transient ischemia in rat, however, did not disclose its use in a method of the present invention (Ross et al., *Neuropharmacology* (2007) 53:638-642; incorporated herein by reference in its entirety).

VRT-018858 is the active metabolite of the selective caspase-1 inhibitor pro-drug, pralnacasan (Ross et al., *Neuropharmacology* (2007) 53:638-642). VRT-018858 may be provided, e.g., by Vertex Pharmaceuticals, Inc. (Cambridge, USA). VRT-018858 is potently selective for group I or inflammatory caspases, with $K_i$ values against caspase-1 and caspase-4 of 1.3 nM and 0.4 nM, respectively (Ross et al.). Further, VRT-018858 exhibits >100-fold selectivity for caspase 1 and caspase-4 against other caspases (Ross et al.). Ross et al. describe injection icy of rats with 2.5, 5, 10, or 20 µg VRT-018858. One of skill in the art will be able to extrapolate such treatment to the treatment of a patient in methods described herein.

39. Caspase-1 Inhibitor IDN-6556

In some embodiments of the present invention a caspase-1 inhibitor for use in a method of the present invention is IDN-6556 or single stereoisomers, mixtures of stereoisomers, pharmaceutically acceptable salts or prodrugs thereof. IDN-6556 (3-{2-(2-tert-Butyl-phenylaminooxalyl)-amino]-propionylamino}-4-oxo-5-(2,3,5,6-tetrafluoro-phenoxy)-pentanoic acid) is a novel irreversible broad-spectrum caspase inhibitor (with activity against all tested human caspases). It shows no inhibition of other classes of proteases or other enzymes or receptors (Hoglen et al., *Pharmacol Exp Ther* (2004) 309:634-640).

Recently, Baskin-Bey et al. described phase II clinical trials of using IDN-6556 in human liver preservation injury however, did not did not disclose its use in a method of the present invention (Baskin-Bey et al., *Am J Transplantation* (2007) 7:218-225; incorporated herein by reference in its entirety). Baskin-Bey et al. showed that IDN-6556 reduced CI/WR (cold ischemia/warm reperfusion)-induced apoptosis and injury in the liver and other organs (Baskin-Bey et al., *Am J Transplantation* (2007) 7:218-225). A phase I clinical trial of IDN-6556 administered to patients with hepatic impairment showed the drug to be well tolerated. In the phase II trial, some patients received IDN-6556 (supplied in the University of Wisconsin (UW) or histidine-tryptophan-ketoglutamate (HTK) solution) at a concentration of 15 µg/mL and perfused through the portal vein. Others received IDN-6556 in the cold storage and flush solutions at a concentration of 5 µg/mL and following liver transplantation, intravenously (0.5 mg/kg) every 6 h for 24 h. Yet others received IDN-6556 (15 µg/mL) in the storage and flush solutions administered at a concentration of 0.5 mg/kg every 6 h for 48 h.

In addition, Pockros et al. (Pockros et al., *Hepatology* (2007) 46(2):324-329; incorporated by reference in its entirety) reported that orally taken or intravenously administered IDN-6556 was well tolerated and efficacious in clinical trial evaluating aminotransferase activity in patients with chronic Hepatitis C. In this trial, IDN-6556 doses ranged from 5 mg to 400 mg daily, given from 1 to 3 times per day.

Thus, one of ordinary skill in the art, will also appreciate that IDN-6556 will also be well tolerated in patients being treated according to a method of the present invention, particular in patients having an HIV-1 infection or suspected of having an HIV-1 infection or having AIDS.

40. CRID as Caspase-1 Inhibitors

In a screen for inhibitors of IL-1β production a novel class of sulfonylurea containing compounds were identified. These so-called cytokine release inhibitory drugs or CRIDs (CP-424,174 and CP-412,245) inhibited the post-translational processing and secretion of IL-1β in response to LPS (lipopolysaccharide) and ATP in human monocytes (Perregaux et al., *J Pharmacol Exp Therapeutics* (2001) 299:187-197). Further studies identified glutathione-S-transferase omega 1 (GSTO1) as a possible target for CRIDs (Laliberte et al., *J Biol Chem* (2003) 278:16567-16578). More recently Coll and O'Neill characterized the inhibitory activity of the CRID CP-456,773 (termed CRID3) against multiple inflammasomes and found that CRID3 inhibited both NLRP3 (Nod-like receptor protein) and AIM2 (Absent in melanoma-2) inflammasomes by preventing ASC (adaptor molecule apoptosis-associated speck-like protein containing a CARD [caspase activation and recruitment domain]) oligomerisation (Coll and O'Neill, *PLos ONE* 6(12) e29539). In addition GSTO1 was found to associate with ASC suggesting that it might play a role in inflammasome signaling and could indeed be a target of CRID3.

In some embodiments of the present invention a caspase-1 inhibitor for use in a method of the present invention is CP-412-245 having Formula 39:

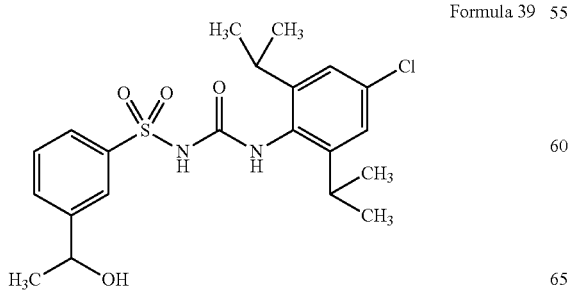

Formula 39

In some embodiments of the present invention a caspase-1 inhibitor for use in a method of the present invention is CP-424,174 having Formula 40:

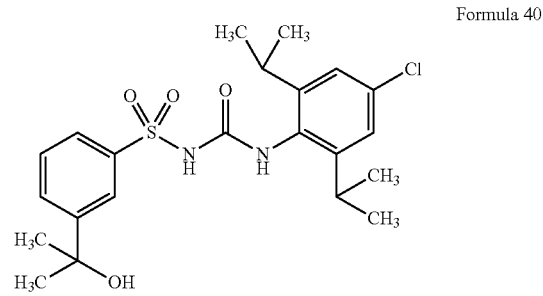 [SMILES: CC(C)c1cc(Cl)cc(C(C)C)c1NC(=O)NS(=O)(=O)c1cccc(C(C)(C)O)c1]

Formula 40

In some embodiments of the present invention a caspase-1 inhibitor for use in a method of the present invention is CRID1 having Formula 41:

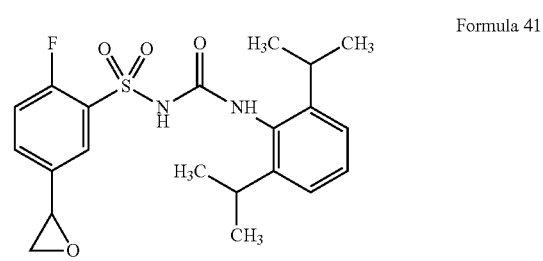 [SMILES: CC(C)c1cccc(C(C)C)c1NC(=O)NS(=O)(=O)c1cc(C2CO2)ccc1F]

Formula 41

CRID1 is known as 1-(4-Chloro-2,6-diisopropylphenyl)-3-[2-fluoro-5-oxiranyl benzenesulfonyl]urea (CP-452,759; Laliberte et al., *J Biol Chem* (2003) 278(19):16567-16578).

In some embodiments of the present invention a caspase-1 inhibitor for use in a method of the present invention is CRID2 having Formula 42:

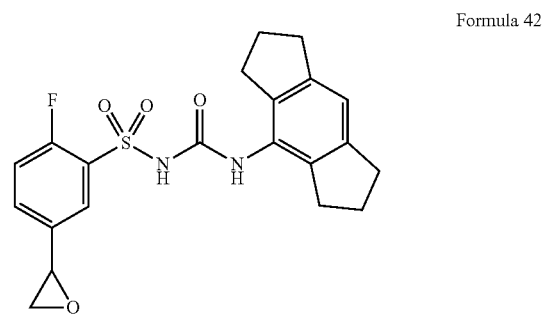 [SMILES: O=C(Nc1c2c(cc3c1CCC3)CCC2)NS(=O)(=O)c1cc(C2CO2)ccc1F]

Formula 42

CRID2 is known as 1-(1,2,3,5,6,7-hexahydro-s-indacen-4-yl)-3-[2-fluoro-5-oxiranylbenzenesulfonyl]urea (CP-470,947; Laliberte et al., *J Biol Chem* (2003) 278(19):16567-16578).

In some embodiments of the present invention a caspase-1 inhibitor for use in a method of the present invention is CRID3. CP-456,773 (CRID3) can be obtained from Amgen, Inc. (Thousand Oaks, Calif., USA) and has Formula 43.

Formula 43

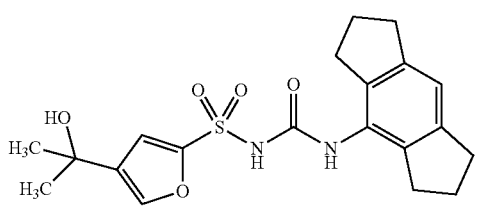

Preparation and purification of CP-456,773 (CRID3) has been described (Laliberte et al., *J Biol Chem* (2003) 278(19): 16567-16578).

CP-412,245, CP-424,174, CRID1, CRID2, and CRID3 can be obtained, e.g., from Pfizer, Inc. (Groton, Conn., USA).

B. Testing Inhibitors

The present invention describes a variety of caspase-1 inhibitors for use in the methods of the present invention. These inhibitors are useful as pharmaceutical agents, especially in the treatment of HIV-1 infection and AIDS and in methods inhibiting death of CD4 T-cells as more fully described herein. Pharmaceutically acceptable salts of the compounds disclosed herein can be used to practice the present invention.

The caspase-1 inhibitors described herein and agents derived therefrom through routine chemical manipulations that are useful for practicing the present invention can be tested for their potential to inhibit the activation and/or activity of caspase-1 using assays described herein (see Examples).

Other useful caspase-1 activity assays and caspase-1 inhibitor assays are available from R&D Systems (Minneapolis, Minn., USA) and are also described in Winter et al. (Winter et al., *Anticancer Res* (2004) 24:1377-1386).

IV. Methods

The caspase-1 inhibitors described herein and agents derived therefrom through routine chemical manipulations are useful for practicing the methods described below. They will be set forth exemplary once for practicing the method for the treatment of HIV-1 infection and/or AIDS. One of skill in the art will appreciate that the caspase-1 inhibitors described herein, can also be used for practicing the other methods described herein.

A. Treatment of HIV-1 Infection and/or AIDS

The present invention provides methods for the treatment of an HIV-1 infection and/or AIDS. The present invention also provides a method for the treatment of a patient having an HIV-1 infection or suspected of having an HIV-1 infection or having AIDS. These methods comprise the step of selecting a patient having an HIV-1 infection or suspected of having an HIV-1 infection or having AIDS and administering to the patient a compound of the invention. Thereby the patient is treated.

In some embodiments of the present invention, the method for the treatment of a patient having an HIV-1 infection or suspected of having an HIV-1 infection or having AIDS comprises the step of administering to the patient having an HIV-1 infection or suspected of having an HIV-1 infection or having AIDS a caspase-1 inhibitor. Thereby the patient is treated.

The invention allows the selection of patients for treatment with a compound described herein, based on an appreciated need of the patient for a treatment of HIV-1 infection or for a treatment of AIDS. In some embodiments this method comprises the step of selecting a patient having an HIV-1 infection or suspected of having an HIV-1 infection or having AIDS and administering to the patient a caspase-1 inhibitor. Thereby the patient is treated.

In some embodiments, the method comprises the step of selecting a patient on the basis of that patient being in need of the inhibition of caspase-1 for the treatment of the HIV-1 infection or AIDS.

In some embodiments of methods for the treatment of HIV-1 infection and/or AIDS, the method comprises administering to a patient in need of such treatment, an effective amount of a caspase-1 inhibitor or a pharmaceutically acceptable salt, prodrug or active derivative of such a substance. The substance in question has been identified as one that is capable of treating HIV-1 infection or AIDS in a patient by their effect on inhibition of activity of caspase-1.

In some embodiments of the method for treating an HIV-1 infection and/or AIDS in a patient, the caspase-1 inhibitor is a caspase-1 inhibitor having Formula 1a or 1b. In some embodiments, the caspase-1 inhibitor is a caspase-1 inhibitor having Formula 2. In some embodiments, the caspase-1 inhibitor is a caspase-1 inhibitor having Formula 3. In some embodiments, the caspase-1 inhibitor is a caspase-1 inhibitor having Formula 4, 4.1, 4.2, or 4.3. In some embodiments, the caspase-1 inhibitor is a caspase-1 inhibitor having Formula 5. In some embodiments, the caspase-1 inhibitor is a caspase-1 inhibitor having Formula 6. In some embodiments, the caspase-1 inhibitor is a caspase-1 inhibitor having Formula 7. In some embodiments, the caspase-1 inhibitor is a caspase-1 inhibitor having Formula 8, 8.1, or 8.2. In some embodiments, the caspase-1 inhibitor is a caspase-1 inhibitor having Formula 9 or 9.1. In some embodiments, the caspase-1 inhibitor is a caspase-1 inhibitor having Formula 10. In some embodiments, the caspase-1 inhibitor is a caspase-1 inhibitor having Formula 11. In some embodiments, the caspase-1 inhibitor is a caspase-1 inhibitor having Formula 12. In some embodiments, the caspase-1 inhibitor is a caspase-1 inhibitor having Formula 13. In some embodiments, the caspase-1 inhibitor is a caspase-1 inhibitor having Formula 14. In some embodiments, the caspase-1 inhibitor is a caspase-1 inhibitor having Formula 15. In some embodiments, the caspase-1 inhibitor is a caspase-1 inhibitor having Formula 16, 16.1, 16.2, 16.3, 16.4, 16.5, 16.6, or 16.7. In some embodiments, the caspase-1 inhibitor is a caspase-1 inhibitor having Formula 17, 17.1, 17.2, 17.3, 17.4, 17.5, 17.6, 17.7, 17.8, 17.9, 17.10, 17.11, 17.12, 17.13, 17.14, 17.15, 17.16, 17.17, 17.18, 17.19, 17.20, 17.21, or 17.22. In some embodiments, the caspase-1 inhibitor is a caspase-1 inhibitor having Formula 18A, 18B, 18.1, or 18.2. In some embodiments, the caspase-1 inhibitor is a caspase-1 inhibitor having Formula 19, 19A, or 19B. In some embodiments, the caspase-1 inhibitor is a caspase-1 inhibitor having Formula 20 or 20A. In some embodiments, the caspase-1 inhibitor is a caspase-1 inhibitor having Formula 21 or 21A. In some embodiments, the caspase-1 inhibitor is a caspase-1 inhibitor having Formula 22 or 22A. In some embodiments, the caspase-1 inhibitor is a caspase-1 inhibitor having Formula 23(I), 23(II), or 23(III). In some embodiments, the caspase-1 inhibitor is a caspase-1 inhibitor having Formula 24. In some embodiments, the caspase-1 inhibitor is a caspase-1 inhibitor having Formula 25. In some embodiments, the caspase-1 inhibitor is a caspase-1 inhibitor having Formula 26. In some embodiments, the caspase-1 inhibitor is a caspase-1 inhibitor having Formula 27. In some embodiments, the caspase-1 inhibitor is a caspase-1 inhibitor having Formula 28. In some embodiments, the caspase-1 inhibitor is a caspase-1 inhibitor having Formula 29. In some embodiments, the caspase-1 inhibitor is a caspase-1 inhibitor having Formula 30. In some embodiments, the caspase-1 inhibitor is a caspase-1 inhibitor having Formula 31A or 31B. In some embodiments, the caspase-1 inhibitor is a caspase-1 inhibitor having Formula 32. In some embodiments, the caspase-1 inhibitor is a caspase-1 inhibitor having Formula 33. In some embodiments, the caspase-1 inhibitor is a caspase-1 inhibitor having Formula 34. In some embodiments, the caspase-1 inhibitor is a caspase-1 inhibitor having Formula 35. In some embodiments, the caspase-1 inhibitor is a caspase-1 inhibitor having Formula 36. In some embodiments, the caspase-1 inhibitor is a caspase-1 inhibitor having Formula 37. In some embodiments, the caspase-1 inhibitor is a caspase-1 inhibitor having Formula 38. In some embodiments, the caspase-1 inhibitor is a caspase-1 inhibitor having Formula 39. In some embodiments, the caspase-1 inhibitor is a caspase-1 inhibitor having Formula 40. In some embodiments, the caspase-1 inhibitor is a caspase-1 inhibitor having Formula 41. In some embodiments, the caspase-1 inhibitor is a caspase-1 inhibitor having Formula 42. In some embodiments, the caspase-1 inhibitor is a caspase-1 inhibitor having Formula 43. In some embodiments, the caspase-1 inhibitor is a caspase-1 inhibitor selected from the compounds depicted in FIGS. 30 and 31. In some embodiments, the caspase-1 inhibitor is a compound disclosed in any of the published EP patent applications, in any of published PCT patent applications, in any of published U.S. patent applications, or in any of the granted U.S. patents disclosed herein and incorporated herein by reference in their entireties.

In some embodiments of the method for treating an HIV-1 infection and/or AIDS in a patient, the caspase-1 inhibitor is selected from the group of caspase-1 inhibitors having Formula 1a, 1b, 2, 3, 4, 4.1, 4.2, 4.3, 5, 6, 7, 8, 8.1, 8.2, 9, 9.1, 10, 11, 12, 13, 14, 15, 16, 16.1, 16.2, 16.3, 16.4, 16.5, 16.6, 16.7, 17, 17.1, 17.2, 17.3, 17.4, 17.5, 17.6, 17.7, 17.8, 17.9, 17.10, 17.11, 17.12, 17.13, 17.14, 17.15, 17.16, 17.17, 17.18, 17.19, 17.20, 17.21, 17.22, 18A, 18B, 18.1, 18.2, 19, 19A, 19B, 20, 20A, 21, 21A, 22, 22A, 23(I), 23(II), 23(III), 24, 25, 26, 27, 28, 29, 30, 31A, 31B, 32, 33, 34, 35, 36, 37, 38, 39, 40, 41, 42, 43, a caspase-1 inhibitor depicted in FIGS. 30 and 31, and combinations thereof.

In some embodiments of this method, the method the patient comprises cells having incomplete HIV-1 nucleic acids.

Formulation, administration, therapeutic effective amounts and dosing of pharmaceutical compositions useful in methods for the treatment of HIV-1 infection and AIDS using a compound of the present invention are described below.

In some embodiments of the method for treating an HIV-1 infection and/or AIDS, the method comprises the step of selecting a patient who has developed a resistance against an antiviral HIV-1 drug. Resistance of an HIV-1 infected patient to an antiviral HIV-1 drug typically is determined by a treating clinician.

In some embodiments of this method, the method comprises the step of administering to the patient an anti HIV-1 compound, such as a HAART compound and as described further below.

In some embodiments of the method for treating an HIV-1 infection and/or AIDS, the method comprises the step of selecting a patient who has a reduced total lymphocyte count of less than 1,000/mm$^3$. In some embodiments of the method for treating an HIV-1 infection and/or AIDS, the method comprises the step of selecting a patient who has a reduced total lymphocyte count of less than 750/mm$^3$. In some embodiments of the method for treating an HIV-1 infection and/or AIDS, the method comprises the step of selecting a patient who has a reduced total lymphocyte count of less than 500/mm$^3$. In some embodiments of the method for treating an HIV-1 infection and/or AIDS, the method comprises the step of selecting a patient who has a reduced T-cell count of less than 500/mm$^3$. In some embodiments of the method for treating an HIV-1 infection and/or AIDS, the method comprises the step of selecting a patient who has a reduced T-cell count of less than 375/mm$^3$. In some embodiments of the method for treating an HIV-1 infection and/or AIDS, the method comprises the step of selecting a patient who has a reduced T-cell count of less than 200/mm$^3$.

B. Preventing Death of CD4 T-Cells

The present invention provides methods for preventing death of a CD4 T-cell in a population of CD4 T-cells comprising HIV-1 infected and uninfected CD4 T-cells.

The methods for preventing death of a CD4 T-cell in a population of CD4 T-cells comprising HIV-1 infected and uninfected CD4 T-cells can be practiced in vitro and in vivo. For practicing the method in vitro, CD4 T-cells may be prepared as human lymphoid aggregate cultures (HLACs) as described herein. In some embodiments, the method comprises the step of contacting a CD4 T-cell in a population of CD4 T-cells comprising HIV-1 infected and uninfected CD4 T-cells with a compound described herein. Thereby the death of a CD4 T-cell in a population of CD4 T-cells comprising HIV-1 infected and uninfected CD4 T-cells is prevented. The survival of CD4 T-cells using a method of the invention can be determined as described herein (e.g., see, Examples).

When practicing the method in vivo, in some embodiments, the method comprises the steps of (a) selecting a patient having a CD4 T-cell in a population of CD4 T-cells comprising HIV-1 infected and uninfected CD4 T-cells and (b) administering to the patient a compound described herein. Thereby the death of a CD4 T-cell in a population of CD4 T-cells comprising HIV-1 infected and uninfected CD4 T-cells is prevented.

In some embodiments of the method for preventing death of a CD4 T-cell in a population of CD4 T-cells comprising HIV-1 infected and uninfected CD4 T-cells, the method comprises the step of selecting a patient who has a reduced total lymphocyte count of less than 1,000/mm$^3$. In other embodiments, the method comprises the step of selecting a patient who has a reduced total lymphocyte count of less than 750/mm$^3$. In yet other embodiments, the method comprises the step of selecting a patient who has a reduced total lymphocyte count of less than 500/mm$^3$. In some embodiments of the method for preventing death of a CD4 T-cell in a population of CD4 T-cells comprising HIV-1 infected and uninfected CD4 T-cells, the method comprises the step of selecting a patient who has a reduced T-cell count of less than 500/mm$^3$. In other embodiments, the method comprises the step of selecting a patient who has a reduced T-cell count of less than 375/mm$^3$. In yet other embodiments, the method comprises the step of selecting a patient who has a reduced T-cell count of less than 200/mm$^3$.

In some embodiments of this method, the CD4 T-cell comprises incomplete HIV-1 nucleic acids.

In some embodiments of this method, the method comprises the step of contacting the CD4 T-cell with a caspase-1 inhibitor, more specifically, with a caspase-1 inhibitor described herein.

In some embodiments of the method of preventing the death of CD4 T-cells, the caspase-1 inhibitor is a caspase-1 inhibitor having Formula 1a or 1b. In some embodiments, the caspase-1 inhibitor is a caspase-1 inhibitor having Formula 2. In some embodiments, the caspase-1 inhibitor is a caspase-1 inhibitor having Formula 3. In some embodiments, the caspase-1 inhibitor is a caspase-1 inhibitor having Formula 4, 4.1, 4.2, or 4.3. In some embodiments, the caspase-1 inhibitor is a caspase-1 inhibitor having Formula 5. In some embodiments, the caspase-1 inhibitor is a caspase-1 inhibitor having Formula 6. In some embodiments, the caspase-1 inhibitor is a caspase-1 inhibitor having Formula 7. In some embodiments, the caspase-1 inhibitor is a caspase-1 inhibitor having Formula 8, 8.1, or 8.2. In some embodiments, the caspase-1 inhibitor is a caspase-1 inhibitor having Formula 9 or 9.1. In some embodiments, the caspase-1 inhibitor is a caspase-1 inhibitor having Formula 10. In some embodiments, the caspase-1 inhibitor is a caspase-1 inhibitor having Formula 11. In some embodiments, the caspase-1 inhibitor is a caspase-1 inhibitor having Formula 12. In some embodiments, the caspase-1 inhibitor is a caspase-1 inhibitor having Formula 13. In some embodiments, the caspase-1 inhibitor is a caspase-1 inhibitor having Formula 14. In some embodiments, the caspase-1 inhibitor is a caspase-1 inhibitor having Formula 15. In some embodiments, the caspase-1 inhibitor is a caspase-1 inhibitor having Formula 16, 16.1, 16.2, 16.3, 16.4, 16.5, 16.6, or 16.7. In some embodiments, the caspase-1 inhibitor is a caspase-1 inhibitor having Formula 17, 17.1, 17.2, 17.3, 17.4, 17.5, 17.6, 17.7, 17.8, 17.9, 17.10, 17.11, 17.12, 17.13, 17.14, 17.15, 17.16, 17.17, 17.18, 17.19, 17.20, 17.21, or 17.22. In some embodiments, the caspase-1 inhibitor is a caspase-1 inhibitor having Formula 18A, 18B, 18.1, or 18.2. In some embodiments, the caspase-1 inhibitor is a caspase-1 inhibitor having Formula 19, 19A, or 19B. In some embodiments, the caspase-1 inhibitor is a caspase-1 inhibitor having Formula 20 or 20A. In some embodiments, the caspase-1 inhibitor is a caspase-1 inhibitor having Formula 21 or 21A. In some embodiments, the caspase-1 inhibitor is a caspase-1 inhibitor having Formula 22 or 22A. In some embodiments, the caspase-1 inhibitor is a caspase-1 inhibitor having Formula 23(I), 23(II), or 23(III). In some embodiments, the caspase-1 inhibitor is a caspase-1 inhibitor having Formula 24. In some embodiments, the caspase-1 inhibitor is a caspase-1 inhibitor having Formula 25. In some embodiments, the caspase-1 inhibitor is a caspase-1 inhibitor having Formula 26. In some embodiments, the caspase-1 inhibitor is a caspase-1 inhibitor having Formula 27. In some embodiments, the caspase-1 inhibitor is a caspase-1 inhibitor having Formula 28. In some embodiments, the caspase-1 inhibitor is a caspase-1 inhibitor having Formula 29. In some embodiments, the caspase-1 inhibitor is a caspase-1 inhibitor having Formula 30. In some embodiments, the caspase-1 inhibitor is a caspase-1 inhibitor having Formula 31A or 31B. In some embodiments, the caspase-1 inhibitor is a caspase-1 inhibitor having Formula 32. In some embodiments, the caspase-1 inhibitor is a caspase-1 inhibitor having Formula 33. In some embodiments, the caspase-1 inhibitor is a caspase-1 inhibitor having Formula 34. In some embodiments, the caspase-1 inhibitor is a caspase-1 inhibitor having Formula 35. In some embodiments, the caspase-1 inhibitor is a caspase-1 inhibitor having Formula 36. In some embodiments, the caspase-1 inhibitor is a caspase-1 inhibitor having Formula 37. In some embodiments, the caspase-1 inhibitor is a caspase-1 inhibitor having Formula 38. In some embodiments, the caspase-1 inhibitor is a caspase-1 inhibitor having Formula 39. In some embodiments, the caspase-1 inhibitor is a caspase-1 inhibitor having Formula 40. In some embodiments, the caspase-1 inhibitor is a caspase-1 inhibitor having Formula 41. In some embodiments, the caspase-1 inhibitor is a caspase-1 inhibitor having Formula 42. In some embodiments, the caspase-1 inhibitor is a caspase-1 inhibitor having Formula 43. In some embodiments, the caspase-1 inhibitor is a caspase-1 inhibitor selected from the compounds depicted in FIGS. 30 and 31. In some embodiments, the caspase-1 inhibitor is a compound disclosed in any of the published EP patent applications, in any of published PCT patent applications, in any of published U.S. patent applications, or in any of the granted U.S. patents disclosed herein and incorporated herein by reference in their entireties.

In some embodiments of the method of preventing the death of CD4 T-cells, the caspase-1 inhibitor is a caspase-1 inhibitor having Formula 1a, 1b, 2, 3, 4, 4.1, 4.2, 4.3, 5, 6, 7, 8, 8.1, 8.2, 9, 9.1, 10, 11, 12, 13, 14, 15, 16, 16.1, 16.2, 16.3, 16.4, 16.5, 16.6, 16.7, 17, 17.1, 17.2, 17.3, 17.4, 17.5, 17.6, 17.7, 17.8, 17.9, 17.10, 17.11, 17.12, 17.13, 17.14, 17.15, 17.16, 17.17, 17.18, 17.19, 17.20, 17.21, 17.22, 18A, 18B, 18.1, 18.2, 19, 19A, 19B, 20, 20A, 21, 21A, 22, 22A, 23(I), 23(II), 23(III), 24, 25, 26, 27, 28, 29, 30, 31A, 31B, 32, 33, 34, 35, 36, 37, 38, 39, 40, 41, 42, 43, a caspase-1 inhibitor depicted in FIGS. 30 and 31 or combinations thereof.

In some embodiments of this method, the method comprises the step of administering to the patient an anti HIV-1 compound, such as a HAART compound and as described further below.

Formulation, administration, therapeutic effective amounts and dosing of pharmaceutical compositions useful in methods for preventing death of a CD4 T-cell in a population of CD4 T-cells comprising HIV-1 infected and uninfected CD4 T-cells using a compound of the present invention are described below.

C. Inhibiting Formation of Bioactive Interleukin Beta

Mammalian interleukin-1 beta (IL-1β) plays an important role in various pathologic processes, including chronic and acute inflammation and autoimmune diseases (Oppenheim et. al. 1986, *Immunology Today*, 7:45-56). IL-1β is synthesized as a cell associated precursor polypeptide (pro-IL-1β) that is unable to bind IL-1 receptors and is biologically inactive (Mosley et al., 1987, *J Biol Chem* 262:2941-2944). By inhibiting conversion of precursor IL-1β to mature IL-1β, the activity of interleukin-1 can be inhibited. Interleukin-1β converting enzyme (ICE), also known as caspase-1, is a protease responsible for the activation of IL-1β (Thornberry et al., 1992, *Nature* 356:768; Yuan et al., 1993, *Cell* 75:641). ICE is a substrate-specific cysteine protease that cleaves the inactive prointerleukin-1 to produce the mature IL-1.

As described herein (see Examples) it was found that in CD4 T-cells, abortive production of HIV-1 reverse transcripts, leads to the production and secretion of bioactive IL-1β, and ultimately to cell death. The present invention provides methods for inhibiting the formation of bioactive IL-1β.

The methods for inhibiting the formation of bioactive interleukin-beta (IL-1β) can be practiced in vitro and in vivo. For practicing the method in vitro, cells, preferably CD4 T-cells, secreting bioactive IL-1β may be prepared as human lymphoid aggregate cultures (HLACs) as described herein. In some embodiments, the method comprises the step of contacting cells secreting IL-1β with a compound described herein. Thereby the formation of bioactive IL-1β is inhibited. Formation of bioactive IL-1β can be determined using assays described herein.

When practicing the method in vivo, in some embodiments, the method comprises the steps of (a) selecting a patient having cells secreting IL-1β and having an HIV-1 infection or being suspected of having an HIV-1 infection or having AIDS and (b) administering to the patient a compound described herein. Thereby the formation of bioactive IL-1β is inhibited.

In some embodiments of this method, cells secreting IL-1β comprise incomplete HIV-1 nucleic acids. In some embodiments of this method, cells secreting IL-1β are infected with HIV-1. In some embodiments of this method, cells secreting IL-1β comprise an HIV-1 expression vector. Suitable HIV-1 expression vectors are described herein.

In some embodiments of this method, the method comprises the step of contacting a cell secreting IL-1β with a caspase-1 inhibitor, more specifically, with a caspase-1 inhibitor described herein.

In some embodiments of the method for inhibiting the formation of bioactive interleukin-beta (IL-1β), the caspase-1 inhibitor is a caspase-1 inhibitor having Formula 1a or 1b. In some embodiments, the caspase-1 inhibitor is a caspase-1 inhibitor having Formula 2. In some embodiments, the caspase-1 inhibitor is a caspase-1 inhibitor having Formula 3. In some embodiments, the caspase-1 inhibitor is a caspase-1 inhibitor having Formula 4, 4.1, 4.2, or 4.3. In some embodiments, the caspase-1 inhibitor is a caspase-1 inhibitor having Formula 5. In some embodiments, the caspase-1 inhibitor is a caspase-1 inhibitor having Formula 6. In some embodiments, the caspase-1 inhibitor is a caspase-1 inhibitor having Formula 7. In some embodiments, the caspase-1 inhibitor is a caspase-1 inhibitor having Formula 8, 8.1, or 8.2. In some embodiments, the caspase-1 inhibitor is a caspase-1 inhibitor having Formula 9 or 9.1. In some embodiments, the caspase-1 inhibitor is a caspase-1 inhibitor having Formula 10. In some embodiments, the caspase-1 inhibitor is a caspase-1 inhibitor having Formula 11. In some embodiments, the caspase-1 inhibitor is a caspase-1 inhibitor having Formula 12. In some embodiments, the caspase-1 inhibitor is a caspase-1 inhibitor having Formula 13. In some embodiments, the caspase-1 inhibitor is a caspase-1 inhibitor having Formula 14. In some embodiments, the caspase-1 inhibitor is a caspase-1 inhibitor having Formula 15. In some embodiments, the caspase-1 inhibitor is a caspase-1 inhibitor having Formula 16, 16.1, 16.2, 16.3, 16.4, 16.5, 16.6, or 16.7. In some embodiments, the caspase-1 inhibitor is a caspase-1 inhibitor having Formula 17, 17.1, 17.2, 17.3, 17.4, 17.5, 17.6, 17.7, 17.8, 17.9, 17.10, 17.11, 17.12, 17.13, 17.14, 17.15, 17.16, 17.17, 17.18, 17.19, 17.20, 17.21, or 17.22. In some embodiments, the caspase-1 inhibitor is a caspase-1 inhibitor having Formula 18A, 18B, 18.1, or 18.2. In some embodiments, the caspase-1 inhibitor is a caspase-1 inhibitor having Formula 19, 19A, or 19B. In some embodiments, the caspase-1 inhibitor is a caspase-1 inhibitor having Formula 20 or 20A. In some embodiments, the caspase-1 inhibitor is a caspase-1 inhibitor having Formula 21 or 21A. In some embodiments, the caspase-1 inhibitor is a caspase-1 inhibitor having Formula 22 or 22A. In some embodiments, the caspase-1 inhibitor is a caspase-1 inhibitor having Formula 23(I), 23(II), or 23(III). In some embodiments, the caspase-1 inhibitor is a caspase-1 inhibitor having Formula 24. In some embodiments, the caspase-1 inhibitor is a caspase-1 inhibitor having Formula 25. In some embodiments, the caspase-1 inhibitor is a caspase-1 inhibitor having Formula 26. In some embodiments, the caspase-1 inhibitor is a caspase-1 inhibitor having Formula 27. In some embodiments, the caspase-1 inhibitor is a caspase-1 inhibitor having Formula 28. In some embodiments, the caspase-1 inhibitor is a caspase-1 inhibitor having Formula 29. In some embodiments, the caspase-1 inhibitor is a caspase-1 inhibitor having Formula 30. In some embodiments, the caspase-1 inhibitor is a caspase-1 inhibitor having Formula 31A or 31B. In some embodiments, the caspase-1 inhibitor is a caspase-1 inhibitor having Formula 32. In some embodiments, the caspase-1 inhibitor is a caspase-1 inhibitor having Formula 33. In some embodiments, the caspase-1 inhibitor is a caspase-1 inhibitor having Formula 34. In some embodiments, the caspase-1 inhibitor is a caspase-1 inhibitor having Formula 35. In some embodiments, the caspase-1 inhibitor is a caspase-1 inhibitor having Formula 36. In some embodiments, the caspase-1 inhibitor is a caspase-1 inhibitor having Formula 37. In some embodiments, the caspase-1 inhibitor is a caspase-1 inhibitor having Formula 38. In some embodiments, the caspase-1 inhibitor is a caspase-1 inhibitor having Formula 39. In some embodiments, the caspase-1 inhibitor is a caspase-1 inhibitor having Formula 40. In some embodiments, the caspase-1 inhibitor is a caspase-1 inhibitor having Formula 41. In some embodiments, the caspase-1 inhibitor is a caspase-1 inhibitor having Formula 42. In some embodiments, the caspase-1 inhibitor is a caspase-1 inhibitor having Formula 43. In some embodiments, the caspase-1 inhibitor is a caspase-1 inhibitor selected from the compounds depicted in FIGS. 30 and 31. In some embodiments, the caspase-1 inhibitor is a compound disclosed in any of the published EP patent applications, in any of published PCT patent applications, in any of published U.S. patent applications, or in any of the granted U.S. patents disclosed herein and incorporated herein by reference in their entireties.

In some embodiments of the method for inhibiting the formation of bioactive interleukin-beta (IL-1β), the caspase-1 inhibitor is a caspase-1 inhibitor having Formula 1a, 1b, 2, 3, 4, 4.1, 4.2, 4.3, 5, 6, 7, 8, 8.1, 8.2, 9, 9.1, 10, 11, 12, 13, 14, 15, 16, 16.1, 16.2, 16.3, 16.4, 16.5, 16.6, 16.7, 17, 17.1, 17.2, 17.3, 17.4, 17.5, 17.6, 17.7, 17.8, 17.9, 17.10, 17.11, 17.12, 17.13, 17.14, 17.15, 17.16, 17.17, 17.18, 17.19, 17.20, 17.21, 17.22, 18A, 18B, 18.1, 18.2, 19, 19A, 19B, 20, 20A, 21, 21A, 22, 22A, 23(I), 23(II), 23(III), 24, 25, 26, 27, 28, 29, 30, 31A, 31B, 32, 33, 34, 35, 36, 37, 38, 39, 40, 41, 42, 43, a caspase-1 inhibitor depicted in FIGS. 30 and 31 or combinations thereof.

In some embodiments of this method, the method comprises the step of administering to the patient an anti HIV-1 compound, such as a HAART compound and as described further below.

Formulation, administration, therapeutic effective amounts and dosing of pharmaceutical compositions useful in methods for inhibiting the formation of bioactive interleukin-beta using a compound of the present invention are described below.

D. Inhibiting Pyroptosis

As described herein (see Examples) it was found that abortive production of HIV-1 reverse transcripts leads to pyroptosis and ultimately to cell death.

The present invention provides methods for inhibiting pyroptosis.

The methods for inhibiting pyroptosis can be practiced in vitro and in vivo. For practicing the method in vitro, cells, preferably CD4 T-cells undergoing pyroptosis may be prepared as human lymphoid aggregate cultures (HLACs) as described herein. In some embodiments, the method comprises the step of contacting cells undergoing pyroptosis with a compound described herein, thereby inhibiting pyroptosis. Inhibition of pyroptosis can be determined using assays described herein.

When practicing the method in vivo, in some embodiments, the method comprises the steps of (a) selecting a patient having cells undergoing pyroptosis and having an HIV-1 infection or being suspected of having an HIV-1 infection or having AIDS and (b) administering to the patient a compound described herein. Thereby the pyroptosis is inhibited.

In some embodiments of this method, cells undergoing pyroptosis comprise incomplete HIV-1 nucleic acids. In some embodiments of this method, cells undergoing pyroptosis are infected with HIV-1. In some embodiments of this method, cells undergoing pyroptosis comprise an HIV-1 expression vector. Suitable HIV-1 expression vectors are described herein.

In some embodiments of this method, the method comprises the step of contacting a cell undergoing pyroptosis with a caspase-1 inhibitor, more specifically, with a caspase-1 inhibitor described herein.

In some embodiments of the method for inhibiting pyroptosis, the caspase-1 inhibitor is a caspase-1 inhibitor having Formula 1a or 1b. In some embodiments, the caspase-1 inhibitor is a caspase-1 inhibitor having Formula 2. In some embodiments, the caspase-1 inhibitor is a caspase-1 inhibitor having Formula 3. In some embodiments, the caspase-1 inhibitor is a caspase-1 inhibitor having Formula 4, 4.1, 4.2, or 4.3. In some embodiments, the caspase-1 inhibitor is a caspase-1 inhibitor having Formula 5. In some embodiments, the caspase-1 inhibitor is a caspase-1 inhibitor having Formula 6. In some embodiments, the caspase-1 inhibitor is a caspase-1 inhibitor having Formula 7. In some embodiments, the caspase-1 inhibitor is a caspase-1 inhibitor having Formula 8, 8.1, or 8.2. In some embodiments, the caspase-1 inhibitor is a caspase-1 inhibitor having Formula 9 or 9.1. In some embodiments, the caspase-1 inhibitor is a caspase-1 inhibitor having Formula 10. In some embodiments, the caspase-1 inhibitor is a caspase-1 inhibitor having Formula 11. In some embodiments, the caspase-1 inhibitor is a caspase-1 inhibitor having Formula 12. In some embodiments, the caspase-1 inhibitor is a caspase-1 inhibitor having Formula 13. In some embodiments, the caspase-1 inhibitor is a caspase-1 inhibitor having Formula 14. In some embodiments, the caspase-1 inhibitor is a caspase-1 inhibitor having Formula 15. In some embodiments, the caspase-1 inhibitor is a caspase-1 inhibitor having Formula 16, 16.1, 16.2, 16.3, 16.4, 16.5, 16.6, or 16.7. In some embodiments, the caspase-1 inhibitor is a caspase-1 inhibitor having Formula 17, 17.1, 17.2, 17.3, 17.4, 17.5, 17.6, 17.7, 17.8, 17.9, 17.10, 17.11, 17.12, 17.13, 17.14, 17.15, 17.16, 17.17, 17.18, 17.19, 17.20, 17.21, or 17.22. In some embodiments, the caspase-1 inhibitor is a caspase-1 inhibitor having Formula 18A, 18B, 18.1, or 18.2. In some embodiments, the caspase-1 inhibitor is a caspase-1 inhibitor having Formula 19, 19A, or 19B. In some embodiments, the caspase-1 inhibitor is a caspase-1 inhibitor having Formula 20 or 20A. In some embodiments, the caspase-1 inhibitor is a caspase-1 inhibitor having Formula 21 or 21A. In some embodiments, the caspase-1 inhibitor is a caspase-1 inhibitor having Formula 22 or 22A. In some embodiments, the caspase-1 inhibitor is a caspase-1 inhibitor having Formula 23(I), 23(II), or 23(III). In some embodiments, the caspase-1 inhibitor is a caspase-1 inhibitor having Formula 24. In some embodiments, the caspase-1 inhibitor is a caspase-1 inhibitor having Formula 25. In some embodiments, the caspase-1 inhibitor is a caspase-1 inhibitor having Formula 26. In some embodiments, the caspase-1 inhibitor is a caspase-1 inhibitor having Formula 27. In some embodiments, the caspase-1 inhibitor is a caspase-1 inhibitor having Formula 28. In some embodiments, the caspase-1 inhibitor is a caspase-1 inhibitor having Formula 29. In some embodiments, the caspase-1 inhibitor is a caspase-1 inhibitor having Formula 30. In some embodiments, the caspase-1 inhibitor is a caspase-1 inhibitor having Formula 31A or 31B. In some embodiments, the caspase-1 inhibitor is a caspase-1 inhibitor having Formula 32. In some embodiments, the caspase-1 inhibitor is a caspase-1 inhibitor having Formula 33. In some embodiments, the caspase-1 inhibitor is a caspase-1 inhibitor having Formula 34. In some embodiments, the caspase-1 inhibitor is a caspase-1 inhibitor having Formula 35. In some embodiments, the caspase-1 inhibitor is a caspase-1 inhibitor having Formula 36. In some embodiments, the caspase-1 inhibitor is a caspase-1 inhibitor having Formula 37. In some embodiments, the caspase-1 inhibitor is a caspase-1 inhibitor having Formula 38. In some embodiments, the caspase-1 inhibitor is a caspase-1 inhibitor having Formula 39. In some embodiments, the caspase-1 inhibitor is a caspase-1 inhibitor having Formula 40. In some embodiments, the caspase-1 inhibitor is a caspase-1 inhibitor having Formula 41. In some embodiments, the caspase-1 inhibitor is a caspase-1 inhibitor having Formula 42. In some embodiments, the caspase-1 inhibitor is a caspase-1 inhibitor having Formula 43. In some embodiments, the caspase-1 inhibitor is a caspase-1 inhibitor selected from the compounds depicted in FIGS. 30 and 31. In some embodiments, the caspase-1 inhibitor is a compound disclosed in any of the published EP patent applications, in any of published PCT patent applications, in any of published U.S. patent applications, or in any of the granted U.S. patents disclosed herein and incorporated herein by reference in their entireties.

In some embodiments of the method for inhibiting pyroptosis, the caspase-1 inhibitor is a caspase-1 inhibitor having Formula 1a, 1b, 2, 3, 4, 4.1, 4.2, 4.3, 5, 6, 7, 8, 8.1, 8.2, 9, 9.1, 10, 11, 12, 13, 14, 15, 16, 16.1, 16.2, 16.3, 16.4, 16.5, 16.6, 16.7, 17, 17.1, 17.2, 17.3, 17.4, 17.5, 17.6, 17.7, 17.8, 17.9, 17.10, 17.11, 17.12, 17.13, 17.14, 17.15, 17.16, 17.17, 17.18, 17.19, 17.20, 17.21, 17.22, 18A, 18B, 18.1, 18.2, 19, 19A, 19B, 20, 20A, 21, 21A, 22, 22A, 23(I), 23(II), 23(III), 24, 25, 26, 27, 28, 29, 30, 31A, 31B, 32, 33, 34, 35, 36, 37, 38, 39, 40, 41, 42, 43, a caspase-1 inhibitor depicted in FIGS. 30 and 31 or combinations thereof.

In some embodiments of this method, the method comprises the step of administering to the patient an anti HIV-1 compound, such as a HAART compound and as described further below.

Formulation, administration, therapeutic effective amounts and dosing of pharmaceutical compositions useful in methods for inhibiting pyroptosis using a compound of the present invention are described below.

E. Combination Therapy

In a preferred embodiment of the present invention, a composition of the invention is used in a method for treating an HIV-1 infection or AIDS in a patient in need of such treatment. Preferably this method is practiced in vivo. Preferably this method is practiced in a host infected with HIV-1, e.g., a human infected with HIV-1. In some embodiments, this method comprises the step of administering to the HIV-1 infected host a therapeutically effective amount of a composition comprising an effective amount of a caspase-1 inhibitor or a pharmaceutically acceptable salt, prodrug or active derivative of such a substance.

Importantly, unlike current antiretroviral drugs designed to interfere with viral components, the caspase-1 inhibitors, do not target HIV-1 itself. Instead these inhibitors target the host CD4 T-cells themselves and thus obviate any potential problems with viral drug resistance. This approach can be used in combination with antiviral drugs, and be particularly useful for treatment of a patient with acute inflammation associated with rapid CD4 T-cell decline, or in a patient who has developed resistance to multiple drugs and for whom few or no therapeutic options remain.

In order to increase the effectiveness of methods for the treatment of an HIV-1 infection and/or AIDS, it may be desirable to combine an inhibitor for caspase-1 activity with other agents effective in the treatment or prevention of HIV-1 infection or AIDS, such as an anti HIV-1 compound. When practiced in vivo, methods of the present invention, optionally comprise the step of administering HAART. Thus, in yet another embodiment of the present invention, a method of treating an HIV-1 infection or AIDS in an HIV-1 infected host in vivo comprises the step of administering highly active antiretroviral therapy (HAART). The current standard of care using HAART is usually a combination of at least three nucleoside reverse transcriptase inhibitors and frequently includes a protease inhibitors, or alternatively a non-nucleoside reverse transcriptase inhibitor. Patients who have low CD4+ cell counts or high plasma RNA levels may require more aggressive HAART. Patients with relatively normal CD4+ cell counts and low to non-measurable levels of plasma HIV RNA over prolonged periods (i.e. slow or non-progressors) may require less aggressive HAART. For antiretroviral-naive patients who are treated with initial antiretroviral regimen, different combinations (or cocktails) of antiretroviral drugs can be used.

Preferably, a composition comprising an inhibitor for the activation and/or activity of caspase-1 may be coadministered with a "cocktail" of nucleoside reverse transcriptase inhibitors, non-nucleoside HIV reverse transcriptase inhibitors, and protease inhibitors, i.e., anti HIV-1 compounds. For example, a composition comprising an inhibitor for the activation and/or activity of caspase-1 may be coadministered with a cocktail of two nucleoside reverse transcriptase inhibitors (e.g. ZIDOVUDINE® (AZT) and LAMIVUDINE® (3TC)), and one protease inhibitor (e.g. INDINAVIR® (MK-639)). A composition comprising an inhibitor for the activation and/or activity of caspase-1 may also be coadministered with a cocktail of one nucleoside reverse transcriptase inhibitor (e.g. STAVUDINE® (d4T)), one non-nucleoside reverse transcriptase inhibitor (e.g. NEVIRAPINE® (BI-RG-587)), and one protease inhibitor (e.g. NELFINAVIR® (AG-1343)). Alternatively, a composition comprising an inhibitor for the activation and/or activity of caspase-1 may be coadministered with a cocktail of one nucleoside reverse transcriptase inhibitor (e.g. ZIDOVUDINE® (AZT)), and two protease inhibitors (e.g. NELFINAVIR® (AG-1343) and SAQINAVIR® (Ro-31-8959)).

In some embodiments, a composition comprising an inhibitor for the activation and/or activity of caspase-1 may be coadministered with an HIV-1 protease inhibitor. Typical suitable protease inhibitors for use in combination therapy include saquinavir (Ro 31-8959) available in hard gel capsules (INVIRASE®) and as soft gel capsules (FORTOVASE®) from Roche Pharmaceuticals, Nutley, N.J. 07110-1199; RITONAVIR® (ABT-538, NORVIR®) from Abbott Laboratories, Abbott Park, Ill. 60064; indinavir (MK-639, CRIXIVAN®) from Merck & Co., Inc., West Point, Pa. 19486-0004; nelfnavir (AG-1343, VIRACEPT®) from Agouron Pharmaceuticals, Inc., La Jolla Calif. 92037-1020; amprenavir (141W94, AGENERASE®), a non-peptide protease inhibitor under development by Vertex Pharmaceuticals, Inc., Cambridge, Mass. 02139-4211 and available from Glaxo-Wellcome, Research Triangle, N.C. under an expanded access program; LASINAVIR® (BMS-234475) available from Bristol-Myers Squibb, Princeton, N.J. 08543 (originally discovered by Novartis, Basel, Switzerland (CGP-61755); DMP-450, a cyclic urea discovered by Dupont and under development by Triangle Pharmaceuticals; BMS-2322623, an azapeptide under development by Bristol-Myers Squibb, Princeton, N.J. 08543, as a 2nd-generation HIV-1 PI; ABT-378 under development by Abbott, Abbott Park, Ill. 60064; and AG-1549 an orally active imidazole carbamate discovered by Shionogi (Shionogi #S-1153) and under development by Agouron Pharmaceuticals, Inc., LaJolla Calif. 92037-1020.

Other antiviral agents for use in combination therapy with a caspase-1 include hydroxyurea, ribavirin, IL-2, IL-12, pentafuside and Yissum Project No. 11607. Hydroxyurea (Droxia), an inhibitor of ribonucleoside triphosphate reductase, the enzyme involved in the activation of T-cells, was discovered at the NCI and is under development by Bristol-Myers Squibb; in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE33653, 4,530,787, 4,569,790, 4,604,377, 4,748,234, 4,752,585, and 4,949,314, and is available under PROLEUKIN® (aldesleukin) from Chiron Corp., Emeryville, Calif. 94608-2997 as a lyophilized powder for IV infusion or sc administration upon reconstitution and dilution with water; a dose of about 1 to about 20 million IU/day, sc is preferred; a dose of about 15 million IU/day, sc is more preferred. IL-12 is disclosed in WO96/25171 and is available from Roche Pharmaceuticals, Nutley, N.J. 07110-1199 and American Home Products, Madison, N.J. 07940; a dose of about 0.5 microgram/kg/day to about 10 microgram/kg/day, sc is preferred. Pentafuside (DP-178, T-20) a 36-amino acid synthetic peptide, is disclosed in U.S. Pat. No. 5,464,933 licensed from Duke University to Trimeris which is developing pentafuside in collaboration with Duke University; pentafuside acts by inhibiting fusion of HIV-1 to target membranes. Pentafuside (3 100 mg/day) is given as a continuous sc infusion or injection together with efavirenz and 2 PI's to HIV-1 positive patients refractory to a triple combination therapy; use of 100 mg/day is preferred. Yissum Project No. 11607, a synthetic protein based on the HIV-1 Vif protein, is under preclinical development by Yissum Research Development Co., Jerusalem 91042, Israel. Ribavirin, 1-β-D-ribofuranosyl-1H-1,2,4-triazole-3-carboxamide, is available from ICN Pharmaceuticals, Inc., Costa Mesa, Calif.; its manufacture and formulation are described in U.S. Pat. No. 4,211,771.

In some embodiments, coadministration comprises administering to a patient (i) a caspase-1 inhibitor and (ii) an anti HIV-1 compound. In some embodiments coadministration comprises administering to a patient (i) a caspase-1 inhibitor having Formula 1a, 1b, 2, 3, 4, 4.1, 4.2, 4.3, 5, 6, 7, 8, 8.1, 8.2, 9, 9.1, 10, 11, 12, 13, 14, 15, 16, 16.1, 16.2, 16.3, 16.4, 16.5, 16.6, 16.7, 17, 17.1, 17.2, 17.3, 17.4, 17.5, 17.6, 17.7, 17.8, 17.9, 17.10, 17.11, 17.12, 17.13, 17.14, 17.15, 17.16, 17.17, 17.18, 17.19, 17.20, 17.21, 17.22, 18A, 18B, 18.1, 18.2, 19, 19A, 19B, 20, 20A, 21, 21A, 22, 22A, 23(I), 23(II), 23(III), 24, 25, 26, 27, 28, 29, 30, 31A, 31B, 32, 33, 34, 35, 36, 37, 38, 39, 40, 41, 42, 43, a caspase-1 inhibitor depicted in FIGS. 30 and 31 or combinations thereof and (ii) an anti HIV-1 compound.

Coadministration in the context of this invention is defined to mean the administration of more than one therapeutic in the course of a coordinated treatment to achieve an improved clinical outcome. Such coadministration may also be coextensive, that is, occurring during overlapping periods of time. Further discussion of such conventional treatment can be found in the art (e.g., Gulick, 1997; *Qual Life Res* 6:471-474; Henry et al., 1997, *Postgrad Med* 102:100-107; Hicks, 1997, *Radiol Clin North Am* 35:995-1005; Goldschmidt, 1996, *Am Fam Physician* 54:574-580).

V. Pharmaceutical Compositions

In one aspect the present invention provides a pharmaceutical composition or a medicament comprising an inhibitor for the activation and/or activity of caspase-1 of the present invention and a pharmaceutically acceptable carrier. A pharmaceutical composition or medicament can be administered to a subject for the treatment of, for example, a condition or disease as described herein.

A pharmaceutical composition may include any combinations of one or more inhibitors for the activation and/or activity of caspase-1.

A. Formulation and Administration

Compounds of the present invention, such as the inhibitors for the activation and/or activity of caspase-1 described herein, are useful in the manufacture of a pharmaceutical composition or a medicament comprising an effective amount thereof in conjunction or mixture with excipients or carriers suitable for either enteral or parenteral application.

As a non-limiting example, in some embodiments of the present invention, a composition comprises a peptide caspase-1 inhibitor.

As a non-limiting example, in some embodiments of the present invention, a composition comprises a non-peptide caspase-1 inhibitor.

As a non-limiting example, in some embodiments of the present invention, a composition comprises caspase-1 inhibitor having Formula 1a or 1b:

Formula 1a and 1b

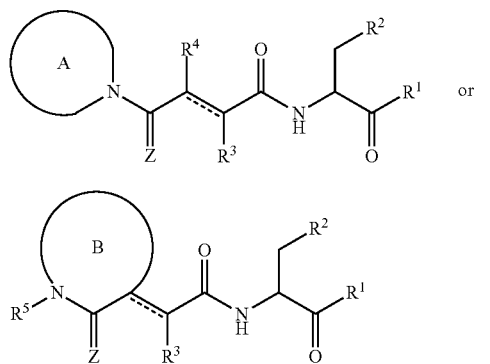

or single stereoisomers, mixtures of stereoisomers, pharmaceutically acceptable salts or prodrugs thereof, wherein: ≈ next to $R^3$ represents a single or double bond; Z is oxygen or sulfur; $R^1$ is hydrogen, $-CHN_2$, $-R$, $-CH_2OR$, $-CH_2SR$, or $-CH_2Y$; R is a $C_{1-12}$ aliphatic, aliphatic, aryl, aralkyl, heterocyclyl, or heterocyclylalkyl; Y is an electronegative leaving group; $R^2$ is $CO_2H$, $CH_2CO_2H$, or esters, amides or isosteres thereof; $R^3$ is a group capable of fitting into the S2 sub-site of a caspase; $R^4$ is hydrogen or a $C_{1-6}$ aliphatic group that is optionally interrupted by $-O-$, $-S-$, $-SO_2-$, $-CO-$, $-NH-$, or $-N(C_{1-4}$ alkyl)-, or $R^3$ and $R^4$ taken together with their intervening atoms optionally form a 3-7 membered ring having 0-2 heteroatoms selected from nitrogen, oxygen or sulfur; Ring A is a nitrogen-containing mono-, bi- or tricyclic ring system having 0-5 additional ring heteroatoms selected from nitrogen, oxygen or sulfur; Ring B is a nitrogen-containing 5-7 membered ring having 0-2 additional ring heteroatoms selected from nitrogen, oxygen or sulfur; $R^5$ is $R^6$, $(CH_2)_nR^6$, $COR^E$, $CO_2R^6$, $SO_2R^6$, $CON(R^6)_2$, or $SO_2N(R^6)_2$; n is one to three; and each $R^6$ is independently selected from hydrogen, an optionally substituted $C_{1-4}$ aliphatic group, an optionally substituted $C_{6-10}$ aryl group, or a mono- or bicyclic heteroaryl group having 5-10 ring atoms.

As a non-limiting example, in some embodiments of the present invention, a composition comprises caspase-1 inhibitor having Formula 2:

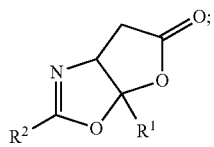

Formula 2 or single stereoisomers, mixtures of stereoisomers, pharmaceutically acceptable salts or prodrugs thereof, wherein $R^1$ is H, $R^4$, haloalkyl, $CHN_2$, $CH_2Cl$, $CH_2F$, $-CH_2OPO(R^4)_2$, $-CH_2OPO(OR^4)_2$, or $-C_{1-2}$alkyl-$R^3$—$R^4$; $R^2$ is a $P_4$—$P_3$—$P_2$, $P_3$—$P_2$, or $P_2$ moiety of a caspase-1 inhibitor; $R^3$ is $-O-$, $-NH-$, $-NR^4-$, $-S-$, or $-O(C=O)-$; $R^4$ is $C_{1-12}$aliphatic, $C_{6-10}$aryl, 5-10 membered heterocyclyl, 5-10 membered heteroaryl, $C_{3-10}$cycloaliphatic, $-(C_{1-6}$alkyl)-$C_{6-10}$aryl, $-(C_{1-6}$ alkyl)-(5-10 membered heteroaryl), $-(C_{1-6}$alkyl)-(5-10 membered heterocyclyl), or $-(C_{1-6}$alkyl)-$C_{3-10}$cycloaliphatic; wherein said $R^4$ group is optionally substituted with 0-5 J and 0-2 $J^2$; or two $R^4$ groups, together with the atom to which they are attached, form a 3-8 membered monocyclic or 8-12 membered bicyclic ring optionally substituted with 0-5 J and 0-2 $J^2$; J is halogen, $-OR'$, $-NO_2$, $-CN$, $-CF_3$, $-OCF_3$, $-R'$, 1,2-methylenedioxy, 1,2-ethylenedioxy, $-N(R')_2$, $-SR'$, $-SOR'$, $SO_2R'$, $-SO_2N(R')_2$, $-SO_3R'$, $C(O)R'$, $-C(O)C(O)R'$, $-C(O)C(O)OR'$, $-C(O)C(O)N(R')_2$, $-C(O)CH_2C(O)R'$, $-C(S)R'$, $-C(S)OR'$, $-C(O)OR'$, $-OC(O)R'$, $-C(O)N(R')_2$, $-OC(O)N(R')_2$, $-C(S)N(R')_2$, $-(CH_2)_{0-2}NHC(O)R'$, $-N(R')N(R')COR'$, $-N(R)N(R)C(O)OR'$, $-N(R')N(R')CON(R')_2$, $-N(R')SO_2R'$, $-N(R')SO_2N(R')_2$, $-N(R')C(O)OR'$, $-N(R')C(O)R'$, $-N(R')C(S)R'$, $-N(R')C(O)N(R')_2$, $-N(R')C(S)N(R')_2$, $-N(COR')COR'$, $-N(OR')R'$, $-CN$, $-C(=NR')N(R)_2$, $-C(O)N(OR')R'$, $-C(=NOR')R'$, $-OP(O)(OR')_2$, $-P(O)(R')_2$, $-P(O)(OR')_2$, or $-P(O)(H)(OR')$; $J_2$ is $=NR'$, $=N(OR')$, $=O$, or $=S$; $R'$ is H, $C_{1-12}$aliphatic, $C_{6-10}$aryl, 5-10 membered heterocyclyl, 5-10 membered heteroaryl, $C_{3-10}$cycloaliphatic, $-(C_{1-6}$alkyl)-$C_{6-10}$aryl, $-(C_{1-6}$alkyl)-(5-10 membered heteroaryl), $-(C_{1-6}$alkyl)-(5-10 membered heterocyclyl), or $-(C_{1-6}$alkyl)-$C_{3-10}$cycloaliphatic; each R' is independently and optionally substituted with 0-5 occurrences of H, $C_{1-6}$alkyl, $CF_3$, halogen, $NO_2$, $OCF_3$, CN, OH, $O(C_{1-6}$alkyl), $NH_2$, $N(C_{1-6}$alkyl), $N(C_{1-6}$alkyl)$_2$, $C(=O)CH_3$, or $C_{1-6}$alkyl optionally interrupted 1 time with a heteroatom selected from O, N, and S; wherein each $C_{1-6}$alkyl is unsubstituted; unless otherwise indicated, any group with suitable valence is optionally substituted with 0-5 J and 0-2 $J^2$.

Benzenesulfonyl-ureas described herein are preferably destined for the manufacture of orally administrable preparations and can be applied as such or in the form of their salts or in the presence of substances causing salt formation. For the formation of salts there can be used: alkaline agents, for instance, alkali metal hydroxides, alkaline earth metal hydroxides, alkali metal carbonates, alkaline earth metal carbonates, alkali metal bicarbonates, alkaline earth metal bicarbonates, but likewise organic bases, particularly tertiary nitrogen bases, if the latter are tolerated by the host.

In some embodiments, a pharmaceutical preparation is a tablet containing in addition to a compound of the invention an adjuvant or carrier such as talc, starch, lactose, tragacanth or magnesium stearate.

In some embodiments, a preparation containing the above-mentioned benzenesulfonyl-ureas as active substance, for instance, a tablet or a powder, with or without the above-mentioned additions, is favorably brought into a suitable dosage unit form. The dose chosen should comply with the activity of the benzenesulfonyl-urea used and the desired effect. Favorably, the dosage per unit amounts to about 0.5 to 100 milligrams, preferably to 2-10 milligrams, but considerably higher or lower dosage units can likewise be used which, if desired, are divided or multiplied prior to application.

Pharmaceutical compositions or medicaments for use in the present invention can be formulated by standard techniques using one or more physiologically acceptable carriers or excipients. Suitable pharmaceutical carriers are described herein and in "*Remington's Pharmaceutical Sciences*" by E. W. Martin. The compounds of the present invention and their physiologically acceptable salts and solvates can be formulated for administration by any suitable route that achieves their intended purpose, including via inhalation, topically, nasally, orally, parenterally, or rectally. Thus, the administration of the pharmaceutical composition may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration. Tablets and capsules can be administered orally, rectally or vaginally.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a small molecule compound of the present invention, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate; (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or *acacia*; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

In some embodiments of the present invention, a tablet suitable for oral administration comprises 0.3 to 100 milligrams, preferably 2 to 10 milligrams, of a caspase-1 inhibitor.

As a non-limiting example, in some embodiments of the present invention, a tablet suitable for oral administration comprises 0.3 to 100 milligrams, preferably 2 to 10 milligrams, of a caspase-1 inhibitor having Formula 1a or 1b:

Formula 1a and 1b

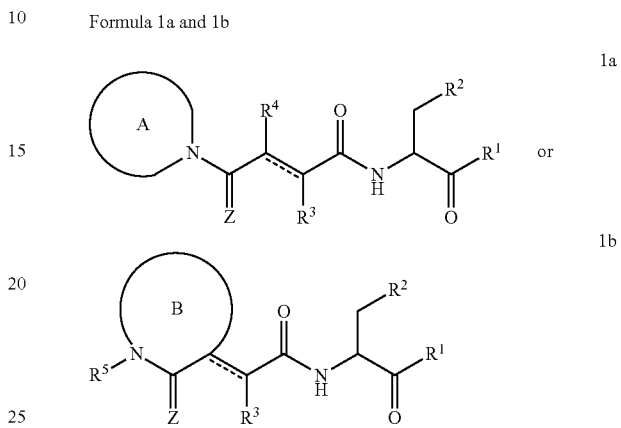

or single stereoisomers, mixtures of stereoisomers, pharmaceutically acceptable salts or prodrugs thereof, wherein: ⁓ next to $R^3$ represents a single or double bond; Z is oxygen or sulfur; $R^1$ is hydrogen, —$CHN_2$, —R, —$CH_2OR$, —$CH_2SR$, or —$CH_2Y$; R is a $C_{1-12}$ aliphatic, aryl, aralkyl, heterocyclyl, or heterocyclylalkyl; Y is an electronegative leaving group; $R^2$ is $CO_2H$, $CH_2CO_2H$, or esters, amides or isosteres thereof; $R^3$ is a group capable of fitting into the S2 sub-site of a caspase; $R^4$ is hydrogen or a $C_{1-6}$ aliphatic group that is optionally interrupted by —O—, —S—, —$SO_2$—, —CO—, —NH—, or —$N(C_{1-4}$ alkyl)-, or $R^3$ and $R^4$ taken together with their intervening atoms optionally form a 3-7 membered ring having 0-2 heteroatoms selected from nitrogen, oxygen or sulfur; Ring A is a nitrogen-containing mono-, bi- or tricyclic ring system having 0-5 additional ring heteroatoms selected from nitrogen, oxygen or sulfur; Ring B is a nitrogen-containing 5-7 membered ring having 0-2 additional ring heteroatoms selected from nitrogen, oxygen or sulfur; $R^5$ is $R^6$, $(CH_2)_nR^6$, $COR^E$, $CO_2R^6$, $SO_2R^6$, $CON(R^6)_2$, or $SO_2N(R^6)_2$; n is one to three; and each $R^6$ is independently selected from hydrogen, an optionally substituted $C_{1-4}$ aliphatic group, an optionally substituted $C_{6-10}$ aryl group, or a mono- or bicyclic heteroaryl group having 5-10 ring atoms.

As a non-limiting example, in some embodiments of the present invention, a tablet suitable for oral administration comprises 0.3 to 100 milligrams, preferably 2 to 10 milligrams, of a caspase-1 inhibitor having Formula 2:

Formula 2

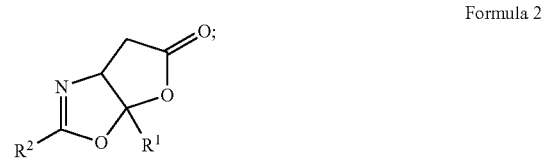

or single stereoisomers, mixtures of stereoisomers, pharmaceutically acceptable salts or prodrugs thereof, wherein $R^1$ is H, $R^4$, haloalkyl, $CHN_2$, $CH_2Cl$, $CH_2F$, —$CH_2OPO(R^4)_2$, —$CH_2OPO(OR^4)_2$, or —$C_{1-2}$alkyl-$R^3$—$R^4$; $R^2$ is a $P_4$—$P_3$—$P_2$, $P_3$—$P_2$, or $P_2$ moiety of a caspase-1 inhibitor; $R^3$ is —O—, —NH—, —NR$^4$—, —S— or —O(C=O)—; $R^4$ is $C_{1-12}$aliphatic, $C_{6-10}$aryl, 5-10 membered heterocyclyl, 5-10 membered heteroaryl, $C_{3-10}$cycloaliphatic, —($C_{1-6}$alkyl)-$C_{6-10}$aryl, —($C_{1-6}$ alkyl)-(5-10 membered heteroaryl), —($C_{1-6}$alkyl)-(5-10 membered heterocyclyl), or —($C_{1-6}$alkyl)-$C_{3-10}$cycloaliphatic; wherein said $R^4$ group is optionally substituted with 0-5 J and 0-2 $J^2$; or two $R^4$ groups, together with the atom to which they are attached, form a 3-8 membered monocyclic or 8-12 membered bicyclic ring optionally substituted with 0-5 J and 0-2 $J^2$; J is halogen, —OR', —NO$_2$, —CN, —CF$_3$, —OCF$_3$, —R', 1,2-methylenedioxy, 1,2-ethylenedioxy, —N(R')$_2$, —SR', —SOR', SO$_2$R', —SO$_2$N(R')$_2$, —SO$_3$R', C(O)R', —C(O)C(O)R', —C(O)C(O)OR', —C(O)C(O)N(R')$_2$, —C(O)CH$_2$C(O)R', —C(S)R', —C(S)OR', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R)N(R)C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —CN, —C(=NR')N(R)$_2$, —C(O)N(OR')R', —C(=NOR')R', —OP(O)(OR')$_2$, —P(O)(R')$_2$, —P(O)(OR')$_2$, or —P(O)(H)(OR'); $J_2$ is =NR', =N(OR'), =O, or =S; R' is H, $C_{1-12}$aliphatic, $C_{6-10}$aryl, 5-10 membered heterocyclyl, 5-10 membered heteroaryl, $C_{3-10}$cycloaliphatic, —($C_{1-6}$alkyl)-$C_{6-10}$aryl, —($C_{1-6}$alkyl)-(5-10 membered heteroaryl), —($C_{1-6}$alkyl)-(5-10 membered heterocyclyl), or —($C_{1-6}$alkyl)-$C_{3-10}$cycloaliphatic; each R' is independently and optionally substituted with 0-5 occurrences of H, $C_{1-6}$alkyl, CF$_3$, halogen, NO$_2$, OCF$_3$, CN, OH, O($C_{1-6}$alkyl), NH$_2$, N($C_{1-6}$alkyl), N($C_{1-6}$alkyl)$_2$, C(=O)CH$_3$, or $C_{1-6}$alkyl optionally interrupted 1 time with a heteroatom selected from O, N, and S; wherein each $C_{1-6}$alkyl is unsubstituted; unless otherwise indicated, any group with suitable valence is optionally substituted with 0-5 J and 0-2 $J^2$.

Compounds of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

Suitable formulations for transdermal application include an effective amount of a compound of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

In some embodiments of the present invention, a pharmaceutical composition or medicament comprises an effective amount of an inhibitor for the activation and/or activity of caspase-1 as described above, and another therapeutic agent, such as a component used for HAART, as described herein. When used with compounds of the invention, such therapeutic agent may be used individually (e.g., a component used for HAART and compounds of the present invention), sequentially (e.g., a component used for HAART and compounds of the present invention for a period of time followed by e.g., a second component used for HAART and compounds of the present invention), or in combination with one or more other such therapeutic agents (e.g., a reverse transcriptase inhibitor used for HAART, a protease inhibitor used for HAART, and compounds of the present invention). Administration may be by the same or different route of administration or together in the same pharmaceutical formulation.

In a some embodiments of the present invention, a pharmaceutical composition comprises (i) a caspase-1 inhibitor or a pharmaceutically acceptable salt, prodrug or active derivative of such a substance and (ii) a pharmaceutically acceptable carrier.

In a some embodiments of the present invention, a pharmaceutical composition comprises (i) a caspase-1 inhibitor or a pharmaceutically acceptable salt, prodrug or active derivative of such a substance, (ii) an inhibitor for use in HAART, and (iii) a pharmaceutically acceptable carrier.

B. Therapeutic Effective Amount and Dosing

In some embodiments of the present invention, a pharmaceutical composition or medicament is administered to a subject, preferably a human, at a therapeutically effective dose to prevent, treat, or control a condition or disease as described herein, such as HIV-1 infection and AIDS. The pharmaceutical composition or medicament is administered to a subject in an amount sufficient to elicit an effective therapeutic response in the subject. An effective therapeutic response is a response that at least partially arrests or slows the symptoms or complications of the condition or disease. An amount adequate to accomplish this is defined as "therapeutically effective dose."

The dosage of active compounds administered is dependent on the species of warm-blooded animal (mammal), preferably a human, the body weight, age, individual condition, surface area of the area to be treated and on the form of administration. The size of the dose also will be determined by the existence, nature, and extent of any adverse effects that accompany the administration of a particular small molecule compound in a particular subject. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of compound accumulation in the body of a subject. In general, dosage may be given once or more daily, weekly, or monthly. Persons of ordinary skill in the art can easily determine optimum dosages, dosing methodologies and repetition rates.

In some embodiments of the present invention, a pharmaceutical composition or medicament comprising compounds of the present invention is administered in a daily dose in the range from about 0.1 mg of each compound per kg of subject weight (0.1 mg/kg) to about 1 g/kg for multiple days. In other embodiments, the daily dose is a dose in the range of about 5 mg/kg to about 500 mg/kg. In yet other embodiments, the daily dose is about 10 mg/kg to about 250 mg/kg. In other embodiments, the daily dose is about 25 mg/kg to about 150 mg/kg. A preferred dose is about 10 mg/kg. The daily dose can be administered once per day or divided into subdoses and administered in multiple doses, e.g., twice, three times, or four times per day. However, as will be appreciated by a skilled artisan, inhibitors for the activation and/or activity of caspase-1 may be administered in different amounts and at different times.

In some embodiments, a tablet comprises from 0.5 to 100 mg of the active ingredient of a compound described herein, preferably from 1 to 50 mg, more preferably from 1.5 to 25 mg, even more preferably from 2 to 10 mg.

To achieve the desired therapeutic effect, compounds may be administered for multiple days at the therapeutically effective daily dose. Thus, therapeutically effective administration of compounds to treat a condition or disease described herein in a subject requires periodic (e.g., daily) administration that continues for a period ranging from three days to two weeks or longer. Typically, compounds will be administered for at least three consecutive days, often for at least five consecutive days, more often for at least ten, and sometimes for 20, 30, 40 or more consecutive days. When used to prevent the appearance or manifestation of a condition or disease described herein, administration of a pharmaceutical composition may be done daily for as long as the appearance or manifestation of the condition or disease is to be prevented. While consecutive daily doses are a preferred route to achieve a therapeutically effective dose, a therapeutically beneficial effect can be achieved even if the compounds are not administered daily, so long as the administration is repeated frequently enough to maintain a therapeutically effective concentration of the compounds in the subject. For example, one can administer the compounds every other day, every third day, or, if higher dose ranges are employed and tolerated by the subject, once a week. A preferred dosing schedule, for example, is administering daily for a week, one week off and repeating this cycle dosing schedule for 3-4 cycles.

Optimum dosages, toxicity, and therapeutic efficacy of compounds described herein may vary depending on the relative potency of individual compounds and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from, for example, cell culture assays and animal studies can be used to formulate a dosage range for use in humans. The dosage of such small molecule compounds lies preferably within a range of circulating concentrations that include the $ED_{50}$ with little or no toxicity. The dosage can vary within this range depending upon the dosage form employed and the route of administration. For any compounds used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of compounds is from about 1 ng/kg to 100 mg/kg for a typical subject.

For the treatment of an HIV-1 infection and/or AIDS or for preventing the death of a CD4 T-cell in a population of CD4 T-cells comprising HIV-1 infected and uninfected CD4 T-cells there may be no fixed dosage regimen for administering a some caspase-1 inhibitor. The patient's viral load or CD4 T-cell count may be measured periodically to determine the minimum effective dose for the patient.

In some embodiments, a starting dose of a caspase-1 inhibitor is 2.5 to 5 mg daily, which may be administered with breakfast or a first main meal. In some embodiments, a maintenance dose for a caspase-1 inhibitor is in the range of 1.25 to 20 mg daily, which may be given as a single dose or in divided doses. Dosage increases should be made in increments of no more than 2.5 mg at weekly intervals based upon the patient's response (such as increasing or lowering viral load, increasing or decreasing CD4 T-cell count). Once-a-day therapy is usually satisfactory, based upon usual meal patterns and the half-life of some caspase-1 inhibitors, some patients, particularly those receiving more than 10 mg daily, may have a more satisfactory response with twice-a-day dosage.

In some embodiments, a starting dose of a caspase-1 inhibitor is 1 to 2 mg daily, which may be administered with breakfast or a first main meal. In some embodiments, a maintenance dose for the caspase-1 inhibitor is in the range of 1 to 4 mg daily, which may be given as a single dose or in divided doses. In some embodiments, the maximum recommended dose is 8 mg once daily. After reaching a dose of 2 mg, dosage increases should be made in increments of no more than 2 mg at 1-2 week intervals based upon the patient's response (such as increasing or lowering viral load, increasing or decreasing CD4 T-cell count). Once-a-day therapy is usually satisfactory, based upon usual meal patterns and the half-life of some caspase-1 inhibitors, some patients, particularly those receiving more than 8 mg daily, may have a more satisfactory response with twice-a-day dosage.

Following successful treatment, it may be desirable to have the subject undergo maintenance therapy to prevent the recurrence of the condition or disease treated.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

VI. Kits

For use in diagnostic, research, and therapeutic applications suggested above, kits are also provided by the invention. In the diagnostic and research applications such kits may include any or all of the following: assay reagents, buffers, a compound of the present invention, a caspase-1 polypeptide, an IL-1β polypeptide, an HIV-1 polypeptide, a caspase-1 nucleic acid, an IL-1β nucleic acid, an HIV-1 nucleic acid, an anti-HIV-1 polypeptide antibody, hybridization probes and/or PCR primers, expression constructs for e.g., a virion, a cell expressing a caspase-1 polypeptide, a cell expressing an HIV-1 polypeptide, a component for use in HAART. A therapeutic product may include sterile saline or another pharmaceutically acceptable emulsion and suspension base.

In some embodiments of the present invention, a kit comprises one or more inhibitors for caspase-1. Optionally, the kit includes one or more components used for HAART as described herein. Typically, these compounds are provided in a container.

This invention provides kits for use in the methods described herein. In some embodiments of the present invention this kit comprises (i) a first container containing an inhibitor for caspase-1 and (ii) an instruction for using the inhibitor for caspase-1 in a method of the present invention. In other embodiments, this kit comprises any of the compounds described herein and above, which will be provided in a separate container.

In addition, a kit may include instructional materials containing directions (i.e., protocols) for the practice of methods of this invention. The instructions may be present in the subject kits in a variety of forms, one or more of which may be present in the kit. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials. Optionally, the instruction comprises warnings of possible side effects and drug-drug or drug-food interactions.

A wide variety of kits and components can be prepared according to the present invention, depending upon the intended user of the kit and the particular needs of the user.

In some embodiments of the present invention, the kit is a pharmaceutical kit and comprises a pharmaceutical composition comprising (i) one or more inhibitors for caspase-1 and (ii) a pharmaceutical acceptable carrier. In other embodiments, the pharmaceutical kit comprises a component for use in HAART as described herein. Pharmaceutical kits optionally comprise an instruction stating that the pharmaceutical composition can or should be used for treating a condition or disease described herein.

Preferred embodiments of this invention are described herein, including the best mode known to the inventors for carrying out the invention. Of course, variations on those preferred embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

As can be appreciated from the disclosure above, the present invention has a wide variety of applications. While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention. The invention is further illustrated by the following examples, which are only illustrative and are not intended to limit the definition and scope of the invention in any way.

VII. Examples

The below examples are meant to illustrate specific embodiments of the methods and compositions described herein and should not be construed as limiting the scope of the invention in any way.

Example 1

General i. Culture and Infection of HLACs

Human tonsil or splenic tissues from routine tonsillectomies were obtained from the National Disease Research Interchange and the Cooperative Human Tissue Network and processed as previously described (Jekle et al., 2003, *J Virol* 77:5846-5854). In brief, tonsils or spleen were minced, passed through a 40-μm cell strainer, and cultured in 96-well U-bottomed polystyrene plates ($2 \times 10^6$ cells/well) in medium (200 μl/well) consisting of RPMI 1640 supplemented with 15% heat-inactivated fetal bovine serum, 100 μg/ml gentamicin, 200 μg/ml ampicillin, 1 mM sodium pyruvate, 1% nonessential amino acids (Mediatech), 2 mM L-glutamine, and 1% fungizone (Invitrogen). All HIV-1 infections were carried out with 20-50 ng of HIV-1 p24$^{gag}$. Cells were incubated with the virus for 12-16 h, washed extensively, and supplemented with fresh medium. After day 5, infections were monitored by measuring p24gag levels in the culture medium using a FLAQ assay (Hayden et al., 2003, *AIDS* 17:629-631). Infected and uninfected cultures were manipulated as described for individual experiments. In "indirect killing" assays, unless otherwise stated, drugs were used at the following concentrations: 5 µM AZT; 250 nM AMD3100; 10 µg/ml T20; 100 nM Efavirenz; 1 µM Nevirapine; 30 µM Raltegravir; 60 µM 118-D-24; 5 µM Amprenavir; 5 µM Saquinavir; 5 µM Indinavir. CFSE-labeled cells were activated with PHA (5 µg/ml) and IL-2 (20 ng/ml) 2 days before mixing with effector cells.

ii. HIV-1 Constructs and Preparation of HIV-1 Virions

To generate replication-competent viruses, pNL4-3, pNLENG1 (David N. Levy, The University of Alabama, Birmingham), WEAU-16, and mutant pNL4-3: ΔVif NL4-3 (also known as pNL-ND) (Adachi et al., 1991, *Arch Virol* 117:45-58; Sakai et al., 1993, *J Virol* 67:1663-1666), TR712, SIM, GIA, GIA-SKY, SKY, pNL4-3 Δenv (an HIV molecular clone lacking the Env gene, constructed by blunting at the NheI site present in the envelope coding region of NL4-3), E478Q (Smith et al., 1999, *J Virol* 73:6573-6581), and pDB653 (Guo et al., 2000, *J Virol* 74:8980-8988) proviral expression DNA were transfected into 293T-cells by the calcium phosphate method. The GIA-SKY DNA was co-transfected with a VSV-G envelope DNA (4:1). The medium was replaced after 16 hours. After 48 hours, the supernatants were collected and clarified by sedimentation, and virions were concentrated by ultracentrifugation, and stored at −80° C. in RPMI 1640 containing 50% fetal bovine serum. All viral stocks were quantitated by measuring p24gag levels by FLAQ assay.

HIV-1 viruses were generated by transfection of proviral DNA into 293T-cells by the calcium phosphate method. Virion-based fusion assay was performed as previously described (Cavrois et al., 2002, *Nat Biotechnol* 20:1151-1154).

iii. FACS Analysis and Gating Strategy

Uninfected cells (5×10$^6$/ml) were labeled with 1 µM CFSE (Molecular Probes C1157), treated with 5 µM AZT for 24 h, and co-cultured with effector cells. CFSE readily diffuses into cells, where intracellular esterases cleave the acetate groups, converting it to a fluorescent, membrane-impermeable dye. This dye is not transferred to adjacent cells and does not affect cellular function. To quantify indirect killing, mixed (CFSE-labeled+effector) cultures were washed in FACS buffer (PBS supplemented with 2 mM EDTA and 2% fetal bovine serum), stained with PE-conjugated anti-CD4, PerCP-conjugated anti-CD19, and APC-conjugated anti-CD8 (all from BD Pharmingen) and fixed in 1% paraformaldehyde. To determine the absolute numbers of the viable CFSE-labeled cells, a standard number of fluorescent beads (Flow-Count Fluorospheres, Beckman Coulter) was added to each cell-suspension sample before data acquisition. Data were collected on a FACS Calibur (BD Biosciences) and analyzed with Flowjo software (Treestar). The level of indirect killing was defined by sequential gating beginning with forward scatter versus side scatter to select live lymphocytes, subgating on the CFSE-positive population, and calculating the numbers of CD4 or CD8 T or B cells, divided by the number of fluorescent beads acquired.

iv. Preparation of Primary WEAU 16-8 HIV-1 Clone

Peripheral blood mononuclear cells (PBMCs) obtained 15 days after the onset of symptoms were used to isolate a molecular proviral clone of HIV-1 (WEAU1.60). A panel of plasma-derived HIV-1 envelopes obtained at various times over the course of disease in this patient was also prepared (Wei et al., 2003, *Nature* 422:307-312). These envelopes were subcloned into the WEAU1.60 backbone to create isogenic WEAU molecular clones. Each of these viruses replicated efficiently in primary PBMC cultures (data not shown). To create the proviral clone WEAU1.60, PBMCs obtained patient WEAU (Clark et al., 1991, *N Engl J Med* 324:954-960) 15 days after the onset of infection were co-cultured with PHA/IL2-stimulated lymphocytes for 14 days and then with an H9 T-cell line for 14 days. The proviral WEAU1.60 was subcloned into pTOPO-XL, and the flanking cellular DNA sequences were removed. Envelope 16-8, isolated 16 days after the onset of symptoms, and a panel of other envelopes derived from patient WEAU at sequential plasma time-points (Wei et al., 2003, *Nature* 422:307-312) were individually subcloned into the pTOPO-XL WEAU1.60 plasmid using two NdeI sites located at positions 6399 and 8813.

v. Virion-Based Fusion Assay

The virion-based fusion assay is performed in three successive steps: (1) incubation of target cells with virions, (2) loading of target cells with the CCF2/AM dye, and (3) development and detection of the BlaM reaction. SupT1 cells (5×10$^5$) were incubated with BlaM-Vpr containing virions (400 ng of p24$^{gag}$ at 37° C. for 2 hours, washed in $CO_2$-independent medium (GibCo BRL), and loaded with CCF2/AM dye as described by the manufacturer (Invitrogen). Briefly, 2 µl of CCF2/AM (1 mM) was mixed with 8 µl of 0.1% acetic acid containing 100 mg/ml Pluronic-F127R and 1 ml of DEEM to constitute the loading solution. Cells were incubated in 100 µl of loading solution for 1 hour at room temperature. After two washes with DEEM, the BlaM reaction was executed for 16 hours at room temperature in 200 µl of DMEM supplemented with 10% FBS and 2.5 mM probenecid, a nonspecific inhibitor of anion transport (Sigma Pharmaceuticals). Finally, the cells were washed once in DMEM and fixed in a 2% solution of paraformaldehyde. The change in emission fluorescence of CCF2 after cleavage by the BlaM-Vpr chimera was monitored by flow cytometry with LSR2 (Becton Dickinson, San Jose, Calif.). Data were collected with DiVa software and analyzed with FlowJo software (Treestar, San Carlos, Calif.).

vi. Spinoculation

Fresh HLAC cells are cultured overnight in a V-bottom 96-well plate (1×10$^6$ cells/well) in the presence of drugs and then chilled on ice. HIV-1 (600-800 ng p24gag/200 µl) is added to each well and mixed with cold cells. The cold temperature allows virion attachment but prevents virion fusion. HIV-coated cells are then tightly packed into a pellet by high-speed centrifugation (1200 g) for 2 hours at 4° C. This step presses the virus between cell membranes, exerting a uniform and consistent attachment. Immediately after centrifugation cells are cultured at 37° C. as a pellet. This step promotes high-level attachment of virions to target cell membranes. Immediately after centrifugation, cells are cultured at 37° C. as a pellet. This step facilitates a coordinated fusion of the attached viruses, generating a pulse of virion entry into the target cells. After 3 days of incubation, the cells are subjected to analysis by flow cytometry.

vii. Isolation of CD4 T-Cells and Taqman-Based QPCR Analysis of HIV-1-Infected CD4 T-Cells Fresh HLACs were washed once with PBS and resuspended with PBS containing 5 mM EDTA and 2% fetal bovine serum. CD4 T-cells were isolated from HLACs by positive selection on CD4 microbeads (Miltenyi) and cultured overnight in 96-well U-bottomed plates (1×10$^6$ cells/well) as described above, and AZT was added to the indicated cell samples. Next day, the rest of the drugs were added to the indicated cell samples at concentrations as described above. Cells were chilled on ice for 15 min and DNAse-treated (Ambion, 60 U/ml, 1 hour, 37° C.) NL4-3 or Δvif NL4-3 virions (200 ng/well) were added. After a 1 hour incubation with virions on ice, cells were spinoculated at 1200 g for 2 hours at 4° C., incubated at 37° C. for 2 hours, washed three times with cold PBS, and resuspended in fresh RPMI with the indicated drugs. Eight or 16 hours after spinoculation, cell pellets were frozen at −80° C. Total DNA was purified from each cell pellet with a DNAse kit (Qiagen). Primer and probe sequences used to detect reverse transcription products are provided herein. QPCR reactions were performed in triplicates in TaqMan universal PCR master mix using each primer at 3.75 µM and probe at 2.5 µM. After 15 minutes at 95° C., reactions underwent 50 cycles of 15 sec at 95° C. followed by 1 min at 60° C. in an ABI Prism 7900HT (Applied Biosystems).

viii. ISRE-GFP H35 Reporter Cells, Microscopy, and Generation of Synthetic HIV-1 Reverse Transcription Intermediates Hepatocyte-derived reporter ISRE-GFP H35 cells were maintained as previously described (King et al., 2007, Lab Chip 7:77-85; Patel et al., 2009, Proc Natl Acad Sci USA 106:12867-12872). For microscopic imaging, ISRE-GFP reporter H35 cells were cultured on 35 mm glass bottom culture dishes (MatTeck) and were treated with AZT (5 µM), Efavirenz (100 nM), or Raltegravir (30 µM) 12 hours before infection. Cells were then infected with 2 µg/ml of replication competent VSV-G pseudotyped NL4-3. After 48 hours incubation at 37° C., cells were fixed in 2% paraformaldehyde at 25° C. for 1 hour, washed with PBS and stained with 10 µg/ml Hoechst 33342 (Invitrogen) and 1 µg/ml 7-AAD (eBioscience) for 15 min at 25° C. Cells were washed 3 times with PBS and were analyzed with an Axio observer Z1 microscope (Zeiss) equipped with an EC Plan NEOFLUAR 10×/0.3 PHM27 objective, filter sets 38HE, 45, and 49, and an Axiocam MRM REV 3.

For generation of synthetic HIV-1 reverse transcription intermediates, PCR products of 150 bp, 500 bp, 1,500 bp, and 3,300 bp were generated using the same reverse primer: 5'-CAGTACAGGCAAAAAGCAGCTGCTTATATG-3' (SEQ ID NO: 21). The following forward primers were used to amplify the corresponding PCR product: 150-5'-GCATC-CGGAGTACTTCAAGAACTGCTGAC-3' (SEQ ID NO: 22); 500-5'-AAGGCAGCTGTAGATCTTAGCC-3' (SEQ ID NO: 23); 1,500-5'-ACTGCTGTGCCTTGGAATGCTAGT-TGGAG-3' (SEQ ID NO: 24); 3,300-5'-ATGAGAGTGAAG-GAGAAGTATCAGCACTTGTGG-3' (SEQ ID NO:25). PCR products were gel purified to ensure no primer carryover. To generate ssDNA, PCR products were heated at 95° C. for 5-10 minutes followed by 10 minutes on ice. To generate HIV-1 pregenomic mRNA, MS HIV-1 RNA containing exons 1, 5, and 7 was cloned into pSP64 Poly(A) (Promega, Madison, Wis., United States). Uncapped or capped HIV-1 mRNA was produced by in vitro transcription with a MEGAscript™ SP6 transcription kit or mMESSAGE mMACHINE® SP6 Kit respectively (Ambion) according to manufacturer's protocol. Full-length polyadenylated transcripts were isolated using an Oligotex mRNA mini kit (Qiagen). Capped RNA was incubated with equimolar amounts of the following primers to mimic the strong stop DNA:RNA hybrid: 5'-CTGCTA-GAGATTTTCCACACTGAC-TAAAAGGGTCTGAGGGATCTCTAGTTACCAGAG TACCACAACAGACGGGCAGAGAC-TACTTTGAGCACTCAAGGCA-3' (SEQ ID NO:26) and 5'-AGCTTTATTGAGGCTTAAGCAGTGGGT-TCCCTAGTTAGCCAGAGAGCTCCCAGGCTC AGATCTGGTCTAACCAGAGAGACC-3' (SEQ ID NO: 27). To generate heteroduplex RNA, uncapped HIV-1 RNA was incubated with equimolar amounts of the following primers: 5'-GGGCTCGCCACTCCCCAGTCCCGCCCAG-GCCACGCCTCCCTGGAAAGTCC-3' (SEQ ID NO: 28); 5'-CCTCCACTCTAACACTTCTCTCT-CAGGGTCATCCATTCCATGCAGGCTCACAGGG-3' (SEQ ID NO:29); 5'-GGCTCAACTGGTACTAGCTTG-TAGCACCATCCAAAGGTCAGTGGATATCTGACCC3' (SEQ ID NO: 30); 5'-GCCAATCAGGGAAGTAGCCTTGT-GTGTGGTAGATCCACAGATCAAGG-3' (SEQ ID NO: 31); 5'-GGGAGTGAATTAGCCCTTCCAGTC-CCCCCTTTTCTTTTAAAAAGTGGCTAAG-3' (SEQ ID NO: 32); 5'-GGTGTGACTGGAAAACCCACCTCTTC-CTCCTCTTGTGCTTCTAGCCAGGC-3' (SEQ ID NO: 33); 5'-GCATTGTTAGCTGCTGTATTGCTACT-TGTGATTGCTCCATGTTTTCTAGG-3' (SEQ ID NO:49); 5'-CCCCATCTGCTGCTGGCTCAGCTCGTCT-CATTCTTTCCCTTACAGCAGGCCATCC-3' (SEQ ID NO:34); 5'-CCACTTGCCACCCATCTTATAG-CAAAATCCTTTCCAAGCCCTGTCTTATTC-3' (SEQ ID NO: 35); 5'-GGCGAATAGCTCTATAAGCTGCTTG-TAATACTTCTATAACCCTATACTGTCCCC-3' (SEQ ID NO: 36). To generate RNA:DNA hybrids, RNA and DNA were mixed together at equimolar amounts, incubated at 95° C. for 5 minutes and allowed to cool to room temperature. For transfection experiments H35 ISRE-GFP cells were plated at a density of 75,000 cells/well in 12 well plates the night before transfection. Cells were transfected with 1 µg of DNA, RNA, or RNA:DNA hybrid with Fugene (Roche) at a ratio of 3:1. 24 hours after transfection cells were harvested and analyzed by flow cytometry for GFP fluorescence. All transfections were performed in triplicate and results are representative of at least three independent experiments. A schematic illustration of the synthetic reverse transcription intermediates is provided in FIG. 14E.

ix. Assays of Intracellular Cytokines and Caspases

HLACs were subjected to intracellular analysis of caspases activity and cytokine expression 3 days after spinoculation with NL4-3. Intracellular caspase-1, -3, -6, -8, and -9 activities were analyzed with a CaspaLux1 E1D2, Phiphilux G1D2, CaspaLux6 J1D2, CaspaLux 8 L1D2, and CaspaLux 9 M1D2 kits (OncoImmunin), respectively, at 37° C. for 15 min, followed by staining with PE anti-CD4, and APC anti-CD8, at 4° C. for 15 min. For annexin V analysis, cells were stained with APC-conjugated annexin V together with PE anti-CD4, FITC anti-CD8, and with 0.5 µg/ml ethidium monoazide (E-1374, Molecular Probes) for 15 min at 4° C. For intracellular cytokine capture, cells were incubated with 2 µM protein transport inhibitor GolgiStop (BD Biosciences) containing monensin, and 5 µg/ml Brefeldin A (EMD biosciences) at 37° C. for 6 hours before analysis. Cells were then stained with anti-CD4 and anti-CD8 antibodies at 4° C. for 15 min, and fixed in 1% paraformaldehyde at 4° C. for 1 hour. Fixed cells were washed extensively with PBS and were stained in 0.2% saponin buffer (PBS+2% FBS+0.2% saponin) containing PE anti-human TNFα (R&D Systems), FITC anti-human IFNβ (PBL Biomedical laboratories), PE anti-human IL-1β (BD Biosciences), or APC anti-phosphorylated p53 at serine 37 (pS37) at 4° C. for 1 hour.

x. Protein Analysis of IL-β Maturation and Secretion

For stimulating the processing and secretion of IL-1, CD4 T-cells were isolated from HLACs by positive selection and treated with 0.5 µM PMA (Phorbol-12-myristate-12-acetate, Calbiochem Cat. #524400) for 6 hours at 37° C. PMA induces large intracellular stores of the 35 kDa pro-IL-1β. Cells were then washed with PBS and treated with 10 µM nigericin (Sigma, Cat. # N7143) overnight at 37° C. The potassium ionophore nigericin mediates an elecroneutral exchange of intracellular $K^+$ ions for extracellular protons, providing a second inflammatory stimulus, which results in the maturation and release of the bioactive 17 kDa IL-1β(Perregaux et al., 1992, *J Immunol* 149:1294-1303; Perregaux and Gabel, 1994, *J Biol Chem* 269:15195-15203).

For assessing the processing and secretion of IL-1β in abortively infected CD4 T-cells, CD4 T-cells were isolated from HLACs as described above, and were spinoculated with or without NL4-3 with the indicated drugs as describes above in vi (Spinoculation) and in FIG. 7B. For intracellular protein analysis, cells were lysed 72 hours after spinoculation in RIPA buffer (150 mM NaCl, 1% Nonidet P-40 (vol/vol), 0.5% AB-deoxycholate (vol/vol), 0.1% SDS (vol/vol), 50 mM Tris-HCl (pH 8), 1 mM DTT), and EDTA-free Protease Inhibitor (Roche Applied Science, Cat. #04 693 132 001). For analysis of secreted IL-1β, supernatants (200 µl/1 million cells) from the rest of the CD4 T-cells were collected five days after spinoculation and analyzed using Western blot. For Western blots we used the Bio-Rad Criterion 15% pre-cast Tris-HCl gels. Primary antibodies used were 1/1000 of the mouse monoclonal anti-human IL-1β (R&D Systems, Cat. # MAB201) and 1/10000 of the mouse monoclonal anti-β-Actin (Sigma, Cat. # A5316).

xi. Caspase-1 and Caspase-3 Enzyme Assays

Several assays for caspase inhibition are known in the art (e.g., WO2001/42216) and described herein.

Assays for caspase inhibition can be based on the cleavage of a fluorogenic substrate by recombinant, purified human caspase-1 or caspase-3. The assays are run in essentially the same way as those reported by Garcia-Calvo et al. (1998, *J Biol Chem* 273:32608-32613), using a substrate specific for each enzyme. The substrate for caspase-1 is Acetyl-Tyr-Val-Ala-Asp-amino-4-methylcoumarin (SEQ ID NO: 37). The substrate for caspase-3 is Acetyl-Asp-Glu-Val-Asp-amino-4-methylcoumarin (SEQ ID NO: 38). The observed rate of enzyme inactivation at a particular inhibitor concentration, $k_{obs}$, is computed by direct fits of the data to the equation derived by Thornberry et al. (1994, *Biochemistry* 33:3943-3939) using a nonlinear least-squares analysis computer program (PRISM 2.0; GraphPad software). To obtain the second order rate constant, $k_{inact}$, $k_{obs}$ values are plotted against their respective inhibitor concentrations and $k_{inact}$ values are subsequently calculated by computerized linear regression.

The effectiveness of compounds against the activity of human recombinant caspase-1 (BIOMOL Research Laboratories, Inc.) can also be measured using fluorescent based assays. 3 nM active enzyme are added to test compounds dissolved in DMSO (at various concentrations) and incubated at room temperature for 30 minutes. The tetrapeptide substrate (Ac-Trp-Glu-His-Asp-AFC, Alexis Biochemicals) is added to a final concentration of 4 µM to initiate the reaction, bringing the final reaction volume to 50 µL. Preferred caspase-1 reaction buffer contains 25 mM HEPES pH 7.4, 0.1% CHAPS, 50 mM KCl and 5 mM β-mercaptoethanol (β-ME). Caspase activity is monitored using Molecular Devices' Microplate Spectrofluorometer Gemini XS over 15-minutes at room temperature. $IC_{50}$ values are calculated using direct fits of the data to a 4-parameter fit using the computer application SOFTmax PRO. $K_{i(apparent)}$ values were calculated according to Kuzmic et al. (2000, *Analytical Biochem* 286:45-50).

The efficacy of caspase-3 inhibitors at the cellular level can also be tested in live Hela cells by the determining ability of compounds to inhibit the proteolytic cleavage of PARP (poly ADP-ribose polymerase). Briefly, in this assay, Hela cells are seeded in 96 well plates and incubated for 4 hours with staurosporine, a well characterized inducer of apoptosis, alone or together with different concentrations of a compound (e.g., 50, 25, 10 and 3 µM). After formaldehyde-based fixation, the cells are stained with a fluorescein-labeled anti-cleaved PARP antibody (Cell signaling, Cat#: 9547) and counterstained with Hoechst 33342 (Invitrogen, Cat#: H3570) to mark all nuclei. Fluorescence images are taken on a Cellomics™ microscope system (Thermo Scientific, Pittsburgh, USA) with the Hoechst stain in the blue channel and the cleaved PARP antibody stain in the green channel. The percentage of cleaved PARP positive cells is determined by calculating the ratio between nuclei with a cleaved PARP antibody staining above a certain threshold and all (Hoechst positive) nuclei. The efficacy of caspase-3 inhibition is determined by calculating the ratio between cleaved PARP positive cells after staurosporine incubation together with compounds and staurosporine incubation without compounds.

xii. Inhibition of IL-1β Secretion Assay

Processing of pre-IL-1β by caspase-1 can be measured in cell culture using a variety of cell sources. Human PBMC obtained from healthy donors provide a mixed population of lymphocyte and mononuclear cells that produce a spectrum of interleukins and cytokines in response to many classes of physiological stimulators.

Experimental Procedure: A test compound is dissolved in dimethyl sulfoxide (DMSO, Sigma #D-2650) to give a 100 mM stock solution. This is diluted in complete medium consisting of RPMI containing 10% heat inactivated FCS (Gibco BRL #10099-141), 2 mM L-Glutamine (Sigma, #G-7513), 100 U penicillin and 100 µg/ml streptomycin (Sigma #P-7539). The final concentration range of the test compound is adjusted from 100 µM down to 6 nM over eight dilution steps. The highest concentration of test compound is equivalent to 0.1% DMSO in the assay. Human PBMC are isolated from Buffy Coats obtained from the blood bank using centrifugation on Ficoll-Paque leukocyte separation medium (Amersham, #17-1440-$O_2$) and the cellular assay is performed in a sterile 96 well flat-bottomed plate (Nunc). Each well contains 100 µl of the cell suspension, $1\times10^5$ cells, 50 µl of compound dilutions and 50 µl of LPS (Sigma #L-3012) at 50 ng/ml final concentration. Controls consist of cells+/−LPS stimulation and a serial dilution of DMSO diluted in the same way as compound. The plates are incubated for 16-18 h at 37° C. in 5% $CO_2$ & 95% humidity atmosphere. After 16-18 h, the supernatants are harvested after centrifuging the plates at 100×g at 18° C. for 15 min and assayed for their IL-1β content. Measurement of mature IL-1β in the supernatant is performed using the Quantikine kits (R&D Systems) according to manufacturer's instructions. Mature IL-1β levels of about 600-1500 pg/ml are observed for PBMCs in positive control wells. The inhibitory potency of the compounds can be represented by an $IC_{50}$ value, which is the concentration of inhibitor at which 50% of the mature IL-1β is detected in the supernatant as compared to the positive controls.

xiii. ELISA for IL-1β

Quantikine kits (R&D Systems) may be used for the measurement of mature IL-1β. Assays are performed according to the manufacturer's directions. Mature IL-1β levels of about 1-3 ng/ml in both PBMC and adherent mononuclear cell positive controls are observed. ELISA assays are performed on 1:5, 1:10 and 1:20 dilutions of supernatants from LPS-positive controls to select the optimal dilution for supernatants in the test panel. The inhibitory potency of compounds can be represented by an $IC_{50}$ value, which is the concentration of inhibitor at which 50% of mature IL-1β is detected in the supernatant as compared to the positive controls.

Suitable antibodies for measuring IL-1β levels by ELISA, include, but are not limited to MAB601 (R&D Systems, Inc.; monoclonal anti-human IL-1β antibody) and BAF201 (R&D Systems, Inc.; biotinylated anti-human IL-1β antibody).

xiv. Caspase 1 Inhibitors

Caspase 1 inhibitors, Z-YVAD-FMK (SEQ ID NO: 16) (Catalog Number FMK005) and Z-WEHD-FMK (SEQ ID NO: 13) (Catalog Number FMK002), Z-VAD-FMK (Catalog Number FMK001), Z-DEVD-FMK (SEQ ID NO: 18) (Catalog Number FMK004), and caspase inhibitor control Z-FA-FMK (Catalog Number FMKC01) used in the examples described herein were obtained from R&D Systems, Inc. (USA).

Example 2

Selective Depletion of CD4 T-Cells by X4-Tropic HIV-1

To explore depletion of CD4 T-cells by HIV-1, HLACs made from freshly dissected human tonsillar tissues were infected with a GFP reporter virus (NLENG1), prepared from the X4-tropic NL4-3 strain of HIV-1. This reporter produces fully replication-competent viruses. An IRES inserted upstream of the Nef gene preserves Nef expression and supports LTR-driven GFP expression (Levy et al., 2004, *Proc Natl Acad Sci USA* 101:4204-4209), allowing simultaneous quantification of the dynamics of HIV-1 infection and T-cell depletion. NL4-3 was selected because tonsillar tissue contains a high percentage of CD4 T-cells expressing CXCR4 (90-100%). Productively infected GFP-positive cells appeared in small numbers 3 days after infection, peaked on days 6-9, and decreased until day 12, when few CD4 T-cells remained in the culture (FIG. 1) Fluorescence-linked antigen quantification (FLAQ) assay of HIV-1 p24 (Hayden et al., 2003, *AIDS* 17:629-631) confirmed the accumulation of viral particles in the medium between day 3 and days 8-9, when a plateau was reached (data not shown). Interestingly, when HIV-1 p24 levels plateaued no more than 1.5% of all cells (about 5% of CD4 T-cells) were GFP-positive. However, although the number of CD4 T-cells was not markedly altered in infected cultures through six days, the culture was almost completely devoid of CD4 T-cells by day 9. CD8 T-cells were not depleted in infected cultures, and CD4 T-cells were not depleted in uninfected cultures. These findings reveal marked and selective depletion of CD4 T-cells in HLAC cultures. However, due to the nature of the assay, it could not have been definitely concluded whether the principal mechanism of depletion involved direct or indirect effects of HIV-1.

Example 3

Extensive Depletion of Non-Productively Infected CD4 T-Cells in HLACs

To determine if indirect killing (formerly indicated as "bystander") of CD4 T-cells accounted for most of the observed cellular depletion, an experimental strategy (Jekle et al., 2003, *J Virol* 77:5846-5854) was employed that unambiguously distinguishes between the death of productively and non-productively infected cells (FIG. 2A). After 6 days of co-culture, survival analysis of CFSE-labeled cells by flow cytometry (FIG. 2B) showed extensive depletion of CD4 T-cells in cultures mixed with HIV-infected cells but not in those mixed with uninfected cells (FIG. 2C). The relative proportion of CD8 T-cells was not altered. CD3+/CD8– T-cells were similarly depleted, indicating that the loss was not an artifact of downregulated surface expression of CD4 following direct infection. Loss of CFSE-labeled CD4 T-cells was prevented by AMD3100, which blocks the engagement of gp120 with CXCR4, but not by the reverse transcriptase inhibitor AZT (AZT prevents productive infection of target cells without affecting viral output from productively infected cells). Thus, productive viral replication is not required for CD4 T-cell death.

Figure 3:
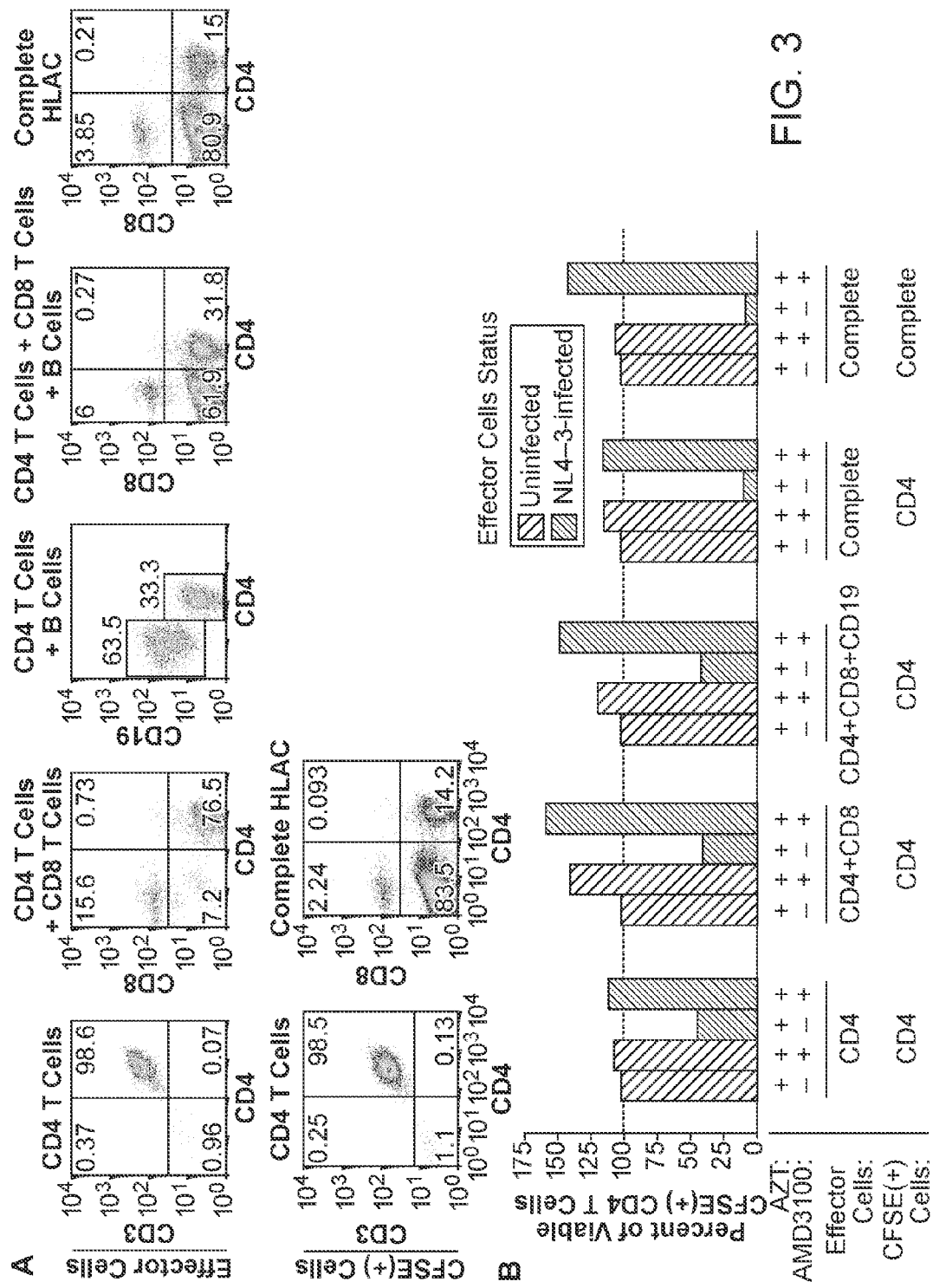
FIG. 3 depicts that CD4 T-cells are sufficient to induce indirect killing in HLAC. (A) CD4 T-cells, CD8 T-cells, and B cells were isolated from HLACs by positive selection on CD4, CD8 and CD19 microbeads (Miltenyi), respectively. The isolated cells were cultured in combinations and proportions that corresponded to their authentic distribution in the complete, undivided HLAC (shown), and were infected with NL4-3 ("Effector Cells"). Effector cells from the complete HLAC were used as a positive control. After 5 days, uninfected complete HLAC and isolated CD4 T-cells were treated with AZT and labeled with CFSE ("CFSE(+) cells"). On day 6, the indicated effectors and the CFSE-labeled cells were co-cultured in the presence of 5 μM AZT or together with 250 nM AMD3100. (B) After 6 days of co-culture, the number of viable CSFE-positive CD4 T-cells was determined by flow cytometry. Percentages are normalized to the number of viable CFSE-positive CD4 T-cells co-cultured with uninfected effectors in the presence of AZT. This experiment is the representative of three independent experiments performed with cells from three different donors.

To estimate the absolute numbers of all CFSE-labeled cell subsets, a standard number of fluorescent beads was added to the cell suspensions (FIG. 2D). In contrast to the sharp decline in CD4 T-cells, the absolute numbers of CD8 T and B-cells were unaltered. Separating the HLAC into distinct cell types revealed that cell death occurred in purified populations of CD4 T-cells suggesting that other cell types did not mediate the killing. (FIG. 3). In all instances, CD4-specific killing was prevented by AMD3100 but not AZT. Importantly, the extent of CD4 T-cell depletion in the presence of AZT was similar to that observed when no antiviral drugs were added (FIG. 2C and FIG. 1, respectively). Together, these results suggest that indirect killing is the predominant mechanism for CD4 T-cell depletion in HIV-infected HLACs.

Example 4

Indirect Killing is an Intrinsic Property of CD4 T-Cells

It was investigated whether indirect killing of CD4 T-cells in HLACs requires the presence of other cell types. To this end, CD4 T-cells, CD8 T-cells, and B cells from complete HLACs were isolated and assessed for the level of indirect killing occurring in single and combined cultures as indicated (FIG. 3A). Interestingly, indirect killing was equally effective in co-cultures containing only CD4 T-cells as found in cultures containing additional CD8 T and B cells (FIG. 3B), suggesting that interactions between CD4 T-cells are sufficient to induce the cell death response. The somewhat greater depletion of CD4 T-cells observed in the complete HLACs may reflect residual anti-CD4 beads bound to infected CD4 T-cells.

Example 5

HIV 201-Mediated Fusion is Necessary for Depletion of Non-Productively Infected CD4 T-Cells Studies with AMD3100 and AZT indicated that indirect CD4 T-cell killing is mediated by events occurring between gp120-CXCR4 binding and reverse transcription. Engagement of the chemokine coreceptor induces conformational changes in gp41, resulting in insertion of viral fusion peptide on gp41 into the target T-cell membrane. To determine if the gp120-CXCR4 interaction alone or later events involving viral fusion are required for indirect killing, the effects of enfuvirtide (T20), a fusion inhibitor that blocks six-helix bundle formation by gp41, a prerequisite for virion fusion and core insertion, were evaluated.

Figure 4:
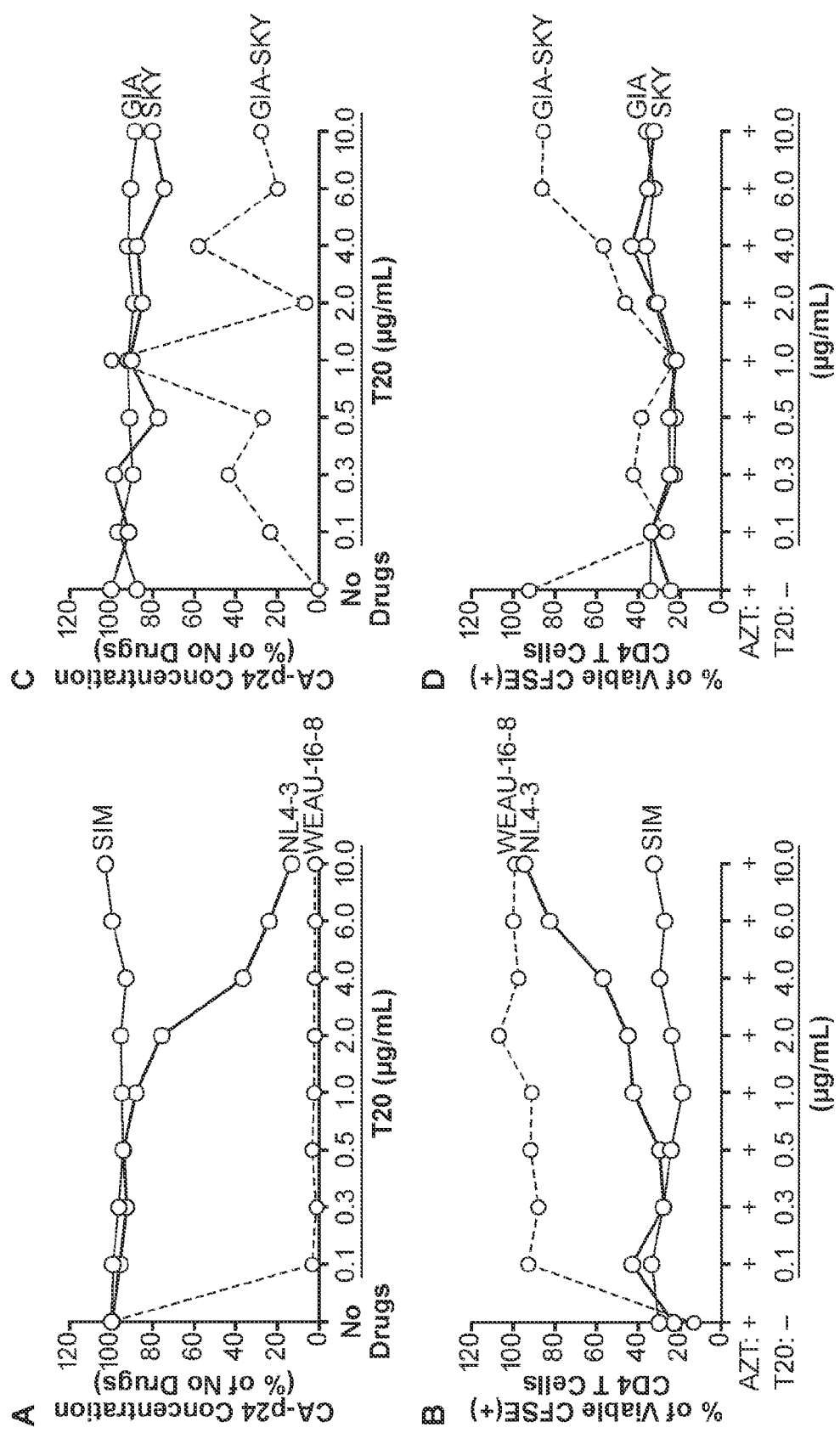
FIG. 4 depicts that HIV-1 fusion is necessary to induce killing of non-productively infected cells. (A and C) Concentrations of T20 that block viral infection. HLACs were infected with the indicated clones of HIV-1 in the presence of the indicated concentrations of T20 or no drugs. One hour before incubation with the virus, cells were pretreated with T20 or left untreated. At 12 hours, cells were washed extensively and cultured under the same conditions. On day 9, the viral concentration was determined using a p24gag FLAQ assay. The amount of p24gag accumulated in the absence of drugs by each viral clone (A) or by SKY (C) was defined as 100%. (B and D) Effect of T20 on indirect killing. CFSE-labeled cells were co-cultured with cells infected with the indicated viral clones in the presence of 5 μM AZT and the indicated concentrations of T20. After 6 days, indirect killing in the mixed cultures was assessed. The number of viable CFSE-positive CD4 T-cells co-cultured with uninfected cells in the presence of AZT was defined as 100% (not shown). To allow successful initial infection the GIA-SKY mutants were pseudotyped with the VSV-G envelope. NL4-3, WT lab-adapted virus; WEAU 16-8, primary virus; SIM, T20-resistant virus; GIA-SKY, T20-dependent virus; GIA and SKY, single-domain mutant viruses. Representative data from three independent experiments with different donors are shown. See also FIG. 5, below.
Figure 5:
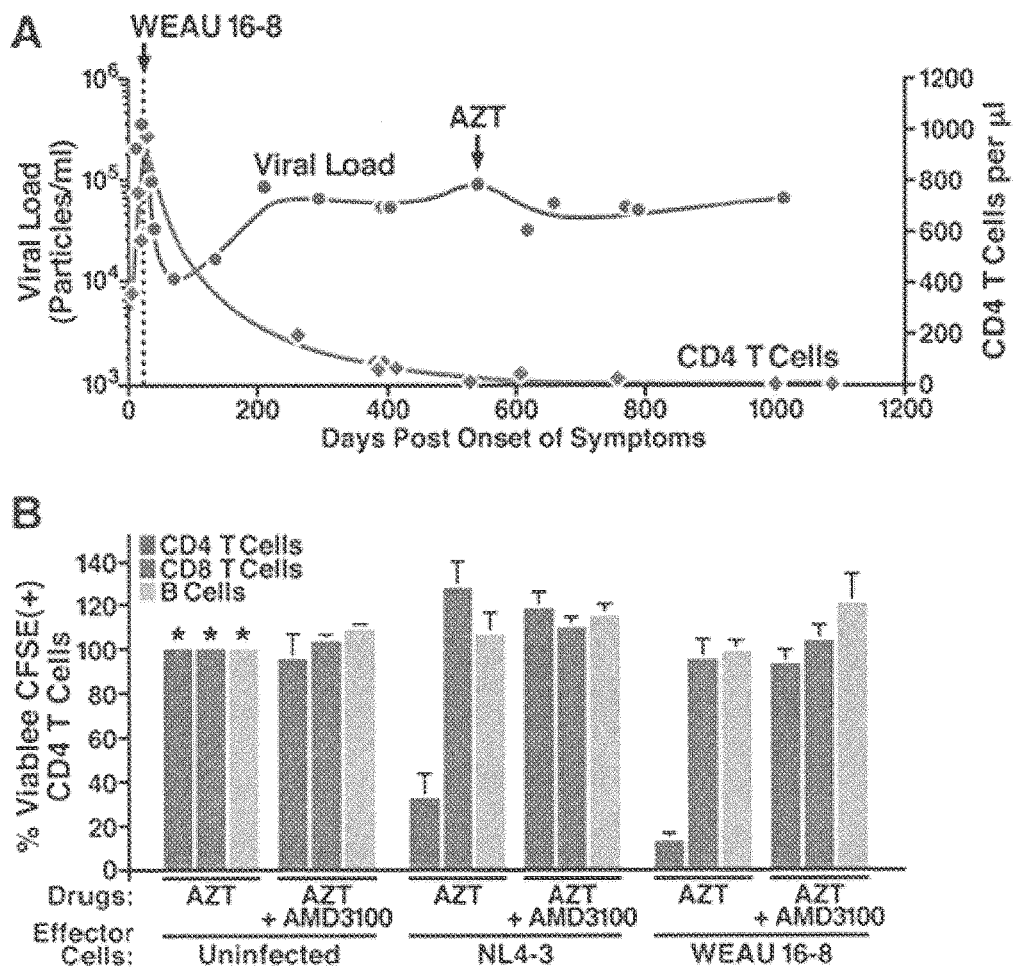
FIG. 5 depicts extensive indirect depletion of CD4 T-cells by a primary HIV-1 isolate. (A) Changes in plasma viral load and CD4 T-cells after symptom onset in patient WEAU, who was positive for HIV-1 p24gag antigen and had early clinical manifestations of acute retroviral syndrome. Arrow indicates when the 16-8 envelope was isolated, and used to derive the WEAU 16-8 subclone. (B) CFSE-labeled cells were co-cultured with cells infected with the primary WEAU 18-6 (R5/X4) viral isolate or the laboratory-adapted viral clone NL4-3 (X4) in the presence of 5 μM AZT or together with 250 nM AMD3100. After 6 days of co-culturing, the number of viable CSFE-positive cells was determined by flow cytometry. Percentages are normalized to the number of viable CFSE-positive cells co-cultured with uninfected cells in the presence of AZT, as depicted by (*). Error bars represent standard deviations obtained for three replicates performed with cells from the same donor.

The optimal concentrations of T20 that block viral infection was first determined (FIG. 4A). In NL4-3-infected cells, T20 began to inhibit infection at concentrations >2 µg/ml; complete inhibition required 10 µg/ml. In cells infected with a primary viral isolate, WEAU 16-8 (FIG. 5, below), infection was completely inhibited by 0.1 µg/ml of T20. T20 did not inhibit infection with a T20-resistant mutant, SIM (Rimsky et al., 1998, *J Virol* 72:986-993), regardless of concentration.

Next, it was investigated the effect of T20 on indirect CD4 T-cell killing (FIG. 4B). In the absence of T20, high levels of indirect killing were observed. T20 concentrations that blocked infection also greatly inhibited indirect killing. T20 did not inhibit indirect killing in cultures containing SIM-infected cells. Thus, blocking gp41-mediated fusion prevents indirect killing.

Next a T20-dependent mutant, GIA-SKY (Baldwin et al., 2004, *J Virol* 78:12428-12437), which fuses only when T20 is present, but cannot initiate a spreading infection in the absence of T20 was examined (FIG. 4C). Consistent with its T20 dependency, in the presence of 1 µg/ml T20, the GIA-SKY mutant readily replicated while growth was inhibited at higher or lower T20 concentrations. The single-domain mutants GIA and SKY exhibited a T20-resistance phenotype similar to that of SIM.

GIA-SKY-infected cells did not induce indirect killing of CD4 T-cells in the absence of T20 (FIG. 4D). Indirect killing was observed in cultures treated with 1 µg/ml T20 but was inhibited at higher or lower concentrations. Since T20-dependent viruses were bound to CXCR4 before T20 was added, these findings argue that CXCR4 signaling is not sufficient to elicit indirect CD4 T-cell killing.

Example 6

High Levels of Indirect Killing by HIV-1 Encoding Primary Envelope from a Rapid AIDS Progressor To better replicate the conditions leading to the loss of non-productively infected CD4 T-cells by HIV-1 in vivo, the indirect killing potential of primary viral isolates obtained from a patient (WEAU) (Clark et al., 1991, *N Engl J Med* 324:954-960), who was classified as a rapid progressor with high viral loads and a rapid decline in CD4 T-cell count, was evaluated (FIG. 5A). WEAU 16-8 virions contained an envelope isolated 16 days after the onset of symptoms that exhibited dual co-receptor tropism (R5/X4). Uninfected CFSE-labeled cells were co-cultured with cells infected with WEAU 16-8 or laboratory adapted NL4-3 or with uninfected cells in the presence of AZT alone or with AMD3100. After 5 days, viable CFSE-positive CD4 and CD8 T-cells and B cells were counted (FIG. 5B). In the presence of AZT alone, depletion of CSFE-positive CD4 T-cells was approximately 20% greater in co-cultures with WEAU 16-8-infected cells than in those with NL4-3-infected cells. In both cases, the number of CFSE-positive CD8 T and B cells remained essentially unchanged. Thus, primary viruses, like the laboratory-adapted NL4-3 virus, induce pronounced indirect killing in lymphoid cultures. Notably, AMD3100 prevented indirect killing induced by the dual-tropic WEAU 16-8 virus, indicating that indirect killing in lymphoid histocultures is primarily mediated by the CXCR4 pathway. TAK779, an antagonist of the CCR5 receptor, had no effect on the observed indirect killing of CD4 T-cells (data not shown).

Example 7

Figure 6:
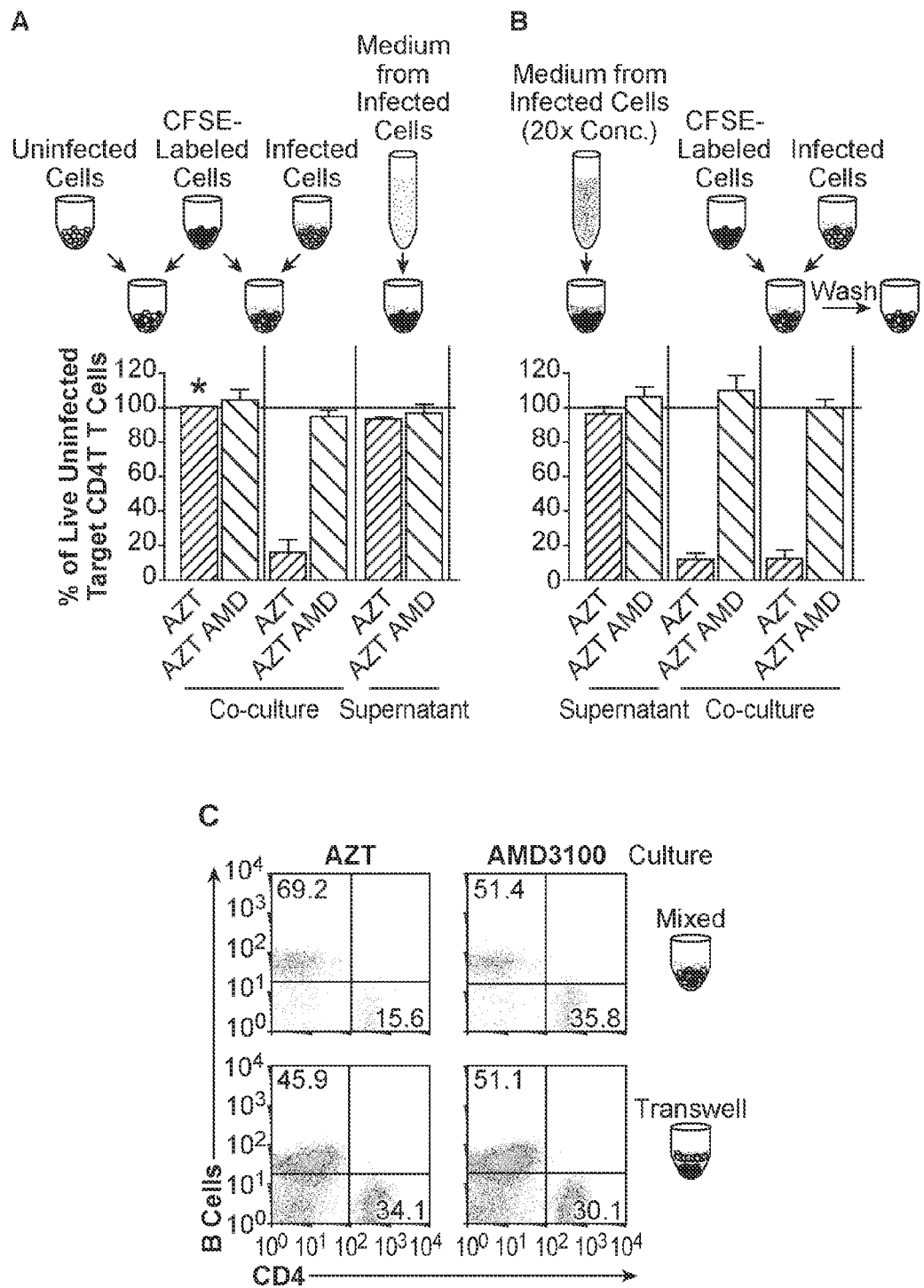
FIG. 6 depicts that killing of non-productively infected CD4 T-cells requires fusion of virions from nearby HIV-1-producing cells. (A) Supernatants from HIV-infected HLACs are less efficient at inducing indirect killing than mixing of HIV-infected and uninfected HLACs. (B) HIV-1 virions released into the medium do not participate in indirect killing. Replacing the mixed culture with fresh RPMI every 24 hours did not impair indirect killing. Challenging HLACs with supernatants containing 20-fold more histoculture-derived virions (1 μg p24/ml) than normally accumulated in mixed cultures containing infected cells (50 ng p24/ml) did not induce indirect killing. Percentages are normalized to the number of viable CFSE-positive cells depicted by (*). (C) CFSE-labeled cells are not killed when HIV-infected HLAC is physically separated by a 1 μm pore transwell system that allows free diffusion of HIV-1 particles. Values represent the levels of viable CFSE-positive cells after 6 days of culture in the presence of the indicated drugs. Red, HIV-infected cells; blue, uninfected cells; green, CFSE-labeled cells. (D) Mature and immature viruses carry equivalent amounts of envelope protein and Blam-Vpr, but differ in their content of capsid and Gag precursor. NL4-3 and TR712 viruses were generated in 293T-cells with or without amprenavir, lysed and subjected to SDS-PAGE immunoblotting analysis for gp120, p55 Gag, p24 CA, Blam-Vpr, and free Blam. (E) Immature viruses have reduced capacity to enter cells. SupT1 cells were mock infected or infected with mature or immature NL4-3 or TR712 virions containing Blam-Vpr. After loading of cells with CCF2 dye, fusion was analyzed by flow cytometry. Percentages are the fraction of cells displaying increased cleaved CCF2 fluorescence, indicating virion fusion. (F) Protease inhibitors inhibit indirect killing. CFSE-labeled cells were co-cultured with NL4-3-infected or uninfected cells in the presence of AZT (5 μM) alone or together with AMD3100 (250 nM). To the indicated cultures were added 5 μM of Amprenavir, Saquinavir, or Indinavir. Percentages are normalized to the number of viable CFSE-positive cells depicted by error bars represent the SD obtained with three independent samples from the same donor. See also FIG. 7, below.
Figure 6:
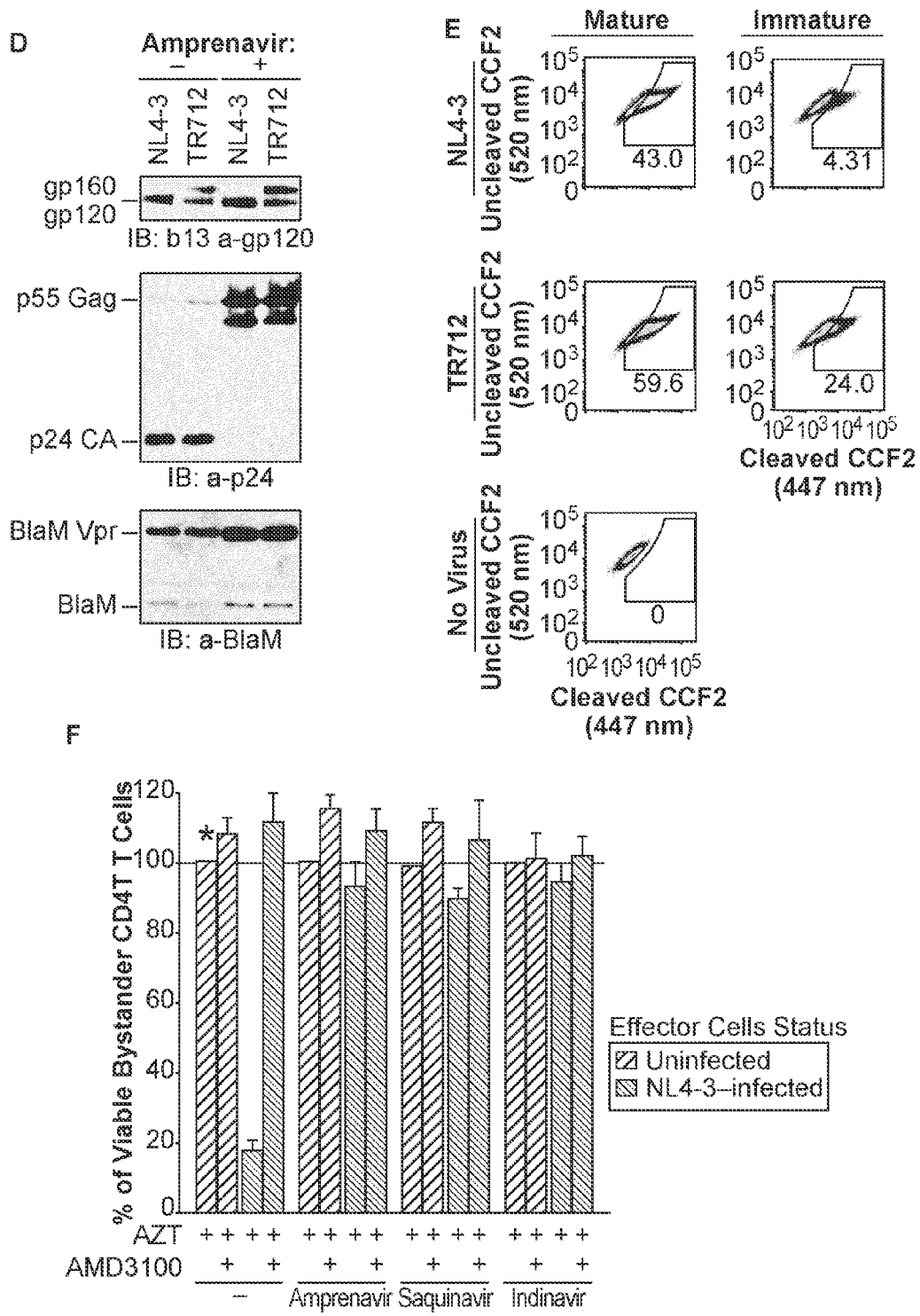

Indirect Killing Requires a Close Interaction of Uninfected and HIV-Infected Cells Next it was examined whether indirect killing requires close contact with HIV-infected cells or instead can be fully supported by virions accumulating in the supernatants of the infected histocultures. It was found that cell-free supernatants from HIV-infected histocultures were much less efficient at inducing indirect killing (FIG. 6A). To exclude the possibility that the concentration of virions in the supernatants was too low, the experiment was repeated using a 20-fold concentrated virion supernatants (1 µg p24/ml) but still failed to detect indirect CD4 T-cell killing (FIG. 6B). Together, these findings suggest that close cell-cell contact is likely required for indirect killing.

To further explore the potential requirement of close cell-cell contact for indirect killing (Sherer et al., 2007, *Nat Cell Biol* 9:310-315; Sourisseau et al., 2007, *J Virol* 81:1000-1012), these assays were repeated using cells that had been washed daily with fresh RPMI to prevent accumulation of HIV-1 virions and soluble factors. Such cell washing did not affect the ability of the resultant infected cells to mediate indirect CD4 T-cell killing (FIG. 6B), suggesting that virions released into the medium do not participate in indirect killing. These findings were confirmed using a transwell culture system. CSFE-labeled cells and HIV-infected cells were mixed or physically separated by a transwell insert with 1 µm pores, which allows free diffusion of virions but not cells. Indirect killing was substantial in the mixed cultures but not in the transwell cultures (FIG. 6C). Together, these findings indicated that indirect killing requires close interaction between CFSE-labeled and HIV-1-infected cells, consistent with in vitro (Garg et al., 2007, *J Biol Chem* 282:16899-16906; Holm and Gabuzda, 2005, *J Virol* 79:6299-6311) and in vivo studies showing that apoptotic non-productively infected cells in human lymph nodes often cluster near productively infected cells (Finkel et al., 1995, *Nat Med* 1:129-134).

Example 8

Indirect Killing Requires Fusion of Virions from Nearby HIV-Producing Cells

Indirect killing required gp41-mediated fusion and close interaction with HIV-infected cells, suggesting that cell death may be caused by the fusion of HIV-1 virions to CD4 T-cells, syncytia formation, or hemifusion (mixing of lipids in the absence of fusion pore formation) mediated by Env present on HIV-infected cells interacting with neighboring CD4 T-cells. HIV-1 virions (Holm et al., 2004, *J Virol* 78:4541-4551; Jekle et al., 2003, *J Virol* 77:5846-5854; Vlahakis et al., 2001, *J Clin Invest* 107:207-215), cell-mediated fusion (LaBonte et al., 2000, *J Virol* 74:10690-10698; Margolis et al., 1995, *AIDS Res Hum Retroviruses* 11:697-704), and hemifusion (Garg et al., 2007, *J Biol Chem* 282:16899-16906) have been proposed to be involved in indirect killing. Therefore, the requirement for cell-cell interaction in indirect killing may be mediated either by effective delivery of HIV-1 virions or by cell-associated Env.

To discriminate between virion-mediated and cell-associated Env induction of indirect killing, the effects of HIV protease inhibitors were tested. These inhibitors act during the budding process, resulting in immature viral particles that cannot fuse with target cells (Wyma et al., 2004, *J Virol* 78:3429-3435). The effect of protease inhibitors on viral maturation was assessed first. NL4-3 viruses carrying a β-lactamase-Vpr (BlaM-Vpr) reporter protein were produced in 293T-cells in the presence or absence of the HIV protease inhibitor amprenavir. A mutant virus, TR712, encoding a form of gp41 lacking 144 of the 150 amino acids in the C-terminal cytoplasmic tail was also produced. This deletion largely relieves the impaired fusogenic properties of immature HIV-1 particles (Wyma et al., 2004, *J Virol* 78:3429-3435). Protein analysis of viral lysates showed that the NL4-3 and TR712 virions appropriately cleaved gp160 to generate gp120 in the presence and absence of amprenavir. However, in the presence of amprenavir, an uncleaved form of p55 Gag polypeptide rather than the mature p24 CA protein accumulated in both NL4-3 and TR712 virions (FIG. 6D). These results confirm that amprenavir treatment of virus producing cells results in the accumulation of immature particles containing normal levels of incorporated Env proteins.

To test the ability of these viruses to fuse with target cells, an HIV virion-based fusion assay was used that measures β-lactamase (BlaM) activity delivered to target cells upon the fusion of virions containing BlaM fused to the Vpr protein (BlaM-Vpr) (Cavrois et al., 2002, *Nat Biotechnol* 20:1151-1154). Immunoblotting for BlaM confirmed that NL4-3 and TR712 virions incorporated Blam-Vpr in the presence or absence of amprenavir (FIG. 6D).

Next, SupT1 cells were infected with mature or amprenavir-treated immature NL4-3 or TR712 virions containing BlaM-Vpr. Immature NL4-3 viruses displayed a 90% decline in fusogenic properties (FIG. 6E). In contrast, immature TR712 retained 40% fusion capacity, indicating that the impaired fusion is not a result of a defective BlaM enzyme. Thus, immature virions generated in the presence of amprenavir display greatly reduced ability to fuse with target cells. Importantly, protease inhibitors did not affect the function of Env proteins expressed on infected cells and did not block cell-cell fusion.

Next the effect of protease inhibitors on indirect killing was investigated. Remarkably, three different protease inhibitors inhibited indirect killing as efficiently as AMD3100 (FIG. 6F). These results indicated that HIV-1 virions, not HIV-infected cells, are responsible for indirect CD4 T-cell killing. Additionally, recapitulating the efficient viral delivery of close cell-cell interactions by spinoculation of free virions resulted in extensive and selective indirect killing of CD4 T-cells while sparing CD8 T-cells and B cells (FIG. 7A-B). Thus, although indirect killing in lymphoid cultures requires a close interaction between non-productively and productively infected cells, this killing involves virions rather than cell-associated Env.

Example 9

Extensive and Selective Indirect Killing of CD4 T-Cells by Spinoculation

Data obtained suggested that indirect killing requires efficient delivery of virions by close cell-cell contact. Notably, the particle-to-infectivity ratio for HIV-1 was quite low ($10^{-3}$ to $10^{-4}$). In contrast, the infectivity of virus producing cells, as measured in co-cultured systems, was approximately $10^2$ to $10^3$ times higher (Dimitrov et al., 1993; *J Virol* 67:2182-2190). Although the mechanism responsible for such distinctive infection capacities is unclear, it is possible that TREX1, a cellular 3' DNA exonuclease plays a role by degrading cytoplasmic reverse transcribed DNA products (Stetson et al., 2008, *Cell* 134:587-598). TREX1 activity in the cytoplasm may create a threshold of DNA products that must be achieved for the initiation of productive infection in permissive cells, or alternatively, to induce cell death in abortively infected cells.

Therefore it was assessed whether the synchronized delivery of large numbers of HIV-1 particles by spinoculation (FIG. 7A) would generate sufficient incomplete reverse transcripts to induce a cytopathic response in CD4 T-cells. Remarkably, spinoculation of HLAC with HIV-1 induced extensive and selective depletion of CD4 T-cells (FIG. 7B). Loss of CD4 T-cells was prevented by efavirenz but not by AZT, indicating that cell death was due to abortive HIV-1 infection. These data demonstrated that efficient viral delivery was key to recapitulate the extensive indirect killing of CD4 T-cells mediated by close cell-cell interactions. Additionally, delivering the virions in such synchronous manner allowed for the evaluation of abortive infection and subsequent cell death in real time. Of note, when high doses of HIV-1 (≥2 μg p24gag/200 μl) are spinoculated, CD4 T-cell killing occurs within 12 hours and is not prevented by efavirenz (data not shown), suggesting that the efavirenz block can be overwhelmed under certain conditions. Nevertheless, T20 prevented CD4 T-cell killing even at such high viral doses, indicating that the observed indirect cell death involved abortive infection.

Example 10

Non-Permissive CD4 T-Cells Die from Abortive Infection

Based on these findings, it was hypothesized that "indirect killing" involves an abortive form of infection, like that which occurs in nonpermissive resting CD4 T-cells. These naive CD4 T-cells exhibit an early post-entry block to HIV-1 infection that can be relieved by activation with phytohemagglutinin (PHA) and interleukin-2 (IL-2) (Kreisberg et al., 2006, *J Exp Med* 203:865-870; Santoni de Sio and Trono, 2009, *PLos One* 4:e6571; Unutmaz et al., 1999, *J Exp Med* 189:1735-1746; Zack et al., 1990, *Cell* 61:213-222). To test this hypothesis, the killing of activated and non-activated CFSE-labeled cells in HLACs was compared.

CFSE-labeled cells were activated with PHA and IL-2 two days before mixing with effector cells, and contained a large percentage of dividing CD25 and CD69 positive cells. Non-activated (resting) CFSE-labeled cells did not divide and typically contained a small percentage of cells expressing CD25 and CD69 (FIG. 8A). Either in the presence or absence of AZT, killing of resting CFSE-labeled CD4 T-cells was robust (FIG. 8B, columns 4+5 and 16+17). In sharp contrast, activated CFSE-labeled CD4 T-cells were not depleted in the absence of AZT, but were extensively depleted in cultures containing AZT (FIG. 8B, columns 10+11 and 22+23). Addition of AMD3100 prevented the AZT-induced killing of activated CFSE-labeled cells, excluding non-specific toxic effects of AZT in the activated cells (FIG. 8B, columns 12 and 24).

The ability of AZT to promote indirect killing of activated CD4 T-cells suggested that cell death is triggered by impaired reverse transcription. To investigate this possibility, the experiment was repeated with two pairs of AZT-resistant HIV-1 clones, 629 and 964 (Larder et al., 1989, *Science* 243:1731-1734). It was first determined that concentrations of 0.5 μM AZT block viral replication in NL4-3-infected and AZT-sensitive clones and achieve half maximal inhibitory effect in AZT-resistant clones (FIGS. 9A-B).

When resting CFSE-labeled cells were used, the extent of killing by the AZT-resistant HIV-1 viruses was similar to that obtained with NL4-3 with or without AZT (FIG. 8C resting CFSE-positive cells), demonstrating a redundant function for endogenous termination of reverse transcription and AZT. Alternatively, when activated CFSE-labeled cells were tested, AZT-resistant HIV-1 clones did not deplete CFSE-labeled CD4 T-cells in the presence of AZT (FIG. 8C, columns 29 and 35).

Example 11

Indirect Killing Requires Elongation of Viral DNA in Abortively Infected CD4 T-Cell In the absence of Vif, human APOBEC3G from virus-producing cells is packaged into HIV-1 particles. Incorporated APOBEC3G blocks HIV-1 infection after initiation of reverse transcription but before the completion of strong-stop DNA synthesis (Bishop et al., 2008, *PLoS Pathog* 4, e1000231; Li et al., 2007, *J Biol Chem* 282:32065-32074), regardless of target cell permissively. Therefore the effect of vif-deficient (Δvif) HIV-1 on resting and activated CD4 T-cells was assessed. Because these particles introduce short reverse transcription products into the target cell, it was tested whether this would be sufficient to elicit indirect killing of activated CD4 T-cells even in the absence of AZT. To test this hypothesis, HLACs were infected with wild type (WT) and Δvif NL4-3 viruses generated in 293T-cells in the absence of APOBEC3G. Particles in supernatants from HIV-infected histocultures were collected after 6 days and subjected to protein analysis (FIG. 9C). Equal amounts of WT and Δvif NL4-3 virions were produced, as shown by the levels of HIV-1 p24$^{gag}$. However, as expected, Δvif NL4-3 virions packaged markedly more endogenous APOBEC3G molecules than WT virions.

Figure 9:
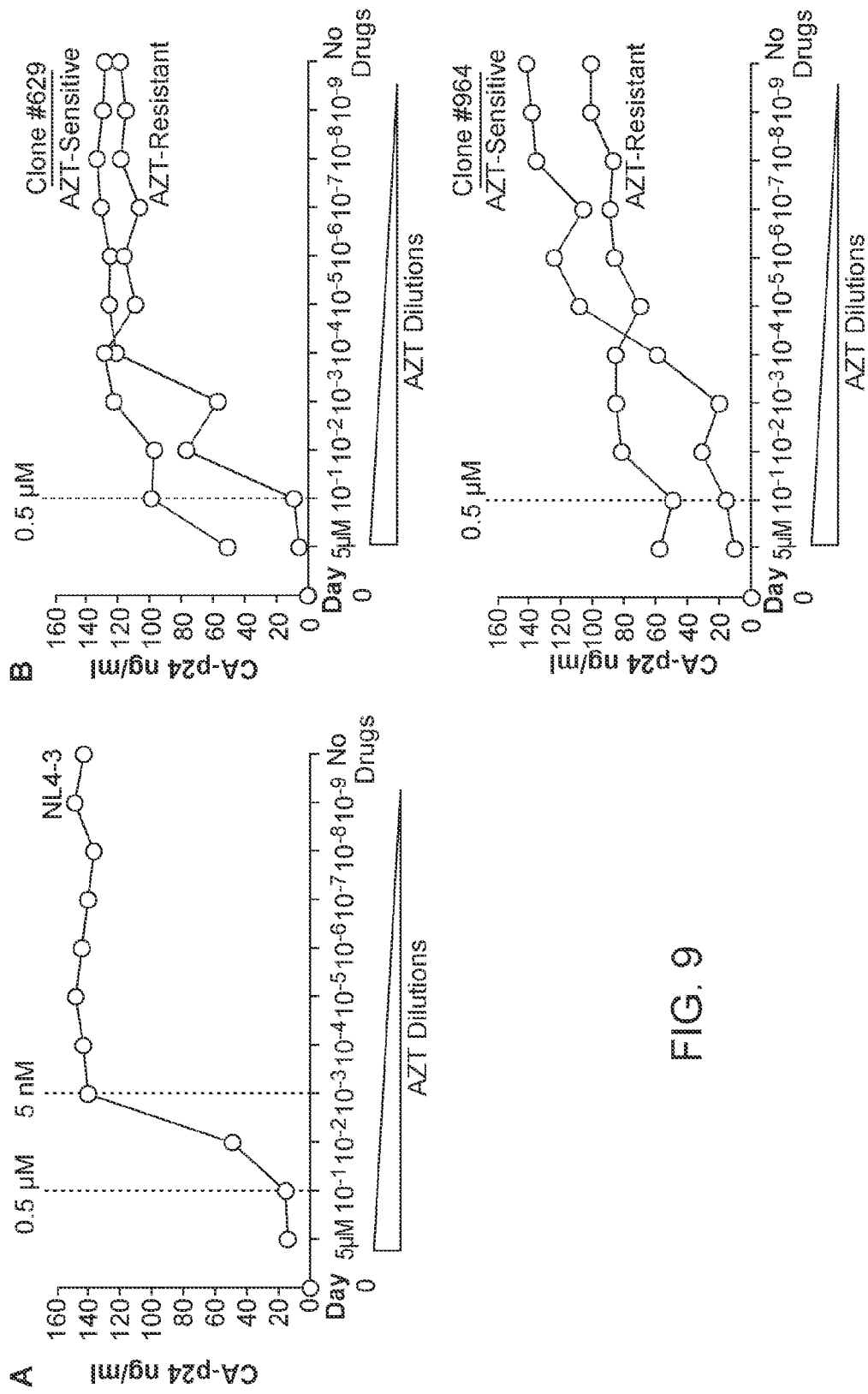
FIG. 9 depicts concentrations of AZT that block viral infection (A, B), demonstrates that indirect killing occurs after strong-stop DNA synthesis (C, D), and shows that HIV-1 clones encoding defective reverse transcription do not kill HLAC CD4 T-cells (E, F). HLACs were infected with viruses derived from the indicated HIV proviral clones in the presence of the indicated concentrations of AZT or in the absence of drugs. Six days after infection the amount of p24$^{gag}$ in the medium was determined by FLAQ assay. The amount of p24$^{gag}$ in the medium after infection wash (day 0) was defined as 0%. (A) In NL4-3-infected cells the maximal inhibitory concentration was 0.5 µM AZT. (B) In cells infected with HIV-1 clones #629 and #964 (Larder et al., 1989, *Science* 243:1731-1734), concentration of 0.5 µM AZT achieved a maximal inhibitory effect in the AZT-sensitive version of these clones, and half maximal inhibitory concentration effect in the AZT-resistant version of these clones. (C) Δvif NL4-3 virions incorporate 100-fold more endogenous APOBEC3G (A3G) than WT virions. Viral incorporation of endogenous A3G was measured by immunoblot analysis of purified NL4-3 and Δvif NL4-3 virions harvested from 1 ml of supernatant from infected HLACs. Doses reflect 1:10 dilutions. Virions were originally generated from 293T-cells that do not express APOBEC3G; therefore, physiological levels of endogenous A3G packaged into newly synthesized virions are shown. p24$^{gag}$ CA levels indicate equivalent virion production by NL4-3 and Δvif NL4-3 in infected HLACs. (D) Killing of abortively infected CD4 T-cells requires elongation of viral DNA. Resting or activated CFSE-labeled cells were co-cultured with cells infected with WT or Δvif NL4-3 in the presence or absence of the following drugs, AZT (5 µM), AMD3100 (250 nM), the NNRTIs Efavirenz (100 nM), and Nevirapine (1 µM), or the integration inhibitors Raltegravir (30 µM) and 118-D-24 (60 µM). Data are representative of four independent experiments performed with cells from four different donors. (E) A method to assess indirect killing in HLAC with non-infectious HIV-1 clones. Fresh human tonsil is processed into HLAC and cells are cultured in suspension. At the same time 293T-cells are transfected with 1 µg HIV-1 DNA in a 24-well plate. After 12 hours, 293T-cells are washed and overlayed with 3×10$^6$ HLAC cells in RPMI in the presence of the indicated drugs. Virus-producing 293T-cells directly interact with target overlaying HLAC cells. After 24 hours, the HLAC suspensions are collected from wells and analyzed by flow cytometry. (F) Indirect killing of HLAC CD4 T-cells by virus-producing 293T-cells. HLAC were cultured with the indicated drugs 3 hours before co-culture with 293T-cells. Percentages are normalized to the number of viable CD4 T-cells in HLAC overlaying non-transfected 293T-cells in the presence of AZT, as depicted by (*). Error bars represent standard error of the mean of three experiments performed using cells from three different HLAC donors.
Figure 10:
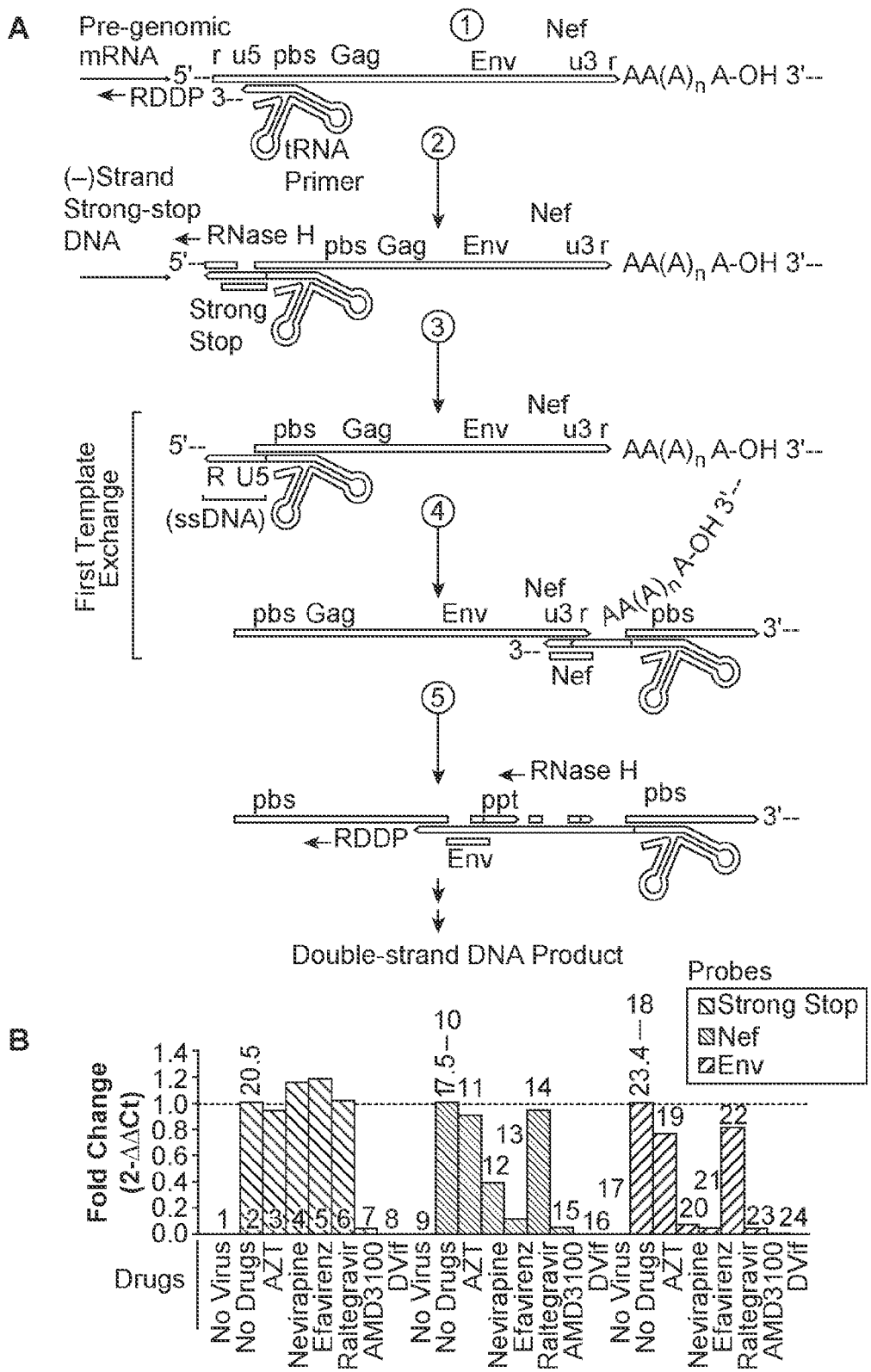
FIG. 10 depicts that cytoplasmic HIV-1 DNA triggers proapoptotic and proinflammatory responses in abortively infected CD4 T-cells. (A) Critical reactions in HIV-1 reverse transcription as detected by probes monitoring different regions within the Strong stop, Nef, and Env DNA fragments. RDDP, RNA-dependent DNA polymerase. Adapted from S. J. Flint et al., Principles Of Virology, 2000 ASM Press, Washington D.C., with permission. (B) NNRTIs prevent accumulation of DNA elongation products. The amount of viral DNA detected by a particular probe was calculated as a fold change relative to cells treated with no drugs (i.e. calibrator). A β-actin probe was used as an internal reference. Mean cycle threshold (Ct) values of calibrator samples are depicted. CD4 T-cells were infected with WT NL4-3 produced in 293T-cells, or with a Δvif NL4-3 collected from supernatants of infected HLAC, as described in FIG. 9C. Data are representative of two independent experiments performed with cells from two different donors. (C and D) Abortive HIV-1 infection generates a coordinated proapoptotic and proinflammatory response involving caspase-3 and caspase-1 activation. HLACs were spinoculated with no virus or with NL4-3 and AZT (5 µM), Efavirenz (100 nM), and T20 (10 µg/ml), as indicated (see FIG. 7A-B). After 3 days, cells were assessed by flow cytometry for intracellular levels of proinflammatory cytokines, serine 37 phosphorylated p53, and activated caspases as indicated. Ethidium monoazide was used to exclude dead and necrotic cells from the annexin V binding analysis. Data are representative of three independent experiments with three different donors. (E) Death of abortively infected CD4 T-cells requires caspase activation. CSFE-labeled cells were co-cultured with effector cells in the presence of 20 µM of Z-VAD-FMK, a general caspase inhibitor, or Z-FA-FMK, a negative control for caspase inhibitors. AZT (5 µM); AMD3100 (250 nM). Percentages are normalized to the number of viable CFSE-positive cells depicted by (*). Error bars represent standard error of the mean of three experiments from three different HLAC donors. (F) Abortive HIV infection promotes the maturation and secretion of IL-1β in tonsillar CD4 T-cells. Isolated tonsillar CD4 T-cells were either untreated, or stimulated with PMA (Phorbol-12-myristate-12-acetate, 0.5 µM) and the potassium ionophore nigericin (10 µM), or spinoculated with or without NL4-3 in the presence of AZT (5 µM), AMD3100 (250 nM), and efavirenz (100 nM) as indicated. After 3 days, half of the cells were lysed and subjected to SDS-PAGE immunoblotting analysis. On day 5, the supernatants from the rest of the cells were collected and subjected to SDS-PAGE immunoblotting analysis. The IL-1β antibody detects the pro-IL-1β (37 kD) and the mature cleaved form (17 kD). Data are the representative results of five independent experiments using tonsillar CD4 T-cells isolated from five different donors. (G) DNA reverse transcription intermediates induce an IFN-stimulatory antiviral innate immune response (ISD). ISRE-GFP reporters were transfected with 1 µg of HIV-1 reverse transcription intermediate products as indicated by numbers (detailed description in FIG. 14E), empty DNA plasmid, or polyinosinic:polycytidylic acid [poly(I:C)], and were analyzed by flow cytometry after 48 hours. Data are representative of three independent experiments; error bars show the SD for three independent samples from the same experiment. See also FIG. 11 and FIG. 13.

Next, cells infected with WT or Δvif NL4-3 HIV-1 were co-cultured with resting or activated CSFE-labeled cells in the presence or absence of AZT, NNRTIs, or AMD3100 (FIG. 9D). Resting CFSE-labeled CD4 T-cells were not extensively depleted by Δvif NL4-3-infected cells when co-cultured with AZT or no drugs (FIG. 10B, columns 9 and 10 vs. 17 and 18). These results suggested that early termination of DNA synthesis by virion-incorporated APOBEC3G prevents the cytopathic response in infected CD4 T-cells.

Figure 8:
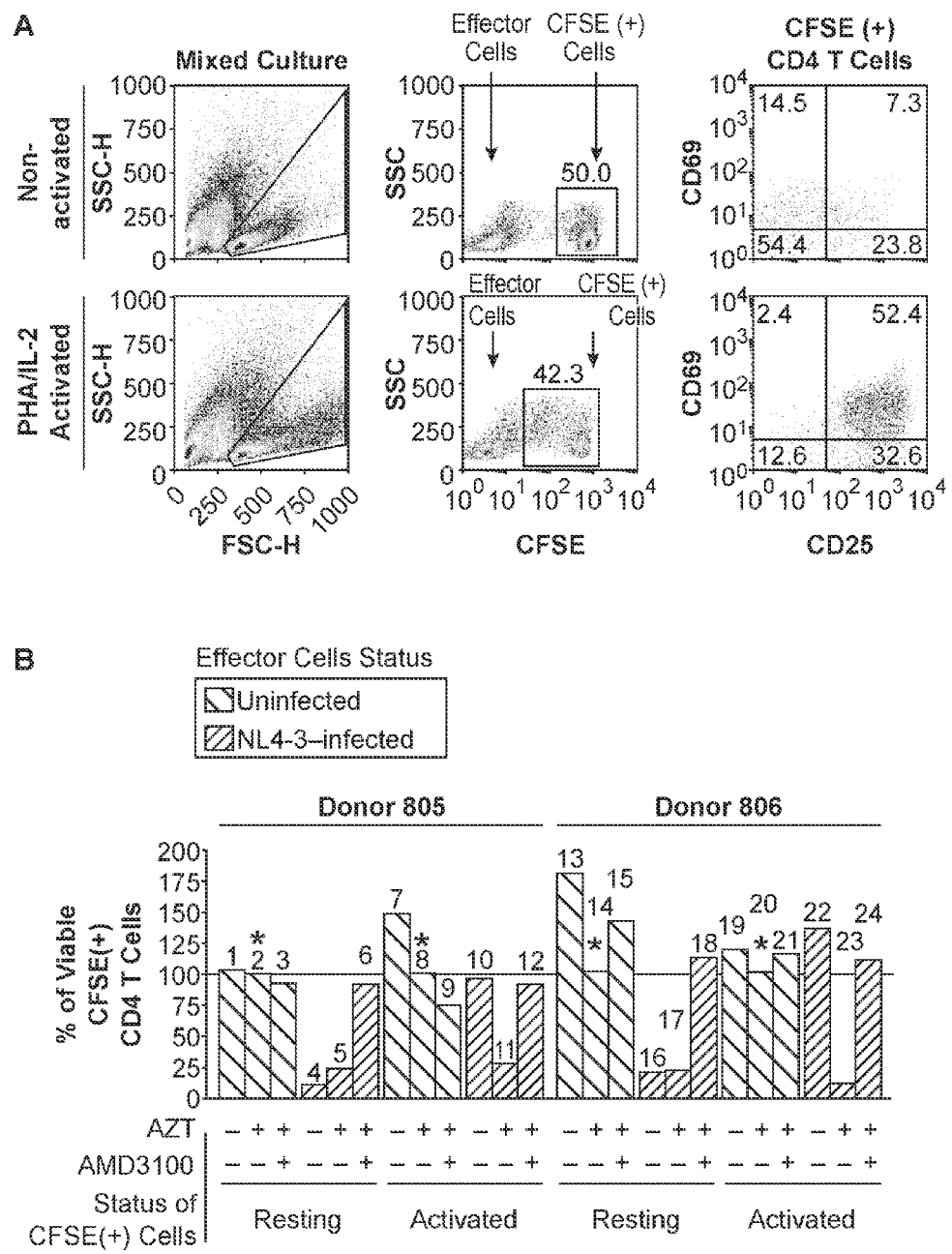
FIG. 8 depicts that death of abortively infected CD4 T-cells is due to impaired reverse transcription. (A) Status of mixed HLACs containing either resting or activated CFSE-labeled cells, 4 days after co-culturing with effector cells. Activated CFSE-labeled cells were stimulated with PHA and IL-2 48 hours before mixing, but not during co-culturing with effector cells. To avoid direct killing of activated CFSE-labeled cells in cultures with no drugs, cell killing was terminated and analyzed 4 days after co-culturing. (B) AZT renders activated CFSE-labeled CD4 T-cells sensitive to indirect killing. Resting or activated CFSE-labeled cells were co-cultured with effector cells in the presence of no drugs, AZT (5 µM) alone, or AZT+AMD3100 (250 nM). Data are from two independent experiments performed with tonsil cells from two different donors. (C) AZT-induced killing is lost when AZT-resistant viruses are tested. Resting or activated CFSE-labeled cells were co-cultured with cells infected with NL4-3 or HIV-1 clones #629 and #964 in the presence of no drugs, AZT (0.5 µM) alone, or AZT+AMD3100 (250 nM). AZT-sensitive and AZT-resistant sub-clones are depicted. Data are representative of three independent experiments with three different donors. (D) NNRTIs prevent killing of abortive infected CD4 T-cells. Resting or activated CFSE-labeled cells were co-cultured with infected or uninfected effector cells, in the presence of no drugs, AZT (5 µM), AMD3100 (250 nM), the NNRTIs Efavirenz (100 nM), and Nevirapine (1 µM), or the integration inhibitors Raltegravir (30 µM) and 118-D-24 (60 µM). Killing of resting CFSE-labeled CD4 T-cells was blocked with equal efficiency by NNRTIs and AMD3100 (columns 15, 16), but not by integration inhibitors (columns 17, 18). In combination, NNRTIs prevented cell death induced by AZT in activated CFSE-labeled cells (compare column 38 to 44 and 45). Data are representative of four independent experiments with four different donors. The absolute numbers of CFSE-labeled CD8 T-cells and B cells was unaltered in these experiments (data not shown). Percentages are normalized to the number of viable CFSE-positive cells depicted by (*). See also FIG. 9, below.

Of note, Δvif NL4-3-infected cells also did not deplete activated CFSE-labeled cells in the absence of drugs (FIG. 8, Panel D, column 41). Moreover, when AZT was added, indirect cell depletion was observed only in cultures containing cells infected with WT HIV-1 (FIG. 8, Panel D, column 34 vs. 42). These results indicate that the termination of reverse transcription before the completion of strong-stop DNA synthesis is not sufficient to generate a cytopathic response.

Example 12

Death of Abortively Infected CD4 T-Cells is Triggered by Premature Termination of Viral DNA Elongation Next it was determined what stage of reverse transcription triggers abortive infection cell death. AZT inhibits DNA elongation but not early DNA synthesis (Arts and Wainberg, 1994, *Antimicrob Agents Chemother* 38:1008-1016). It was examined whether blocking early DNA synthesis with non-nucleoside reverse transcriptase inhibitors (NNRTIs) would have the same effect as AZT. Impaired reverse transcription may also lead to abortive integration, causing chromosomal DNA breaks and a genotoxic response. To exclude this possibility, integrase inhibitors were used. To discriminate between the cytopathic response induced by endogenous termination of reverse transcription and the response induced by AZT, resting and activated CFSE-labeled cells were separately assessed.

Remarkably, the NNRTIs, efavirenz and nevirapine, blocked indirect killing of resting CD4 T-cells as efficiently as AMD3100 (FIG. 8D, columns 15 and 16). These findings suggested that allosteric inhibition of reverse transcriptase induced by these NNRTI's interrupts reverse transcription sufficiently early to abrogate the death response. In contrast, the integrase inhibitors raltegravir and 118-D-24 did not prevent abortive infection killing (FIG. 8D, columns 17 and 18), suggesting that cell death involves signals generated prior to viral integration. NNRTIs also protected activated CFSE-labeled cells from death induced by AZT (FIG. 8D, column 38 vs. columns 44 and 45), demonstrating that a certain degree of DNA synthesis is required to elicit the cytopathic response.

This notion was further strengthened in findings obtained with vif-deficient (Δvif) HIV-1 particles where reverse transcription is inhibited during strong-stop DNA synthesis due to incorporated APOBEC3G (A3G) (Bishop et al., 2008, *PLos Pathog* 4:e1000231; Li et al., 2007, *J Biol Chem* 282: 32065-32074). Abortively infected CD4 T-cells were not depleted by Δvif NL4-3-infected cells (FIG. 9C-D), indicating that termination of reverse transcription before the completion of strong-stop DNA synthesis is not sufficient to generate a cytopathic response. Other HIV-1 mutants containing substitutions in RNase H and nucleocapsid that promote early defects in reverse transcription failed to elicit indirect CD4 T-cell killing (FIGS. 9E-F). Together, these findings indicate that accumulation of reverse-transcribed DNA, rather than any inherent activity of the HIV-1 proteins, is the key factor that triggers the death response.

Example 13

Reverse-Transcribed Viral DNA is Required for Killing of Abortively Infected CD4 T-Cells To further confirm the role of viral DNA synthesis in indirect killing, viruses harboring genetic mutations that interrupt reverse transcription were examined. First, the clone E478Q contains a point mutation in the catalytic site of the RNase H domain of reverse transcriptase that compromises its RNase H activity. It fuses into the target cells but cannot reverse transcribe beyond the very early strong-stop products (Smith et al., 1999, *J Virol* 73:6573-6581). Second, the pDB653 proviral clone contains mutations in the zinc finger domains of the nucleocapsid (NC) protein and is defective in reverse transcription synthesis and viral RNA packaging (Guo et al., 2000, *J Virol* 74:8980-8988). Because these viruses are not competent for multiple rounds of viral replication, it was not possible to use traditional HLAC culture conditions. Instead, the system was modified by overlaying HLAC cells on a monolayer of 293T-cells that had been transfected with these proviral clones (FIG. 9E). Using this approach which did not require a spreading viral infection, extensive and selective depletion of HLAC CD4 T-cells was observed when 293T-cells were transfected with NL4-3 (FIG. 9F). Loss of CD4 T-cells occurred both in the presence and absence of AZT, but was completely blocked by addition of efavirenz or AMD3100 (FIG. 9, panel F, columns 5-8), indicating that the observed cell death involves abortive HIV-1 infection. Transfection of E478Q and pDB653 HIV-1 clones did not result in depletion of CD4 T-cells (FIG. 9, Panel F, columns 9-11 and 13-16, respectively), indicating that RNA-directed DNA synthesis is key for generating a cytopathic response.

Further, the TR712 HIV-1 clone that encodes a truncated c-terminal domain in gp41 was examined. Transfections with the TR712 HIV-1 clone markedly depleted HLAC CD4 T-cells (FIG. 9, panel F, column 17-20). Because immature TR712 viruses retain their capacity to fuse in the presence of protease inhibitors, the ability of such immature TR712 viruses to mediate killing of CD4 T-cells was tested. To this end, the experiment with the TR712 clone in the presence of the protease inhibitor amprenavir was repeated. This process generated fusion competent virions containing immature, unprocessed capsid proteins. Remarkably, amprenavir prevented CD4 T-cell killing by TR712 viruses (FIG. 9, panel F, columns 21-24), suggesting that fusion of immature particles do not induce a cytopathic response. Previous studies have shown that HIV particles with irregular core morphologies (Tang et al., 2001, *J Virol* 75:9357-9366) and altered stabilities (Fitzon et al., 2000, *Virology* 268:294-307; Stremlau et al., 2004, *Nature* 427:848-853) are unable to undergo reverse transcription in cells. Hence, reverse transcription of immature TR712 viruses was likely disrupted after entry, preventing induction of the cytopathic response. Together, these results suggested that accumulation of reverse-transcribed DNA, rather than the mere delivery of HIV-1 components into CD4 T-cells, is the key factor that initiates the cytopathic response.

Example 14

HIV-1 Env-Receptor Interactions are not Required for Indirect Killing of CD4 T-Cells Some models of indirect CD4 T-cell death have implicated HIV Env-receptor interactions (Holm et al., 2004, *J Virol* 78:4541-4551; Jekle et al., 2003, *J Virol* 77:5846-5854; Perfettini et al., 2005, *Cell Death Differ* 12 Suppl 1:916-923; Vlahakis et al., 2001, *J Clin Invest* 107:207-215; Vlahakis et al., 2003, *J Infect Dis* 188: 1455-1460). In studies exploring whether HIV-1 Env was essential, it was first found that transfection of an HIV-1 clone lacking the Env gene (NL4-3 Δenv) failed to deplete HLAC CD4 T-cells (FIG. 9, panel F, columns 25-28). However, replacement of HIV Env with the amphotropic Env of Moloney Murine Leukemia Virus (MLV) restored CD4 T-cell killing (FIG. 9, panel F, columns 29-30), demonstrating that cell death does not obligatory require HIV-1 Env binding to its surface receptors. In contrast, co-expression of the vesicular stomatitis virus glycoprotein (VSV-G), which mediates viral entry within acidified endosomes, did not result in CD4 T-cell killing, These findings are in agreement with previous studies showing that VSV-G fuses very poorly to resting CD4 T-cells (Yu et al., 2009, *PLoS Pathog* 5:e1000633). Thus, although HIV-1 Env-receptor interactions are not required for indirect killing, these findings highlighted the importance of the HIV envelope for infection of resting lymphoid CD4 T-cells.

Example 15

Abortively Infected CD4 T-Cells Commence but do not Complete Reverse Transcription Next the status of HIV-1 reverse transcription in tonsillar CD4 T-cells after infection was examined. Specifically, the effect on reverse transcription after treatment with NNRTIs, such as efavirenz and nevirapine, which prevent the death of abortively infected CD4 T-cells, or with AZT or integrase inhibitor (raltegravir) that do not prevent CD4 T-cell death, was investigated. Taqman-based quantitative real-time PCR (QPCR) was used to quantify the synthesis of reverse transcription products in isolated CD4 T-cells from HLAC 16 hours after infection with NL4-3. Specific QPCR primers and probes were designed (Table 1) to monitor sequential steps in reverse transcription including generation of strong-stop DNA, first template exchange (Nef), and DNA strand elongation (Env) (FIG. 10A)

TABLE 1

The primer and probe sets used for Taqman-based quantitative real-time PCR of HIV-1 reverse transcription cDNA products

| | Strong-stop (R/U5) region | |
|---|---|---|
| F42 | 5'-GGCTAACTAGGGAACCCACTGC-3' | SEQ ID NO: 39 |
| R98 | 5'-CAACAGACGGGCACACACTACT-3' | SEQ ID NO: 40 |
| P65 | 5'-(6~FAM)-TAAGCCTCAATAAAGCTTGCCTTGA GTGCTC-(MGBNFQ)-3' | SEQ ID NO: 41 |

Nef (Nef/U3) region. This amplicon is located 170 nucleotides downstream to the repeat (R) sequence, after cDNA synthesis proceeds first strand transfer

| F554 | 5'-TTGACAGCCGCCTAGCATT-3' | SEQ ID NO: 42 |
|---|---|---|
| F591 | 5'-TTGAAGTACTCCGGATGCAGC-3' | SEQ ID NO: 43 |
| P574 | 5'-(6~FAM)-CATCACGTGGCCCGAG-(MGBNFQ)-3' | SEQ ID NO: 44 |

Env region. This amplicon is located 3023 nucleotides downstream to the repeat (R) sequence, after cDNA synthesis proceeds first strand transfer.

| F286 | 5'-TGGACAAATGACATGGTAGAACAGA-3' | SEQ ID NO: 45 |
|---|---|---|
| R339 | 5'-TTTACACATGGCTTTAGGCTTTGA-3' | SEQ ID NO: 46 |
| P313 | 5'-(6~FAM)-CATGAGGATATAATCAGTTTATGG-(MGBNFQ)-3' | SEQ ID NO: 47 |

Reverse transcription products corresponding to strong-stop DNA were similar in untreated CD4 T-cells or cells treated with AZT, NNRTIs, or raltegravir but were greatly reduced in cells treated with AMD3100 or in cultures infected with Δvif NL4-3 where arrest occurs prior to the completion of strong-stop DNA synthesis (FIG. 10B, columns 1-8). In contrast, the accumulation of later reverse transcription products detected by the Nef and Env probes were dramatically inhibited by the NNRTIs but not by raltegravir. Levels of Nef (FIG. 10B, columns 10+11) and Env (columns 18+19) DNA products were similar in untreated cells and cells treated with AZT, indicating that reverse transcription in most tonsillar CD4 T-cells naturally terminates during DNA chain elongation, coinciding with the block induced by AZT. The minor inhibition detected by AZT is likely due to a small number of permissive CD4 T-cells in the culture. These results show that abortively infected CD4 T-cells accumulate incomplete reverse transcription products representative of DNA strand elongation. Blocking earlier steps of reverse transcription by NNRTIs or by genetic mutations like deletion of Vif or mutation of RNase H restricts accumulation of such products, and prevents abortive infection-induced cell death (FIG. 11A).

Example 16

DNA Reverse Transcription Intermediates Elicit a Coordinated Proapoptotic and Proinflammatory Response in Abortively Infected CD4 T-Cells Next it was evaluated whether HIV-mediated indirect killing of CD4 T-cells is associated with deregulation of cytokine production or a DNA damage response. To facilitate a vigorous and synchronized killing effect, HLACs were spinoculated with NL4-3 virions in the presence of various antiviral drugs. Interestingly, based on immunostaining after cytokine capture, abortively infected CD4 T-cells expressed IFN-α, and high levels of the proinflammatory interleukin 1β (IL-1β), but not tumor necrosis factor (TNFα) (FIG. 10C). Phosphorylation of S37 p53 was not observed, suggesting that abortive HIV-1 infection does not induce a DNA damage cascade. Abortively infected CD4 T-cells also displayed caspase-1 and caspase-3 activity along with appearance of annexin V (FIG. 10D). T20 and efavirenz but not AZT prevented activation of these caspases, indicating that apoptosis was induced by abortive HIV-1 infection. Cell death was completely prevented by Z-VAD-FMK, a pan-caspase inhibitor, suggesting that caspase activation is required for the observed cytopathic response (FIG. 10E). Such mode of cytokine production and caspase activation was not observed in CD8 T or B cells.

Next it was examined whether abortive HIV-1 infection signals for the maturation and secretion of IL-1β. In cells IL-1β activity is rigorously controlled. Cells can be primed to express inactive pro-IL-1β by various proinflammatory signals. However, the release of bioactive IL-1β requires a second signal leading to activation of inflammasomes, cleavage of pro-IL-1β by caspase-1 and secretion of the bioactive 17 kDa form of IL-1β (Schroder and Tschopp, 2010, *Cell*, 140: 821-832). Interestingly, western blot analysis revealed high amounts of intracellular pro-IL-1β in untreated CD4 T-cells, suggesting that tonsillar CD4 T-cells are primed to release proinflammatory mediators (FIG. 10F). Stimulating the CD4 T-cells with PMA and nigericin induced further accumulation of pro-IL-1β and promoted the maturation and release of the bioactive 17 kDa IL-1β into the supernatant. Remarkably, infection of CD4 T-cells with NL4-3 in the presence of AZT similarly resulted in maturation and release of the bioactive 17 kDa IL-1β into the supernatant. This response was completely prevented by efavirenz and AMD3100, suggesting that abortive HIV-1 infection signals the maturation and release of bioactive IL-1β in these CD4 T-cells.

To identify the nature of the nucleic acid species that trigger these responses, a recently described H35 rat hepatocyte cell line containing an IFN-sensitive response element (ISRE) linked to GFP (Patel et al., 2009, *Proc Natl Acad Sci USA* 106:12867-12872) was used. H35 cells were first infected with pseudotyped VSV-G HIV-1 virions. These virions induced GFP expression and cell death in the presence or absence of AZT. Importantly, the expression of both GFP and cell death response were blocked by efavirenz but not raltegravir (FIG. 13D). Thus, the H35 system successfully reconstitutes the cytokine and cytopathic response observed in tonsillar CD4 T-cells. Next the various HIV-1 reverse transcription intermediates were synthesized and tested for their ability to activate the ISRE-GFP reporter. Interestingly, none of the RNA-containing oligonucleotides stimulated the ISRE-GFP reporter expression above baseline. In sharp contrast, ssDNA and dsDNA oligonucleotides longer than 500 bases in length, which corresponded to reverse transcription intermediates produced during DNA elongation, evoked a potent ISRE-GFP activation (FIG. 10G). Similarly, when cells were stimulated with poly(I:C), a synthetic double-stranded RNA known to activate IRF3 via the RIG-I pathway elicited a comparable ISRE-GFP response. Taken together, these findings indicate that reverse transcription intermediates generated during DNA chain elongation induce a coordinated proapoptotic and proinflammatory innate immune response involving caspase-3 and caspase-1 activation in abortively infected CD4 T-cells.

Example 17

Abortive HIV-1 Infection Represents a General Mechanism of CD4 T-Cell Depletion in Human Lymphoid Organs To confirm that the cytopathic effect mediated by abortive HIV-1 infection is not limited to tonsillar tissue, indirect CD4 T-cell killing in HLACs formed from fresh human splenic tissue was assessed. Of note, effector spleen cells were completely refractory to HIV infection (data not shown), which necessitated activation with PHA and IL-2 before infection with NL4-3. Nevertheless, non-activated CSFE-labeled spleen CD4 T-cells were extensively depleted in cultures containing HIV-infected spleen HLACs (FIG. 11 B, C). Loss of CFSE-labeled CD4 T-cells was robust in the absence of drugs or in the presence of AZT, indicating that productive viral replication was not required for CD4 T-cell death in spleen. Remarkably, addition of efavirenz prevented the loss of CD4 T-cells as efficiently as AMD3100, indicating that cell death involved abortive infection. The integrase inhibitors raltegravir did not prevent CD4 T-cell killing demonstrating that signaling for cell death occurs before viral integration.

Lymphocytes continuously circulate between one peripheral lymphoid organ and another via the lymph and blood. After leaving one organ and entering second, productively infected CD4 T-cells may come into contact with a new pool of uninfected lymphocytes. To simulate these conditions, infected human tonsil cells were co-cultured with resting (non-activated) CSFE-labeled human spleen cells. It was observed that resting spleen CD4 T-cells were massively depleted by HIV-infected tonsil cells in the absence of drugs or in the presence of AZT. Further, it was found that the addition of efavirenz, but not raltegravir, prevented this loss of CD4 T-cells. These findings support a mechanism of cell death involving abortive HIV infection. Taken together, these results demonstrated that abortive HIV infection is a general mechanism of CD4 T-cell depletion, which plays a significant role in the overall cytopathicity induced by HIV-1.

Example 18

HIV-1 Infection Activates Innate Proapoptotic and Proinflammatory Responses in Human Lymphoid CD4 T-Cells Human lymphoid aggregate cultures (HLACs, Doitsh et al., 2010, *Cell*, 143(5):789-801) were left uninfected or infected with NL4-3, an X4-tropic strain of HIV-1, in the presence of AZT (5 μM), efavirenz (100 nM), or T20 (10 μg/ml), as indicated. After 3 days, infected CD4 T-cells displayed evidence of caspase-1 and caspase-3 activity and annexin V positivity, but caspase 6, 8, and 9 were not activated. Of note, T20 and efavirenz but not AZT prevented activation of these caspases, indicating that apoptosis was induced by non-productive HIV-1 infection. Data for this experiment are depicted in FIGS. 13A and 14B, C.

Example 19

Death of HIV-Infected CD4 T-Cells Requires Caspase Activation

Different members of the caspase family play key roles in inflammation and mammalian apoptosis. The proapoptotic caspases are comprised of caspase-3, -6 and -7, while the proinflammatory caspases correspond to caspase-1, -4 and -5. Caspase inhibitors were used to assess whether caspase activation is required for indirect CD4 T-cell killing. HIV-infected HLACs were cultured in the presence of Z-VAD-FMK (a pan-caspase inhibitor) or Z-FA-FMK (negative control). CD4 T-cell death was blocked by Z-VAD-FMK but persisted in the presence of Z-FA-FM. Values are mean±SEM of three experiments with cells from three HLAC donors. Remarkably, CD4 T-cell death was completely prevented by addition of Z-VAD-FMK, a general caspase inhibitor (FIGS. 13B, 14A). This finding indicated that activation of one or more caspase was required to induce cell death. Interestingly, specific inhibition of caspase-3 with Z-DEVD-FMK reduced cell death by only 50% raising the possibility that multiple caspase signaling cascades may be involved in the observed killing of CD4 T-cells. These studies further revealed that caspase-1 is activated in response to abortive HIV-1 infection, raising a possible role for both caspase-3 and caspase-1 in CD4 T-cells cytopathology.

Inflammasome-dependent caspase-1 activity can result in a highly inflammatory form of cell death known as pyroptosis, which results in cleavage of IL-1β and IL-18 and early changes in membrane permeability leading to release of these inflammatory cytokines. Pyroptosis occurs most frequently upon infection with intracellular pathogens (Schroder and Tschopp, 2010, *Cell*, 140:821-832)

Example 20

HIV-1 Infection Promotes the Maturation and Secretion of IL-1β in Lymphoid CD4 T-Cells In panel FIG. 13C, it is shown that infected CD4 T-cells also displayed IFN-β expression and high-level expression of IL-1β but not TNFα. The absence of phospho-S37 p53 suggested that abortive HIV-1 infection does not induce a DNA damage cascade. In panel FIG. 13D, it is shown that isolated tonsillar CD4 T-cells were left untreated or stimulated with 0.5 μM PMA (to further induce intracellular stores of 35-kDa pro-IL-1β) and 10 μM nigericin, (a potassium ionophore used as a second inflammatory stimulus to trigger maturation and release of the bioactive 17-kDa IL-1β in primed cells). Cultures were infected with NL4-3 in the presence of the indicated antiviral drugs. After 3 days, half the cells were lysed and analyzed by SDS-PAGE and immunoblotting with anti IL-1β and anti-β-actin (loading control). On day 5, supernatants from the remaining cells were analyzed by SDS-PAGE and immunoblotting with anti-IL-1β antibodies. Untreated CD4 T-cells displayed high levels of intracellular pro-IL-1β consistent with their primed status. Infection with NL4-3 in the presence of AZT also resulted in release of bioactive 17-kDa IL-1β, as observed after treatment with PMA+nigericin. This response was blocked by efavirenz and AMD3100 (250 nM). Thus, non-productive HIV-1 infection induces maturation and release of bioactive IL-1β in lymphoid CD4 T-cells. Data for this experiment are depicted in FIGS. 13C and 13D.

Example 21

Pro-IL-1β is Abundantly Expressed in Lymphoid CD4 T-Cells but not in CD8 T or B Cells Levels of intracellular pro-IL-1β were assessed in HLACs from fresh tonsils and spleen tissue from different donors (FIG. 13E). Asterisks indicate samples in which dead cells were removed by Ficoll-Hypaque gradient centrifugation. CD4 T, CD8 T, and B cells were isolated from donor 2100 by positive selection with microbeads and analyzed for pro-IL-1β expression. High levels of intracellular pro-IL-1β were found in purified CD4 T-cells but not in CD8 T or B cells (rectangle). Data for this experiment are depicted in FIG. 13E.

Example 22

Caspase-1 Inhibitors Efficiently Inhibit Inflammation in Human Lymphoid CD4 T-Cells Isolated tonsillar CD4 T-cells were treated overnight with nigericin (10 μM) to provide a second inflammatory stimulus, resulting in maturation and release of bioactive 17-kDa IL-1β. Supernatants from the cell cultures were subjected to SDS-PAGE and immunoblotting. 17-kDa IL-1β was released after treatment with nigericin, but not with calcium ionophore A23187 or the nonspecific cation ionophore monensin. Thus, while these cells are primed, they must receive the appropriate proinflammatory signal for pro-IL-1β processing and release. IL-1β release was blocked by pre-treatment with the pan-caspase inhibitor Z-VAD and by the caspase-1 inhibitors Z-WEHD (SEQ ID NO: 12) and Z-YVAD (SEQ ID NO: 15), consistent with inflammasome-associated caspase-1 processing of IL-1β. Data for this experiment are depicted in FIG. 13F.

Example 23

Caspase-1 Inhibitors Efficiently Inhibit CD4 T-Cell Death in HIV-1-Infected Human Lymphoid Tissues HLACs were left uninfected or infected with HIV-1 (NL4-3 clone) in the presence of AZT, efavirenz, AMD3100, or caspase inhibitors (20 μM each), as indicated in FIG. 16. After 3 days, the percentages of viable CD4 T cells in the cultures were determined by flow cytometry. CD4 T-cell death in HIV-1-infected cultures was prevented by the pan-caspase inhibitor Z-VAD ("Pan-Caspase" in FIG. 16A) and by the caspase-1 inhibitor (Z-WEHD, "Caspase 1" in FIG. 16A) as efficiently as by efavirenz and AMD3100, but not by the Z-FA-FM (commercial negative control; "Control" in FIG. 16A) and caspase-6 inhibitor. Treatment with caspase-3 inhibitor (Z-DEVD; "Caspase 3" in FIG. 16A) prevented the death of only 50% CD4 T-cell population.

HLACs were left uninfected or infected with NL4-3 in the presence of no drugs, efavirenz, AMD3100, or caspase inhibitors (50 µM or 100 µM), as indicated in FIG. 16B. After 3 days, the percentages of viable CD4 T cells in the cultures were determined by flow cytometry. CD4 T-cell death in HIV-infected cultures was prevented by the caspase-1 inhibitor (Caspase-II inhibitor, Calbiochem; "Caspase 1" in FIG. 16B) as efficient as by efavirenz and AMD3100. In these experiments, treatment with the caspase-3 inhibitor (Z-DEVD; "Caspase" 3 in FIG. 16B) did not prevent the death of HIV-1-infected CD4 T cells.

Caspase-1 activation can lead to a highly inflammatory form of cell death called pyroptosis. To gain insight into how CD4 T cells die, it was determined whether HIV infection in CD4 T cells induce pyroptosis cell death, as measured by lactate dehydrogenase (LDH) release. HLACs were left uninfected or infected with NL4-3 in the presence of no drugs, efavirenz, AMD3100, or caspase inhibitors (50 µM or 100 µM), as indicated in FIG. 16C. After 3 days, the supernatants were assayed for the cytosolic enzyme lactate dehydrogenase (LDH) and the LDH released by dying cells was quantified. HIV-1-infected CD4 T cells released high levels of LDH, compared to uninfected cells FIG. 16C). These data suggest that pyroptosis is the predominant form of CD4 T-cell death after HIV-1 infection. LDH was not released from infected cells treated with efavirenz. AMD3100, or caspase-1 inhibitor (Caspase-II inhibitor, Calbiochem; "Caspase 1 in FIG. 16C). Treatment with caspase-3 inhibitor (Z-DEVD; "Caspase 3" in FIG. 16C) did not prevent the LDH release from HIV-1 infected cells.

Example 24

Perspective

The mechanism through which HIV-1 kills CD4 T-cells, a hallmark of AIDS, has been a topic of vigorous research and one of the most pressing questions for the field over the last 28 years (Thomas, 2009; *Nat Med* 15:855-859). In this study, Applicants investigated the mechanism of HIV-1-mediated killing in lymphoid tissues, which carry the highest viral burdens in infected patients. Applicants used HLACs formed with fresh human tonsil cells and an experimental strategy that clearly distinguishes between direct and indirect mechanisms of CD4 T-cell depletion. Applicants now demonstrate that indirect cell killing involving abortive HIV infection of CD4 T-cells accounts for the vast majority of cell death occurring in lymphoid tissues. No more than about 5% of the CD4 T-cells are productively infected, but virtually all the remaining CD4 T-cells are abortively infected ultimately leading to caspase-mediated cell death. Equivalent findings were observed in HLACs formed with fresh human spleen (FIGS. 11B-C), indicating this mechanism of CD4 T-cell depletion can be generalized to other lymphoid tissues.

The massive depletion of non-productively infected CD4 T-cells is in contrast to their survival after infection of intact blocks of tonsillar tissue in human lymphoid histoculture (HLH) (Drivel et al., 2003; *AIDS Res Hum Retroviruses* 19:211-216). This result probably reflects differences between the HLH and the HLAC experimental systems. In HLH, the complex three-dimensional spatial cellular organization of lymphoid tissue is preserved, but cellular movement and interaction are restricted, both of which are required for indirect killing. In HLAC, the tissue is dispersed, and cells are free to interact, resulting in a rapid and robust viral spread. While the mechanism triggering indirect CD4 T-cell death is certainly identical in both settings, HLH allows only a slow, nearly undetectable progression of indirect CD4 T-cell death. In HLAC, this process is accelerated, allowing the outcome to be detected in a few days. Interestingly, indirect killing was also less efficient when peripheral blood cells were tested (data not shown). It is possible that cellular factors specifically produced in lymphoid organs are required to accelerate indirect killing of peripheral blood CD4 T-cells.

Figure 7:
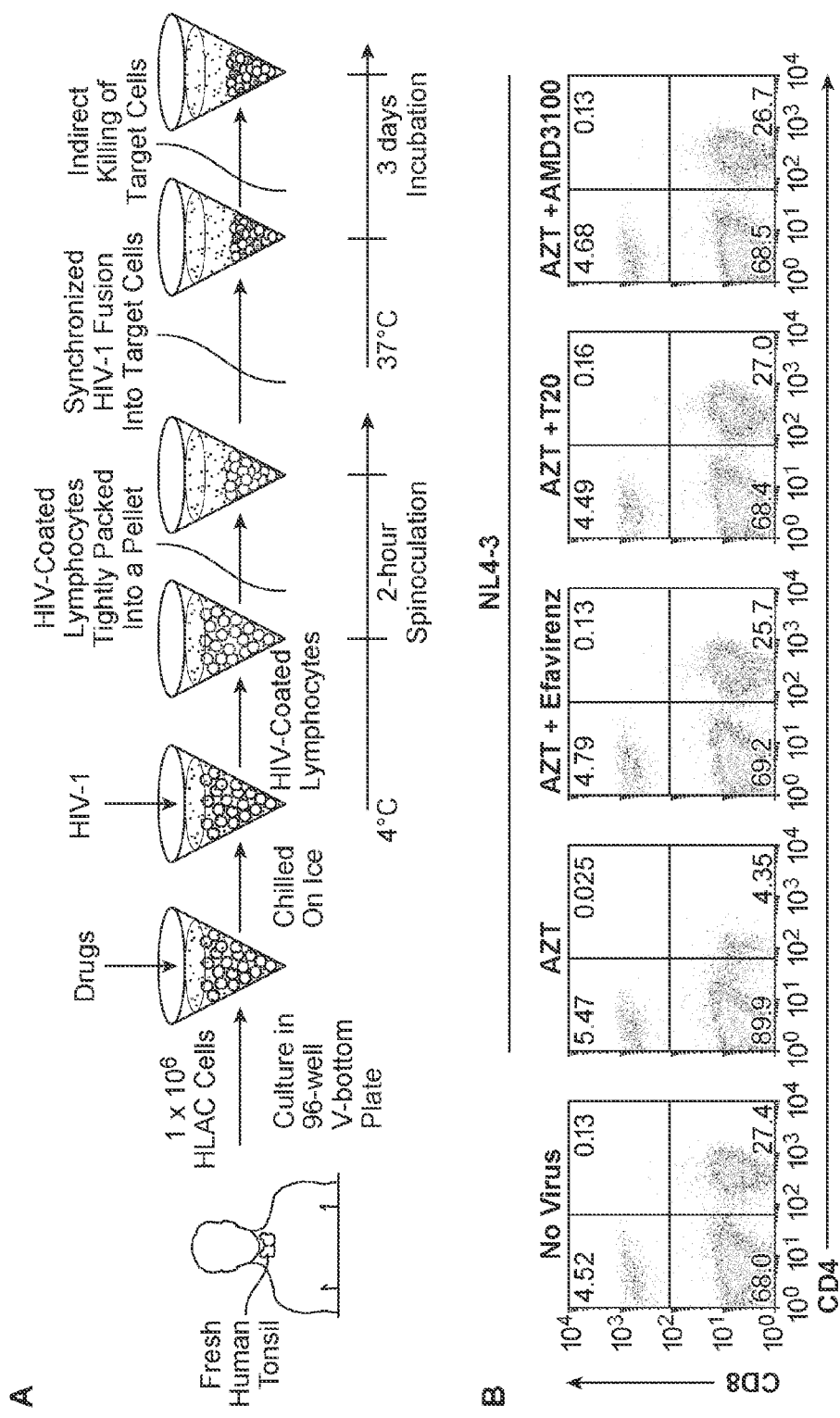
FIG. 7 depicts that spinoculation efficiently recapitulates indirect CD4 T-cell killing (A, B) and that protease inhibitors do not block syncytia formation. (A) The spinoculation procedure. (B) Flow cytometry of viable CD4 versus CD8-T-cells in HLAC three days after spinoculation in the presence of the indicated drugs. Data represent live-gated cells, based on the forward-scatter versus side-scatter profile of the complete culture. Of note, apoptotic cells were included in the analysis of caspases activity and cytokine expression (FIG. 10E, F). Drugs concentrations: AZT 5 μM; Efavirenz 100 nM; AMD3100 250 nM; T20 10 μg/ml. The data are representative results of six independent experiments with six different donors. Note that HIV-spinoculated CD4 T-cells were readily killed in the presence of AZT but not efavirenz, T20 or AMD3100. (C) Highly permissive SupT1 CD4 T leukemic cells were infected with NL4-3 and cultivated for 3 days to allow substantial infection but not syncytia formation. After 3 days, cells were treated with 5 μM AZT, 250 nM AMD3100, 10 μg/ml T20, 5 μM amprenavir, 5 μM saquinavir, or 5 μM indinavir or were left untreated. After 2.5 days of additional culture, the extent of syncytia formation in each sample was evaluated by light microscopy. Note that protease inhibitors inhibited indirect killing as efficiently as AMD3100 and T20, but did not alter the function of Env proteins expressed on the surface of infected cells (i.e., allow syncytia formation), indicating that the killing signal is not delivered directly through the infected cells. Results are representative of three independent experiments.
Figure 7:
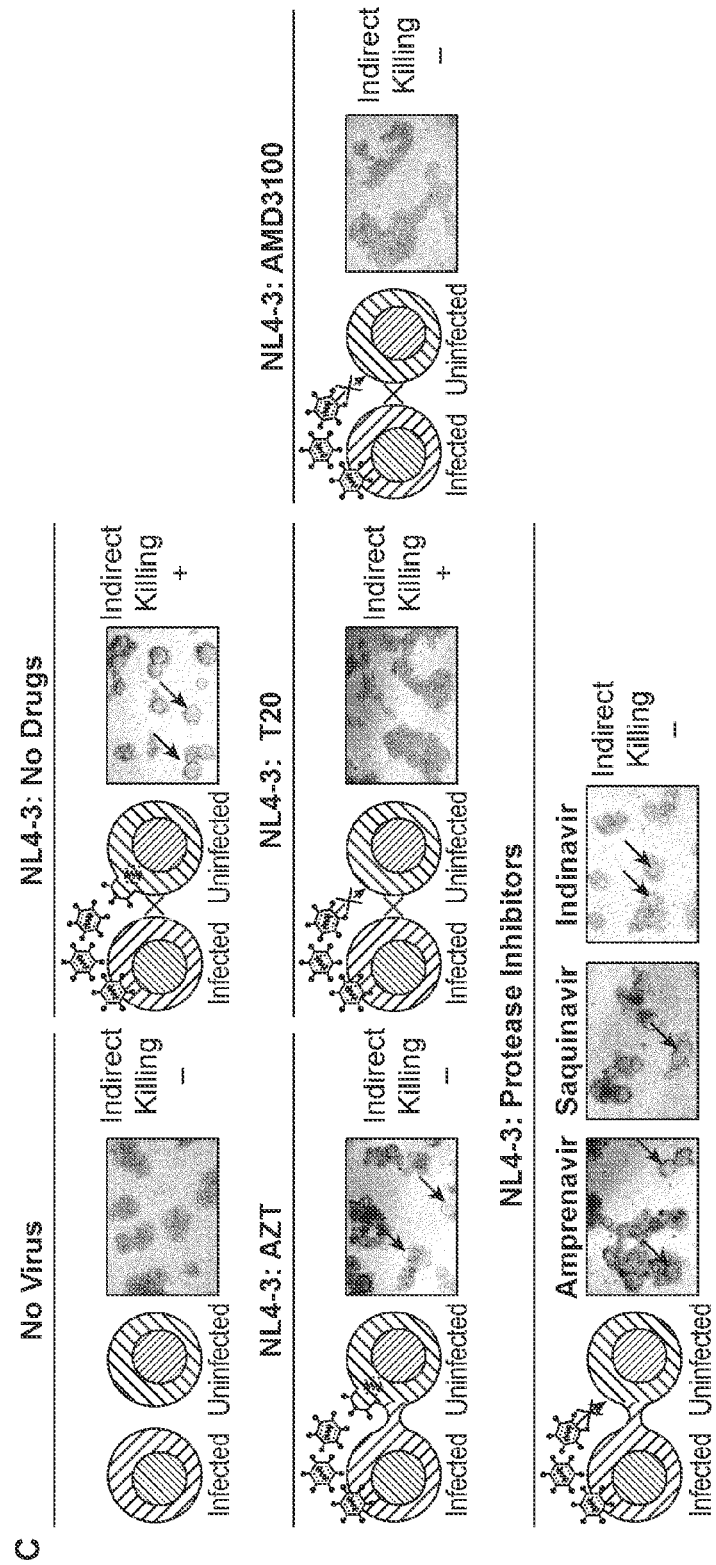

Several mechanisms have been proposed to explain indirect CD4 T-cell killing during HIV infection. Applicants' finding that CD4 T-cell death is blocked by entry and fusion inhibitors but not by AZT, strongly suggested that such killing involves non-productive infection of CD4 T-cells. Therefore, Applicants focused on events that occur after HIV-1 entry. Our investigations demonstrate that abortive viral DNA synthesis occurring in nonpermissive, quiescent CD4 tonsil T-cells, plays a key role in the cell death response. Conversely, in the small subset of permissive target cells, reverse transcription is not interrupted, minimizing the accumulation and subsequent detection of such reverse transcription intermediates (FIG. 7).

Interrupted or slowed reverse transcription may create persistent exposure to cytoplasmic DNA products that elicit an antiviral innate immune response coordinated by activation of type I IFNs (Stetson and Medzhitov, 2006; *Immunity* 24:93-103). Such activation, termed IFN-stimulatory DNA (ISD) response, may be analogous to the type I IFN response triggered by the RIG-I-like receptor (RLR) family of RNA helicases that mediate a cell-intrinsic antiviral defense (Rehwinkel and Reis e Sousa, 2010; *Science* 327:284-286). The results herein suggest that abortive HIV-1 infection also stimulates activation of caspase-3, which is linked to apoptosis, and caspase-1, which promotes the processing and secretion of the proinflammatory cytokines like IL-1β. It is certainly possible that pyroptosis elicited in response to caspase-1 activation also contributes to the observed cytopathic response (Schroder and Tschopp, 2010; *Cell* 140:821-832). The release of inflammatory cytokines during CD4 T-cell death could also contribute to the state of chronic inflammation that characterizes HIV infection. This inflammation may fuel further viral spread by recruiting uninfected lymphocytes to the inflamed zone. While this innate response was likely designed to protect the host, it is subverted in the case of HIV infection and importantly contributes to the immunopathogenic effects characteristic of HIV infection and AIDS.

Such antiviral pathways comprise an unrecognized cell-intrinsic retroviral detection system (Manel et al., 2010, *Nature* 467:214-217; Stetson et al., 2008, *Cell* 134:587-598). Viral RNA in infected cells is recognized by members of the RIG-I-like family of receptors that detect specific RNA patterns like uncapped 5' triphosphate (Rehwinkel and Reis e Sousa, 2010, *Science* 327:284-286). Although uncapped RNA intermediates are generated by the HIV-1 RNase H, they contain a 5' monophosphate and therefore may be not recognized by the RIG-I system (FIG. 10G). In contrast to RNA receptors, intracellular sensing of viral DNA remains poorly understood. Consequently, it is unclear how HIV-1 DNA intermediates are detected in the cytoplasm of abortively infected CD4 T-cells. AIM2 (absent in melanoma 2) was recently identified as a cytoplasmic dsDNA receptor that induces cell death in macrophages through activation of caspase-1 in inflammasomes (Hornung et al., 2009, *Nature* 458:514-518). Applicants' preliminary investigations have not supported a role for AIM2 in cell death induced by abortive HIV infection (not shown) suggesting the potential involvement of a different DNA-sensing mechanism.

In summary, both productive and nonproductive forms of HIV infection contribute to the pathogenic effects of this lentivirus. The relative importance of these different cell death pathways might well vary with the stage of HIV infection. For example, direct infection and death might predominate during acute infection where CCR5-expressing memory CD4 T-cells in gut-associated lymphoid tissue are effectively depleted. Conversely, the CXCR4-dependent indirect killing we describe in tonsil tissue may reflect later stages of HIV-induced disease where a switch to CXCR4 coreceptor usage occurs in approximately 50% of infected subjects. The current study demonstrates how a cytopathic response involving abortive viral infection of resting nonpermissive CD4 T-cells can lead not only to CD4 T-cell depletion but also to the release of proinflammatory cytokines. The ensuing recruitment of new target cells to the site of inflammation may fuel a vicious cycle of continuing infection and CD4 T-cell death centrally contributing to HIV pathogenesis.

All publications, including but not limited to patents and patent applications, cited in this specification and in the specifications of the corresponding priority applications, U.S. Appl. Ser. No. 61/572,883, filed Jul. 22, 2011, U.S. Appl. Ser. No. 61/511,023, filed Jul. 23, 2011, and U.S. Appl. Ser. No. 61/575,324, filed Aug. 17, 2011, to the extent that they provide exemplary procedural or other details supplementary to those set forth herein, are specifically incorporated herein by reference as if each individual publication were specifically and individually indicated to be incorporated by reference herein as though fully set forth.

What is claimed is:

1. A method for ameliorating a symptom of a Human Immunodeficiency Virus-Type 1 (HIV-1) infection in a patient having an HIV-1 infection, the method comprising the step of:

(a) administering to a patient having an HIV-1 infection a pharmaceutical composition comprising a pharmaceutically effective amount of a compound having the formula:

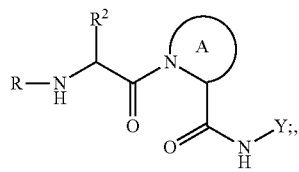

Formula 7 wherein Y is

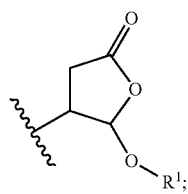

$R^1$ is H, $C_{1-12}$aliphatic, $C_{3-10}$cycloaliphatic, $C_{6-10}$aryl, 5-10 membered heterocyclyl, 5-10 membered heteroaryl, $(C_{3-10}$cycloalkyl$)$-$(C_{1-12}$aliphatic$)$-, cycloalkenyl-$(C_{1-12}$aliphatic$)$-, $(C_{6-10}$aryl$)$-$(C_{1-12}$aliphatic$)$-, (5-10 membered heterocyclyl)-$(C_{1-12}$ aliphatic)-, or (5-10 membered heteroaryl)-$(C_{1-12}$aliphatic)-, wherein any hydrogen atom is optionally and independently replaced by $R^8$ and any set of two hydrogen atoms bound to the same atom is optionally and independently replaced by carbonyl;

Ring A is

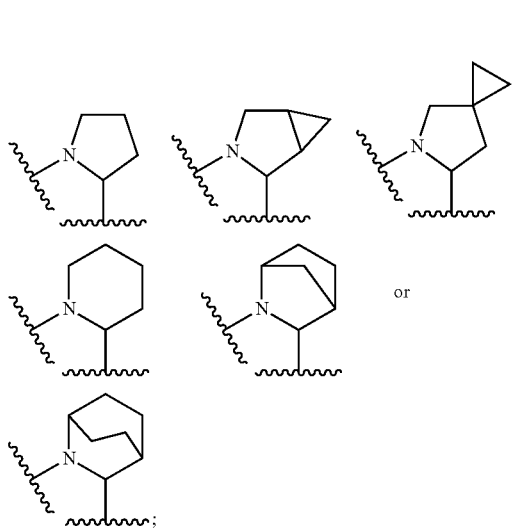

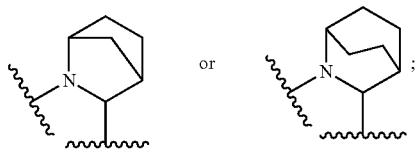

wherein, in each ring, any hydrogen atom is optionally and independently replaced by $R^4$ and any set of two hydrogen atoms bound to the same atom is optionally and independently replaced by carbonyl;

when Ring A is

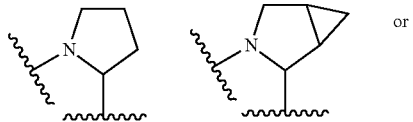

then

R is $R^3C(O)—$, HC(O), $R^3SO_2—$, $R^3OC(O)$, $(R^3)_2NC(O)$, $(R^3)(H)NC(O)$, $R^3C(O)C(O)—$, $R^3—$, $(R^3)_2NC(O)C(O)$, $(R^3)(H)NC(O)C(O)$, or $R^3OC(O)C(O)—$; and $R^3$ is $C_{1-12}$aliphatic, $C_{3-10}$cycloaliphatic, $C_{6-10}$aryl, 5-10 membered heterocyclyl, 5-10 membered heteroaryl, $(C_{3-10}$cycloaliphatic$)$-$(C_{1-12}$aliphatic$)$-, $(C_{6-10}$aryl$)$-$(C_{1-12}$aliphatic$)$-, (5-10 membered heterocyclyl)-$(C_{1-12}$aliphatic$)$-, or (5-10 membered heteroaryl)-$(C_{1-12}$aliphatic$)$-; or two $R^3$ groups bound to the same atom form together with that atom a 3-10 membered aromatic or nonaromatic ring; wherein any ring is optionally fused to an $C_{6-10}$aryl, 5-10 membered heteroaryl, $C_{3-10}$cycloalkyl, or 5-10 membered heterocyclyl; wherein up to 3 aliphatic carbon atoms may be replaced by a group selected from O, N, $NR^9$, S, SO, and $SO_2$, wherein $R^3$ is substituted with up to 6 substituents independently selected from $R^8$;

when Ring A is

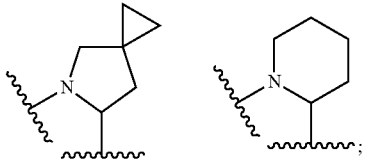

then

R is $R^3C(O)—$, as shown below:

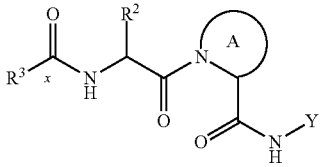

and $R^3$ is phenyl, thiophene, or pyridine, wherein each ring is optionally substituted with up to 5 groups independently selected from $R^{8'}$, and wherein at least one position on the phenyl, thiophene, or pyridine adjacent to bond x is substituted by $R^{12}$, wherein $R^{12}$ has no more than 5 straight-chained atoms;

$R^4$ is halogen, $—OR^9$, $—NO_2$—CN—$CF_3$, $—OCF_1$, $—R^9$, 1,2-methylenedioxy, 1,2-ethylenedioxy, $—N(R^9)_2$, $—SR^9$, $—SOR^9$, $—SO_2R^9$—$SO_2N(R^9)_2$, $—SO_3R^9$, $—C(O)R^9$, $—C(O)C(O)R^9$, $—C(O)C(O)OR^9$, $—C(O)C(O)N(R^9)_2$, $—C(O)CH_2C(O)R^9$, $—C(S)R^9$, $—C(S)OR^9$, $—C(O)OR^9$, $—OC(O)R^9$, $—C(O)N(R^9)_2$, $—OC(O)N(R^9)_2$, $—C(S)N(R^9)_2$, $—(CH_2)_{0-2}NHC(O)R^9$, $—N(R^9)N(R^9)COR^9$, $—N(R^9)N(R^9)C(O)OR^9$, $—N(R^9)N(R^9)CON(R^9)_2$, $—N(R^9)SO_2R^9$, $—N(R^9)SO_2N(R^9)_2$, $—N(R^9)C(O)OR^9$, $—N(R^9)C(O)R^9$, $—N(R^9)C(S)R^9$, $—N(R^9)C(O)N(R^9)_2$, $—N(R^9)C(S)N(R^9)_2$—$N(COR^9)COR^9$, $—N(OR^9)R^9$, $—C(=NH)N(R^9)_2$, $—C(O)N(OR^9)R^9$, $—C(=NOR^9)R^9$, $—OP(O)(OR^9)_2$, $—P(O)(R^9)_2$, $—P(O)(OR^9)_2$, or $—P(O)(H)(OR^9)$;

$R^2$ is $—C(R^5)(R^6)(R^7)$, $C_{6-10}$aryl, 5-10 membered heteroaryl, or $C_{3-7}$ cycloalkyl;

$R^5$ is H or a $C_{1-6}$ straight-chained or branched alkyl;

$R^6$ is H or a $C_{1-6}$ straight-chained or branched alkyl;

$R^7$ is $—CF_3$, $—C_{3-7}$cycloalkyl, $C_{6-10}$aryl, 5-10 membered heteroaryl, heterocycle, or a $C_{1-6}$ straight-chained or branched alkyl, wherein each carbon atom of the alkyl is optionally and independently substituted with $R^{10}$;

or $R^5$ and $R^7$ taken together with the carbon atom to which they are attached form a 3-10 membered cycloaliphatic;

$R^8$ and $R^{8'}$ are each independently halogen, $—OR^9$, $—NO_2$, $—CN$, $—CF_3$, $—OCF_3$, $—R^9$, 1,2-methylenedioxy, 1,2-ethylenedioxy, $—N(R^9)_2$, $—SR^9$, $—SOR^9$, $—SO_2R^9$, $—SO_2N(R^9)_2$—$SO_3R^9$, $—C(O)R^9$, $—C(O)C(O)R^9$, $—C(O)C(O)OR^9$, $—C(O)C(O)N(R^9)_2$, $—C(O)CH_2C(O)R^9$, $—C(S)R^9$, $—C(S)OR^9$, $—C(O)OR^9$, $—OC(O)R^9$, $—C(O)N(R^9)_2$, $—OC(O)N(R^9)_2$, $—C(S)N(R^9)_2$, $—(CH_2)_{0-2}NHC(O)R^9$, $—N(R^9)N(R^9)COR^9$, $—N(R^9)N(R^9)C(O)OR^9$, $—N(R^9)N(R^9)CON(R^9)_2$, $—N(R^9)SO_2R^9$, $—N(R^9)SO_2N(R^9)_2$, $—N(R^9)C(O)OR^9$, $—N(R^9)C(O)R^9$, $—N(R^9)C(S)R^9$, $—N(R^9)C(O)N(R^9)_2$, $—N(R^9)C(S)N(R^9)_2$, $—N(COR^9)COR^9$, $—N(OR^9)R^9$, $—C(=NH)N(R^9)_2$, $—C(O)N(OR^9)R^9$, $—C(=NOR^9)R^9$, $—OP(O)(OR^9)_2$, $—P(O)(R^9)_2$, $—P(O)(OR^9)_2$, and $—P(O)(H)(OR^9)$;

$R^9$ is hydrogen, $C_{1-12}$aliphatic, $C_{3-10}$cycloaliphatic, $C_{6-10}$aryl, 5-10 membered heterocyclyl, 5-10 membered heteroaryl, $(C_{3-10}$cycloaliphatic$)$-$(C_{1-12}$aliphatic$)$-, $(C_{6-10}$aryl$)$-$(C_{1-12}$aliphatic$)$-, (5-10 membered heterocyclyl)-$(C_{1-12}$aliphatic$)$-, or heteroaryl-$(C_{1-12}$aliphatic$)$-; wherein any hydrogen atom is optionally and independently replaced by $R^{13}$ and any set of two hydrogen atoms bound to the same atom is optionally and independently replaced by carbonyl;

$R^{10}$ is halogen, $-OR^{11}$, $-NO_2$, $-CN$, $-CF_3$ $-OCF_3$, $-R^{11}$, or $-SR^{11}$; wherein $R^{11}$ is $C_{1-4}$-aliphatic-;

$R^{11}$ is $C_{1-4}$-aliphatic-; and $R^{12}$ is halogen, $-OR^{11}$, $-NO_2$ $-CN$ $-CF_3$ $-OCF_3$, $-R^{11}$, or $-SR^9$;

$R^{13}$ is $-OR^{11}$, $-NO_2$, $-CN$, $-CF_3$, $-OCF_3$, $-R^{11}$, 1,2-methylenedioxy, 1,2-ethylenedioxy, $-N(R^{11})_2$, $-SR^{11}$, $-SOR^{11}$, $-SO_2R^{11}$ $-SO_2N(R^{11})_2$ $-SO_3R^{11}$, $-C(O)R^{11}$, $-C(O)C(O)R^{11}$, $-C(O)C(O)OR^{11}$, $-C(O)C(O)N(R^{11})_2$, $-C(O)CH_2C(O)R^{11}$ $-C(S)R^{11}$, $-C(S)OR^{11}$, $-C(O)OR^{11}$, $-OC(O)R^{11}$, $-C(O)N(R^{11})_2$, $-OC(O)N(R^{11})_2$, $-C(S)N(R^{11})_2$, $-(CH_2)_{0-2}NHC(O)R^{11}$, $-N(R^{11})N(R^{11})COR^{11}$, $-N(R^{11})N(R^{11})C(O)OR^{11}$, $-N(R^{11})N(R^{11})CON(R^{11})_2$, $-N(R^{11})SO_2R^{11}$, $-N(R^{11})SO_2N(R^{11})_2$, $-N(R^{11})C(O)OR^{11}$, $-N(R^{11})C(O)R^{11}$, $-N(R^{11})C(S)R^{11}$, $-N(R^{11})C(O)N(R^{11})_2$, $-N(R^{11})C(S)N(R^{11})_2$, $-N(COR^{11})COR^{11}$, $-N(OR^{11})R^{11}$, $-C(=NH)N(R^{11})_2$, $-C(O)N(OR^{11})R^{11}$, $-C(=NOR^{11})R^{11}$, $-OP(O)(OR^{11})_2$, $-P(O)(R^{11})_2$, $-P(O)(OR^{11})_2$, and $-P(O)(H)(OR^{11})$; $R^{11}$ is hydrogen, $C_{1-12}$ aliphatic, $C_{3-10}$cycloaliphatic, $C_{6-10}$aryl, 5-10 membered heterocyclyl, 5-10 membered heteroaryl, $(C_{3-10}$cycloaliphatic$)$-$(C_{1-12}$aliphatic$)$, $(C_{6-10}$aryl$)$-$(C_{1-12}$aliphatic$)$-, (5-10 membered heterocyclyl)-$(C_{1-12}$aliphatic$)$-, or heteroaryl-$(C_{1-12}$aliphatic$)$-;

or single stereoisomers, mixtures of stereoisomers, or pharmaceutically acceptable salts thereof;

whereby the symptom of the HIV-1 infection in the patient having the HIV-1 infection is ameliorated.

2. The method according to claim 1, wherein the compound has the following formula:

Formula 19

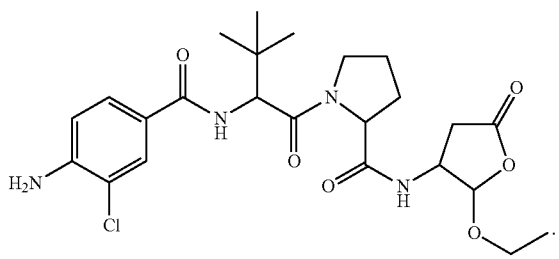

3. The method according to claim 2, wherein a stereoisomer of the compound of Formula 19 is selected from the group consisting of:

Formula 19A

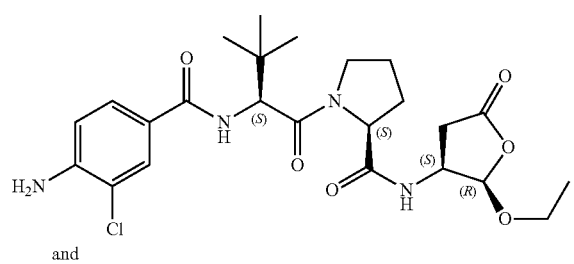

and

Formula 19B

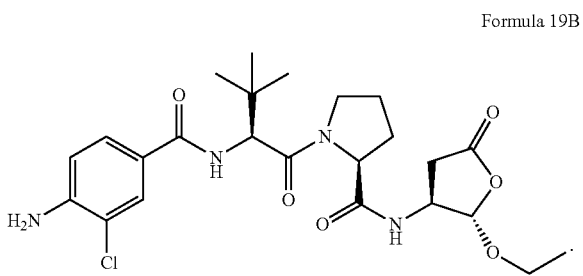

4. The method according to claim 1, wherein the pharmaceutical composition comprises a mixture of stereoisomers having the formula:

Formula 19A

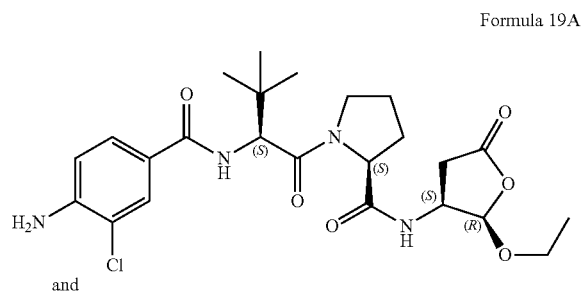

and

Formula 19B

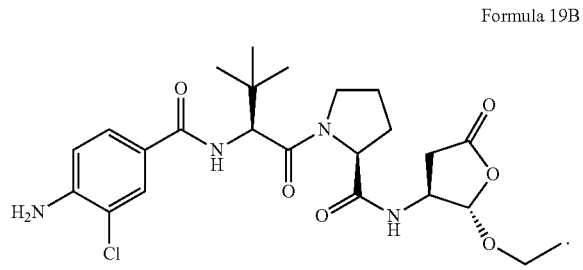

5. The method according to claim 1, wherein the method further comprises the step of:
(b) administering to the patient highly active antiretroviral therapy (HAART).

6. The method according to claim 5, wherein steps (a) and (b) are performed by co-administration.

7. The method according to claim 1, wherein the method further comprises the step of:
(b) administering to the patient an anti-HIV-1 compound.

8. The method according to claim 7, wherein steps (a) and (b) are performed by co-administration.

9. The method according to claim 7, wherein the anti-HIV-1 compound is selected from the group consisting of a nucleoside reverse transcriptase inhibitor, a non-nucleoside reverse transcriptase inhibitor, and a protease inhibitor.

10. The method according to claim 9, wherein the nucleoside reverse transcriptase inhibitor is selected from the group consisting of a compound having formula a compound having formula

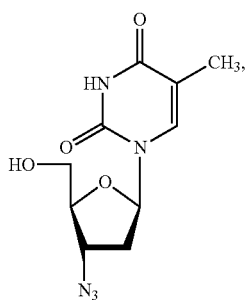 [SMILES: Cc1cn([C@H]2C[C@@H](N=[N+]=[N-])[C@@H](CO)O2)c(=O)[nH]c1=O]

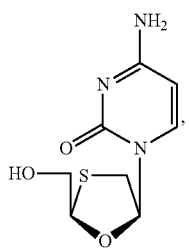 [SMILES: Nc1ccn([C@@H]2CS[C@H](CO)O2)c(=O)n1]

and a compound having formula

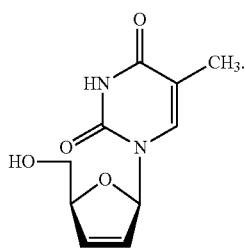 [SMILES: Cc1cn([C@H]2C=C[C@@H](CO)O2)c(=O)[nH]c1=O]

11. The method according to claim 9, wherein the non-nucleoside reverse transcriptase inhibitor is a compound having formula

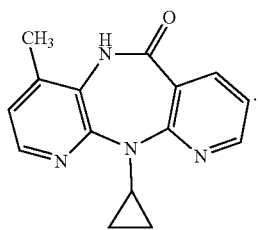 [SMILES: Cc1ccnc2c1NC(=O)c1cccnc1N2C1CC1]

12. The method according to claim 9, wherein the protease inhibitor is selected from the group consisting of a compound having formula

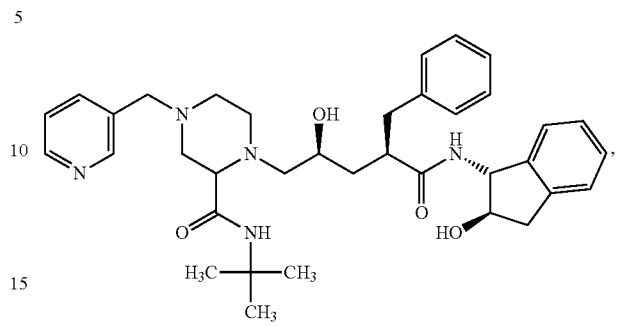

a compound having formula

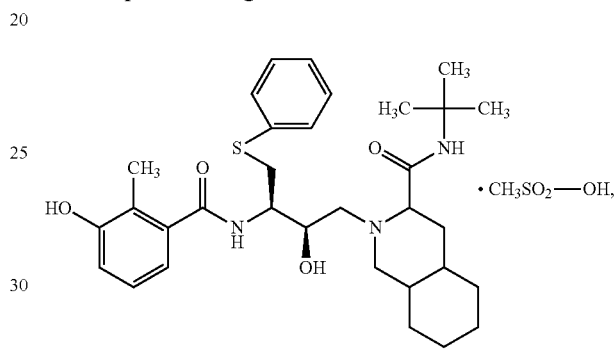

a compound having formula

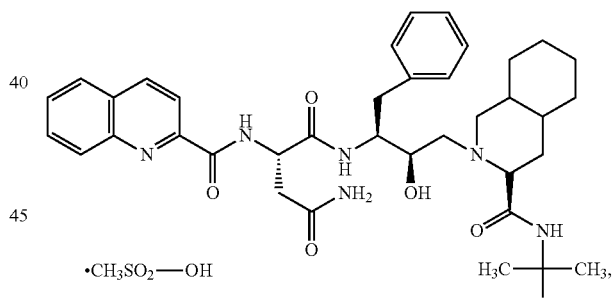

a compound having formula

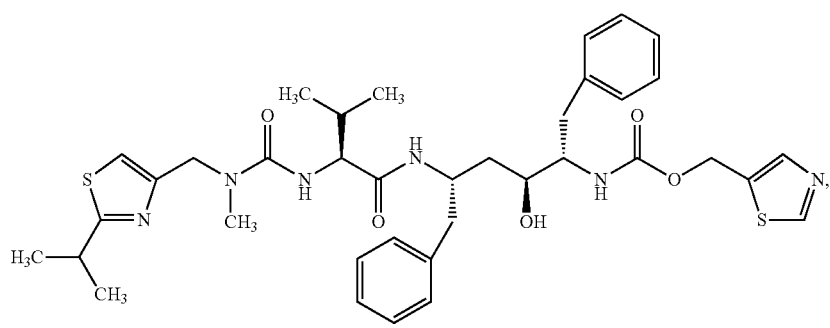

a compound having formula

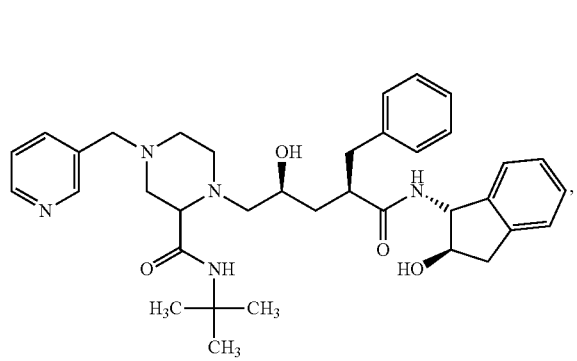

a compound having formula

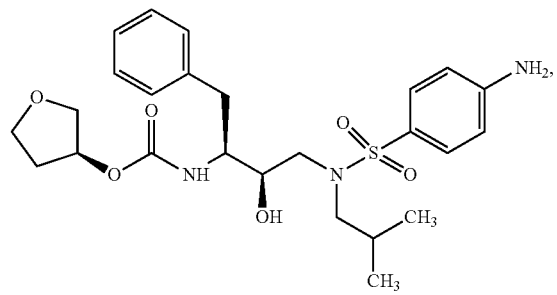 [SMILES: CC(C)CN(C[C@@H](O)[C@H](Cc1ccccc1)NC(=O)O[C@H]1CCOC1)S(=O)(=O)c1ccc(N)cc1]

a compound having formula

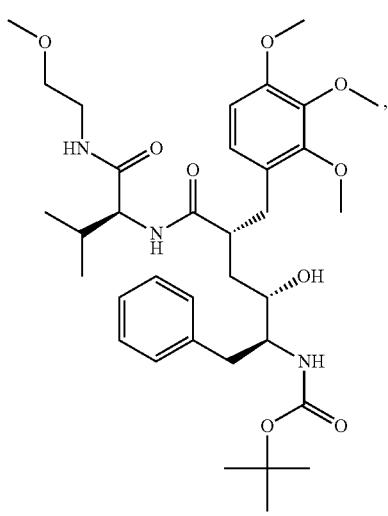

a compound having formula

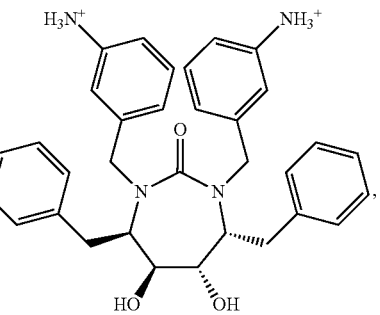

an azapeptide,
a compound having formula

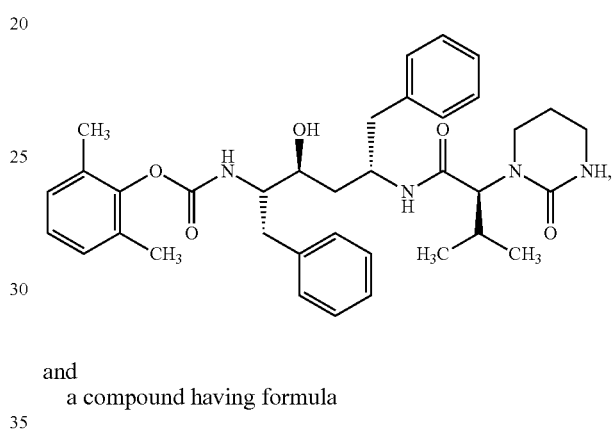

and
a compound having formula

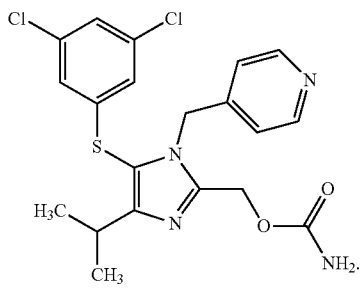 [SMILES: CC(C)c1nc(COC(N)=O)n(Cc2ccncc2)c1Sc1cc(Cl)cc(Cl)c1]

13. The method according to claim 7, wherein the anti-HIV-1 compound is selected from the group consisting of hydroxyurea, ribavirin, interleukin (IL)-2, IL-12, pentafuside (DP-178, T-20), and Yissum Project No. 11607.

14. The method according to claim 1, wherein step (a) comprises administering the pharmaceutical composition via a route selected from the group consisting of orally, rectally, vaginally, intradermal, subdermal, intravenously, intramuscularly, intranasal, intracerebral, intratracheal, intraarterial, intraperitoneal, intravesical, intrapleural, intracoronary or parenteral.

15. The method according to claim 1, wherein step (a) comprises administering the pharmaceutical composition in form of a tablet or capsule.

16. The method according to claim 1, wherein step (a) comprises administering the pharmaceutical composition in form of a liquid preparation.

17. The method according to claim 1, wherein the pharmaceutical composition further comprises a component selected from the group consisting of a preservative, an adjuvant, a stabilizing agent, a wetting agent, an emulsifying agent, a solution promoter, a salt for regulating osmotic pressure, a buffer, a diluent, a filler, a lubricant, a binder, a disintegrate, an absorbent, a colorant, a flavor compound and a sweetener.

18. The method according to claim 1, wherein step (a) comprises administering the compound in an amount of between about 5 to 500 mg.

19. The method according to claim 1, wherein step (a) comprises administering the compound to the patient in a range selected from the group consisting of from about 0.1 mg/kg of patient weight to about 1 g/kg of patient weight, from about 5 mg/kg of patient weight to about 500 mg/kg of patient weight, from about 10 mg/kg of patient weight to about 250 mg/kg of patient weight, and from about 25 mg/kg of patient weight to about 150 mg/kg of patient weight.

20. The method according to claim 1, wherein step (a) comprises administering the compound in an amount of about 10 mg/kg of patient weight.

21. The method according to claim 1, wherein step (a) comprises administering the compound to the patient for a period comprising at least three consecutive days, at least five consecutive days, at least 10 consecutive days, at least 20 consecutive days, at least 30 consecutive days or at least 40 consecutive days.

22. The method according to claim 1, wherein the symptom of the HIV-1 infection is a reduced CD4 T-cell count and the method further comprising the step of:
(b) measuring the patient's CD4 T-cell count.

23. The method according to claim 22, wherein the patient has a reduced T-cell count of less than 1,000/mm$^3$.

24. The method according to claim 1, wherein the symptom of the HIV-1 infection is an increased interleukin (IL)-1β level and the method further comprising the step of:
(b) measuring the patient's IL-1β level.

25. The method according to claim 1, wherein the patient has developed a resistance against an anti-HIV-1 compound.

26. A method for preventing reduction of a CD4 T-cell count in a subject having a Human Immunodeficiency Virus Type-1 (HIV-1) infection, the method comprising the step of:
(a) administering to a subject having an HIV-1 infection a pharmaceutical composition comprising a pharmaceutically effective amount of a compound having the formula:

Formula 7

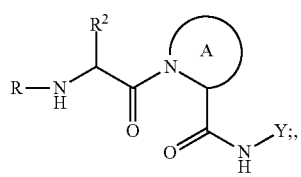

wherein Y is

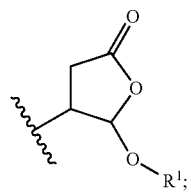

$R^1$ is H, $C_{1-12}$aliphatic, $C_{3-10}$cycloaliphatic, $C_{6-10}$aryl, 5-10 membered heterocyclyl, 5-10 membered heteroaryl, ($C_{3-10}$cycloalkyl)-($C_{1-12}$aliphatic)-, cycloalkenyl-($C_{1-12}$aliphatic)-, ($C_{6-10}$aryl)-($C_{1-12}$aliphatic)-, (5-10 membered heterocyclyl)-($C_{1-12}$ aliphatic)-, or (5-10 membered heteroaryl)-($C_{1-12}$aliphatic)-, wherein any hydrogen atom is optionally and independently replaced by $R^8$ and any set of two hydrogen atoms bound to the same atom is optionally and independently replaced by carbonyl;

Ring A is

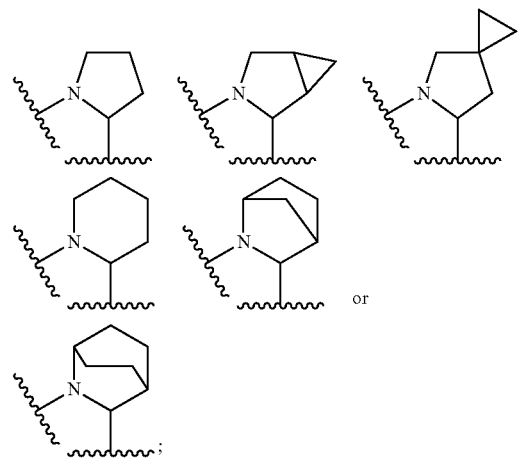

wherein, in each ring, any hydrogen atom is optionally and independently replaced by $R^4$ and any set of two hydrogen atoms bound to the same atom is optionally and independently replaced by carbonyl;

when Ring A is

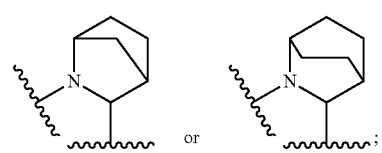 [SMILES: *C1C2CCC(C2)N1* ; *C1C2CCC(CC2)N1*]

then

R is $R^3$C(O)—, HC(O), $R^3$SO$_2$—, $R^3$OC(O), $(R^3)_2$NC(O), $(R^3)$(H)NC(O), $R^3$C(O)C(O)—, $R^3$—, $(R^3)_2$NC(O)C(O), $(R^3)$(H)NC(O)C(O), or $R^3$OC(O)C(O)—; and $R^3$ is $C_{1-12}$aliphatic, $C_{3-10}$cycloaliphatic, $C_{6-10}$aryl, 5-10 membered heterocyclyl, 5-10 membered heteroaryl, ($C_{3-10}$cycloaliphatic)-($C_{1-12}$aliphatic)-, ($C_{6-10}$aryl)-($C_{1-12}$aliphatic)-, (5-10 membered heterocyclyl)-($C_{1-12}$aliphatic)-, or (5-10 membered heteroaryl)-($C_{1-12}$aliphatic)-; or two $R^3$ groups bound to the same atom form together with that atom a 3-10 membered aromatic or nonaromatic ring; wherein any ring is optionally fused to an $C_{6-10}$aryl, 5-10 membered heteroaryl, $C_{3-10}$cycloalkyl, or 5-10 membered heterocyclyl; wherein up to 3 aliphatic carbon atoms may be replaced by a group selected from O, N, NR$^9$, S, SO, and SO$_2$, wherein $R^3$ is substituted with up to 6 substituents independently selected from $R^8$;

when Ring A is

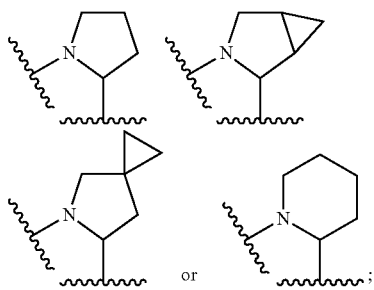

or then
R is $R^3C(O)-$, as shown below:

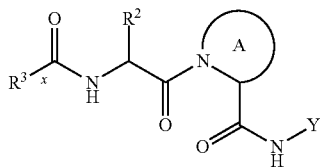

and $R^3$ is phenyl, thiophene, or pyridine, wherein each ring is optionally substituted with up to 5 groups independently selected from $R^{8'}$, and wherein at least one position on the phenyl, thiophene, or pyridine adjacent to bond x is substituted by $R^{12}$, wherein $R^{12}$ has no more than 5 straight-chained atoms;

$R^4$ is halogen, $-OR^9$, $-NO_2-CN-CF_3$, $-OCF_1$, $-R^9$, 1,2-methylenedioxy, 1,2-ethylenedioxy, $-N(R^9)_2$, $-SR^9$, $-SOR^9$, $-SO_2R^9-SO_2N(R^9)_2$, $-SO_3R^9$, $-C(O)R^9$, $-C(O)C(O)R^9$, $-C(O)C(O)OR^9$, $-C(O)C(O)N(R^9)_2$, $-C(O)CH_2C(O)R^9$, $-C(S)R^9$, $-C(S)OR^9$, $-C(O)OR^9$, $-OC(O)R^9$, $-C(O)N(R^9)_2$, $-OC(O)N(R^9)_2$, $-C(S)N(R^9)_2$, $-(CH_2)_{0-2}NHC(O)R^9$, $-N(R^9)N(R^9)COR^9$, $-N(R^9)N(R^9)C(O)OR^9$, $-N(R^9)N(R^9)CON(R^9)_2$, $-N(R^9)SO_2R^9$, $-N(R^9)SO_2N(R^9)_2$, $-N(R^9)C(O)OR^9$, $-N(R^9)C(O)R^9$, $-N(R^9)C(S)R^9$, $-N(R^9)C(O)N(R^9)_2$, $-N(R^9)C(S)N(R^9)_2-N(COR^9)COR^9$, $-N(OR^9)R^9$, $-C(=NH)N(R^9)_2$, $-C(O)N(OR^9)R^9$, $-C(=NOR^9)R^9$, $-OP(O)(OR^9)_2$, $-P(O)(R^9)_2$, $-P(O)(OR^9)_2$, or $-P(O)(H)(OR^9)$;

$R^2$ is $-C(R^5)(R^6)(R^7)$, $C_{6-10}$aryl, 5-10 membered heteroaryl, or $C_{3-7}$ cycloalkyl;

$R^5$ is H or a $C_{1-6}$ straight-chained or branched alkyl;

$R^6$ is H or a $C_{1-6}$ straight-chained or branched alkyl;

$R^7$ is $-CF_3$, $-C_{3-7}$cycloalkyl, $C_{6-10}$aryl, 5-10 membered heteroaryl, heterocycle, or a $C_{1-6}$ straight-chained or branched alkyl, wherein each carbon atom of the alkyl is optionally and independently substituted with $R^{10}$;

or $R^5$ and $R^7$ taken together with the carbon atom to which they are attached form a 3-10 membered cycloaliphatic;

$R^8$ and $R^{8'}$ are each independently halogen, $-OR^9$, $-NO_2$, $-CN$, $-CF_3$, $-OCF_3$, $-R^9$, 1,2-methylenedioxy, 1,2-ethylenedioxy, $-N(R^9)_2$, $-SR^9$, $-SOR^9$, $-SO_2R^9$, $-SO_2N(R^9)_2-SO_3R^9$, $-C(O)R^9$, $-C(O)C(O)R^9$, $-C(O)C(O)OR^9$, $-C(O)C(O)N(R^9)_2$, $-C(O)CH_2C(O)R^9$, $-C(S)R^9$, $-C(S)OR^9$, $-C(O)OR^9$, $-OC(O)R^9$, $-C(O)N(R^9)_2$, $-OC(O)N(R^9)_2$, $-C(S)N(R^9)_2$, $-(CH_2)_{0-2}NHC(O)R^9$, $-N(R^9)N(R^9)COR^9$, $-N(R^9)N(R^9)C(O)OR^9$, $-N(R^9)N(R^9)CON(R^9)_2$, $-N(R^9)SO_2R^9$, $-N(R^9)SO_2N(R^9)_2$, $-N(R^9)C(O)OR^9$, $-N(R^9)C(O)R^9$, $-N(R^9)C(S)R^9$, $-N(R^9)C(O)N(R^9)_2$, $-N(R^9)C(S)N(R^9)_2$, $-N(COR^9)COR^9$, $-N(OR^9)R^9$, $-C(=NH)N(R^9)_2$, $-C(O)N(OR^9)R^9$, $-C(=NOR^9)R^9$, $-OP(O)(OR^9)_2$, $-P(O)(R^9)_2$, $-P(O)(OR^9)_2$, and $-P(O)(H)(OR^9)$;

$R^9$ is hydrogen, $C_{1-12}$aliphatic, $C_{3-10}$cycloaliphatic, $C_{6-10}$aryl, 5-10 membered heterocyclyl, 5-10 membered heteroaryl, $(C_{3-10}$cycloaliphatic)-$(C_{1-12}$aliphatic)-, $(C_{6-10}$aryl)-$(C_{1-12}$aliphatic)-, (5-10 membered heterocyclyl)-$(C_{1-12}$aliphatic)-, or heteroaryl-$(C_{1-12}$aliphatic)-; wherein any hydrogen atom is optionally and independently replaced by $R^{13}$ and any set of two hydrogen atoms bound to the same atom is optionally and independently replaced by carbonyl;

$R^{10}$ is halogen, $-OR^{11}$, $-NO_2$, $-CN$, $-CF_3-OCF_3$, $-R^{11}$, or $-SR^{11}$; wherein $R^{11}$ is $C_{1-4}$-aliphatic-;

$R^{11}$ is $C_{1-4}$-aliphatic-; and $R^{12}$ is halogen, $-OR^{11}$, $-NO_2-CN-CF_3-OCF_3$, $-R^{11}$, or $-SR^9$;

$R^{13}$ is $-OR^{11}$, $-NO_2$, $-CN$, $-CF_3$, $-OCF_3$, $-R^{11}$, 1,2-methylenedioxy, 1,2-ethylenedioxy, $-N(R^{11})_2$, $-SR^{11}$, $-SOR^{11}$, $-SO_2R^{11}-SO_2N(R^{11})_2-SO_3R^{11}$, $-C(O)R^{11}$, $-C(O)C(O)R^{11}$, $-C(O)C(O)OR^{11}$, $-C(O)C(O)N(R^{11})_2$, $-C(O)CH_2C(O)R^{11}-C(S)R^{11}$, $-C(S)OR^{11}$, $-C(O)OR^{11}$, $-OC(O)R^{11}$, $-C(O)N(R^{11})_2$, $-OC(O)N(R^{11})_2$, $-C(S)N(R^{11})_2$, $-(CH_2)_{0-2}NHC(O)R^{11}$, $-N(R^{11})N(R^{11})COR^{11}$, $-N(R^{11})N(R^{11})C(O)OR^{11}$, $-N(R^{11})N(R^{11})CON(R^{11})_2$, $-N(R^{11})SO_2R^{11}$, $-N(R^{11})SO_2N(R^{11})_2$, $-N(R^{11})C(O)OR^{11}$, $-N(R^{11})C(O)R^{11}$, $-N(R^{11})C(S)R^{11}$, $-N(R^{11})C(O)N(R^{11})_2$, $-N(R^{11})C(S)N(R^{11})_2$, $-N(COR^{11})COR^{11}$, $-N(OR^{11})R^{11}$, $-C(=NH)N(R^{11})_2$, $-C(O)N(OR^{11})R^{11}$, $-C(=NOR^{11})R^{11}$, $-OP(O)(OR^{11})_2$, $-P(O)(R^{11})_2$, $-P(O)(OR^{11})_2$, and $-P(O)(H)(OR^{11})$; $R^{11}$ is hydrogen, $C_{1-12}$ aliphatic, $C_{3-10}$cycloaliphatic, $C_{6-10}$aryl, 5-10 membered heterocyclyl, 5-10 membered heteroaryl, $(C_{3-10}$cycloaliphatic)-$(C_{1-12}$aliphatic), $(C_{6-10}$aryl)-$(C_{1-12}$aliphatic)-, (5-10 membered heterocyclyl)-$(C_{1-12}$aliphatic)-, or heteroaryl-$(C_{1-12}$aliphatic)-;

or single stereoisomers, mixtures of stereoisomers, or pharmaceutically acceptable salts thereof;

whereby the CD4 T-cell count in the subject having the HIV-1 infection after performing the step of administering the pharmaceutical composition is higher or not reduced compared to the CD4 T-cell count in the subject having the HIV-1 infection before performing the step of administering the pharmaceutical composition.

27. The method according to claim 26, wherein the compound has the following formula:

Formula 19

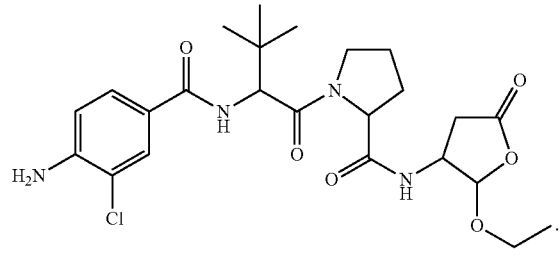

28. The method according to claim 27, wherein a stereoisomer of the compound of Formula 19 is selected from the group consisting of:

Formula 19A

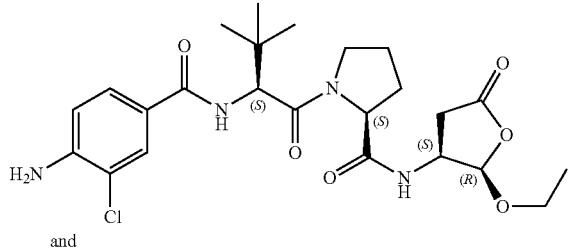

and

Formula 19B

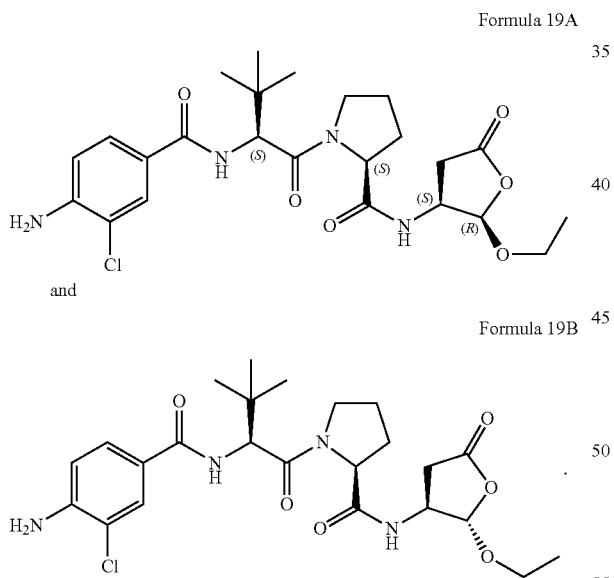

29. The method according to claim 26, wherein the pharmaceutical composition comprises a mixture of stereoisomers having the formula:

Formula 19A and

Formula 19B

30. The method according to claim 26, wherein the method further comprises the step of:
(b) administering to the subject highly active antiretroviral therapy (HAART).

31. The method according to claim 30, wherein steps (a) and (b) are performed by co-administration.

32. The method according to claim 26, wherein the method further comprises the step of:
(b) administering to the subject an anti-HIV-1 compound.

33. The method according to claim 32, wherein steps (a) and (b) are performed by co-administration.

34. The method according to claim 32, wherein the anti-HIV-1 compound is selected from the group consisting of a nucleoside reverse transcriptase inhibitor, a non-nucleoside reverse transcriptase inhibitor, and a protease inhibitor.

35. The method according to claim 34, wherein the nucleoside reverse transcriptase inhibitor is selected from the group consisting of a compound having formula

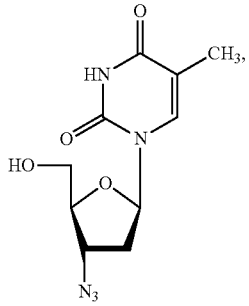

a compound having formula

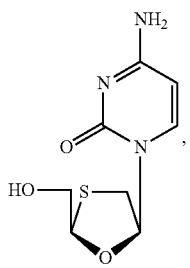 [SMILES: Nc1ccn([C@@H]2CS[C@H](CO)O2)c(=O)n1]

and a compound having formula

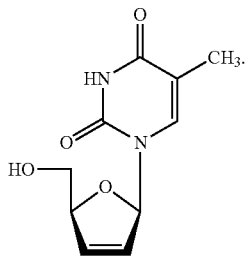 [SMILES: Cc1cn([C@H]2C=C[C@@H](CO)O2)c(=O)[nH]c1=O]

36. The method according to claim 34, wherein the non-nucleoside reverse transcriptase inhibitor is a compound having formula

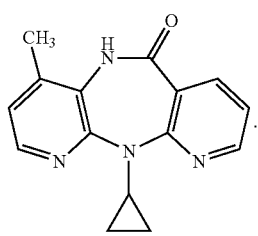 [SMILES: Cc1ccnc2c1NC(=O)c1cccnc1N2C1CC1]

37. The method according to claim 34, wherein the protease inhibitor is selected from the group consisting of a compound having formula
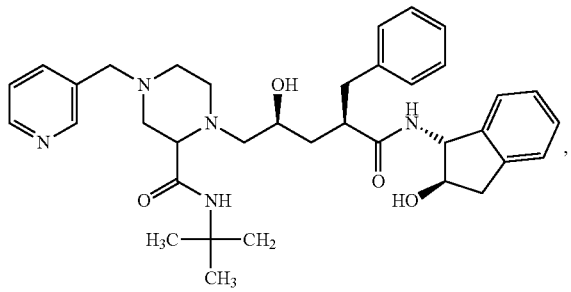
a compound having formula
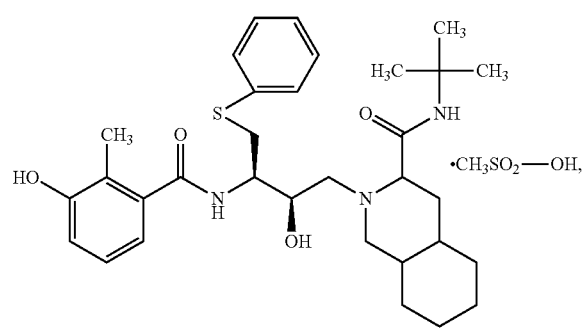
a compound having formula
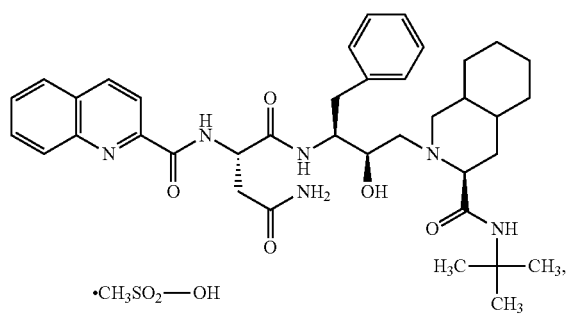
a compound having formula
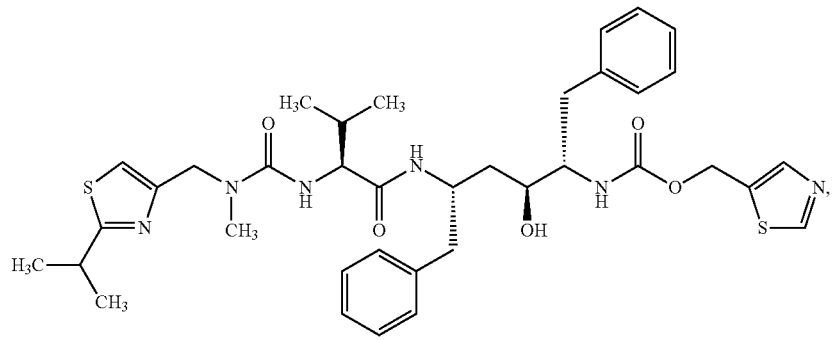 [SMILES: CC(C)c1nc(CN(C)C(=O)N[C@H](C(=O)N[C@@H](Cc2ccccc2)C[C@H](O)[C@H](Cc2ccccc2)NC(=O)OCc2cncs2)C(C)C)cs1]
a compound having formula
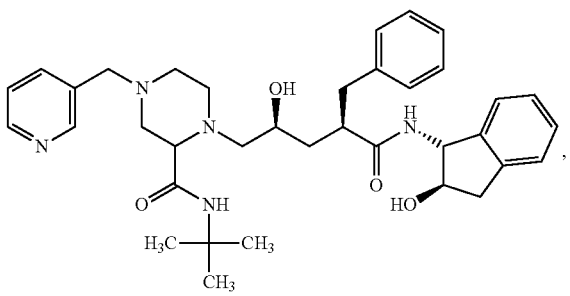
a compound having formula
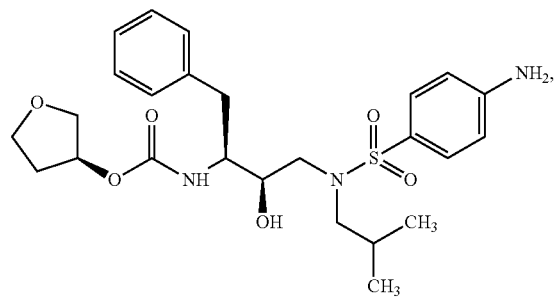 [SMILES: CC(C)CN(C[C@@H](O)[C@H](Cc1ccccc1)NC(=O)O[C@H]1CCOC1)S(=O)(=O)c1ccc(N)cc1]
a compound having formula
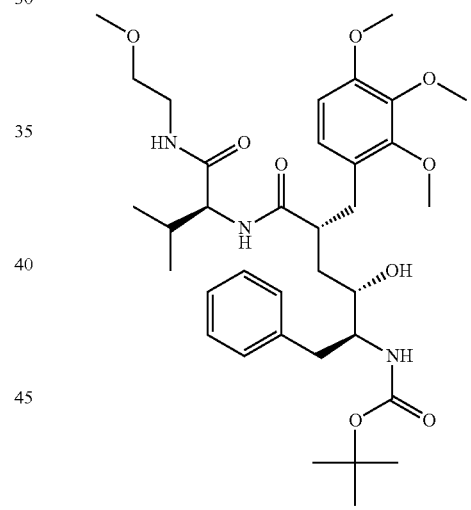

a compound having formula

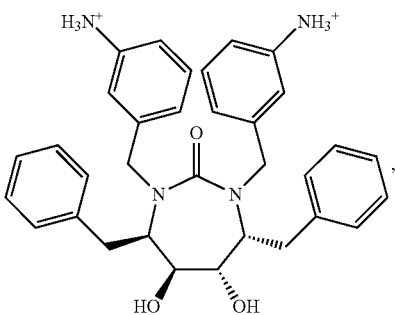 [SMILES: [NH3+]c1cccc(CN2C(=O)N(Cc3cccc([NH3+])c3)[C@H](Cc3ccccc3)[C@H](O)[C@@H](O)[C@H]2Cc2ccccc2)c1]

an azapeptide,
a compound having formula

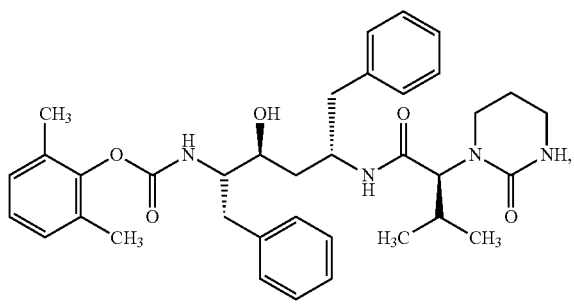

and
a compound having formula

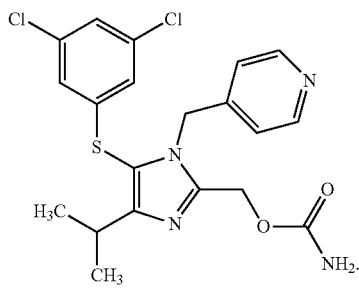 [SMILES: CC(C)c1nc(COC(N)=O)n(Cc2ccncc2)c1Sc1cc(Cl)cc(Cl)c1]

38. The method according to claim 32, wherein the anti-HIV-1 compound is selected from the group consisting of hydroxyurea, ribavirin, interleukin (IL)-2, IL-12, pentafuside (DP-178, T-20), and Yissum Project No. 11607.

39. The method according to claim 26, wherein step (a) comprises administering the pharmaceutical composition via a route selected from the group consisting of orally, rectally, vaginally, intradermal, subdermal, intravenously, intramuscularly, intranasal, intracerebral, intratracheal, intraarterial, intraperitoneal, intravesical, intrapleural, intracoronary or parenteral.

40. The method according to claim 26, wherein step (a) comprises administering the pharmaceutical composition in form of a tablet or capsule.

41. The method according to claim 26, wherein step (a) comprises administering the pharmaceutical composition in form of a liquid preparation.

42. The method according to claim 26, wherein the pharmaceutical composition further comprises a component selected from the group consisting of a preservative, an adjuvant, a stabilizing agent, a wetting agent, an emulsifying agent, a solution promoter, a salt for regulating osmotic pressure, a buffer, a diluent, a filler, a lubricant, a binder, a disintegrate, an absorbent, a colorant, a flavor compound and a sweetener.

43. The method according to claim 26, wherein step (a) comprises administering the compound in an amount of between about 5 to 500 mg.

44. The method according to claim 26, wherein step (a) comprises administering the compound to the subject in a range selected from the group consisting of from about 0.1 mg/kg of subject weight to about 1 g/kg of subject weight, from about 5 mg/kg of subject weight to about 500 mg/kg of subject weight, from about 10 mg/kg of subject weight to about 250 mg/kg of subject weight, and from about 25 mg/kg of subject weight to about 150 mg/kg of subject weight.

45. The method according to claim 26, wherein step (a) comprises administering the compound in an amount of about 10 mg/kg of subject weight.

46. The method according to claim 26, wherein step (a) comprises administering the compound to the subject for a period comprising at least three consecutive days, at least five consecutive days, at least 10 consecutive days, at least 20 consecutive days, at least 30 consecutive days or at least 40 consecutive days.

47. The method according to claim 26, further comprising the step of:
(b) measuring the subject's CD4 T-cell count.

48. The method according to claim 26, wherein the subject has a reduced T-cell count of less than $1,000/mm^3$.

49. The method according to claim 26, further comprising the step of:
(b) measuring the subject's interleukin-1β level.

50. The method according to claim 26, wherein the subject has developed a resistance against an anti-HIV-1 compound.

51. A method for prophylactic treatment of a subject, the method comprising the step of:
(a) administering to a subject a pharmaceutical composition comprising a pharmaceutically effective amount of a compound having the formula:

Formula 7

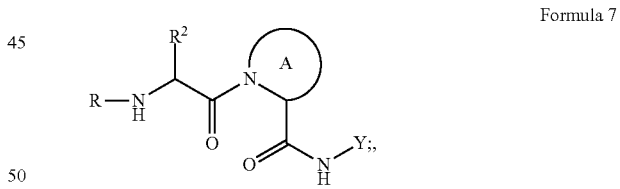

wherein Y is

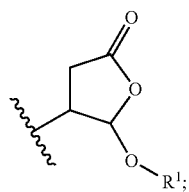

$R^1$ is H, $C_{1-12}$aliphatic, $C_{3-10}$cycloaliphatic, $C_{6-10}$aryl, 5-10 membered heterocyclyl, 5-10 membered heteroaryl, ($C_{3-10}$cycloalkyl)-($C_{1-12}$aliphatic)-, cycloalkenyl-($C_{1-12}$aliphatic)-, ($C_{6-10}$aryl)-($C_{1-12}$aliphatic)-, (5-10 membered heterocyclyl)-($C_{1-12}$ aliphatic)-, or (5-10 membered heteroaryl)-($C_{1-12}$aliphatic)-, wherein any hydrogen atom is optionally and independently replaced by $R^8$ and any set of two hydrogen atoms bound to the same atom is optionally and independently replaced by carbonyl;

Ring A is

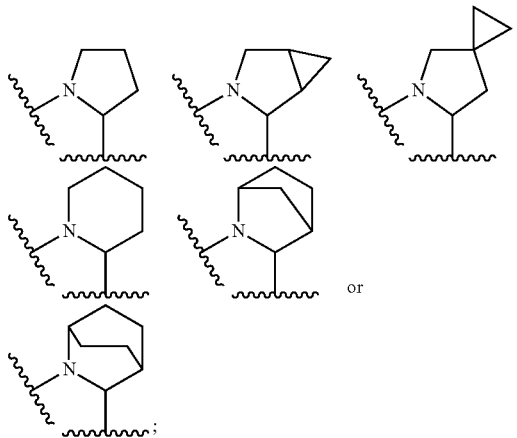

wherein, in each ring, any hydrogen atom is optionally and independently replaced by $R^4$ and any set of two hydrogen atoms bound to the same atom is optionally and independently replaced by carbonyl;

when Ring A is

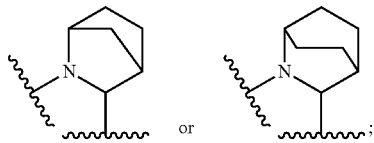 [SMILES: *C1C2CCC(C2)N1* ; *C1C2CCC(CC2)N1*]

then

R is $R^3C(O)$—, HC(O), $R^3SO_2$—, $R^3OC(O)$, $(R^3)_2NC(O)$, $(R^3)(H)NC(O)$, $R^3C(O)C(O)$—, $R^3$—, $(R^3)_2NC(O)C(O)$, $(R^3)(H)NC(O)C(O)$, or $R^3OC(O)C(O)$—; and $R^3$ is $C_{1-12}$aliphatic, $C_{3-10}$cycloaliphatic, $C_{6-10}$aryl, 5-10 membered heterocyclyl, 5-10 membered heteroaryl, ($C_{3-10}$cycloaliphatic)-($C_{1-12}$aliphatic)-, ($C_{6-10}$aryl)-($C_{1-12}$aliphatic)-, (5-10 membered heterocyclyl)-($C_{1-12}$aliphatic)-, or (5-10 membered heteroaryl)-($C_{1-12}$aliphatic)-; or two $R^3$ groups bound to the same atom form together with that atom a 3-10 membered aromatic or nonaromatic ring; wherein any ring is optionally fused to an $C_{6-10}$aryl, 5-10 membered heteroaryl, $C_{3-10}$cycloalkyl, or 5-10 membered heterocyclyl; wherein up to 3 aliphatic carbon atoms may be replaced by a group selected from O, N, $NR^9$, S, SO, and $SO_2$, wherein $R^3$ is substituted with up to 6 substituents independently selected from $R^8$;

when Ring A is

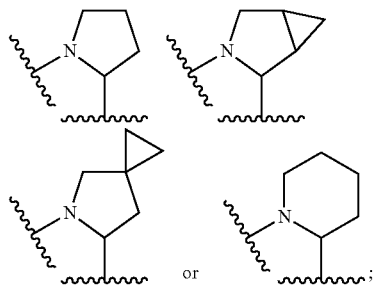

then
R is $R^3C(O)$—, as shown below:

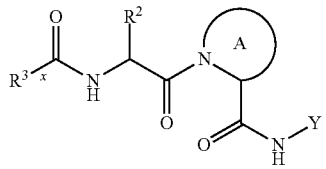

and $R^3$ is phenyl, thiophene, or pyridine, wherein each ring is optionally substituted with up to 5 groups independently selected from $R^{8'}$, and wherein at least one position on the phenyl, thiophene, or pyridine adjacent to bond x is substituted by $R^{12}$, wherein $R^{12}$ has no more than 5 straight-chained atoms;

$R^4$ is halogen, —$OR^9$, —$NO_2$—CN—$CF_3$, —$OCF_1$, —$R^9$, 1,2-methylenedioxy, 1,2-ethylenedioxy, —$N(R^9)_2$, —$SR^9$, —$SOR^9$, —$SO_2R^9$—$SO_2N(R^9)_2$, —$SO_3R^9$, —$C(O)R^9$, —$C(O)C(O)R^9$, —$C(O)C(O)OR^9$, —$C(O)C(O)N(R^9)_2$, —$C(O)CH_2C(O)R^9$, —$C(S)R^9$, —$C(S)OR^9$, —$C(O)OR^9$, —$OC(O)R^9$, —$C(O)N(R^9)_2$, —$OC(O)N(R^9)_2$, —$C(S)N(R^9)_2$, —$(CH_2)_{0-2}NHC(O)R^9$, —$N(R^9)N(R^9)COR^9$, —$N(R^9)N(R^9)C(O)OR^9$, —$N(R^9)N(R^9)CON(R^9)_2$, —$N(R^9)SO_2R^9$, —$N(R^9)SO_2N(R^9)_2$, —$N(R^9)C(O)OR^9$, —$N(R^9)C(O)R^9$, —$N(R^9)C(S)R^9$, —$N(R^9)C(O)N(R^9)_2$, —$N(R^9)C(S)N(R^9)_2$—$N(COR^9)COR^9$, —$N(OR^9)R^9$, —$C(=NH)N(R^9)_2$, —$C(O)N(OR^9)R^9$, —$C(=NOR^9)R^9$, —$OP(O)(OR^9)_2$, —$P(O)(R^9)_2$, —$P(O)(OR^9)_2$, or —$P(O)(H)(OR^9)$;

$R^2$ is —$C(R^5)(R^6)(R^7)$, $C_{6-10}$aryl, 5-10 membered heteroaryl, or $C_{3-7}$ cycloalkyl;

$R^5$ is H or a $C_{1-6}$ straight-chained or branched alkyl;

$R^6$ is H or a $C_{1-6}$ straight-chained or branched alkyl;

$R^7$ is —$CF_3$, —$C_{3-7}$cycloalkyl, $C_{6-10}$aryl, 5-10 membered heteroaryl, heterocycle, or a $C_{1-6}$ straight-chained or branched alkyl, wherein each carbon atom of the alkyl is optionally and independently substituted with $R^{10}$;

or $R^5$ and $R^7$ taken together with the carbon atom to which they are attached form a 3-10 membered cycloaliphatic;

$R^8$ and $R^{8'}$ are each independently halogen, —$OR^9$, —$NO_2$, —CN, —$CF_3$, —$OCF_3$, —$R^9$, 1,2-methylenedioxy, 1,2-ethylenedioxy, —$N(R^9)_2$, —$SR^9$, —$SOR^9$, —$SO_2R^9$, —$SO_2N(R^9)_2$—$SO_3R^9$, —$C(O)R^9$, —$C(O)C(O)R^9$, —$C(O)C(O)OR^9$, —$C(O)C(O)N(R^9)_2$, —$C(O)CH_2C(O)R^9$, —$C(S)R^9$, —$C(S)OR^9$, —$C(O)OR^9$, —$OC(O)R^9$, —$C(O)N(R^9)_2$, —$OC(O)N(R^9)_2$, —$C(S)N(R^9)_2$, —$(CH_2)_{0-2}NHC(O)R^9$, —$N(R^9)N(R^9)COR^9$, —$N(R^9)N(R^9)C(O)OR^9$, —$N(R^9)N(R^9)CON(R^9)_2$, —N(R⁹)SO₂R⁹, —N(R⁹)SO₂N(R⁹)₂, —N(R⁹)C(O)OR⁹, —N(R⁹)C(O)R⁹, —N(R⁹)C(S)R⁹, —N(R⁹)C(O)N(R⁹)₂, —N(R⁹)C(S)N(R⁹)₂, —N(COR⁹)COR⁹, —N(OR⁹)R⁹, —C(=NH)N(R⁹)₂, —C(O)N(OR⁹)R⁹, —C(=NOR⁹)R⁹, —OP(O)(OR⁹)₂, —P(O)(R⁹)₂, —P(O)(OR⁹)₂, and —P(O)(H)(OR⁹);

R⁹ is hydrogen, C₁₋₁₂aliphatic, C₃₋₁₀cycloaliphatic, C₆₋₁₀aryl, 5-10 membered heterocyclyl, 5-10 membered heteroaryl, (C₃₋₁₀cycloaliphatic)-(C₁₋₁₂aliphatic)-, (C₆₋₁₀aryl)-(C₁₋₁₂aliphatic)-, (5-10 membered heterocyclyl)-(C₁₋₁₂aliphatic)-, or heteroaryl-(C₁₋₁₂aliphatic)-; wherein any hydrogen atom is optionally and independently replaced by R¹³ and any set of two hydrogen atoms bound to the same atom is optionally and independently replaced by carbonyl;

R¹⁰ is halogen, —OR¹¹, —NO₂, —CN, —CF₃—OCF₃, —R¹¹, or —SR¹¹; wherein R¹¹ is C₁₋₄-aliphatic-;

R¹¹ is C₁₋₄-aliphatic-;

R¹² is halogen, —OR¹¹, —NO₂—CN—CF₃—OCF₃, —R¹¹, or —SR⁹;

R¹³ is —OR¹¹, —NO₂, —CN, —CF₃, —OCF₃, —R¹¹, 1,2-methylenedioxy, 1,2-ethylenedioxy, —N(R¹¹)₂, —SR¹¹, —SOR¹¹, —SO₇R¹¹—SO₂N(R¹¹)₂—SO₃R¹¹, —C(O)R¹¹, —C(O)C(O)R¹¹, —C(O)C(O)OR¹¹, —C(O)C(O)N(R¹¹)₂, —C(O)CH₂C(O)R¹¹—C(S)R¹¹, —C(S)OR¹¹, —C(O)OR¹¹, —OC(O)R¹¹, —C(O)N(R¹¹)₂, —OC(O)N(R¹¹)₂, —C(S)N(R¹¹)₂, —(CH₂)₀₋₂NHC(O)R¹¹, —N(R¹¹)N(R¹¹)COR¹¹, —N(R¹¹)N(R¹¹)C(O)OR¹¹, —N(R¹¹)N(R¹¹)CON(R¹¹)₂, —N(R¹¹)SO₂R¹¹, —N(R¹¹)SO₂N(R¹¹)₂, —N(R¹¹)C(O)OR¹¹, —N(R¹¹)C(O)R¹¹, —N(R¹¹)C(S)R¹¹, —N(R¹¹)C(O)N(R¹¹)₂, —N(R¹¹)C(S)N(R¹¹)₂, —N(COR¹¹)COR¹¹, —N(OR¹¹)R¹¹, —C(=NH)N(R¹¹)₂, —C(O)N(OR¹¹)R¹¹, —C(=NOR¹¹)R¹¹, —OP(O)(OR¹¹)₂, —P(O)(R¹¹)₂, —P(O)(OR¹¹)₂, and —P(O)(H)(OR¹¹); R¹¹ is hydrogen, C₁₋₁₂ aliphatic, C₃₋₁₀cycloaliphatic, C₆₋₁₀aryl, 5-10 membered heterocyclyl, 5-10 membered heteroaryl, (C₃₋₁₀cycloaliphatic)-(C₁₋₁₂aliphatic), (C₆₋₁₀aryl)-(C₁₋₁₂aliphatic)-, (5-10 membered heterocyclyl)-(C₁₋₁₂aliphatic)-, or heteroaryl-(C₁₋₁₂aliphatic)-;

or single stereoisomers, mixtures of stereoisomers, or pharmaceutically acceptable salts thereof;

whereby the prophylactic treatment reduces development of a pathological condition associated with or developing in a subject as a consequence of a Human Immunodeficiency Virus Type-1 (HIV-1) infection or AIDS compared to a subject having an HIV-1 infection or AIDS without having received administration of the pharmaceutical composition.

52. The method according to claim 51, wherein the compound has the following formula:

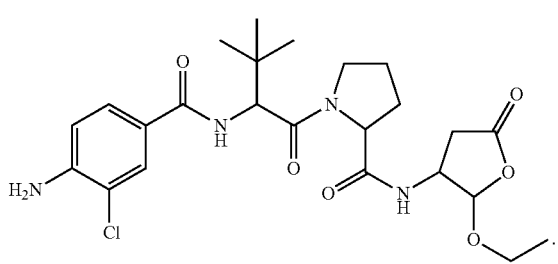

Formula 19

53. The method according to claim 51, wherein a stereoisomer of the compound of Formula 19 is selected from the group consisting of:

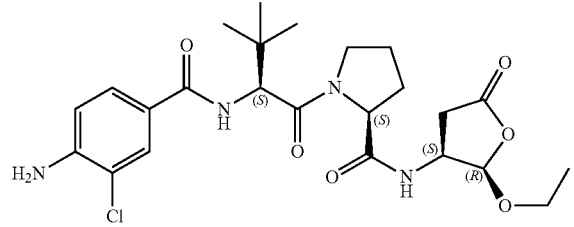

Formula 19A and

Formula 19B

54. The method according to claim 51, wherein the pharmaceutical composition comprises a mixture of stereoisomers having the formula:

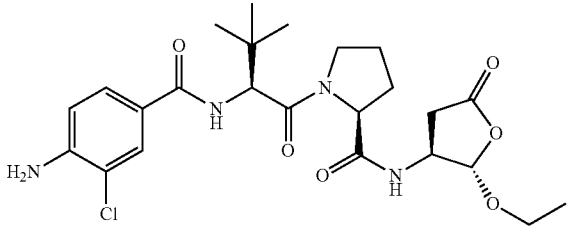

Formula 19A and

Formula 19B

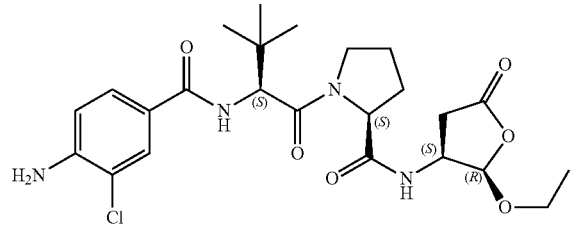

55. The method according to claim 51, wherein the method further comprises the step of:
(b) administering to the subject highly active antiretroviral therapy (HAART).

56. The method according to claim 55, wherein steps (a) and (b) are performed by co-administration.

57. The method according to claim 51, wherein the method further comprises the step of:

(b) administering to the subject an anti-HIV-1 compound.

58. The method according to claim 57, wherein steps (a) and (b) are performed by co-administration.

59. The method according to claim 57, wherein the anti-HIV-1 compound is selected from the group consisting of a nucleoside reverse transcriptase inhibitor, a non-nucleoside reverse transcriptase inhibitor, and a protease inhibitor.

60. The method according to claim 59, wherein the nucleoside reverse transcriptase inhibitor is selected from the group consisting of a compound having formula

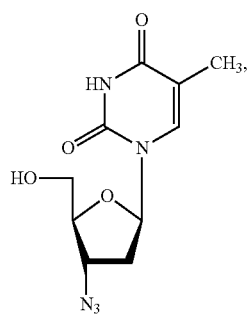 [SMILES: Cc1cn([C@H]2C[C@@H](N=[N+]=[N-])[C@@H](CO)O2)c(=O)[nH]c1=O]

a compound having formula

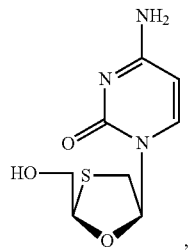

and a compound having formula

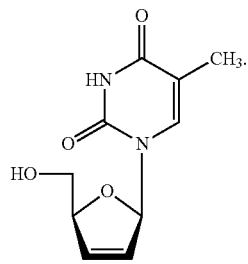 [SMILES: Cc1cn([C@H]2C=C[C@@H](CO)O2)c(=O)[nH]c1=O]

61. The method according to claim 59, wherein the non-nucleoside reverse transcriptase inhibitor is a compound having formula

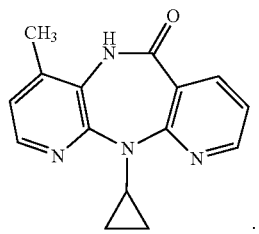 [SMILES: Cc1ccnc2c1NC(=O)c1cccnc1N2C1CC1]

62. The method according to claim 59, wherein the protease inhibitor is selected from the group consisting of a compound having formula

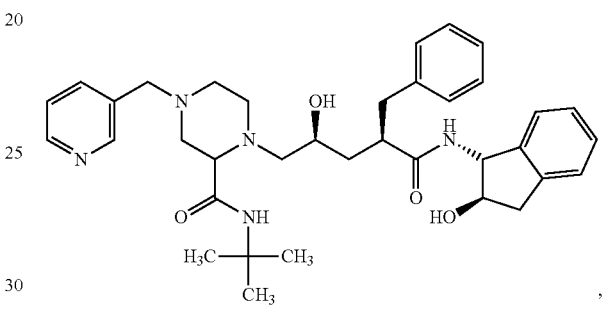

a compound having formula

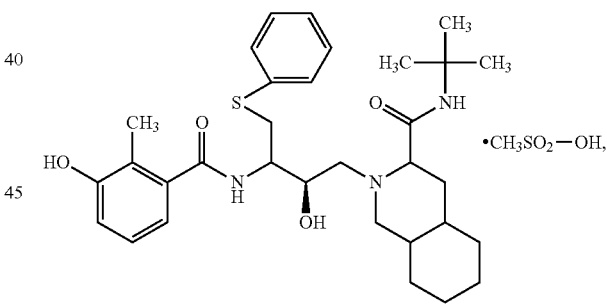

a compound having formula

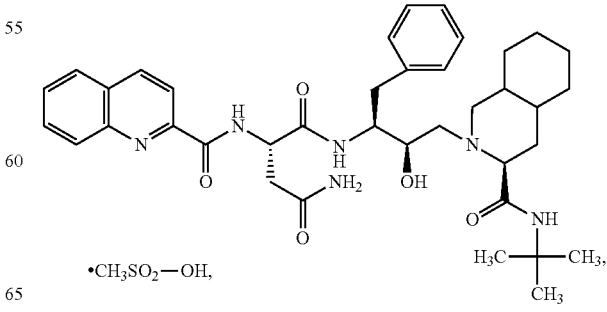

a compound having formula
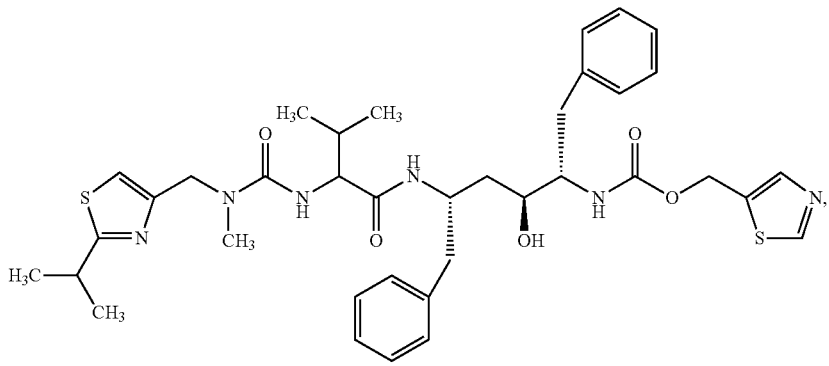 [SMILES: CC(C)c1nc(CN(C)C(=O)NC(C(=O)N[C@@H](Cc2ccccc2)C[C@H](O)[C@H](Cc2ccccc2)NC(=O)OCc2cncs2)C(C)C)cs1]
a compound having formula
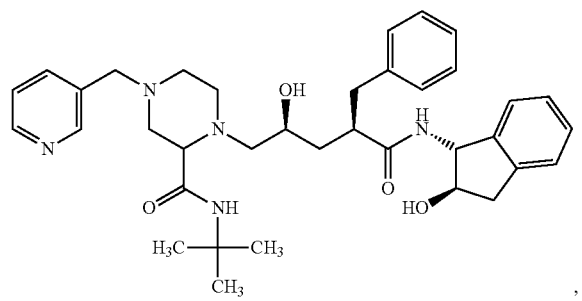
a compound having formula
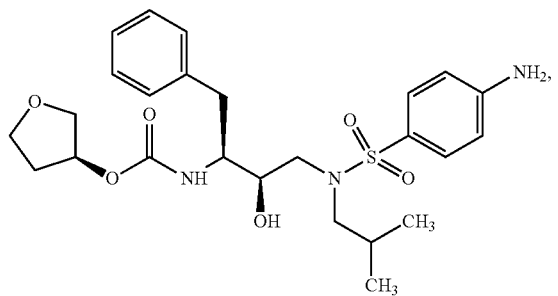 [SMILES: CC(C)CN(C[C@@H](O)[C@H](Cc1ccccc1)NC(=O)O[C@H]1CCOC1)S(=O)(=O)c1ccc(N)cc1]
a compound having formula
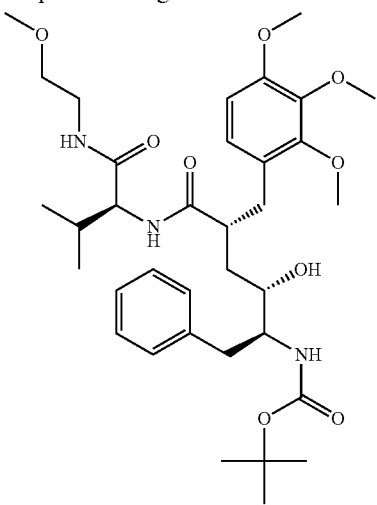
a compound having formula
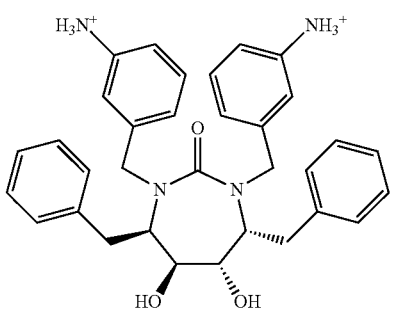
an azapeptide,
a compound having formula
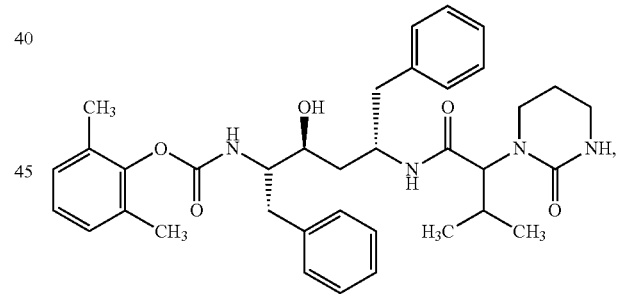
and
a compound having formula
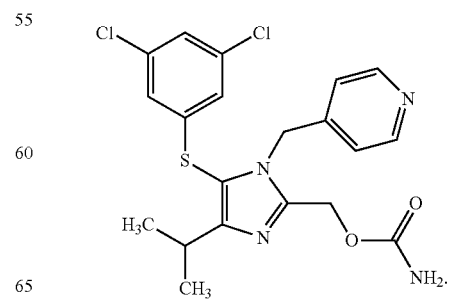

63. The method according to claim 57, wherein the anti-HIV-1 compound is selected from the group consisting of hydroxyurea, ribavirin, interleukin (IL)-2, IL-12, pentafuside (DP-178, T-20), and Yissum Project No. 11607.

64. The method according to claim 51, wherein step (a) comprises administering the pharmaceutical composition via a route selected from the group consisting of orally, rectally, vaginally, intradermal, subdermal, intravenously, intramuscularly, intranasal, intracerebral, intratracheal, intraarterial, intraperitoneal, intravesical, intrapleural, intracoronary or parenteral.

65. The method according to claim 51, wherein step (a) comprises administering the pharmaceutical composition in form of a tablet or capsule.

66. The method according to claim 51, wherein step (a) comprises administering the pharmaceutical composition in form of a liquid preparation.

67. The method according to claim 51, wherein the pharmaceutical composition further comprises a component selected from the group consisting of a preservative, an adjuvant, a stabilizing agent, a wetting agent, an emulsifying agent, a solution promoter, a salt for regulating osmotic pressure, a buffer, a diluent, a filler, a lubricant, a binder, a disintegrate, an absorbent, a colorant, a flavor compound and a sweetener.

68. The method according to claim 51, wherein step (a) comprises administering the compound in an amount of between about 5 to 500 mg.

69. The method according to claim 51, wherein step (a) comprises administering the compound to the subject in a range selected from the group consisting of from about 0.1 mg/kg of subject weight to about 1 g/kg of subject weight, from about 5 mg/kg of subject weight to about 500 mg/kg of subject weight, from about 10 mg/kg of subject weight to about 250 mg/kg of subject weight, and from about 25 mg/kg of subject weight to about 150 mg/kg of subject weight.

70. The method according to claim 51, wherein step (a) comprises administering the compound in an amount of about 10 mg/kg of subject weight.

71. The method according to claim 51, wherein step (a) comprises administering the compound to the subject for a period comprising at least three consecutive days, at least five consecutive days, at least 10 consecutive days, at least 20 consecutive days, at least 30 consecutive days or at least 40 consecutive days.

72. The method according to claim 51, further comprising the step of:
(b) measuring the subject's CD4 T-cell count.

73. The method according to claim 72, wherein the subject has a reduced T-cell count of less than $1,000/mm^3$.

74. The method according to claim 51, method further comprising the step of:
(b) measuring the subject's IL-1β level.

75. The method according to claim 51, wherein the subject has developed a resistance against an anti-HIV-1 compound.

* * * * *